US010441290B2

(12) United States Patent
Rudakov et al.

(10) Patent No.: US 10,441,290 B2
(45) Date of Patent: Oct. 15, 2019

(54) IMPLANTABLE LUMINAL DEVICES

(71) Applicant: ArtVentive Medical Group, Inc., San Marcos, CA (US)

(72) Inventors: Leon Rudakov, San Marcos, CA (US); Andrew Black, Johnsburg, IL (US); Andrew R. Leopold, Hawthorn Woods, IL (US); Kelly Jensen, Palatine, IL (US)

(73) Assignee: ArtVentive Medical Group, Inc., San Marcos, CA (US)

( * ) Notice: Subject to any disclaimer, the term of this patent is extended or adjusted under 35 U.S.C. 154(b) by 179 days.

(21) Appl. No.: 15/583,956

(22) Filed: May 1, 2017

(65) Prior Publication Data

US 2017/0296198 A1    Oct. 19, 2017

Related U.S. Application Data

(60) Division of application No. 14/304,869, filed on Jun. 13, 2014, now Pat. No. 9,636,116, which is a
(Continued)

(51) Int. Cl.
*A61B 17/12* (2006.01)
(52) U.S. Cl.
CPC .... *A61B 17/12109* (2013.01); *A61B 17/1204* (2013.01); *A61B 17/1214* (2013.01); *A61B 17/1215* (2013.01); *A61B 17/12036* (2013.01); *A61B 17/12136* (2013.01); *A61B 17/12145* (2013.01); *A61B 17/12172* (2013.01); *A61B 17/12177* (2013.01); *A61B 2017/1205* (2013.01)

(58) Field of Classification Search
CPC .......... A61B 17/12036; A61B 17/1204; A61B 17/12109; A61B 17/12022; A61B 17/1214; A61B 17/12145; A61B 2017/1205; A61B 2017/12054; A61B 2002/9505; A61B 2002/9511
See application file for complete search history.

(56) References Cited

U.S. PATENT DOCUMENTS 3,805,767 A    4/1974    Erb
3,868,956 A    3/1975    Alfidi et al.
(Continued)

FOREIGN PATENT DOCUMENTS

DE    202008007775 U1    8/2008
EP    1166721 A2    1/2002
(Continued)

OTHER PUBLICATIONS

Aydogan, Transcatheter Embolization Treatment of Coronary Arteriovenous Fistulas, Asian Cardiovascular & Thoracic Annals, 2003, pp. 63-67, vol. 11, No. 1.
(Continued)

*Primary Examiner* — Alexander J Orkin
(74) *Attorney, Agent, or Firm* — Natha S. Smith; Danai N. Mhembere; Morgan, Lewis & Bockius LLP

(57) ABSTRACT

An implant may include a frame and a cover to facilitate endoluminal vessel occlusion, selective release of embolic material toward a target region, and/or endoluminal stenting. The frame of the implant provides radial expansion properties to secure the cover within a body vessel. The cover and/or the frame can occlude flow of a fluid through the body vessel.

19 Claims, 69 Drawing Sheets

Related U.S. Application Data continuation-in-part of application No. 14/101,171, filed on Dec. 9, 2013, now Pat. No. 9,737,308.

(60) Provisional application No. 61/835,406, filed on Jun. 14, 2013, provisional application No. 61/835,461, filed on Jun. 14, 2013, provisional application No. 61/836,061, filed on Jun. 17, 2013, provisional application No. 61/900,321, filed on Nov. 5, 2013, provisional application No. 61/904,376, filed on Nov. 14, 2013, provisional application No. 61/904,379, filed on Nov. 14, 2013, provisional application No. 61/939,659, filed on Feb. 13, 2014.

(56) References Cited

U.S. PATENT DOCUMENTS

| | | |
|---|---|---|
| 3,877,434 A | 4/1975 | Ferguson et al. |
| 3,918,431 A | 11/1975 | Sinnreich |
| 4,013,063 A | 3/1977 | Bucalo |
| 4,245,623 A | 1/1981 | Erb |
| 4,503,569 A | 3/1985 | Dotter |
| 4,553,545 A | 11/1985 | Maass et al. |
| 4,649,922 A | 3/1987 | Wiktor |
| 4,682,592 A | 7/1987 | Thorsgard |
| 4,705,517 A | 11/1987 | DiPisa, Jr. |
| 4,706,671 A | 11/1987 | Weinrib |
| 4,733,665 A | 3/1988 | Palmaz |
| 4,739,762 A | 4/1988 | Palmaz |
| 4,768,507 A | 9/1988 | Fischell et al. |
| 4,776,337 A | 10/1988 | Palmaz |
| 4,800,882 A | 1/1989 | Gianturco |
| 4,827,946 A | 5/1989 | Kaali et al. |
| 4,878,906 A | 11/1989 | Lindemann et al. |
| 4,913,141 A | 4/1990 | Hillstead |
| 4,969,890 A | 11/1990 | Sugita et al. |
| 5,037,427 A | 8/1991 | Harada et al. |
| 5,065,751 A | 11/1991 | Wolf |
| 5,089,005 A | 2/1992 | Harada |
| 5,102,417 A | 4/1992 | Palmaz |
| 5,147,370 A | 9/1992 | McNamara et al. |
| 5,177,075 A | 1/1993 | Suto et al. |
| 5,234,437 A | 8/1993 | Sepetka |
| 5,242,451 A | 9/1993 | Harada et al. |
| 5,242,452 A | 9/1993 | Inoue |
| 5,304,198 A | 4/1994 | Samson |
| 5,324,306 A | 6/1994 | Makower et al. |
| 5,334,210 A | 8/1994 | Gianturco |
| 5,342,387 A | 8/1994 | Summers |
| 5,372,600 A | 12/1994 | Beyar et al. |
| 5,417,708 A | 5/1995 | Hall et al. |
| 5,474,089 A | 12/1995 | Waynant |
| 5,476,505 A | 12/1995 | Limon |
| 5,499,995 A | 3/1996 | Teirstein |
| 5,536,274 A | 7/1996 | Neuss |
| 5,562,641 A | 10/1996 | Flomenblit et al. |
| 5,562,698 A | 10/1996 | Parker |
| 5,601,818 A | 2/1997 | Freeman et al. |
| 5,607,445 A | 3/1997 | Summers |
| 5,656,036 A | 8/1997 | Palmaz |
| 5,674,287 A | 10/1997 | Slepian et al. |
| 5,693,083 A | 12/1997 | Baker et al. |
| 5,702,419 A | 12/1997 | Berry et al. |
| 5,725,552 A | 3/1998 | Kotula et al. |
| 5,733,329 A | 3/1998 | Wallace et al. |
| 5,772,668 A | 6/1998 | Summers et al. |
| 5,782,860 A | 7/1998 | Epstein et al. |
| 5,797,952 A | 8/1998 | Klein |
| 5,797,953 A | 8/1998 | Tekulve |
| 5,830,222 A | 11/1998 | Makower |
| 5,842,621 A | 12/1998 | Gschwind |
| 5,868,782 A | 2/1999 | Frantzen |
| 5,902,266 A | 5/1999 | Leone et al. |
| 5,922,009 A | 7/1999 | Epstein et al. |
| 5,925,063 A | 7/1999 | Khosravi |
| 5,925,074 A | 7/1999 | Gingras et al. |
| 5,928,260 A | 7/1999 | Chin et al. |
| 5,944,738 A | 8/1999 | Amplatz et al. |
| 5,954,766 A | 9/1999 | Zadno-Azizi et al. |
| 5,957,929 A | 9/1999 | Brenneman |
| 5,976,179 A | 11/1999 | Inoue |
| 5,979,446 A | 11/1999 | Loy |
| 6,010,517 A | 1/2000 | Baccaro |
| 6,019,779 A | 2/2000 | Thorud et al. |
| 6,024,765 A | 2/2000 | Wallace et al. |
| 6,056,770 A | 5/2000 | Epstein et al. |
| 6,059,825 A | 5/2000 | Hobbs et al. |
| 6,083,257 A | 7/2000 | Taylor et al. |
| 6,117,157 A | 9/2000 | Tekulve |
| 6,123,715 A | 9/2000 | Amplatz |
| 6,168,622 B1 | 1/2001 | Mazzocchi |
| 6,190,353 B1 | 2/2001 | Makower et al. |
| 6,210,338 B1 | 4/2001 | Afremov et al. |
| 6,214,042 B1 | 4/2001 | Jacobsen et al. |
| 6,241,678 B1 | 6/2001 | Afremov et al. |
| 6,241,758 B1 | 6/2001 | Cox |
| 6,245,090 B1 | 6/2001 | Gilson et al. |
| 6,248,122 B1 | 6/2001 | Klumb et al. |
| 6,258,119 B1 | 7/2001 | Hussein et al. |
| 6,277,103 B1 | 8/2001 | Lauer |
| 6,283,983 B1 | 9/2001 | Makower et al. |
| 6,334,864 B1 | 1/2002 | Amplatz et al. |
| 6,346,118 B1 | 2/2002 | Baker et al. |
| 6,361,558 B1 | 3/2002 | Hieshima et al. |
| 6,368,339 B1 | 4/2002 | Amplatz |
| 6,371,953 B1 | 4/2002 | Beyar et al. |
| 6,371,979 B1 | 4/2002 | Beyar et al. |
| 6,402,760 B1 | 6/2002 | Fedida |
| 6,402,772 B1 | 6/2002 | Amplatz et al. |
| 6,432,116 B1 | 8/2002 | Callister et al. |
| 6,432,127 B1 | 8/2002 | Kim et al. |
| 6,447,531 B1 | 9/2002 | Amplatz |
| 6,451,025 B1 | 9/2002 | Jervis |
| 6,454,780 B1 | 9/2002 | Wallace |
| 6,464,712 B1 | 10/2002 | Epstein et al. |
| 6,468,301 B1 | 10/2002 | Amplatz et al. |
| 6,485,524 B2 | 11/2002 | Strecker |
| 6,488,700 B2 | 12/2002 | Klumb et al. |
| 6,506,204 B2 | 1/2003 | Mazzocchi |
| 6,514,285 B1 | 2/2003 | Pinchasik |
| 6,533,805 B1 | 3/2003 | Jervis |
| 6,550,480 B2 | 4/2003 | Feldman et al. |
| 6,554,849 B1 | 4/2003 | Jones et al. |
| 6,562,064 B1 | 5/2003 | deBeer |
| 6,572,643 B1 | 6/2003 | Gharibadeh |
| 6,572,648 B1 | 6/2003 | Klumb et al. |
| 6,579,303 B2 | 6/2003 | Amplatz |
| 6,585,760 B1 | 7/2003 | Fogarty |
| 6,599,308 B2 | 7/2003 | Amplatz |
| 6,602,271 B2 | 8/2003 | Adams et al. |
| 6,616,675 B1 | 9/2003 | Evard et al. |
| 6,623,518 B2 | 9/2003 | Thompson et al. |
| 6,629,981 B2 | 10/2003 | Bui et al. |
| 6,638,243 B2 | 10/2003 | Kupiecki |
| 6,638,257 B2 | 10/2003 | Amplatz |
| 6,638,293 B1 | 10/2003 | Makower et al. |
| 6,645,237 B2 | 11/2003 | Klumb et al. |
| 6,656,207 B2 | 12/2003 | Epstein et al. |
| 6,660,020 B2 | 12/2003 | Wallace et al. |
| 6,660,032 B2 | 12/2003 | Klumb et al. |
| 6,663,666 B1 | 12/2003 | Quiachon et al. |
| 6,682,546 B2 | 1/2004 | Amplatz |
| 6,689,148 B2 | 2/2004 | Sawhney et al. |
| 6,702,846 B2 | 3/2004 | Mikus et al. |
| 6,719,781 B1 | 4/2004 | Kim |
| 6,790,218 B2 | 9/2004 | Jayaraman |
| 6,790,223 B2 | 9/2004 | Reever |
| 6,849,081 B2 | 2/2005 | Sepetka et al. |
| 6,872,211 B2 | 3/2005 | White et al. |
| 6,890,341 B2 | 5/2005 | Dieck et al. |
| 6,899,730 B1 | 5/2005 | Rivelli, Jr. |
| 6,936,058 B2 | 8/2005 | Forde et al. |
| 6,974,473 B2 | 12/2005 | Barclay et al. |
| 6,984,244 B2 | 1/2006 | Perez et al. |

(56) References Cited

U.S. PATENT DOCUMENTS

| | | |
|---|---|---|
| 7,001,409 B2 | 2/2006 | Amplatz |
| 7,011,643 B2 | 3/2006 | Villafana et al. |
| 7,011,671 B2 | 3/2006 | Welch |
| 7,144,408 B2 | 12/2006 | Keegan et al. |
| 7,152,605 B2 | 12/2006 | Khairkhahan et al. |
| 7,220,270 B2 | 5/2007 | Sawhney et al. |
| 7,270,668 B2 | 9/2007 | Andreas et al. |
| 7,276,077 B2 | 10/2007 | Zadno-Azizi et al. |
| 7,294,146 B2 | 11/2007 | Chew et al. |
| 7,303,571 B2 | 12/2007 | Makower et al. |
| 7,387,641 B2 | 6/2008 | Schmitt |
| 7,396,362 B2 | 7/2008 | Jervis |
| 7,398,780 B2 | 7/2008 | Callister et al. |
| 7,434,578 B2 | 10/2008 | Dillard et al. |
| 7,458,986 B2 | 12/2008 | Schmitt |
| 7,476,232 B2 | 1/2009 | Deal |
| 7,582,100 B2 | 9/2009 | Johnson et al. |
| 7,597,704 B2 | 10/2009 | Frazier et al. |
| 7,604,649 B2 | 10/2009 | McGuckin, Jr. et al. |
| 7,632,291 B2 | 12/2009 | Stephens et al. |
| 7,647,930 B2 | 1/2010 | Ginn |
| 7,651,521 B2 | 1/2010 | Ton et al. |
| 7,666,204 B2 | 2/2010 | Thornton et al. |
| 7,682,673 B2 | 3/2010 | Houston et al. |
| 7,691,124 B2 | 4/2010 | Balgobin |
| 7,699,056 B2 | 4/2010 | Tran et al. |
| 7,740,616 B2 | 6/2010 | Smith et al. |
| 7,771,463 B2 | 8/2010 | Ton et al. |
| 7,785,343 B2 | 8/2010 | Johnson et al. |
| 7,785,631 B2 | 8/2010 | Roser et al. |
| 7,789,860 B2 | 9/2010 | Brady et al. |
| 7,789,892 B2 | 9/2010 | Johnson et al. |
| 7,803,177 B2 | 9/2010 | Hartley et al. |
| 7,854,747 B2 | 12/2010 | Johnson et al. |
| 7,862,602 B2 | 1/2011 | Licata et al. |
| 7,955,343 B2 | 6/2011 | Makower et al. |
| 7,967,837 B2 | 6/2011 | Vale |
| 7,985,250 B2 | 7/2011 | Kaufmann et al. |
| 7,992,565 B2 | 8/2011 | McGuckin, Jr. et al. |
| 8,016,870 B2 | 9/2011 | Chew et al. |
| 8,016,880 B2 | 9/2011 | Cook et al. |
| 8,043,357 B2 | 10/2011 | Hartley |
| 8,100,958 B2 | 1/2012 | Fischer et al. |
| 8,110,267 B2 | 2/2012 | Houston et al. |
| 8,114,114 B2 | 2/2012 | Belson |
| 8,118,852 B2 | 2/2012 | Melsheimer |
| 8,142,456 B2 | 3/2012 | Rosqueta et al. |
| 8,162,970 B2 | 4/2012 | Gilson et al. |
| 8,226,679 B2 | 7/2012 | Johnson et al. |
| 8,226,704 B2 | 7/2012 | Caro et al. |
| 8,298,257 B2 | 10/2012 | Sepetka et al. |
| 8,308,754 B2 | 11/2012 | Belson |
| 8,323,305 B2 | 12/2012 | Epstein et al. |
| 8,323,350 B2 | 12/2012 | Nissl |
| 8,328,840 B2 | 12/2012 | Gailloud et al. |
| 8,333,783 B2 | 12/2012 | Braun et al. |
| 8,333,796 B2 | 12/2012 | Tompkins et al. |
| 8,343,167 B2 | 1/2013 | Henson |
| 8,348,994 B2 | 1/2013 | Leopold et al. |
| 8,382,771 B2 | 2/2013 | Gellman et al. |
| 8,382,821 B2 | 2/2013 | Richter |
| 8,398,700 B2 | 3/2013 | Leopold et al. |
| 8,425,549 B2 | 4/2013 | Lenker et al. |
| 8,430,904 B2 | 4/2013 | Belson |
| 8,663,301 B2 | 3/2014 | Riina et al. |
| 8,808,342 B2 | 8/2014 | Ludwig |
| 8,834,544 B2 | 9/2014 | Gerrans et al. |
| 9,247,942 B2 | 2/2016 | Rudakov et al. |
| 2001/0000798 A1 | 5/2001 | Denardo |
| 2001/0007946 A1 | 7/2001 | Lenker et al. |
| 2001/0031981 A1 | 10/2001 | Evans et al. |
| 2001/0037146 A1 | 11/2001 | Lau et al. |
| 2001/0044648 A1 | 11/2001 | Wolinsky et al. |
| 2001/0046518 A1 | 11/2001 | Sawhney |
| 2002/0007206 A1 | 1/2002 | Bui et al. |
| 2002/0091439 A1 | 7/2002 | Baker et al. |
| 2002/0099437 A1 | 7/2002 | Anson et al. |
| 2002/0107565 A1 | 8/2002 | Greenhalgh |
| 2002/0123765 A1 | 9/2002 | Sepetka et al. |
| 2002/0128707 A1 | 9/2002 | Kavteladze et al. |
| 2002/0143362 A1 | 10/2002 | Macoviak et al. |
| 2002/0173839 A1 | 11/2002 | Leopold et al. |
| 2002/0177855 A1 | 11/2002 | Greene et al. |
| 2002/0198588 A1 | 12/2002 | Armstrong et al. |
| 2003/0114922 A1 | 6/2003 | Iwasaka et al. |
| 2003/0125798 A1 | 7/2003 | Martin |
| 2003/0130684 A1 | 7/2003 | Brady et al. |
| 2003/0153972 A1 | 8/2003 | Helmus |
| 2003/0158515 A1 | 8/2003 | Gonzalez et al. |
| 2003/0163146 A1 | 8/2003 | Epstein et al. |
| 2003/0171801 A1 | 9/2003 | Bates |
| 2003/0187474 A1 | 10/2003 | Keegan et al. |
| 2003/0187495 A1 | 10/2003 | Cully et al. |
| 2003/0212452 A1 | 11/2003 | Zadno-Azizi et al. |
| 2003/0216679 A1 | 11/2003 | Wolf et al. |
| 2003/0229366 A1 | 12/2003 | Reggie et al. |
| 2004/0010282 A1 | 1/2004 | Kusleika |
| 2004/0023415 A1 | 2/2004 | Sokolov et al. |
| 2004/0029994 A1 | 2/2004 | Cheng et al. |
| 2004/0044360 A1 | 3/2004 | Lowe |
| 2004/0055606 A1 | 3/2004 | Hendricksen et al. |
| 2004/0073252 A1 | 4/2004 | Goldberg et al. |
| 2004/0147869 A1 | 7/2004 | Wolf et al. |
| 2004/0153118 A1 | 8/2004 | Clubb et al. |
| 2004/0158308 A1 | 8/2004 | Hogendijk et al. |
| 2004/0193141 A1 | 9/2004 | Leopold et al. |
| 2004/0220663 A1 | 11/2004 | Riveili |
| 2004/0225286 A1 | 11/2004 | Elliott |
| 2004/0243219 A1 | 12/2004 | Fischer et al. |
| 2004/0249342 A1 | 12/2004 | Khosravi et al. |
| 2004/0254517 A1 | 12/2004 | Quiroz-Mercado et al. |
| 2004/0260384 A1 | 12/2004 | Allen |
| 2005/0027305 A1 | 2/2005 | Shiu et al. |
| 2005/0033409 A1 | 2/2005 | Burke et al. |
| 2005/0043759 A1 | 2/2005 | Chanduszko |
| 2005/0049608 A1 | 3/2005 | Aznoian et al. |
| 2005/0051163 A1 | 3/2005 | Deem et al. |
| 2005/0055079 A1 | 3/2005 | Duran |
| 2005/0055082 A1 | 3/2005 | Ben Muvhar et al. |
| 2005/0113902 A1 | 5/2005 | Geiser et al. |
| 2005/0137681 A1 | 6/2005 | Shoemaker et al. |
| 2005/0165442 A1 | 7/2005 | Thinnes et al. |
| 2005/0192616 A1 | 9/2005 | Callister et al. |
| 2005/0209675 A1 | 9/2005 | Ton et al. |
| 2005/0288684 A1 | 12/2005 | Aronson et al. |
| 2006/0009798 A1 | 1/2006 | Callister et al. |
| 2006/0052822 A1 | 3/2006 | Mirizzi et al. |
| 2006/0111771 A1 | 5/2006 | Ton et al. |
| 2006/0111801 A1 | 5/2006 | Weare et al. |
| 2006/0119714 A1 | 6/2006 | Tamura et al. |
| 2006/0149359 A1 | 7/2006 | Richter et al. |
| 2006/0162731 A1 | 7/2006 | Wondka et al. |
| 2006/0178727 A1 | 8/2006 | Richter |
| 2006/0184089 A1 | 8/2006 | Makower et al. |
| 2006/0195175 A1 | 8/2006 | Bregulla |
| 2006/0200191 A1 | 9/2006 | Zadno-Azizi |
| 2006/0241675 A1 | 10/2006 | Johnson et al. |
| 2006/0241690 A1 | 10/2006 | Amplatz et al. |
| 2007/0038178 A1 | 2/2007 | Kusleika |
| 2007/0043419 A1 | 2/2007 | Nikolchev et al. |
| 2007/0060946 A1 | 3/2007 | Keegan et al. |
| 2007/0088388 A1 | 4/2007 | Opolski et al. |
| 2007/0112381 A1 | 5/2007 | Figulla et al. |
| 2007/0118209 A1 | 5/2007 | Strecker |
| 2007/0129753 A1 | 6/2007 | Quinn et al. |
| 2007/0135826 A1 | 6/2007 | Zaver et al. |
| 2007/0150471 A1 | 6/2007 | Ferrera |
| 2007/0156224 A1 | 7/2007 | Cioanta et al. |
| 2007/0163601 A1 | 7/2007 | Pollock et al. |
| 2007/0168018 A1 | 7/2007 | Amplatz et al. |
| 2007/0168019 A1 | 7/2007 | Amplatz et al. |
| 2007/0203503 A1 | 8/2007 | Salahieh et al. |
| 2007/0221230 A1 | 9/2007 | Thompson et al. |
| 2007/0239191 A1 | 10/2007 | Ramzipoor |

(56) References Cited

U.S. PATENT DOCUMENTS

| | | |
|---|---|---|
| 2007/0247680 A1 | 10/2007 | Nakane et al. |
| 2007/0265656 A1 | 11/2007 | Amplatz et al. |
| 2007/0265658 A1 | 11/2007 | Nelson et al. |
| 2008/0017201 A1 | 1/2008 | Sawhney |
| 2008/0045996 A1 | 2/2008 | Makower et al. |
| 2008/0046092 A1 | 2/2008 | Davis et al. |
| 2008/0086214 A1 | 4/2008 | Hardin et al. |
| 2008/0103522 A1 | 5/2008 | Steingisser et al. |
| 2008/0132906 A1 | 6/2008 | Rasmussen |
| 2008/0178890 A1 | 7/2008 | Townsend et al. |
| 2008/0200945 A1 | 8/2008 | Amplatz et al. |
| 2008/0215087 A1 | 9/2008 | Pavcnik et al. |
| 2008/0221600 A1 | 9/2008 | Dieck et al. |
| 2008/0221657 A1 | 9/2008 | Laroya et al. |
| 2008/0221666 A1 | 9/2008 | Licata et al. |
| 2008/0269719 A1 | 10/2008 | Balgobin et al. |
| 2008/0302368 A1 | 12/2008 | McGuckin, Jr. et al. |
| 2009/0005847 A1 | 1/2009 | Adams |
| 2009/0018562 A1 | 1/2009 | Amplatz et al. |
| 2009/0018636 A1 | 1/2009 | Gailloud et al. |
| 2009/0024072 A1 | 1/2009 | Criado et al. |
| 2009/0025820 A1 | 1/2009 | Adams |
| 2009/0030497 A1 | 1/2009 | Metcalf et al. |
| 2009/0043330 A1 | 2/2009 | To |
| 2009/0062841 A1 | 3/2009 | Amplatz et al. |
| 2009/0078270 A1 | 3/2009 | Meier et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0131959 A1 | 5/2009 | Rolland |
| 2009/0132020 A1 | 5/2009 | Watson |
| 2009/0138078 A1 | 5/2009 | Paul, Jr. et al. |
| 2009/0157053 A1 | 6/2009 | Davis et al. |
| 2009/0171386 A1 | 7/2009 | Amplatz et al. |
| 2009/0178682 A1 | 7/2009 | Tal et al. |
| 2009/0187214 A1 | 7/2009 | Amplatz et al. |
| 2009/0209855 A1 | 8/2009 | Drilling et al. |
| 2009/0210047 A1 | 8/2009 | Amplatz et al. |
| 2009/0210048 A1 | 8/2009 | Amplatz et al. |
| 2009/0216185 A1 | 8/2009 | Gregorich et al. |
| 2009/0240326 A1 | 9/2009 | Wilson et al. |
| 2009/0276029 A1 | 11/2009 | Caro et al. |
| 2009/0276039 A1 | 11/2009 | Meretei |
| 2009/0277455 A1 | 11/2009 | Lee-Sepsick et al. |
| 2009/0281610 A1 | 11/2009 | Parker |
| 2010/0006105 A1 | 1/2010 | Carter et al. |
| 2010/0030321 A1 | 2/2010 | Mach |
| 2010/0049307 A1 | 2/2010 | Ren |
| 2010/0057194 A1 | 3/2010 | Ryan |
| 2010/0063578 A1 | 3/2010 | Ren et al. |
| 2010/0063582 A1 | 3/2010 | Rudakov |
| 2010/0089406 A1 | 4/2010 | Kachiguina |
| 2010/0094395 A1 | 4/2010 | Kellett |
| 2010/0106235 A1 | 4/2010 | Kariniemi et al. |
| 2010/0114307 A1 | 5/2010 | Agnew et al. |
| 2010/0121370 A1 | 5/2010 | Kariniemi |
| 2010/0174269 A1 | 7/2010 | Tompkins et al. |
| 2010/0198328 A1 | 8/2010 | Hartley et al. |
| 2010/0223046 A1 | 9/2010 | Bucchieri et al. |
| 2010/0223048 A1 | 9/2010 | Lauder |
| 2010/0249691 A1 | 9/2010 | Van Der Mooren et al. |
| 2010/0268201 A1 | 10/2010 | Tieu et al. |
| 2010/0268260 A1 | 10/2010 | Riina et al. |
| 2010/0294282 A1 | 11/2010 | Chu et al. |
| 2010/0312268 A1 | 12/2010 | Belson |
| 2010/0318178 A1 | 12/2010 | Rapaport et al. |
| 2010/0324585 A1 | 12/2010 | Miles et al. |
| 2010/0324586 A1 | 12/2010 | Miles et al. |
| 2010/0324587 A1 | 12/2010 | Miles et al. |
| 2010/0324588 A1 | 12/2010 | Miles et al. |
| 2011/0029067 A1 | 2/2011 | McGuckin, Jr. et al. |
| 2011/0040371 A1 | 2/2011 | Hanssen et al. |
| 2011/0092997 A1 | 4/2011 | Kang |
| 2011/0124958 A1 | 5/2011 | Nelson |
| 2011/0125132 A1 | 5/2011 | Krolik et al. |
| 2011/0172697 A1 | 7/2011 | Jonsson |
| 2011/0202087 A1 | 8/2011 | Vale |
| 2011/0202129 A1 | 8/2011 | Fofsell |
| 2011/0218479 A1 | 9/2011 | Rottenberg et al. |
| 2011/0264132 A1 | 10/2011 | Strauss et al. |
| 2011/0264195 A1 | 10/2011 | Griswold |
| 2011/0282343 A1 | 11/2011 | Kunis |
| 2011/0301630 A1 | 12/2011 | Hendriksen et al. |
| 2011/0313506 A1 | 12/2011 | Ray et al. |
| 2011/0319906 A1 | 12/2011 | Rudakov et al. |
| 2012/0010556 A1 | 1/2012 | Faul et al. |
| 2012/0022572 A1 | 1/2012 | Braun et al. |
| 2012/0083822 A1 | 4/2012 | Anukhin et al. |
| 2012/0089102 A1 | 4/2012 | Chomas et al. |
| 2012/0089216 A1 | 4/2012 | Rapaport et al. |
| 2012/0095489 A1 | 4/2012 | Rudakov et al. |
| 2012/0101510 A1 | 4/2012 | Lenker et al. |
| 2012/0116350 A1 | 5/2012 | Strauss et al. |
| 2012/0123511 A1 | 5/2012 | Brown |
| 2012/0123514 A1 | 5/2012 | Kunis |
| 2012/0143301 A1 | 6/2012 | Maslanka et al. |
| 2012/0172911 A1 | 7/2012 | Welch |
| 2012/0192872 A1 | 8/2012 | Rudakov et al. |
| 2012/0209310 A1 | 8/2012 | Chen et al. |
| 2012/0239077 A1 | 9/2012 | Zaver et al. |
| 2012/0245614 A1 | 9/2012 | Drasler |
| 2012/0245620 A1 | 9/2012 | Gilson et al. |
| 2012/0245668 A1 | 9/2012 | Kariniemi et al. |
| 2012/0253120 A1 | 10/2012 | Callister et al. |
| 2012/0259354 A1 | 10/2012 | Kellett |
| 2012/0277842 A1 | 11/2012 | Kunis |
| 2012/0283768 A1 | 11/2012 | Cox et al. |
| 2012/0289988 A1 | 11/2012 | Riina et al. |
| 2012/0289994 A1 | 11/2012 | Larson et al. |
| 2012/0296408 A1 | 11/2012 | Jones et al. |
| 2012/0316584 A1 | 12/2012 | Miles et al. |
| 2012/0330347 A1 | 12/2012 | Becking et al. |
| 2012/0330348 A1 | 12/2012 | Strauss et al. |
| 2013/0053758 A1 | 2/2013 | Kibbe |
| 2013/0053879 A1 | 2/2013 | Gailloud et al. |
| 2013/0102996 A1 | 4/2013 | Strauss |
| 2013/0103074 A1 | 4/2013 | Riina et al. |
| 2013/0109987 A1 | 5/2013 | Kunis et al. |
| 2013/0116774 A1 | 5/2013 | Strauss et al. |
| 2013/0123899 A1 | 5/2013 | Leopold et al. |
| 2013/0178889 A1 | 7/2013 | Miles et al. |
| 2013/0204282 A1 | 8/2013 | Nelson |
| 2013/0204311 A1 | 8/2013 | Kunis |
| 2013/0289714 A1 | 10/2013 | Strauss et al. |
| 2014/0058435 A1 | 2/2014 | Jones |
| 2014/0073903 A1 | 3/2014 | Weber et al. |
| 2014/0128780 A1 | 5/2014 | Kennedy et al. |
| 2014/0207180 A1 | 7/2014 | Ferrera |
| 2014/0215792 A1 | 8/2014 | Leopold et al. |
| 2014/0222059 A1 | 8/2014 | Leopold et al. |
| 2014/0257369 A1 | 9/2014 | Leopold et al. |
| 2014/0277085 A1 | 9/2014 | Mirigian et al. |
| 2014/0371716 A1 | 12/2014 | Rudakov |
| 2014/0371777 A1 | 12/2014 | Rudakov et al. |
| 2014/0371778 A1 | 12/2014 | Rudakov et al. |
| 2015/0057700 A1 | 2/2015 | Chen et al. |
| 2015/0157329 A1 | 6/2015 | Rudakov et al. |
| 2015/0157333 A1 | 6/2015 | Leopold et al. |
| 2015/0223821 A1 | 8/2015 | Rudakov et al. |
| 2015/0290437 A1 | 10/2015 | Rudakov et al. |
| 2015/0313602 A1 | 11/2015 | Rudakov |
| 2015/0342611 A1 | 12/2015 | Leopold et al. |
| 2016/0022272 A1 | 1/2016 | Rudakov et al. |
| 2016/0101271 A1 | 4/2016 | Rudakov et al. |

FOREIGN PATENT DOCUMENTS

| | | |
|---|---|---|
| EP | 1188413 | 3/2002 |
| EP | 1317908 A2 | 6/2003 |
| EP | 1600110 A1 | 11/2005 |
| EP | 1707233 A2 | 10/2006 |
| EP | 1752112 A1 | 2/2007 |
| EP | 1813196 A1 | 8/2007 |
| EP | 1820436 A2 | 8/2007 |

(56) References Cited

FOREIGN PATENT DOCUMENTS

| EP | 1852073 A1 | 11/2007 |
|---|---|---|
| EP | 2248471 A1 | 11/2010 |
| EP | 2366362 A1 | 9/2011 |
| EP | 2366363 A1 | 9/2011 |
| EP | 2366364 A1 | 9/2011 |
| EP | 2404580 A1 | 1/2012 |
| EP | 2583636 A1 | 4/2013 |
| GB | 2404860 A | 2/2005 |
| GB | 2494820 A | 3/2013 |
| JP | H 07-000405 | 1/1995 |
| JP | H 07-185011 A | 7/1995 |
| JP | 2006-181015 A | 7/2006 |
| JP | 2010-532180 A | 10/2010 |
| JP | 2012-525859 A | 10/2012 |
| WO | WO-83/00997 A1 | 3/1983 |
| WO | WO-92/14408 A1 | 9/1992 |
| WO | WO-94/000179 A1 | 1/1994 |
| WO | WO-95/24158 A1 | 9/1995 |
| WO | WO-95/25480 A1 | 9/1995 |
| WO | WO-95/32018 A1 | 11/1995 |
| WO | WO-96/18361 A1 | 6/1996 |
| WO | WO-97/13463 A1 | 4/1997 |
| WO | WO-97/13471 A1 | 4/1997 |
| WO | WO-97/27893 A1 | 8/1997 |
| WO | WO-97/27897 A1 | 8/1997 |
| WO | WO-97/27898 A1 | 8/1997 |
| WO | WO-97/31672 A1 | 9/1997 |
| WO | WO-98/08456 A1 | 3/1998 |
| WO | WO-98/31308 A1 | 7/1998 |
| WO | WO-98/34546 A1 | 8/1998 |
| WO | WO-98/46115 A2 | 10/1998 |
| WO | WO-98/46119 A1 | 10/1998 |
| WO | WO-99/12484 A1 | 3/1999 |
| WO | WO-99/23976 A1 | 5/1999 |
| WO | WO-99/25273 A1 | 5/1999 |
| WO | WO-99/44542 A2 | 9/1999 |
| WO | WO-99/48545 A1 | 9/1999 |
| WO | WO-99/49793 A1 | 10/1999 |
| WO | WO-99/49910 A2 | 10/1999 |
| WO | WO-99/62430 A1 | 12/1999 |
| WO | WO-00/09195 A1 | 2/2000 |
| WO | WO-00/16847 A1 | 3/2000 |
| WO | WO-00/27303 A2 | 5/2000 |
| WO | WO-00/67671 A1 | 11/2000 |
| WO | WO-01/032254 A1 | 5/2001 |
| WO | WO-01/64112 A1 | 9/2001 |
| WO | WO-01/080776 A1 | 11/2001 |
| WO | WO-01/080777 A2 | 11/2001 |
| WO | WO-01/89413 A2 | 11/2001 |
| WO | WO-02/03889 | 1/2002 |
| WO | WO-03/001970 A2 | 1/2003 |
| WO | WO-03/073961 A1 | 9/2003 |
| WO | WO-03/073962 A1 | 9/2003 |
| WO | WO-03/101518 A1 | 12/2003 |
| WO | WO-2004/006804 A1 | 1/2004 |
| WO | WO-2004/073557 A2 | 9/2004 |
| WO | WO-2005/020786 A2 | 3/2005 |
| WO | WO-2005/092241 A1 | 10/2005 |
| WO | WO-2005/117755 A2 | 12/2005 |
| WO | WO-2006/017470 A2 | 2/2006 |
| WO | WO-2006/028943 A1 | 3/2006 |
| WO | WO-2006/031602 A1 | 3/2006 |
| WO | WO-2006/034153 A2 | 3/2006 |
| WO | WO-2006/039216 A2 | 4/2006 |
| WO | WO-2006/074163 A2 | 7/2006 |
| WO | WO-2006/096342 A1 | 9/2006 |
| WO | WO-2006/134354 A1 | 12/2006 |
| WO | WO-2007/061927 A2 | 5/2007 |
| WO | WO-2007/070544 A2 | 6/2007 |
| WO | WO-2007/085373 A1 | 8/2007 |
| WO | WO-2007/127351 A1 | 11/2007 |
| WO | WO-2007/149844 A2 | 12/2007 |
| WO | WO-2008/010197 A2 | 1/2008 |
| WO | WO-2008/022327 A2 | 2/2008 |
| WO | WO-2008/100790 A2 | 8/2008 |
| WO | WO-2008/112501 A2 | 9/2008 |
| WO | WO-2008/153653 A1 | 12/2008 |
| WO | WO-2009/061419 A1 | 5/2009 |
| WO | WO-2009/064618 A1 | 5/2009 |
| WO | WO-2009/077845 A2 | 6/2009 |
| WO | WO-2009/088905 A1 | 7/2009 |
| WO | WO-2009/124288 A1 | 10/2009 |
| WO | WO-2009/126747 A1 | 10/2009 |
| WO | WO-2010/009019 A1 | 1/2010 |
| WO | WO-2010/047644 A1 | 4/2010 |
| WO | WO-2010/075565 A2 | 7/2010 |
| WO | WO-2010/085344 A1 | 7/2010 |
| WO | WO-2010/096717 A1 | 8/2010 |
| WO | WO-2010/130617 A1 | 11/2010 |
| WO | WO-2010/135352 A1 | 11/2010 |
| WO | WO-2010/146581 A1 | 12/2010 |
| WO | WO-2010/148246 A2 | 12/2010 |
| WO | WO-2011/011581 A2 | 1/2011 |
| WO | WO-2011/153304 A1 | 12/2011 |
| WO | WO-2011/159913 A2 | 12/2011 |
| WO | WO-2011/163157 A2 | 12/2011 |
| WO | WO-2012/002944 A1 | 1/2012 |
| WO | WO-2012/040380 A1 | 3/2012 |
| WO | WO-2012/054065 A1 | 4/2012 |
| WO | WO-2012/067724 A1 | 5/2012 |
| WO | WO-2012/109367 A1 | 8/2012 |
| WO | WO-2012/111137 A1 | 8/2012 |
| WO | WO-2012/120490 A2 | 9/2012 |
| WO | WO-2012/131672 A2 | 10/2012 |
| WO | WO-2012/134761 A1 | 10/2012 |
| WO | WO-2012/135859 A2 | 10/2012 |
| WO | WO-2012/166804 A1 | 12/2012 |
| WO | WO-2013/055703 A1 | 4/2013 |
| WO | WO-2013/059511 A1 | 4/2013 |
| WO | WO-2013/067299 A1 | 5/2013 |

OTHER PUBLICATIONS

Berguer et al., Cure by Combination of Operation and Detachable Intravascular Balloon, Ann. Surg. Jul. 1982, pp. 65-68, vol. 196, No. 1.

Cheng et al., Minimally Invasive Keyhole Approach for Removal of a Migratory Balloon Complicated by Endovascular Embolization of a Carotid-Cavernous Fistula, Minim. Invasive Neurosurgl, 2006, pp. 305-308, vol. 49.

DeSouza et al., Embolization with detachable Balloons—Applications outside the head, Clinical Radiology, Apr. 21, 1992, pp. 170-175, vol. 46.

Ferro et al, Percutaneous Transcatheter Embolization of a Large Pulmonary Arteriovenous Fistula with an Amplatzer Vascular Plug, Cardovacs Intervent Radiol, 2007, pp. 328-331, vol. 30.

Hawkins et al., The Permeability of Detachable Latex Rubber Balloons—An In Vitro Study, Investigative Radiology, Dec. 1987, pp. 969-972, vol. 22.

Hirai et al., Emergency Balloon Embolization for Carotid Artery Rupture Secondary to Postoperative Infection, Cardiovasc Intervent Radiol, 1996, pp. 50-52, vol. 19.

Kadir et al., Therapeutic Embolization of the Kidney with Detachable Silicone Balloons, The Journal of Urology, Jan. 1983, pp. 11-13, vol. 129.

Kallmes et al., The Use of Hydrocoil for Parent Artery Occlusion, AJNR Am J Neuroradiol, Sep. 2004, pp. 1409-1410, vol. 25.

Kaufman, et al., Detachable Balloon-modified Reducing Stent to Treat Hepatic Insufficiency after Transjugular Intrahepatic Portosystemic Shunt Creation, J Vasc Intery Radiol., May 2003, pp. 635-638, vol. 14, No. 5.

Luo, Chao-Bao et al., Endovascular Treatment of the Carotid Artery Rupture with Massive Hemorrhage, J. Chin Med Assoc., Mar. 2003.

Makita, et al., Guide-Wire-directed Detachable Balloon: Clinical Application in Treatment of Varicoceles, Radiology, 1992, pp. 575-577, vol. 183.

Marshall et al., Treatment of Traumatic Renal Arteriovenous Fistulas by Detachable Silicone Balloon Embolization, The Journal of Urology, Aug. 1979, pp. 237-239, vol. 122.

(56) References Cited

OTHER PUBLICATIONS

Perala et al., Comparison of Early Deflation Rate of Detachable Latex and Silicone Balloons and Observations on Persistent Varicocele, J. Vasc. Interv. Radiol. Sep.-Oct. 1998, pp. 761-765, vol. 9, No. 5.
Pollak et al., Clinical Results of Transvenous Systemic Embolotherapy with a Neuroradiologic Detachable Balloon, Radiology, May 1994, pp. 477-482, vol. 191, No. 2.
Reidy et al., Transcatherer occlusion of coronary to bronchial anastomosis by detachable balloon combined with coronary angioplasty at same procedure, Brit Heart J. 1983, pp. 284-287, vol. 49.
Reidy et al., Transcatheter occlusion of a Blalock-Taussig shunt with a detachable balloon in a child, Bri Heart Journal, 1983, pp. 101-103, vol. 50.
Ross et al., The Vascular Plug: A New Device for Parent Artery Occlusion, AJNR Am J Neuroradiol, Feb. 2007, pp. 385-386, vol. 28.
Serbinenko, F.A., Balloon Catheterization and Occlusion of Major Cerebral Vessels, J. Neurosurg. Aug. 1974, pp. 125-145, vol. 41.
Tasar, et al., Intrahepatic arterioportal fistula and its treatment with detachable balloon and transcatheter embolization with coils and microspheres, Journal of Clinical Imaging, 2005, pp. 325-330, vol. 29.
Wehman, et al., Giant Cerebral Aneurysms: Endovascular Challenges, Neurosurgery, Nov. 2006, pp. S125-S138, vol. 59, No. 5.
White, et al., Occlusion of Varicoceles with Detachable Balloons, Radiology, May 1981, pp. 327-334, vol. 139.
Serbinenko, F.A., Occlusion by Balooning of Sacular Aneurysms of the Cerebral Arteries, Vopr, Neirokhir, Jul.-Aug. 1974, pp. 8-15, vol. 4.
Serebinko, F.A., Balloon Occlusion of Cavernous Portion of the Carotid Artery as a Method of Treating Carotid Cavity Anastomoses, Vopr. Neirokhir, Nov.-Dec. 1971, pp. 3-9, vol. 6.

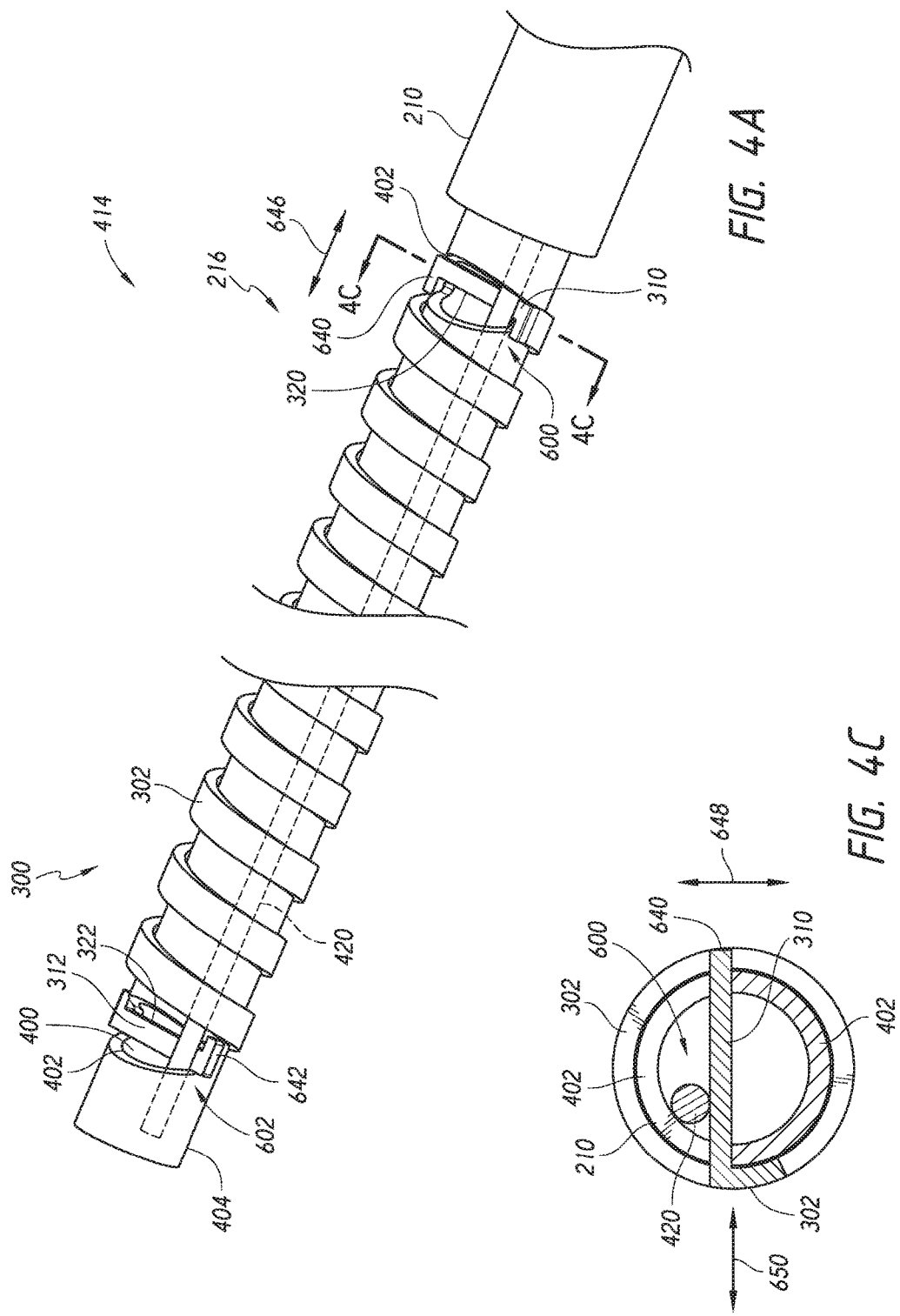

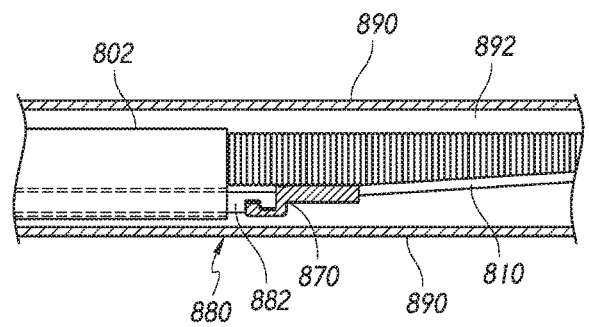
FIG. 14
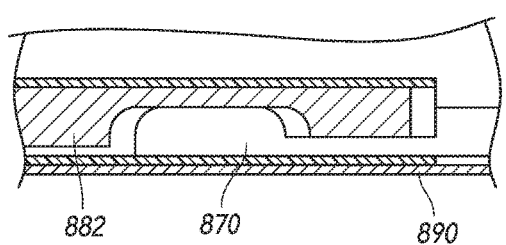 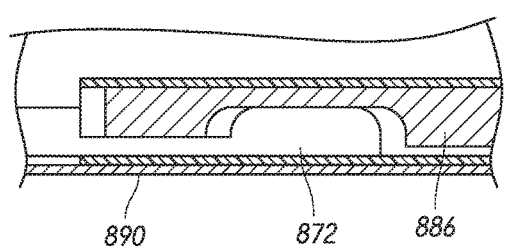
FIG. 15A　　　　　　　FIG. 15B

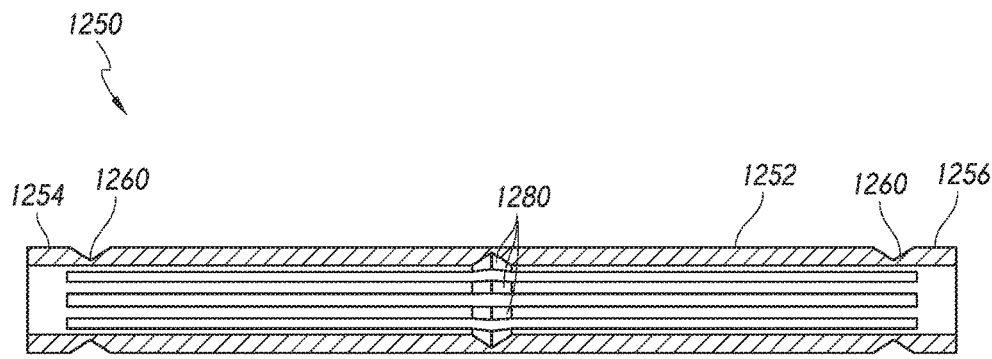
FIG. 23A
FIG. 23B
FIG. 23C
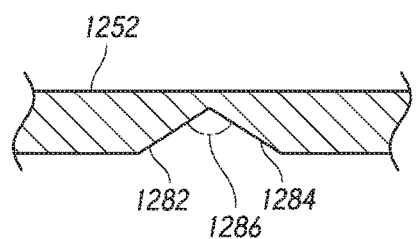
FIG. 23D
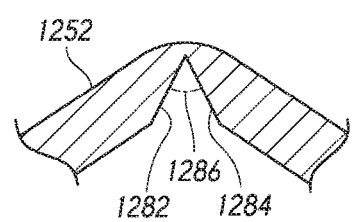
FIG. 23E

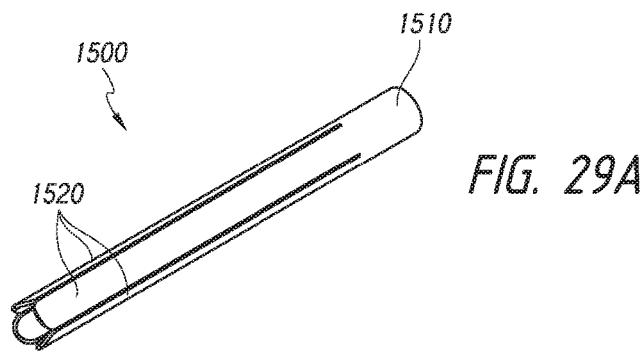
FIG. 29A
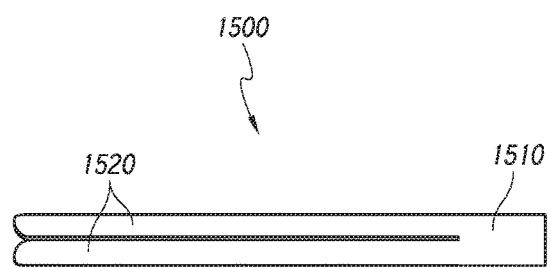
FIG. 29B
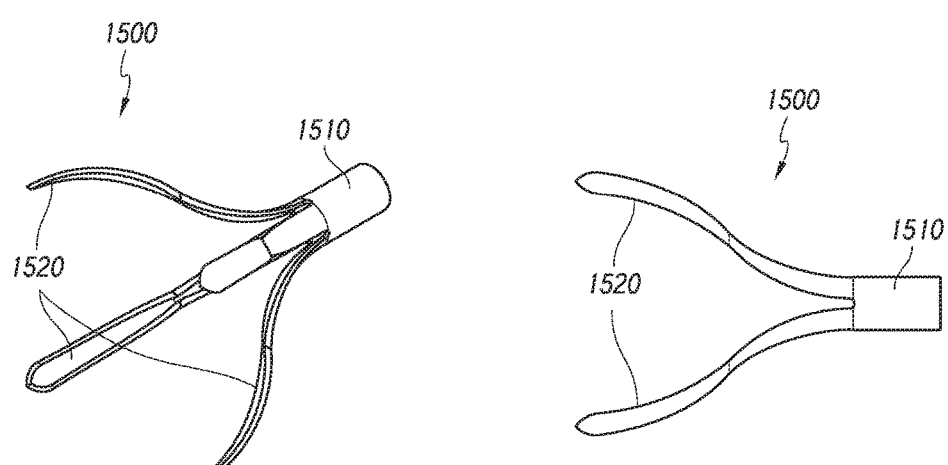
FIG. 29C
FIG. 29D

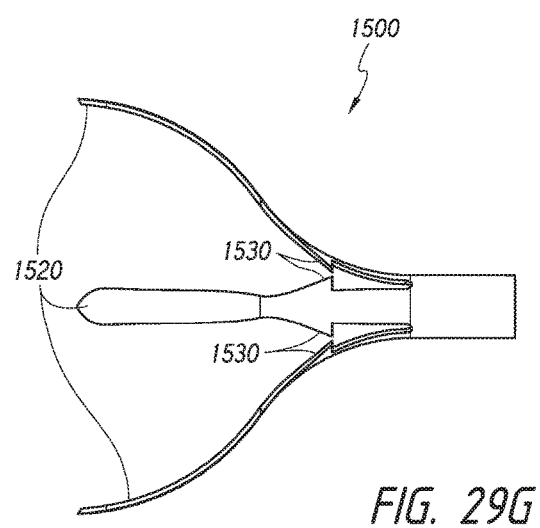
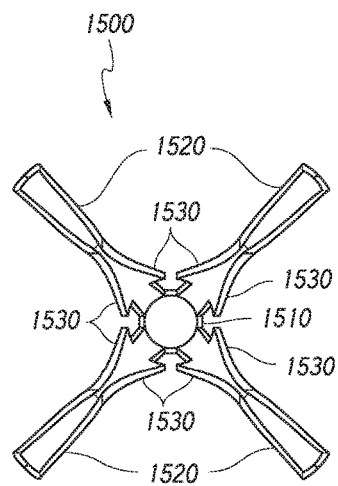
FIG. 29G          FIG. 29H
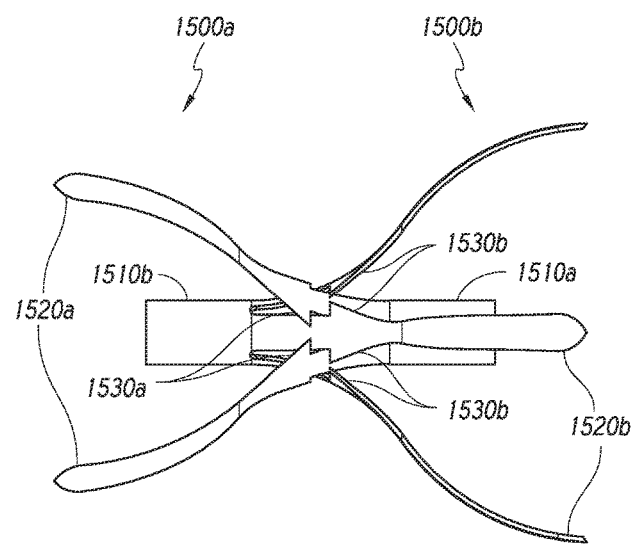
FIG. 29I

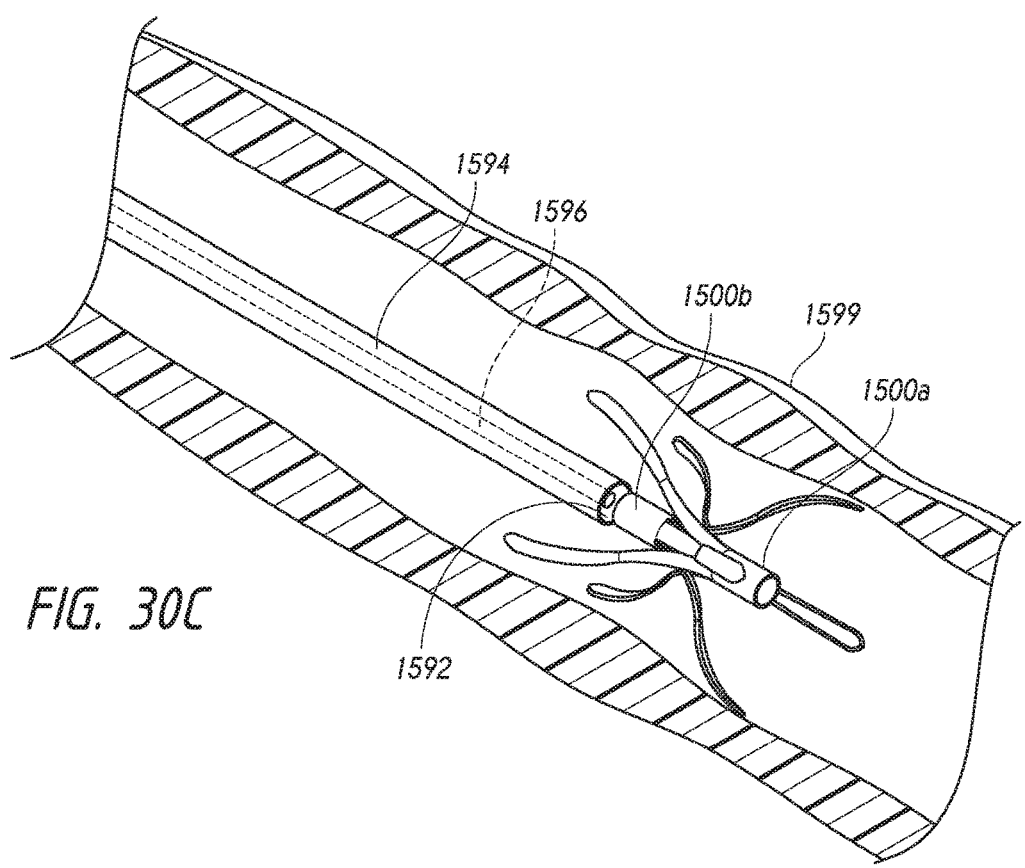

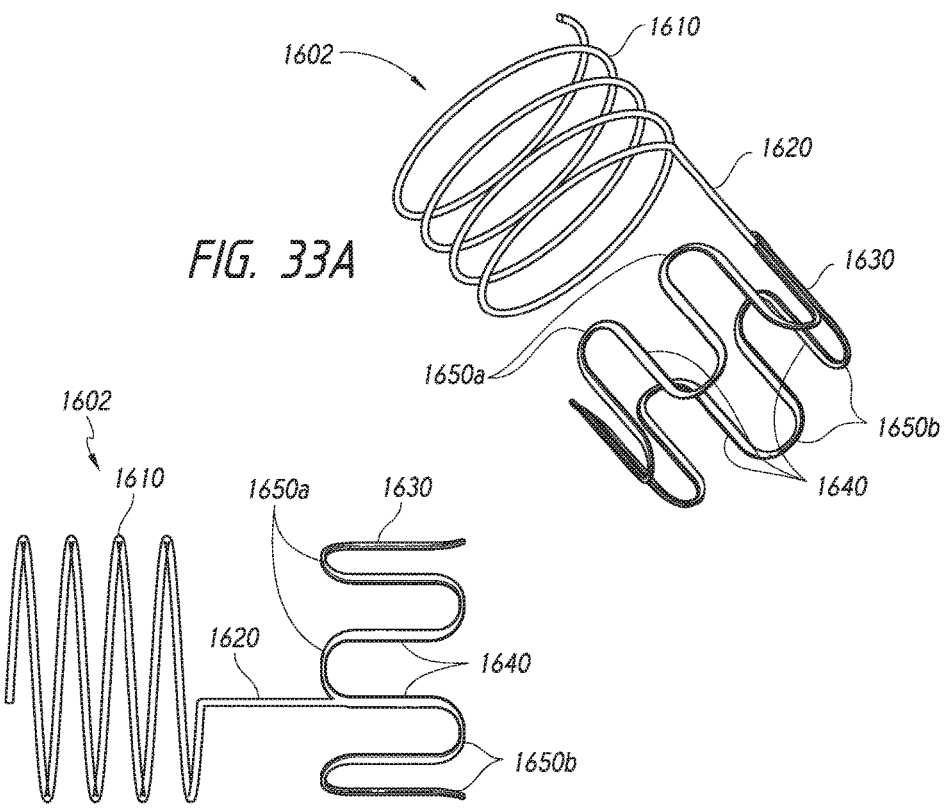
FIG. 33A
FIG. 33B
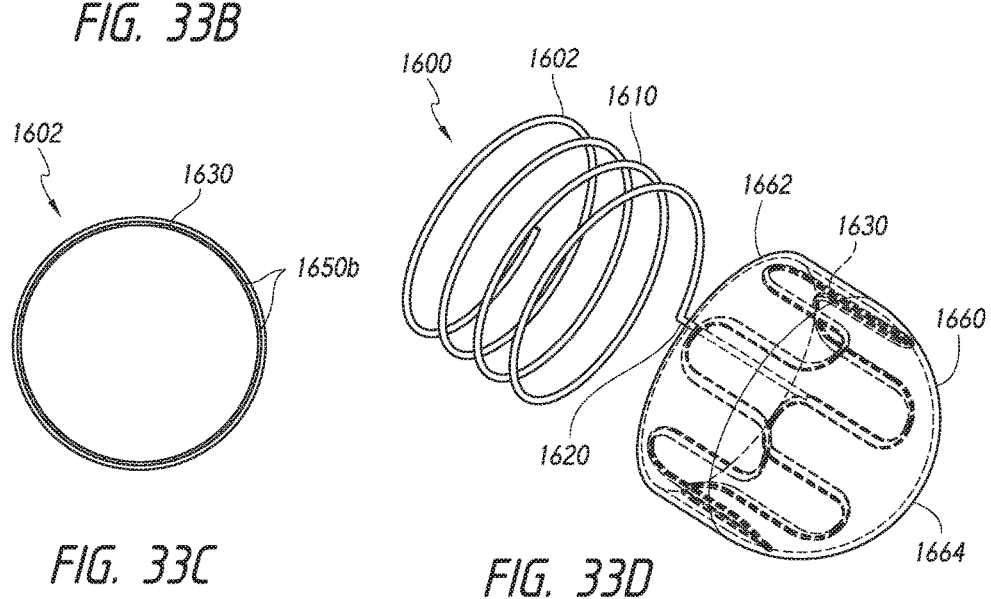
FIG. 33C
FIG. 33D

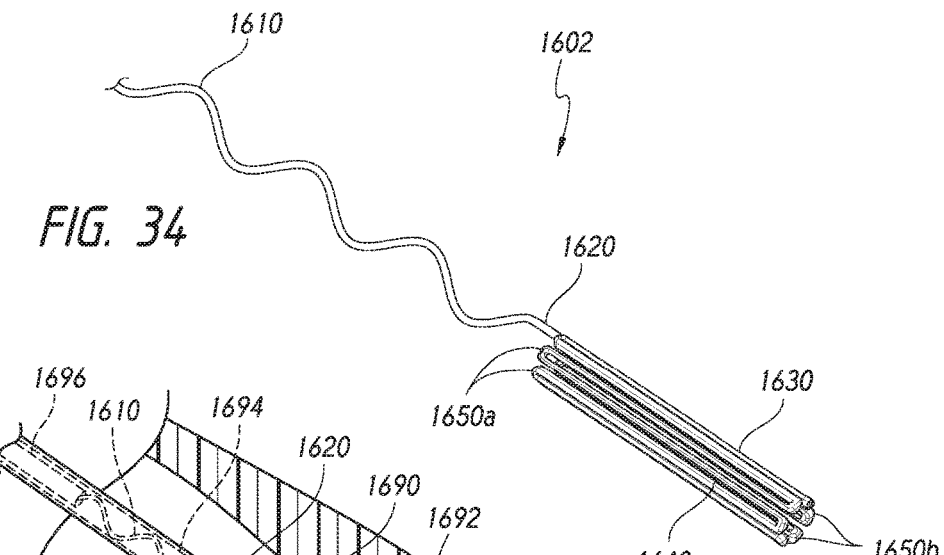
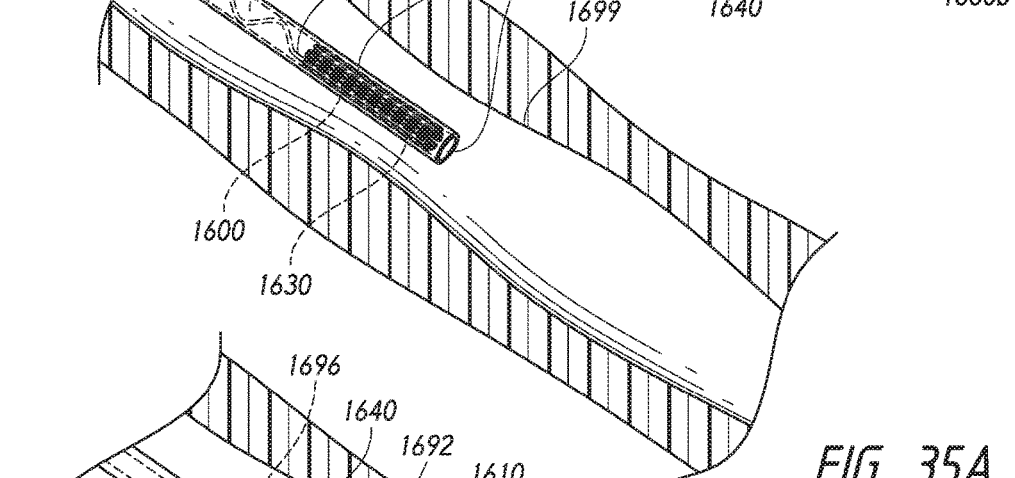
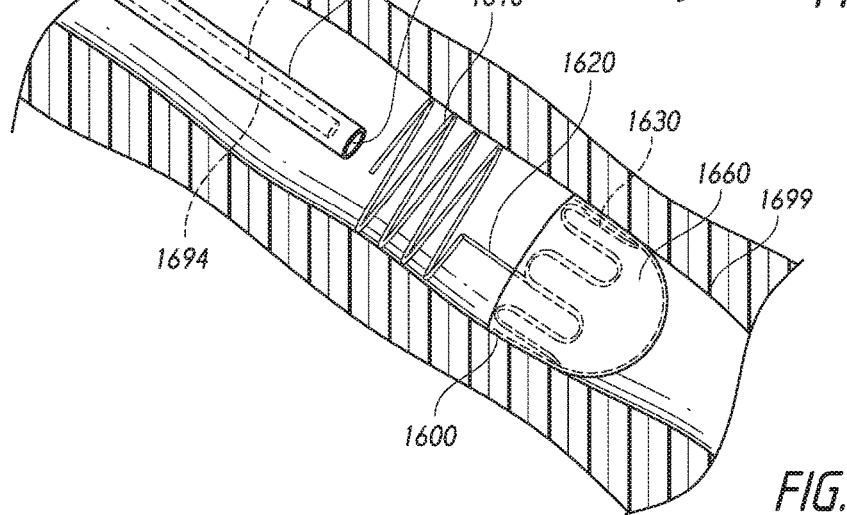

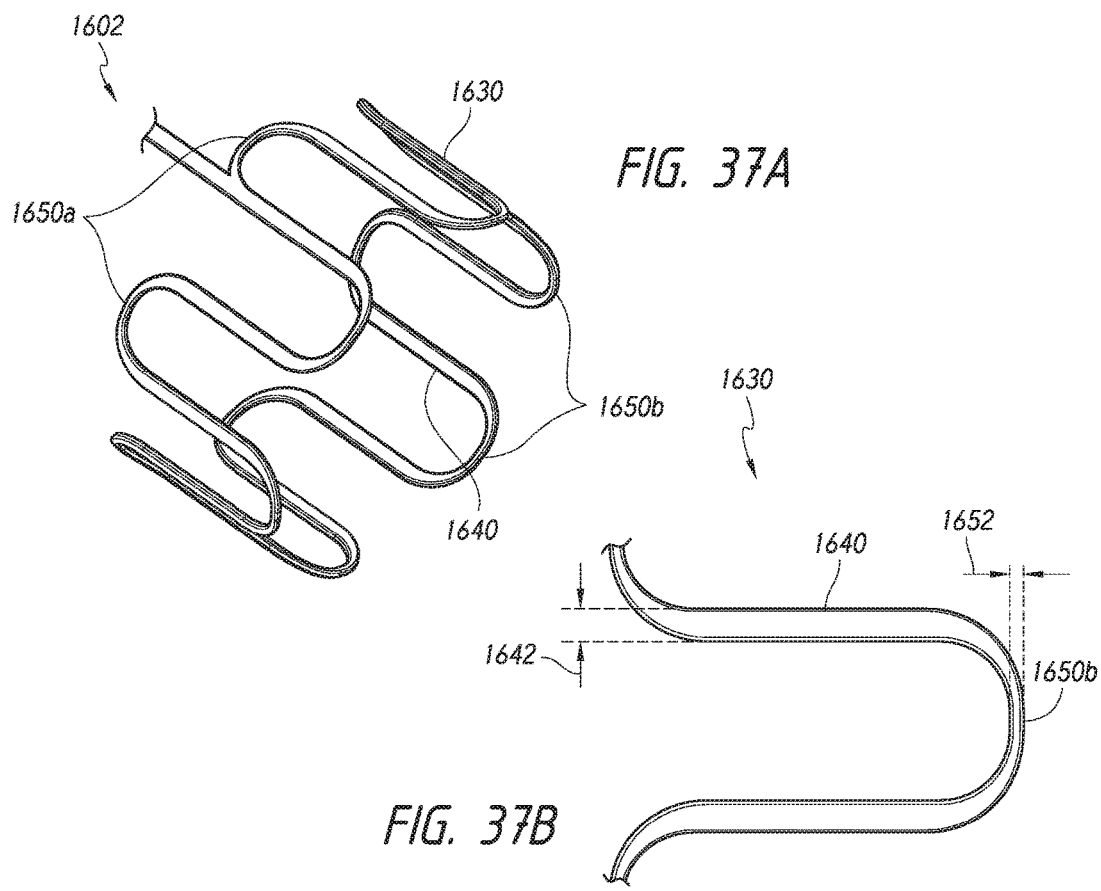
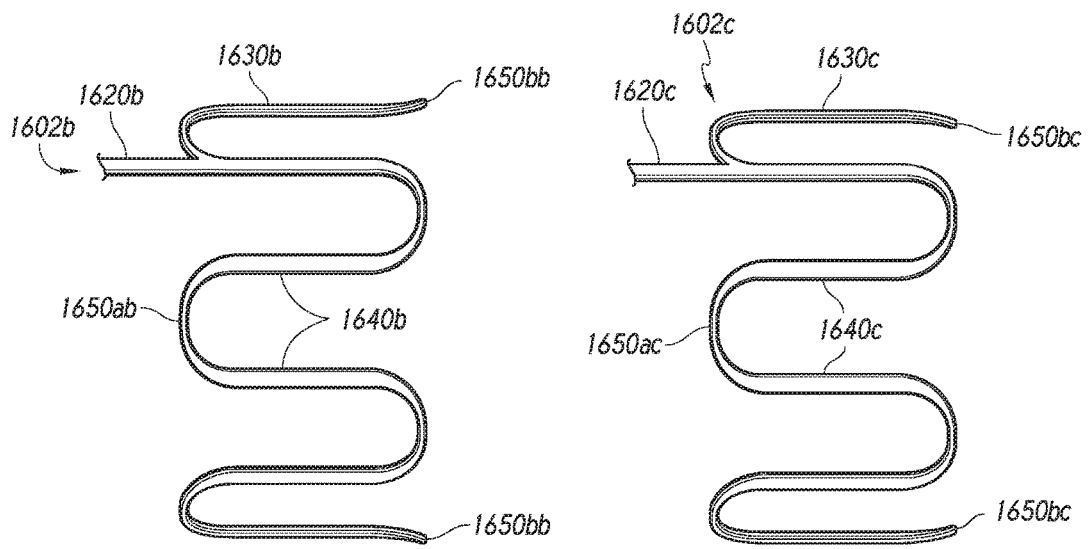
FIG. 37A
FIG. 37B
FIG. 38
FIG. 39

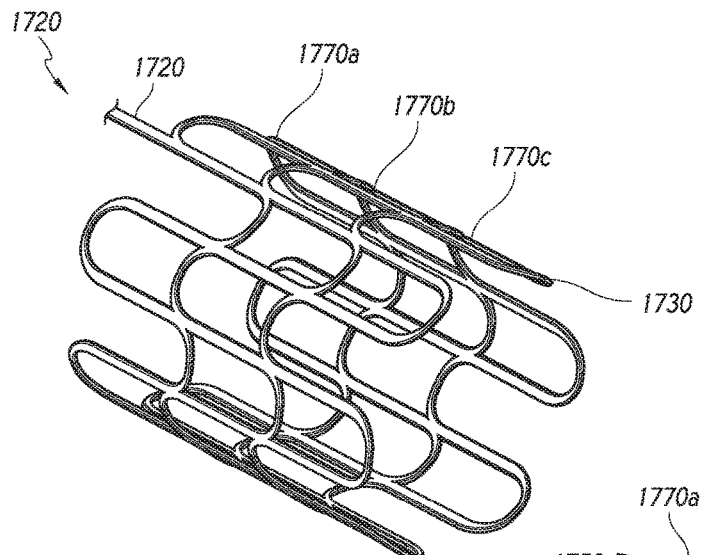
FIG. 40A
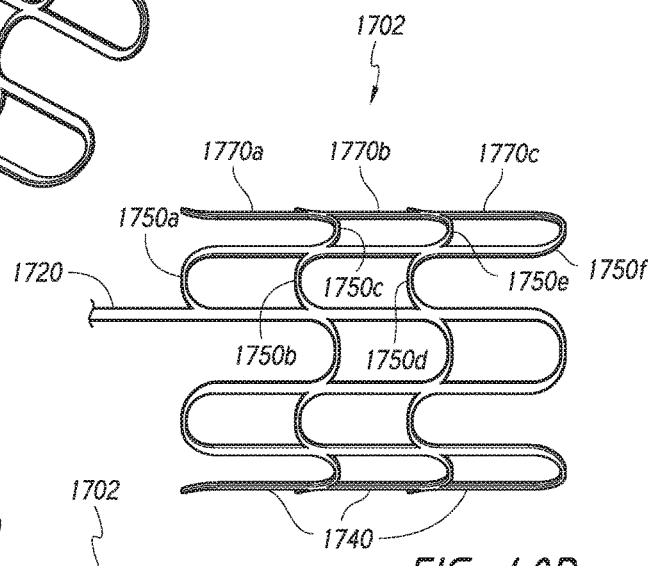
FIG. 40B
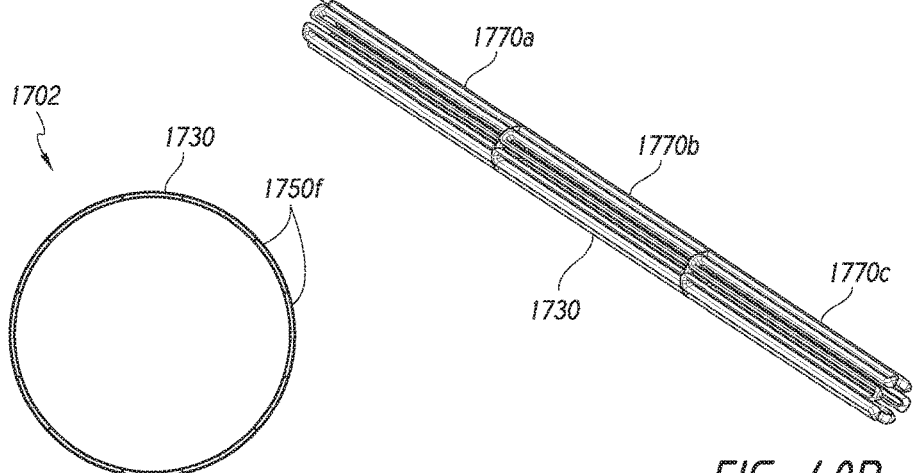
FIG. 40C
FIG. 40D

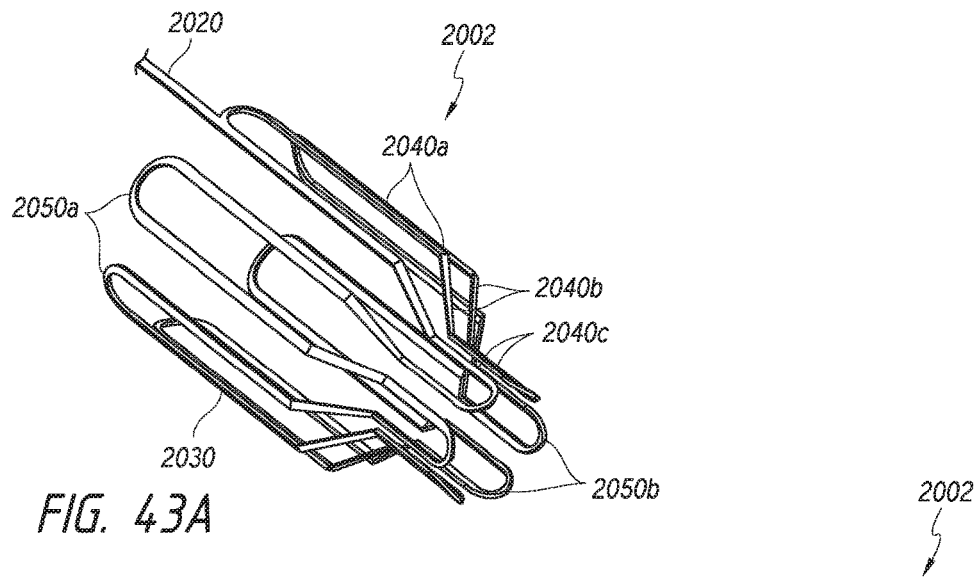
FIG. 43A
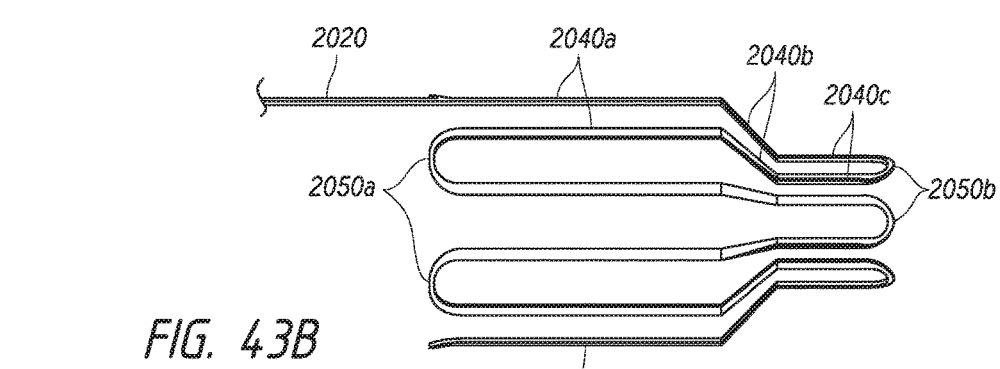
FIG. 43B
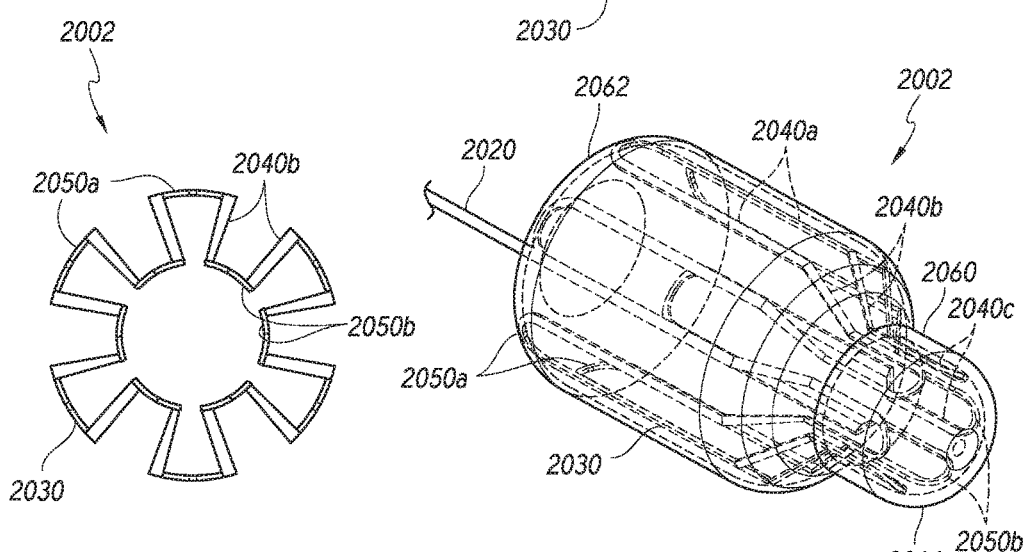
FIG. 43C
FIG. 43D

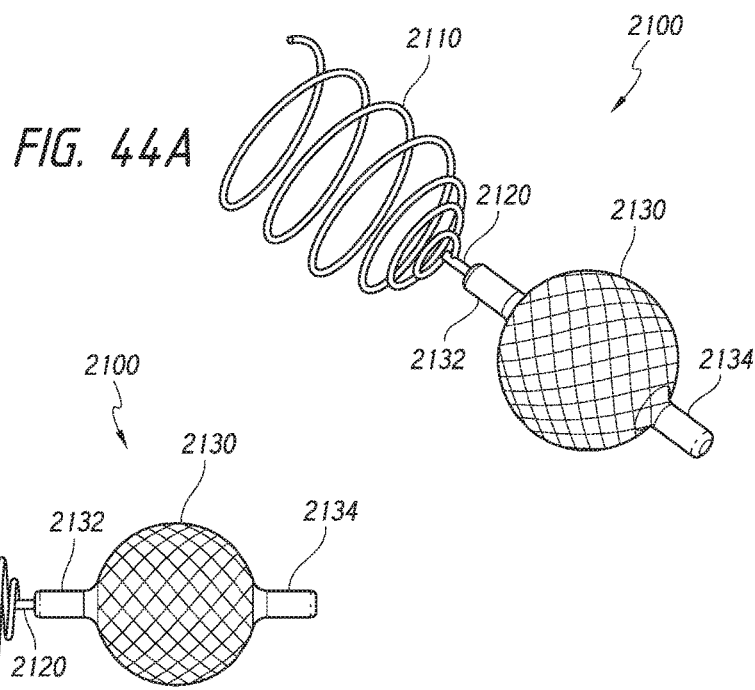
FIG. 44A
FIG. 44B
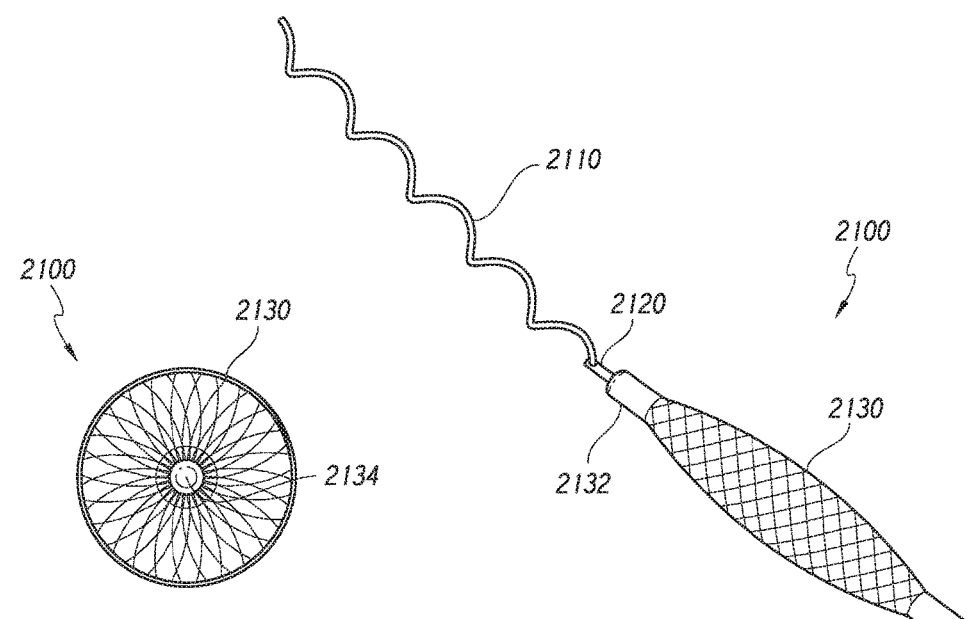
FIG. 44C
FIG. 44D

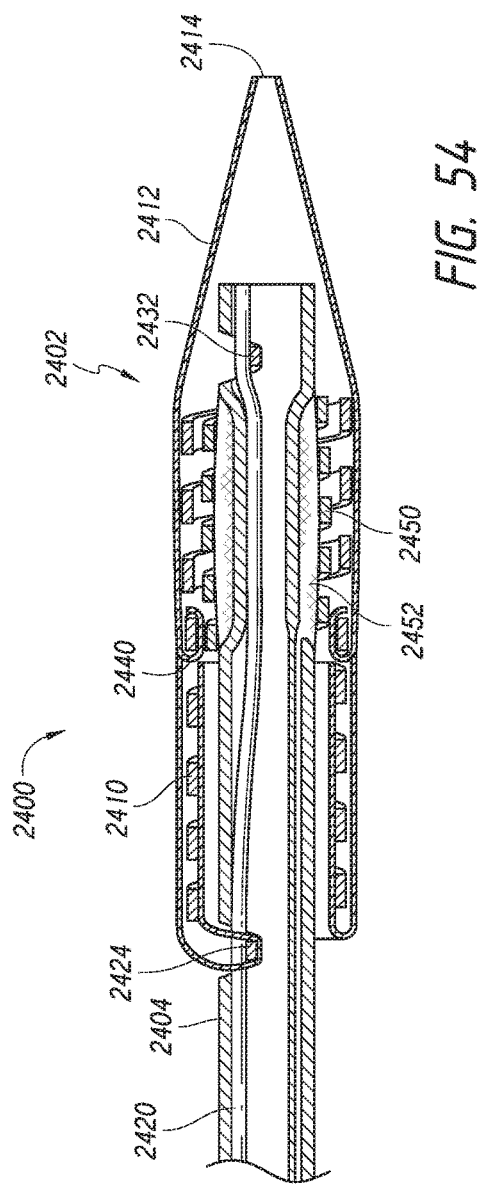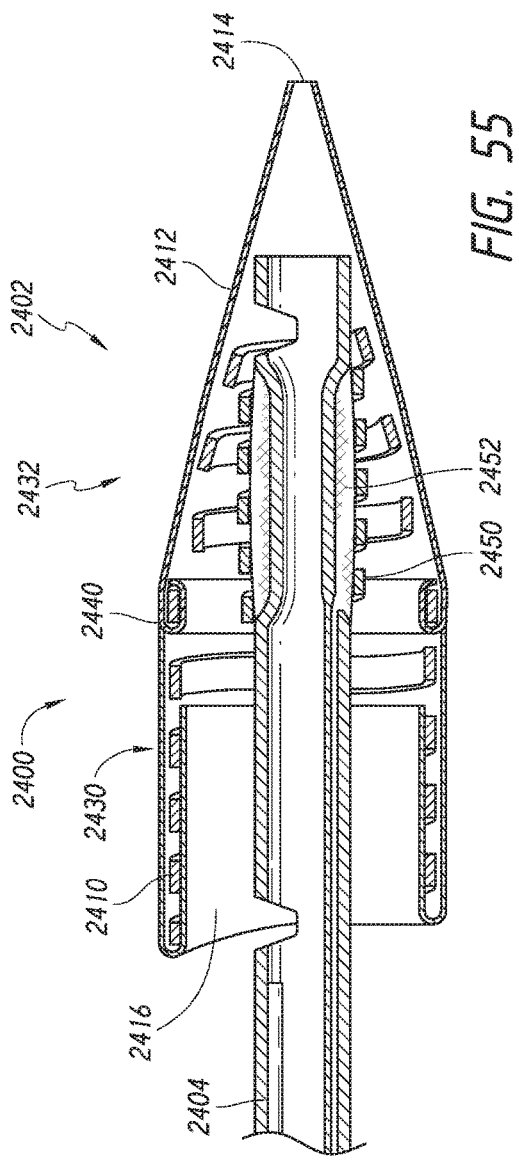

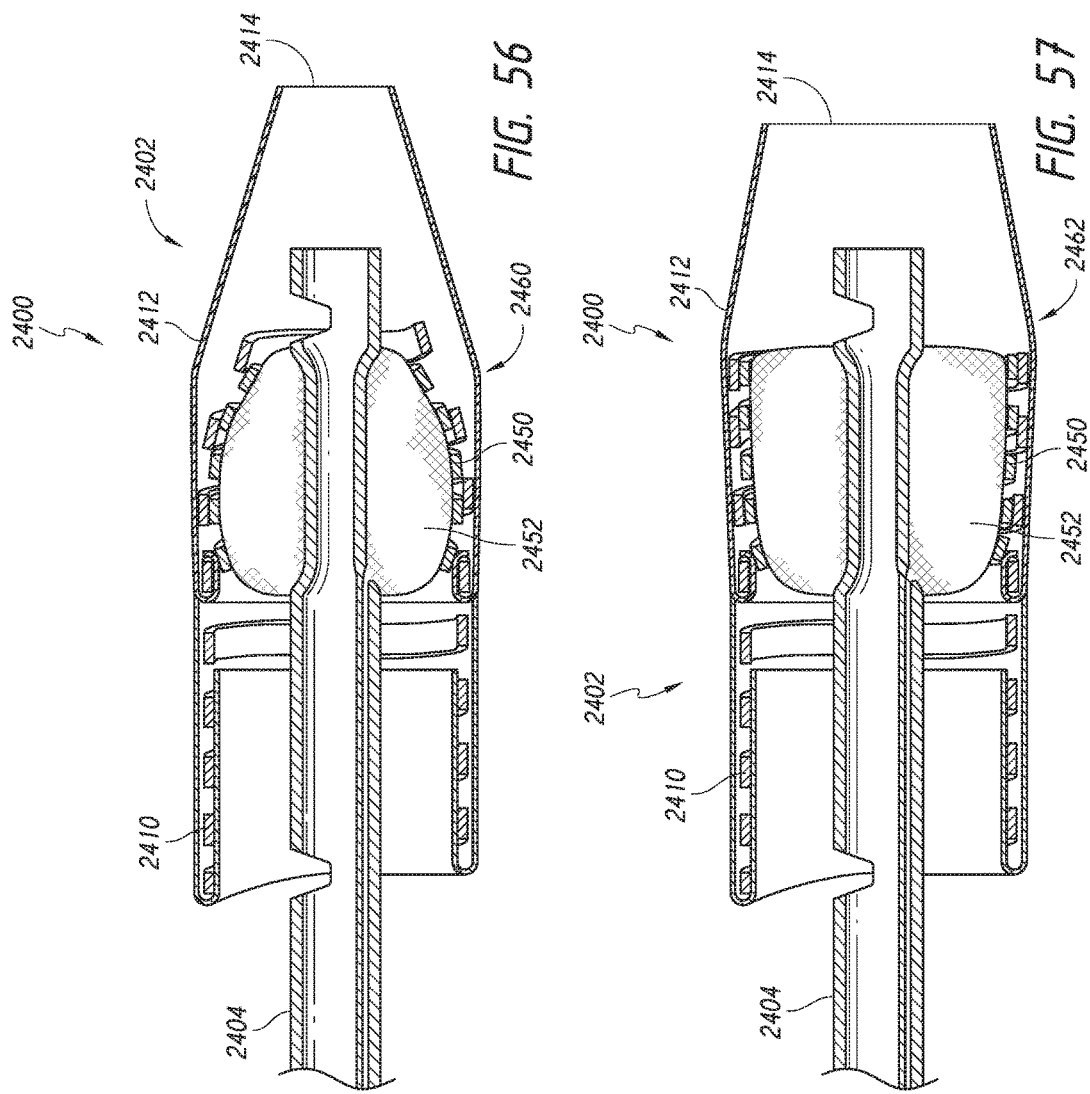

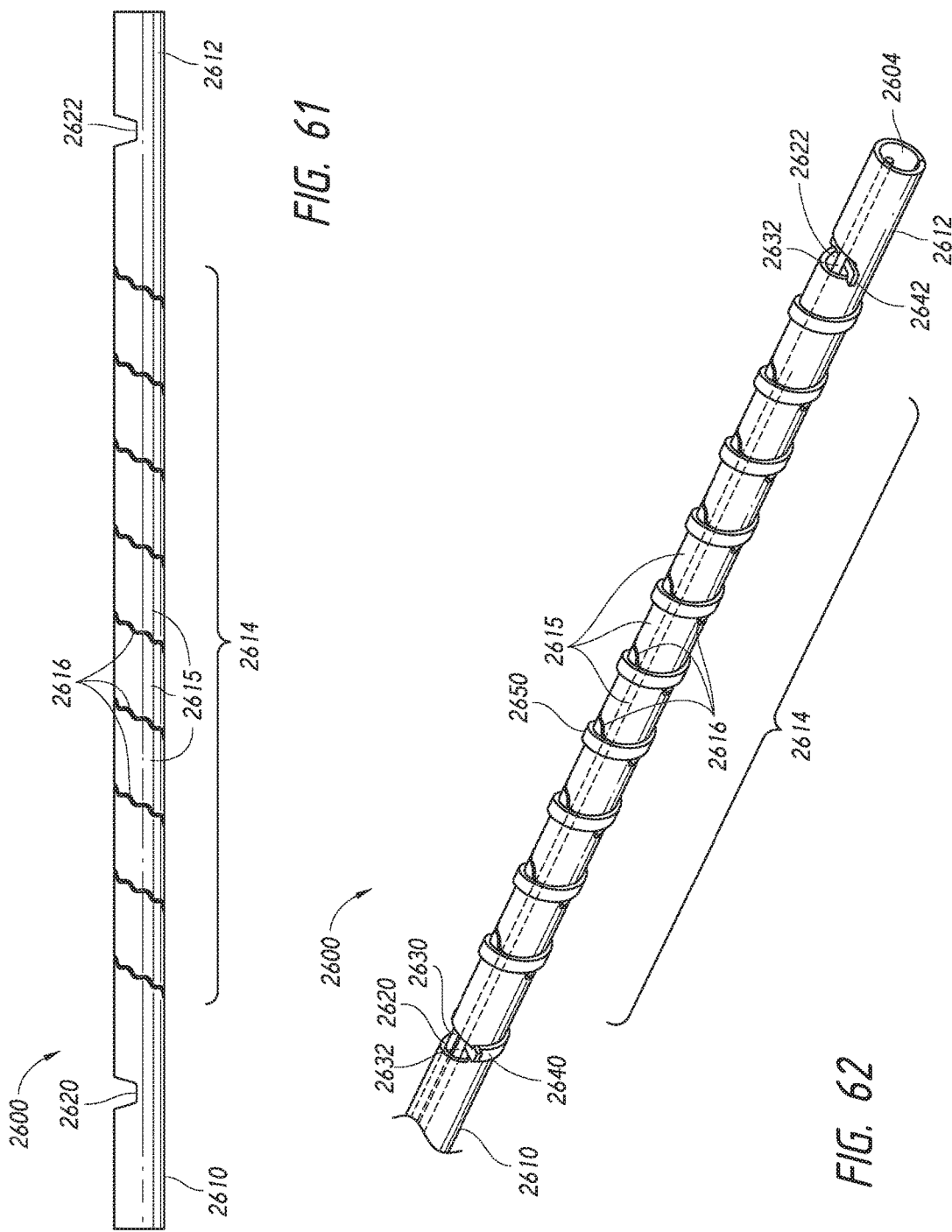

IMPLANTABLE LUMINAL DEVICES

CROSS-REFERENCE TO RELATED APPLICATIONS

This application is a divisional of U.S. patent application Ser. No. 14/304,869, filed on Jun. 13, 2014, which claims the benefit of priority as a continuation-in-part of U.S. patent application Ser. No. 14/101,171, filed on Dec. 9, 2013, and claims the benefit of priority as a nonprovisional of U.S. Provisional Application No. 61/835,406, filed on Jun. 14, 2013, U.S. Provisional Application No. 61/835,461, filed on Jun. 14, 2013, U.S. Provisional Application No. 61/836,061, filed on Jun. 17, 2013, U.S. Provisional Application No. 61/900,321, filed on Nov. 5, 2013, U.S. Provisional Application No. 61/904,376, filed on Nov. 14, 2013, U.S. Provisional Application No. 61/904,379, filed on Nov. 14, 2013, and U.S. Provisional Application No. 61/939,659, filed on Feb. 13, 2014, the entirety of each of which is incorporated herein by reference.

FIELD

The subject technology relates generally to apparatuses and methods for blood vessel occlusion and vascular stenting.

BACKGROUND

Rapid, well-controlled, and safe methods to limit bleeding in vessels have encouraged the development of endovascular devices and techniques, and their introduction into clinical practice. Early devices used balloons, either non-detachable or later detachable, in order to block vessels, for example, in the treatment of carotid-cavernous fistulas and saccular aneurysms.

Typically made from latex or silicone, balloons are delivered to a desired location in a vessel, then inflated in order to physically occlude the vessel. While other devices have since been developed, balloon occlusion remains in use, and is indicated for use in treating a variety of life-threatening conditions, including for example, giant cerebral and skull base aneurysms, traumatic and non-traumatic vessel injury or rupture, vertebro-vertebral arteriovenous fistulas, and pre-operative tumor resections.

Detachable balloons are also useful clinically in procedures outside of neurological intervention. For example, balloons can be useful in flow reduction procedures such as shunt occlusion in patients with transjugular intrahepatic portosystemic shunts and hepatic insufficiency, intrahepatic arterioportal fistulas, treatment of varicoceles, shunt occlusion in patients with a Blalock-Taussig shunt, obliteration of pulmonary arteriovenous fistulas, arteriovenous malformations or aortopulmonary anastomoses, coronary arteriovenous fistulas, or renal arteriovenous fistulas. Detachable balloons are also used in preoperative devascularization before surgical resection of organs such as the kidney.

Calibrated flow reduction is required during treatment of various medical conditions. For example, distal splenorenal shunt procedure (DSRS) (i.e., splenorenal shunt procedure or Warren shunt), is a surgical procedure in which the distal splenic vein attached to the left renal vein. This procedure can be used to treat portal hypertension, its main complication (esophageal varices), and other medical conditions, such as in pediatric patients with surgically created cardiac or pulmonary shunts (congenital heart disease).

Another related medical procedure is the transjugular intrahepatic portosystemic shunt or transjugular intrahepatic portosystemic stent shunting (commonly abbreviated as "TIPS" or "TIPSS") is an artificial channel within the liver that establishes communication between the inflow portal vein and the outflow hepatic vein. It is used to treat portal hypertension (which is often due to liver cirrhosis). Portal hypertension is a hypertension (high blood pressure) involving the portal vein system, which is composed by the portal vein, and its branches and tributaries. Portal hypertension may frequently lead to life threatening upper gastrointestinal bleeding (esophageal varices) and the buildup of fluid within the abdomen (ascites).

Normal values for portal vein pressure are between five and ten mmHg. Anything over 10 mmHg is elevated, while hypertension is over 12 mmHg. In clinical practice, the pressure is not measured directly until the decision to place a TIPS has been made. Corrected sinusoidal pressure (that is the wedged hepatic vein pressure minus free hepatic vein pressure) has generally been accepted as the minimally invasive gold standard for assessing the severity of portal hypertension.

A TIPS procedure becomes necessary when portal hypertension causes the left gastric vein and the umbilical vein to dilate, which causes venous blood to flow in reverse. This leads to varices in the esophagus and stomach, which in turn can lead to bleeding.

A TIPS procedure decreases the effective vascular resistance of the liver. The result is a reduced pressure drop across the liver sinusoids and a decreased portal venous pressure. This, in turn, lessens the pressure on the blood vessels in the esophagus so that future bleeding is less likely to occur. The reduced pressure also makes less fluid develop, although this benefit may take weeks or months to occur.

In order to perform TIPS procedure, an interventional radiologist creates the shunt using an image-guided endovascular (via the blood vessels) approach, with the jugular vein as the usual percutaneous entry site. In a TIPS procedure, a needle is introduced (via the jugular vein) and a tract is passed from the hepatic vein into the portal vein. Thereafter, the tract is dilated with a balloon. After placement of the tract, portal pressure is reduced and the coronary and umbilical veins no longer fill.

SUMMARY

Some embodiments provided herein relate to vessel occlusion by delivery of radially expandable implant frames that achieve immediate total occlusion of blood flow. Frame configurations, expected delivered and expanded dimensions, and a description of target anatomy of some embodiments is provided.

Additionally, some embodiments provided herein relate to implantation in small blood vessels, such as from about 3 mm to about 20 mm, from about 5 mm to about 15 mm, or from about 7 mm to about 11 mm. The target delivery profile can be from about 2 Fr to about 6 Fr, and in some embodiments, from about 3 Fr to about 5 Fr.

Further embodiments can provide vascular stenting for vessels that are from about 3 mm to about 16 mm, from about 5 mm to about 13 mm, and in some embodiments, from about 7 mm to about 11 mm. The target delivery profile can be from about 2 Fr to about 8 Fr, about 3 Fr to about 7 Fr, from about 4 Fr to about 6 Fr, or in some embodiments, about 5 Fr. Additionally, expansion of the implant can provide sufficient radial force against the inside wall of a vein. Some embodiments can comprise features or means configured to minimize backflow of blood or minimize venous insufficiency. For example, treatment applications for embodiments of the device can include ilio-femoral venous obstruction and chronic iliac venous outflow obstruction as a result of venous disease.

Embodiments of the implants provided herein can be manufactured via several methods including shape-setting of drawn wire, chemical etching of a NiTi sheet of material, laser cutting of a tubular member, such as a material sheet or tubing, and/or electrical discharge machining (EDM) of a tubular member, such as a material sheet or tubing.

The implants disclosed herein can comprise flexible and/or shape memory materials such that they may be distorted from an expanded shape to a smaller diameter or straight shape to allow for delivery to a target location by way of a minimally invasive catheter-based approach.

In accordance with some embodiments, the implant can comprise a frame and a cover material. The cover material can comprise ePTFE tubing, film, and/or suture for attachment purposes. Additionally, the cover material may be fibrous, mesh-like, or impermeable in density.

The implant frame and/or implant cover can comprise a collagen coating or collagen treatment to improve anchoring of the implant in the target vessel. The collagen can be configured to promote cell adhesion to implant materials, thereby facilitating improved support for the implant and vessel structure while acting as an anti-migration feature for the implant.

The implant frame can comprise a straight or constant diameter, a tapering diameter, or sections of variable diameter extending over its length, which can facilitate anchoring within a vessel and optimal deployment function.

Embodiments of the systems and devices disclosed herein address the unmet need for a device that can provide a fast, precise and reliable way to close a bodily lumen. The endoluminal occlusion system can include two major subsystems: a guide sheath assembly and an implant carrier assembly. The implant carrier assembly can include an implant device and a handle assembly. Embodiments of the present disclosure can also comprise various features disclosed in U.S. Pat. No. 8,328,840, issued on Dec. 11, 2012, the entirety of which is incorporated herein by reference.

A single wire can be shaped in a back-and-forth pattern around a circumference. The shape can be set to an expanded diameter to fill the circumference of a blood vessel. The ends of the wire can be welded or otherwise attached such that there is a continuous construct around the full circumference. The design can be intended to allow a high ratio of expansion, while maintaining a radial force at all points around the circumference of the blood vessel in order to seal blood flow. The construct can be covered with a non-permeable material, sealed at one or both ends to occlude blood flow. The cover can be silicone rubber, ePTFE, or urethane, and designed to have a tight fit around the expanded construct. The construct size can be chosen based on endoluminal size at the implant location, expected to be a minimum 25% greater in diameter than the endoluminal diameter.

An expandable feature (braid, balloon, or other construct) with a non-permeable cover can be attached to a filament shaped into a coil. The expandable feature can utilize shaped or otherwise positioned wires such that axial compression of the expandable feature causes a diameter increase intended for occlusion of a blood vessel. The expandable feature can alternatively increase in diameter by internal pressure caused by an expandable gel or other material, or insertion of liquid. The coil can be shape set to a corresponding diameter relative to the expandable feature, and acts to anchor the expandable occlusion feature within a blood vessel or vascular malformation such as fistula, etc.

According to some embodiments, medical methods and apparatuses are provided for controlling or modifying a pressure gradient between blood vessels. Further, some embodiments can provide an adjustable implant that can be modified to provide a desired pressure gradient. The implant can be adjusted from a first non-zero flow rate to a second non-zero flow rate, and in some embodiments, from the second non-zero flow rate to a third non-zero flow rate, to provide a variety of gradient options. For example, the implant can be modified in situ. Further, some embodiments can provide methods and implants for adjusting a hepatic venous pressure gradient (HVPG) between the portal and hepatic veins in a transjugular intrahepatic portosystemic procedure. Such methods and apparatuses can be configured to adjust or maintain the HVPG equal to or below about 10 mmHg.

Frame configurations, expected delivered and expanded dimensions, and a description of target anatomy of some embodiments are provided. Aspects of implants, catheters, and delivery devices that can be utilized in combination with the implants, systems, methods, and features disclosed herein are disclosed in: U.S. patent application Ser. No. 12/826,593, filed on Jun. 29, 2010 (086538-0012); U.S. patent application Ser. No. 13/367,338, filed on Feb. 6, 2012 (086538-0018); U.S. patent application Ser. No. 12/906,993, filed on Oct. 18, 2010 (086538-0014); U.S. patent application Ser. No. 13/828,974, filed on Mar. 14, 2013 (086538-0030); U.S. patent application Ser. No. 61/836,061, filed on Jun. 17, 2013 (086538-0038); U.S. patent application Ser. No. 14/044,794, filed on Oct. 2, 2013 (086538-0039); U.S. patent application Ser. No. 14/281,797, filed on May 19, 2014 (086538-0055); U.S. patent application Ser. No. 61/835,406, filed on Jun. 14, 2013 (086538-0032); U.S. patent application Ser. No. 61/904,376, filed on Nov. 14, 2013 (086538-0041); U.S. patent application Ser. No. 61/904,379, filed on Nov. 14, 2013 (086538-0043); U.S. patent application Ser. No. 61/835,461, filed on Jun. 14, 2013 (086538-0034); U.S. patent application Ser. No. 61/900,321, filed on Nov. 5, 2013 (086538-0040); and U.S. patent application Ser. No. 14/101,171, filed on Dec. 9, 2013 (086538-0046), the entireties of which are incorporated herein by reference.

Some embodiments can provide vascular implantation for vessels that are from about 2 mm to about 16 mm, from about 5 mm to about 13 mm, and in some embodiments, from about 7 mm to about 11 mm. The target delivery profile can be from about 2 Fr to about 8 Fr, about 3 Fr to about 7 Fr, from about 4 Fr to about 6 Fr, or in some embodiments, about 5 Fr. Additionally, expansion of the implant can provide sufficient radial force against the inside wall of a vein. Some embodiments can comprise features or means configured to minimize backflow of blood or minimize venous insufficiency. For example, treatment applications for embodiments of the implant can include ilio-femoral venous obstruction and chronic iliac venous outflow obstruction as a result of venous disease.

The implant may serve as a calibrated flow and pressure reduction tool in some embodiments. Some embodiments of the implant can be used for purposes of tumor devascularization, reducing traumatic bleeding or hemorrhage, high-flow vascular malformations, vascular or airway volume reduction procedures, treatment of a target lesion, treatment and embolization of incompetent venous systems in low extremities (i.e., legs and lower abdominal area), treatment varicose veins in the leg (i.e., great saphenous vein and spider veins in deeper system), attending to other indications such as arterio-venous malformation (AVM), pelvic varices, etc.

Further, some embodiments provide an implant delivery system that comprises a catheter having a flexible, torque-resistant tip over which an implant frame may be secured and delivered to a target treatment site. Some embodiments also relate to engagement mechanisms whereby an implant can be engaged relative to a delivery catheter and actuation mechanisms for releasing the implant from the engagement.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 55. The other clauses can be presented in a similar manner.

Clause 1. An expandable device for delivery to a target location in a body vessel, comprising: a first elongate member having (i) a first portion extending along an arcuate path in a clockwise circumferential direction, (ii) a second portion extending along an arcuate path in a counterclockwise circumferential direction, and (iii) a third portion interconnecting the first and second portions; and a second elongate member coupled to the first elongate member, the second member having (i) a first portion extending along an arcuate path in a counterclockwise circumferential direction, (ii) a second portion extending along an arcuate path in a clockwise circumferential direction, and (iii) a third portion interconnecting the first and second portions, wherein the first member third portion is coupled to the second member third portion to interconnect the first and second members, and wherein the first and second portions of the first and second members are spaced apart from each other to collectively define a frame having a central lumen extending therethrough.

Clause 2. The device of Clause 1, wherein the first portions of the first and second elongate members collectively define a first support element, and the second portions of the first and second elongate members collectively define a second support element, wherein the first support element has a cross-sectional profile different from the second support element.

Clause 3. The device of Clause 2, wherein the first and second support elements are circular.

Clause 4. The device of Clause 2, wherein the first and second elongate members each comprise fourth portions that interconnect the second portions with respective fifth portions, the fifth portion of the first elongate member extending along at least a portion of a cylindrical path in a clockwise circumferential direction, the fifth portion of the second elongate member extending along at least a portion of a cylindrical path in a counterclockwise circumferential direction, wherein the fifth portions of the first and second elongate members collectively form a third support element having a cross-sectional profile different from a cross-sectional profile of at least one of the first support element or the second support element.

Clause 5. The device of Clause 4, wherein the first, second, and third support elements are circular and have diameters different from each other.

Clause 6. The device of any of the previous Clauses, wherein in a relaxed position, the first portion and the second portion of the first elongate member both extend substantially parallel relative to each other and transversely relative to the third portion of the first elongate member, and wherein the first portion and the second portion of the second elongate member both extend substantially parallel relative to each other and transversely to the third portion of the second elongate member.

Clause 7. The device of any of the previous Clauses, wherein the frame is substantially conical.

Clause 8. The device of any of the previous Clauses, wherein the frame is substantially tubular.

Clause 9. The device of any of the previous Clauses, wherein the first and second members are configured to form a substantially tubular member in an expanded state and to be drawn into a substantially linear member in a delivery state.

Clause 10. The device of any of the previous Clauses, wherein the first and second members comprise pluralities of first, second, and third portions, and wherein the first and second members are interconnected along a length of the frame at respective third portions thereof.

Clause 11. The device of any of the previous Clauses, wherein the first and second members each define a respective portion of a cylindrical shape, the first and second members being interconnected to form a substantially cylindrical frame.

Clause 12. The device of any of the previous Clauses, wherein the third portions of the first and second members are coupled using a weld, adhesive, cuff, coil, or ring.

Clause 13. The device of any of the previous Clauses, wherein the device comprises a cover.

Clause 14. The device of any of the previous Clauses, wherein the device comprises a graft extending at least partially about the helical member.

Clause 15. The device of any of the previous Clauses, wherein the device comprises a graft extending around the helical member in a substantially tubular configuration and having opposing open end portions.

Clause 16. The device of any of the previous Clauses, wherein the device comprises a plurality of apertures and at least one filament extending between the apertures to form a web along at least a portion of the device.

Clause 17. The device of any of the previous Clauses, wherein the device comprises a partial cover positioned on the frame.

Clause 18. The device of any of the previous Clauses, further comprising a proximal coupling mechanism extending proximally from the first support element and a distal coupling mechanism extending distally from the third support element.

Clause 19. An expandable device for delivery to a target location in a body vessel, comprising: first, second, and third support elements, each comprising at least one wire extending in a circumferential direction to form a loop, each of the support elements extending generally orthogonally relative to a longitudinal axis of the device when the device is in a relaxed state; a first axial element interconnecting the first and second support elements at a first circumferential position; and a second axial element interconnecting the second and third support elements at a second circumferential position, offset from the first circumferential position by about 180°; wherein the first, second, and third support elements are resiliently biased to the relaxed state from a collapsed state in which the device extends in a substantially linear configuration.

Clause 20. The device of Clause 19, wherein the first, second, and third support elements comprise annular rings.

Clause 21. The device of any of Clauses 19-20, wherein the first, second, and third support elements comprise a pair of wires extending symmetrically about an axis of the device.

Clause 22. The device of any of Clauses 19-21, wherein the first and second axial elements comprise a pair of wires extending symmetrically about an axis of the device.

Clause 23. The device of any of Clauses 19-22, further comprising a proximal coupling mechanism extending proximally from the first support element and a distal coupling mechanism extending distally from the third support element.

Clause 24. An delivery system for delivering the expandable device of any of the previous Clauses, the system comprising a catheter having proximal and distal engagement mechanisms, the proximal and distal engagement mechanisms being releasably engageable with proximal and distal coupling portions of the device.

Clause 25. An expandable device for delivery to a target location in a body vessel, comprising an elongate helical member extending in a helical path and having a cross-sectional shape in which an axial width is less than a radial thickness.

Clause 26. The device of Clause 25, wherein the elongate helical member is configured to form a substantially tubular member in an expanded state and to be drawn into a substantially linear member in a delivery state.

Clause 27. The device of any of Clauses 25-26, wherein the helical member is configured to comprise a variable pitch.

Clause 28. The device of any of Clauses 25-27, wherein the helical member is configured to comprise a substantially constant pitch.

Clause 29. The device of any of Clauses 25-28, wherein the device comprises a cover.

Clause 30. The device of any of Clauses 25-29, wherein the device comprises a cover extending between the first and second members.

Clause 31. The device of any of Clauses 25-30, wherein the device comprises an occlusive structure extending at least partially about the helical member.

Clause 32. The device of any of Clauses 25-31, wherein the device comprises an occlusive structure extending around the helical member in a substantially tubular configuration and having opposing open end portions.

Clause 33. The device of any of Clauses 25-32, wherein the device comprises a plurality of apertures and at least one filament extending between the apertures to form a web along at least a portion of the device.

Clause 34. An implant delivery system, comprising the device of any of Clauses 25-33 and a catheter having a distal end portion and a deployment aperture extending through a sidewall of the catheter, the deployment aperture comprising a cross-sectional longitudinal width that is less than its cross-sectional axial height, wherein a distal end portion of the device is positioned within the deployment aperture.

Clause 35. The system of Clause 34, wherein a longitudinal axis of the aperture extends substantially orthogonally relative to the sidewall of the catheter.

Clause 36. The system of any of Clauses 34-35, wherein a longitudinal axis of the aperture extends transversely relative to the sidewall of the catheter.

Clause 37. A method of implanting an intraluminal device, comprising: advancing a catheter to a target location within a body vessel, the catheter having a distal end portion and a deployment aperture extending through a sidewall of the catheter, the catheter having a lumen in which the device is disposed, the device comprising a cross-sectional profile with a first dimension greater than a second dimension; and advancing the device out of the catheter through the deployment aperture with the cross-sectional profile oriented such that the first dimension extends in an axial dimension.

Clause 38. The method of Clause 37, wherein the cross-sectional profile is substantially rectangular.

Clause 39. The method of any of Clauses 37-38, wherein the device extends through the aperture in a direction substantially perpendicular relative to an outer surface of the catheter.

Clause 40. The method of any of Clauses 37-39, wherein a longitudinal axis of the device extends through the aperture substantially orthogonally relative to an outer surface of the catheter.

Clause 41. The method of any of Clauses 37-40, wherein a longitudinal axis of the device extends through the aperture in substantially transverse relative to an outer surface of the catheter.

Clause 42. The method of any of Clauses 37-41, further comprising placing a cover into the vessel.

Clause 43. The method of any of Clauses 37-42, further comprising positioning a graft at least partially about the helical member.

Clause 44. The method of any of Clauses 37-43, further comprising positioning a graft at least partially around the helical member in a substantially tubular configuration, the graft having opposing open end portions.

Clause 45. The method of any of Clauses 37-44, wherein the device comprises a plurality of apertures and at least one filament extending between the apertures to form a web along at least a portion of the device.

Clause 46. The method of any of Clauses 37-45, further comprising positioning a partial cover on the frame.

Clause 47. An expandable device for delivery to a target location in a body vessel, comprising: a proximal end portion; a distal end portion; a plurality of filaments attached to each of the proximal end portion and the distal end portion, extending helically about a central axis, and defining, in an expanded state, a proximal face, a distal face, and a cylindrical middle section between the proximal face and the distal face; and a cover disposed on a portion of the middle section and one of the proximal face and the distal face.

Clause 48. The expandable device of Clause 47, wherein each of the plurality of filaments extends in a helical direction that is the same as a helical direction of every other of the plurality of filaments.

Clause 49. The expandable device of any of Clauses 47-48, wherein the cover is disposed on each of the proximal face, the distal face, and the middle section.

Clause 50. The expandable device of any of Clauses 47-49, wherein the cover is attached to one of the proximal end portion and the distal end portion.

Clause 51. The expandable device of any of Clauses 47-50, wherein the cover blocks fluid flow from a region outside of the filaments to a region enclosed by the filaments.

Clause 52. The expandable device of any of Clauses 47-51, wherein the proximal face and the distal face each define a surface transverse to the central axis.

Clause 53. The expandable device of any of Clauses 47-52, further comprising a wire fixedly attached to one of the proximal end portion and a distal end portion, the wire being slidably connected to the other of the proximal end portion and the distal end portion.

Clause 54. The expandable device of any of Clauses 47-53, wherein the filaments have a compressed state, in which the filaments define a compressed diameter, less than an expanded diameter in the expanded state.

Clause 55. The expandable device of any of Clauses 47-54, wherein proximal end portion is attached to a distal end portion of a second expandable device by a connector.

Clause 56. An expandable device for delivery to a target location in a body vessel, comprising: a proximal end portion; a distal end portion; a plurality of struts attached to each of the proximal end portion and the distal end portion, extending longitudinally along a portion of a circumferential path, and defining, in an expanded state, a proximal face, a distal face, and an equator between the proximal face and the distal face; and a cover disposed on one of the proximal face and the distal face.

Clause 57. The expandable device of Clause 56, wherein the cover is disposed on each of the proximal face, the distal face, and the equator.

Clause 58. The expandable device of any of Clauses 56-57, wherein the cover is attached to one of the proximal end portion and the distal end portion.

Clause 59. The expandable device of any of Clauses 56-58, wherein the cover blocks fluid flow from a region outside of the struts to a region enclosed by struts.

Clause 60. The expandable device of any of Clauses 56-59, wherein the proximal face and the distal face each define a hemispherical section.

Clause 61. The expandable device of any of Clauses 56-60, further comprising a wire fixedly attached to one of the proximal end portion and a distal end portion, the wire being slidably connected to the other of the proximal end portion and the distal end portion.

Clause 62. The expandable device of any of Clauses 56-61, wherein the filaments have a compressed state, in which the struts define a compressed diameter, less than an expanded diameter in the expanded state.

Clause 63. The expandable device of any of Clauses 56-62, wherein each of the plurality of struts forms a proximal notch on an outer surface thereof at the proximal end portion and wherein each of the plurality of struts forms a distal notch on an outer surface thereof at the distal end portion.

Clause 64. The expandable device of any of Clauses 56-63, wherein each of the plurality of struts forms a middle notch on an inner surface thereof and between the proximal end portion and the distal end portion.

Clause 65. An expandable device for delivery to a target location in a body vessel, comprising: a hub; a plurality of filaments having a compressed state, such that the filaments extend axially from a side of the hub, and an expanded state, such that the filaments extend radially outwardly from the side of the hub; an expander being movable by a control rod from a first location distal of the filaments, such that the filaments are in the compressed state, to a second location, proximal of the first location and in which the expander contacts the filaments to transition the filaments to the expanded state; and a cover disposed across the plurality of filaments.

Clause 66. The expandable device of Clause 65, wherein the control rod is movable axially within the hub.

Clause 67. The expandable device of any of Clauses 65-66, wherein the filaments define an inner cross-sectional dimension in the compressed state, and the expander has an outer cross-sectional dimension greater than the inner cross-sectional dimension.

Clause 68. The expandable device of any of Clauses 65-67, wherein, in the expanded state, the filaments extend axially and radially from the side of the hub.

Clause 69. The expandable device of any of Clauses 65-68, further comprising: an enlarged member attached to the expander; an inner protrusion within the hub, configured to allow the enlarged member to move proximally through the hub past the inner protrusion and configured to prevent the enlarged member from moving distally through the hub past the inner protrusion.

Clause 70. The expandable device of Clause 69, wherein the enlarged member comprises a tooth having proximal slope and a distal side, and wherein the inner protrusion comprises a flexible pawl configured to ride up the proximal slope of the tooth and engage the distal side of the tooth.

Clause 71. The expandable device of any of Clauses 65-70, wherein the hub is attached to a hub of a second expandable device by a connector.

Clause 72. The expandable device of any of Clauses 65-71, wherein control rod is releasably attached to the enlarged member.

Clause 73. The expandable device of any of Clauses 65-72, wherein the expandable device tends to the compressed state when unrestrained.

Clause 74. A method of delivering an expandable device to a target location in a body vessel, comprising: providing a catheter to the target location, the catheter carrying the expandable device in a compressed state; and pulling an expander proximally relative to a hub of the expandable device, such that filaments extending distally from the hub expand radially outwardly from the hub to an expanded state, in which a cover over the filaments occludes fluid flow through the body vessel.

Clause 75. The method of Clause 74, wherein pulling the expander comprises pulling a control rod, connected to the expander, proximally through the hub.

Clause 76. The method of any of Clauses 74-75, wherein pulling the expander comprises pulling an enlarged member, connected to the expander, proximally past an inner protrusion within the hub, such that the inner protrusion prevents the enlarged member from moving distally through the hub past the inner protrusion.

Clause 77. The method of any of Clauses 74-76, wherein pulling the expander comprises pulling a control rod, connected to the expander, proximally through the hub.

Clause 78. The method of any of Clauses 74-77, further comprising: delivering a supplemental device within the body vessel, the supplemental device facing a direction opposite a direction of the expandable device; connecting the supplemental device to the expandable device.

Clause 79. An expandable device for delivery to a target location in a body vessel, comprising: a hub; a plurality of proximal filaments having a compressed state, such that the proximal filaments extend proximally and axially from a proximal side of the hub, and an expanded state, such that the proximal filaments extend radially outwardly from the proximal side of the hub; a proximal expander being movable by a control rod from a first location proximal of the proximal filaments, such that the proximal filaments are in the compressed state, to a second location, distal of the first location and in which the expander contacts the proximal filaments to transition the proximal filaments to the expanded state; a proximal cover disposed across the plurality of proximal filaments; a plurality of distal filaments having a compressed state, such that the distal filaments extend distally and axially from a distal side of the hub, and an expanded state, such that the distal filaments extend radially outwardly from the distal side of the hub; a distal expander being movable from a first location distal of the distal filaments, such that the distal filaments are in the compressed state, to a second location, proximal of the first location and in which the expander contacts the distal filaments to transition the distal filaments to the expanded state; and a distal cover disposed across the plurality of the distal filaments.

Clause 80. The expandable device of Clause 79, wherein the control rod is movable axially within the hub.

Clause 81. The expandable device of any of Clauses 79-80, wherein, in the expanded state, the filaments extend axially and radially from the side of the hub.

Clause 82. The expandable device of any of Clauses 79-81, further comprising: an enlarged member attached to the control rod; a lumen, within the proximal expander, configured to allow the enlarged member to move proximally through the proximal expander and configured to prevent the enlarged member from moving distally through the proximal expander.

Clause 83. The expandable device of Clause 82, wherein the enlarged member comprises a tooth having proximal slope and a distal side, and wherein the lumen comprises a flexible pawl configured to ride up the proximal slope of the tooth and engage the distal side of the tooth.

Clause 84. The expandable device of any of Clauses 79-83, wherein control rod is releasably attached to the enlarged member.

Clause 85. The expandable device of any of Clauses 79-84, wherein the expandable device tends to the compressed state when unrestrained.

Clause 86. A method of delivering an expandable device to a target location in a body vessel, comprising: providing a catheter to the target location, the catheter carrying the expandable device in a compressed state; and pulling a distal expander proximally relative to a distal expander of the expandable device, such that distal filaments extending distally from the hub and proximal filaments extending proximally from the hub expand radially outwardly from the hub to an expanded state, in which a cover over the proximal filaments and the distal filaments occludes fluid flow through the body vessel.

Clause 87. The method of Clause 86, wherein pulling the distal expander comprises pulling a control rod, connected to the distal expander, proximally through the proximal expander.

Clause 88. The method of any of Clauses 86-87, wherein pulling the expander comprises pulling an enlarged member, connected to the expander, proximally past the proximal expander, such that the proximal expander prevents the enlarged member from moving distally into the proximal expander.

Clause 89. An expandable device for delivery to a target location in a body vessel, comprising: a hub; a plurality of arms having a compressed state, such that the arms extend axially from a side of the hub, and an expanded state, such that the arms extend axially and radially outwardly from the side of the hub.

Clause 90. The expandable device of Clause 89, wherein the expandable device tends to the expanded state when unrestrained.

Clause 91. The expandable device of any of Clauses 89-90, wherein the arms are symmetrically distributed about a circumference of the hub.

Clause 92. The expandable device of any of Clauses 89-91, wherein the device has, in the expanded state, a maximum cross-sectional dimension at terminal ends of the arms.

Clause 93. A method of delivering expandable devices to a target location in a body vessel, comprising: providing a catheter to the target location, the catheter carrying a first expandable device and a second expandable device within a lumen of the catheter; advancing the first expandable device out of a distal port of the catheter, such that first arms of the first expandable device expand from a proximal orientation to a radial orientation; advancing the second expandable device out of the distal port of the catheter, such that second arms of the second expandable device expand from a distal orientation to a radial orientation, such that the first expandable device and the second expandable device overlap axially and such that each first arm is disposed between circumferentially adjacent second arms.

Clause 94. The method of Clause 93, wherein, while in the catheter, the first arms extend proximally from a first hub of the first expandable device and the second arms extend distally from a second hub of the second expandable device.

Clause 95. The method of any of Clauses 93-94, wherein advancing the first expandable device comprises pushing the first expandable device with the second expandable device.

Clause 96. The method of any of Clauses 93-95, wherein advancing the first expandable device comprises pushing the first arms with the second arms.

Clause 97. The method of any of Clauses 93-96, wherein advancing the second expandable device comprises pushing the second expandable device with a pusher disposed within the lumen and proximal to the second expandable device.

Clause 98. The method of Clause 97, further comprising, after advancing the second expandable device, detaching the pusher from the second expandable device.

Clause 99. The method of any of Clauses 93-98, wherein the first expandable device is advanced such that the first arms are angularly offset relative to the second arms while within the lumen.

Clause 100. The method of any of Clauses 93-99, wherein the second expandable device is advanced such that the first arms are angularly offset relative to the second arms while out of the port.

Clause 101. The method of any of Clauses 93-100, further comprising, after advancing the first expandable device and before advancing the second expandable device, advancing the catheter distally.

Clause 102. The method of any of Clauses 93-101, further comprising advancing the first expandable device toward the second expandable device such that first prongs extending from sides of the first arms engage second prongs extending from sides of the second arms.

Clause 103. The method of Clause 102, wherein advancing the first expandable device toward the second expandable comprises moving the first and second prongs past each other.

Clause 104. The method of any of Clauses 102-103, wherein edges of the first and second prongs are oriented to limit or prevent separation of the first and second expandable devices after the first and second prongs engage each other.

Clause 105. The method of any of Clauses 93-104, further comprising advancing the first expandable device toward the second expandable device with a tether detachably connected to at least one of the first expandable device and the second expandable device.

Clause 106. The method of any of Clauses 93-105, further comprising advancing the first expandable device toward the second expandable device with a band connected to the first expandable device and the second expandable device, the band being configured to shorten axially.

Clause 107. An expandable device for delivery to a target location in a body vessel, comprising: a first helical member having a proximal end portion, a distal end portion, and a first lumen extending between the proximal and distal end portions, the first helical member having an axial width that is greater than its radial thickness; and a second helical member having a proximal end portion coupled to first member proximal end portion, the second coil having axial width that is greater than its radial thickness, the second helical member extending radially within the first lumen.

Clause 108. The device of Clause 107, wherein each of the first helical member and the second helical member comprises a flat coil following a helical path.

Clause 109. The device of any of Clauses 107-108, wherein each of the first helical member and the second helical member comprises a substantially rectangular cross-sectional shape.

Clause 110. The device of any of Clauses 107-109, further comprising a first coupling member interconnecting the first helical member and the second helical member at an end portion of the device.

Clause 111. The device of any of Clauses 107-110, further comprising a second coupling member interconnecting the first helical member and the second helical member between the proximal end portion of the device and the distal end portion of the device.

Clause 112. The device of any of Clauses 107-111, wherein the first member radially overlaps the second member.

Clause 113. The device of any of Clauses 107-112, wherein the device is configured to form a substantially tubular member in an expanded state and to be drawn into a substantially linear member in a delivery state.

Clause 114. The device of any of Clauses 107-113, wherein the device comprises a cover attached to the device.

Clause 115. The device of any of Clauses 107-114, wherein the device comprises a cover extending radially between the first and second helical members.

Clause 116. The device of any of Clauses 107-115, wherein the device comprises a plurality of apertures and at least one filament extending between the apertures to form a web along at least a portion of the device.

Clause 117. An expandable device for delivery to a target location in a body vessel, comprising: at least one elongate member configured to form a frame defining a lumen, the elongate member comprising a plurality of apertures along a length thereof; and a filament extending through the plurality of apertures to form a mesh boundary on frame.

Clause 118. The device of Clause 117, wherein the frame is substantially cylindrical and the mesh boundary defines a portion of a substantially cylindrical surface.

Clause 119. The device of any of Clauses 117-118, wherein the filament comprises an elastic material.

Clause 120. The device of any of Clauses 117-119, wherein the frame extends in a substantially helical path to define a plurality of loops, and wherein the filament extends from a first aperture of the frame, across a lumen of the frame, and to a second aperture of the frame.

Clause 121. The device of Clause 120, wherein the filament extends across the lumen in a direction transverse to a central axis of the frame.

Clause 122. The device of any of Clauses 117-121, wherein the at least one elongate member comprises a coil formed from a flat wire.

Clause 123. The device of any of Clauses 117-122, wherein the filament interconnects a cover with the at least one elongate member, the cover extending along at least a portion of the device frame.

Clause 124. The device of any of Clauses 117-123, wherein the device comprises a cover.

Clause 125. The device of any of Clauses 117-124, wherein the device comprises a graft extending at least partially about the helical member.

Clause 126. The device of any of Clauses 117-125, wherein the device comprises a graft extending around the helical member in a substantially tubular configuration and having opposing open end portions.

Clause 127. The device of any of Clauses 117-126, wherein the device comprises a partial cover positioned on the frame.

Clause 128. An expandable device for delivery to a target location in a body vessel, comprising: a cover having an interior region and an open end; and a filament having (i) an expanded state in which the filament forms windings of a helical shape from a first side to a second side and within the interior region of the cover to hold the cover against a wall of the vessel and (ii) a compressed state, in which the filament is substantially linear.

Clause 129. The expandable device of Clause 128, wherein the first side has a first cross-sectional dimension, the second side has a second cross-sectional dimension, and a middle section between the first side and the second side has a middle cross-sectional dimension greater than each of the first cross-sectional dimension and the second cross-sectional dimension.

Clause 130. The expandable device of any of Clauses 128-129, wherein the helical shape is spherical.

Clause 131. The expandable device of any of Clauses 128-130, wherein the filament comprises a first end region and a second end region each forming a straight portion in the expanded state.

Clause 132. The expandable device of any of Clauses 128-131, wherein the cover has a closed end.

Clause 133. An delivery system to deliver an expandable device to a target location in a body vessel, comprising: a catheter having a lumen and a port; a cover having an interior region, a first end releasably attached to the catheter, and a second, closed end distal to the port; and a filament in a compressed, substantially linear state within the lumen, the filament being configured to expand when released from the catheter to form windings of a helical shape from a first side to a second side and within the interior region of the cover to hold the cover against a wall of the vessel.

Clause 134. The expandable device of Clause 133, wherein the interior portion is accessible to the lumen via the port.

Clause 135. The expandable device of any of Clauses 133-134, wherein the helical shape is spherical.

Clause 136. The expandable device of any of Clauses 133-135, wherein the filament comprises a first end region and a second end region, each forming a straight portion in the expanded state.

Clause 137. A method of delivering an expandable device to a target location in a body vessel, comprising: providing a catheter to the target location, the catheter having a first end of a cover attached to the catheter and a second, closed end distal to the catheter; advancing a filament from a compressed, substantially linear state within a lumen of the catheter to an expanded state forming windings of a helical shape from a first side to a second side and within an interior region of the cover, holding the cover against a wall of the vessel; and releasing the first end of the cover from the catheter.

Clause 138. The method of Clause 137, wherein the advancing comprises forming a straight portion in each of a first end region and a second end region of the filament while in the expanded state.

Clause 139. The method of any of Clauses 137-138, wherein the advancing comprises forming a spherical helix with the filament.

Clause 140. The method of any of Clauses 137-139, further comprising withdrawing the catheter from the body vessel.

Clause 141. The method of any of Clauses 137-140, wherein the second end of the cover is closed.

Clause 142. An assembly for delivering an implant to a target location in a body vessel, comprising: a catheter having a lumen and a distal port; a first expandable device disposed within the lumen and comprising (i) a first hub and (ii) a plurality of first arms extending proximally from the first hub, the first arms being configured to extend radially outwardly when released from the catheter; and a second expandable device disposed within the lumen proximal of the first expandable device and comprising (i) a second hub and (ii) a plurality of second arms extending distally from the second hub, the second arms being configured to extend radially outwardly when released from the catheter.

Clause 143. The assembly of Clause 142, further comprising a push or disposed within the lumen and proximal to the second expandable device.

Clause 144. The assembly of any of Clauses 142-143, wherein the first arms are angularly offset relative to the second arms.

Clause 145. The assembly of any of Clauses 142-144, further comprising a pusher disposed within the lumen and proximal to the second expandable device.

Clause 146. The assembly of Clause 145, wherein the pusher is detachably connected to the second hub.

Clause 147. The assembly of any of Clauses 142-146, wherein the first expandable device is deployable from the catheter while the second expandable device remains within the lumen.

Clause 148. The assembly of any of Clauses 142-147, wherein terminal ends of the first expandable device and the second expandable device provide complementary profiles, such that the first arms are angularly offset relative to the second arms when the first expandable device applies a force to the second expandable device.

Clause 149. The assembly of any of Clauses 142-148, wherein the first arms comprise first prongs extending from sides of the first arms, and second arms comprise second prongs extending from sides of the second arms.

Clause 150. The assembly of Clause 149, wherein edges of the first and second prongs are oriented to allow the first and second prongs to move past each other as the first and second expandable devices engage each other.

Clause 151. The assembly of any of Clauses 149-150, wherein edges of the first and second prongs are oriented to limit or prevent separation of the first and second expandable devices after the first and second expandable devices engage each other.

Clause 152. The assembly of any of Clauses 142-151, further comprising a tether detachably connected to at least one of the first expandable device and the second expandable device.

Clause 153. The assembly of any of Clauses 142-152, further comprising a band connected to the first expandable device and the second expandable device and configured to shorten axially when the first expandable device and the second expandable device are released from the catheter.

Clause 154. An implant, comprising: a proximal anchor; a distal anchor; a connection bridge connecting the proximal anchor to the distal anchor; an occlusive cover comprising an open proximal end and a closed distal end, wherein a portion of the occlusive cover is located about an outer radial surface of at least a portion of the distal anchor.

Clause 155. The implant of Clause 154, wherein the proximal anchor, in an unrestrained configuration, forms a helical coil winding about a central axis of the implant.

Clause 156. The implant of any of Clauses 154-155, wherein the distal anchor, in an unrestrained configuration, forms an undulating and circumferentially continuous path.

Clause 157. The implant of any of Clauses 154-156, wherein the distal anchor comprises a plurality of struts, the plurality of struts being connected to each other by proximal bends and distal bends.

Clause 158. The implant of Clause 157, wherein a circumferential width of each of the plurality of struts exceeds an axial width of the proximal bends and distal bends.

Clause 159. The implant of any of Clauses 157-158, wherein each of the plurality of struts is connected to (i) a first adjacent strut by one of the proximal bends and (ii) a second adjacent strut by one of the distal bends.

Clause 160. The implant of any of Clauses 157-159, wherein each of the plurality of struts is parallel to a central axis of the implant.

Clause 161. The implant of any of Clauses 154-160, wherein at least a portion of the connection bridge extends parallel to the central axis of the implant.

Clause 162. The implant of any of Clauses 154-161, wherein a radially smallest inner cross-sectional dimension of the distal anchor is located only at a distal end of the distal anchor, a proximal end of the distal anchor, or a middle section of the distal anchor.

Clause 163. The implant of any of Clauses 154-162, wherein a radially largest outer cross-sectional dimension of the distal anchor is located only at a distal end of the distal anchor, a proximal end of the distal anchor, or a middle section of the distal anchor.

Clause 164. The implant of any of Clauses 154-163, wherein the distal anchor comprises a plurality of circumferential rings, each of the plurality of circumferential rings forming a circumferentially continuous undulating path.

Clause 165. The implant of any of Clauses 154-164, wherein the connection bridge comprises a hoop that extends at least partially circumferentially about a central axis of the implant, over radially outward surfaces of first portions of the distal anchor and under radially inward surfaces of second portions of the distal anchor.

Clause 166. The implant of any of Clauses 154-165, wherein the distal anchor comprises a proximal section having a first outer cross-sectional dimension and a distal section that tapers along an axial length from the first outer cross-sectional dimension to a second outer cross-sectional dimension, less than the first outer cross-sectional dimension.

Clause 167. The implant of any of Clauses 154-166, wherein the distal anchor comprises a proximal section having a first outer cross-sectional dimension, a middle section that tapers along an axial length from the first outer cross-sectional dimension to a second outer cross-sectional dimension, less than the first outer cross-sectional dimension, and a distal section having the second outer cross-sectional dimension.

Clause 168. A method, comprising: advancing an implant within a body vessel to a target location, the implant comprising a proximal anchor, a distal anchor, and an occlusive cover; expanding the distal anchor until the occlusive cover is held radially between an outer surface of the distal anchor and a wall of the body vessel; and expanding the proximal anchor until the proximal anchor contacts the wall.

Clause 169. The method of Clause 168, wherein advancing the implant comprises restraining the implant in a collapsed configuration within a lumen of a catheter.

Clause 170. The method of any of Clauses 168-169, wherein expanding the distal anchor comprises advancing the distal anchor out of a lumen of the catheter through a distal port of the catheter.

Clause 171. The method of any of Clauses 168-170, wherein expanding the proximal anchor comprises advancing the proximal anchor out of a lumen of the catheter through a distal port of the catheter.

Clause 172. The method of any of Clauses 168-171, wherein expanding the distal anchor comprises allowing a plurality of longitudinal struts of the distal anchor to move radially outwardly.

Clause 173. The method of any of Clauses 168-172, wherein expanding the proximal anchor comprises advancing the proximal anchor out of a lumen of the catheter through a distal port of the catheter.

Clause 174. An implant, comprising: an anchor comprising a plurality of struts connected to each other by proximal bends and distal bends, the anchor forming an undulating and circumferentially continuous path; an occlusive cover comprising an open proximal end and a closed distal end, wherein a portion of the occlusive cover is located about an outer radial surface of at least a portion of the anchor.

Clause 175. The implant of Clause 174, wherein a circumferential width of each of the plurality of struts exceeds an axial width of the proximal bends and distal bends.

Clause 176. The implant of any of Clauses 174-175, wherein each of the plurality of struts is connected to (i) a first adjacent strut by one of the proximal bends and (ii) a second adjacent strut by one of the distal bends.

Clause 177. The implant of any of Clauses 174-176, wherein each of the plurality of struts is parallel to a central axis of the implant.

Clause 178. The implant of any of Clauses 174-177, wherein a radially smallest inner cross-sectional dimension of the anchor is located only at a distal end of the anchor, a proximal end of the anchor, and/or a middle section of the anchor.

Clause 179. The implant of any of Clauses 174-178, wherein a radially largest outer cross-sectional dimension of the anchor is located only at a distal end of the anchor, a proximal end of the anchor, or a middle section of the anchor.

Clause 180. The implant of any of Clauses 174-179, wherein the anchor further comprises a plurality of circumferential rings, each of the plurality of circumferential rings forming a circumferentially continuous undulating path.

Clause 181. The implant of any of Clauses 174-180, wherein the anchor comprises a proximal section having a first inner cross-sectional dimension and a distal section that tapers along an axial length from the first inner cross-sectional dimension to a second inner cross-sectional dimension, less than the first inner cross-sectional dimension.

Clause 182. The implant of any of Clauses 174-181, wherein the anchor comprises a proximal section having a first inner cross-sectional dimension, a middle section that tapers along an axial length from the first inner cross-sectional dimension to a second inner cross-sectional dimension, less than the first inner cross-sectional dimension, and a distal section having the second inner cross-sectional dimension.

Clause 183. A method, comprising: advancing an implant within a body vessel to a target location, the implant comprising an anchor and an occlusive cover, the anchor comprising a plurality of struts connected to each other by proximal bends and distal bends, the anchor forming an undulating and circumferentially continuous path; and expanding the anchor until the occlusive cover is held radially between an outer surface of the anchor and a wall of the body vessel.

Clause 184. The method of Clause 183, wherein advancing the implant comprises restraining the implant in a collapsed configuration within a lumen of a catheter.

Clause 185. The method of any of Clauses 183-184, wherein expanding the anchor comprises advancing the anchor out of a lumen of the catheter through a distal port of the catheter.

Clause 186. The method of any of Clauses 183-185, wherein expanding the anchor comprises allowing the plurality of struts to move radially outwardly.

Clause 187. An implant, comprising: a proximal anchor forming, in an unrestrained configuration, a helical coil winding about a central axis of the implant; a braided member having a center at the central axis, the braided member forming, in the unrestrained configuration, a sphere; and a connection bridge extending along the central axis and connecting the proximal anchor to the braided member.

Clause 188. The implant of Clause 187, further comprising an occlusive cover over the braided, spherical member.

Clause 189. A method, comprising: advancing an implant within a body vessel to a target location, the implant comprising a proximal anchor and a braided member; expanding the braided member until the braided member forms a sphere and contacts a wall of the body vessel; and expanding the proximal anchor until the proximal anchor forms a helical coil and contacts the wall.

Clause 190. The method of Clause 189, wherein expanding the anchor comprises advancing the anchor out of a lumen of the catheter through a distal port of the catheter.

Clause 191. An adjustable shunt system, comprising: a support member having a lumen and an outflow section, the support member being configured for placement in a body lumen, the outflow section comprising a distal aperture configured to restrict flow through the support member; and a valve component, disposed within the support member lumen, being movable within the outflow section between first and second positions, wherein in the first position, the valve component abuts at least a portion of the outflow section such that the distal aperture defines a first size permitting a non-zero flow rate therethrough, and in the second position, the valve component abuts the outflow section such that the distal aperture defines a second size, greater than the first size.

Clause 192. The system of Clause 191, wherein the valve component comprises a rigid structure having a fixed outer profile.

Clause 193. The system of any of Clauses 191-192, wherein the valve component comprises a rigid structure having a fixed outer profile.

Clause 194. The system of any of Clauses 191-193, wherein the outflow section comprises a plurality of movable leaflets biased towards a closed position, the leaflets being movable from the closed position to adjust the size of the aperture.

Clause 195. The system of any of Clauses 191-194, wherein the support member comprises a balloon-expandable structure, the outflow section being expandable such that the aperture increases from the first size to the second size.

Clause 196. The system of Clause 195, wherein valve component comprises a balloon-expandable structure, the valve component being expandable from the first position to the second position to expand the outflow section and expand the aperture to the second size.

Clause 197. The system of any of Clauses 191-196, wherein the outflow section comprises a substantially conical shape, and the valve component is slidable within the lumen such that in the first position, the outflow section has a first cone angle and in the second position, the outflow section has a second cone angle greater than the first cone angle.

Clause 198. The system of any of Clauses 191-197, wherein the valve component comprises an engagement structure configured to engage with the support member for fixing the valve component relative to the support member.

Clause 199. The system of any of Clauses 191-198, wherein the support member is configured to expand from a collapsed configuration to an expanded configuration for placement in a body lumen.

Clause 200. An adjustable shunt system, comprising: a support member having a lumen and an outflow section, the support member being configured for placement in a body lumen, the outflow section comprising a distal aperture configured to restrict flow through the support member; and a valve component, disposed within the support member lumen, being movable within the outflow section aperture between first and second positions, the valve component having an adjustable distal aperture being movable between a first size, permitting a non-zero flow rate therethrough, and a second size greater than the first size.

Clause 201. The system of Clause 200, wherein the outflow section aperture comprises a fixed diameter.

Clause 202. The system of Clause 201, wherein the valve component comprises a plurality of flexible leaflets deflectable from the first position to the second position to change the size of the valve component aperture.

Clause 203. The system of Clause 202, wherein the leaflets are configured to converge toward each other when the valve component is moved from the first position to the second position.

Clause 204. The system of Clause 201, wherein the valve component comprises a helical ribbon member movable from the first position to the second position to change the size of the valve component aperture.

Clause 205. The system of Clause 204, wherein the helical ribbon member comprises a first portion coupled to the support member and a free, second portion configured such that distal movement through the support member aperture constricts the ribbon member and reduces the size of the valve component aperture.

Clause 206. The system of any of Clauses 200-205, wherein the valve component comprises an engagement member configured to engage with a corresponding engagement member of the support member to axially restrain movement of the valve component relative to the support member.

Clause 207. The system of any of Clauses 200-206, wherein the outflow section aperture comprises a substantially conical shape.

Clause 208. A method of shunting comprising: advancing a shunt into a first vessel to provide a flow pathway from the first vessel into a second vessel; and adjusting a valve component of the shunt to control a flow resistance through an aperture of the valve component into the second vessel.

Clause 209. The method of Clause 208, wherein the advancing comprises advancing a shunt through a hepatic vein into a portal vein such that a first end of the shunt is disposed in the hepatic vein and a second end of the shunt is disposed in the portal vein.

Clause 210. The method of Clause 209, further comprising permitting expansion of the shunt to provide the flow pathway from the hepatic vein to the portal vein.

Clause 211. The method of any of Clauses 208-210, further comprising adjusting the position of the valve component within the shunt to modify a flow resistance through the shunt.

Clause 212. The method of Clause 211, wherein the adjusting the position of the valve component comprises detaching the valve component from a first position within the shunt and reattaching the valve component to the shunt at a second position within the shunt.

Clause 213. The method of any of Clauses 208-212, further comprising adjusting a shape of the valve component within the shunt to modify a flow resistance through the shunt.

Clause 214. The method of any of Clauses 208-213, further comprising adjusting the size of the aperture of the valve component to modify a flow resistance through the shunt.

Clause 215. The method of Clause 214, wherein the adjusting the size of the aperture comprises dilating the aperture with a balloon.

Clause 216. An assembly for delivering an implant to a target location within a body lumen, comprising: a catheter comprising a proximal portion, a distal portion, and a helical coil extending in a first helical direction and connecting the proximal portion to the distal portion, the coil being defined by a kerf between adjacent windings of the coil; and an implant comprising a first end portion, a second end portion, a torsion state, and a relaxed state, wherein the implant is biased to the relaxed state and wherein, while the implant is in the torsion state, the proximal portion engages the first end portion, the distal portion engages the second end portion, and the implant applies a torque to the catheter.

Clause 217. The assembly of Clause 216, wherein the kerf has a non-linear profile following a helical path.

Clause 218. The assembly of any of Clauses 216-217, wherein the implant further comprises a helical member extending in a second helical direction, opposite the first helical direction.

Clause 219. The assembly of any of Clauses 216-218, wherein, while the implant is in the torsion state, the adjacent windings of the coil are configured to contact each other.

Clause 220. The assembly of any of Clauses 216-219, wherein, while the implant is in the relaxed state, the adjacent windings of the coil are configured to be separated from each other.

Clause 221. The assembly of any of Clauses 216-220, wherein, while the implant is in the relaxed state, the proximal portion is configured to disengage from the first end portion and/or the distal portion is configured to disengage from the second end portion.

Clause 222. The assembly of any of Clauses 216-221, wherein, the non-linear profile comprises an undulating profile.

Clause 223. The assembly of any of Clauses 216-222, wherein, the non-linear profile comprises a triangular profile.

Clause 224. The assembly of any of Clauses 216-223, wherein, the non-linear profile comprises a sawtooth profile.

Clause 225. The assembly of any of Clauses 216-224, wherein the middle portion is configured to flex by separating the adjacent windings of the coil on a side of the middle section.

Clause 226. A method of delivering an implantable device to a target location in a body lumen, comprising: advancing a catheter, holding an implant in a torsion state, to the target location, wherein a proximal portion of the catheter engages a first end portion of the implant, a distal portion of the catheter engages a second end portion of the implant, and the implant applies a torque to the catheter, the catheter having a helical kerf defining opposing sides along a helical coil; and disengaging the first end portion from the proximal portion and/or the second end portion from the distal portion, such that the implant achieves a relaxed state.

Clause 227. The method of Clause 226, wherein the kerf has a non-linear profile following a helical path.

Clause 228. The method of any of Clauses 226-227, wherein the torque causes the opposing sides of adjacent windings of the coil between the proximal portion and the distal portion to be pulled toward each other.

Clause 229. A method of assembling an implant delivery system, comprising: providing an implant, in a relaxed state, to a catheter having a kerf extending in a first helical direction and defining opposing sides along a helical coil; engaging a first end portion of the implant with a proximal portion of the catheter; and engaging a second end portion of the implant with a distal portion of the catheter, such that the implant is held in a torsion state by the catheter, and such that the implant applies a torque to the catheter.

Clause 230. The method of Clause 229, wherein the kerf has a non-linear profile following a helical path.

Clause 231. The method of any of Clauses 229-230, wherein the torque causes the opposing sides of adjacent windings of the coil between the proximal portion and the distal portion to be pulled toward each other.

Clause 232. The assembly of any of Clauses 229-231, wherein the implant further comprises a helical member extending in a second helical direction, opposite the first helical direction.

Clause 233. An assembly for delivering an implant to a target location within a body lumen, comprising: a catheter comprising a proximal portion, a distal portion, and a plurality of filaments extending in a first helical direction and connecting the proximal portion to the distal portion; and an implant comprising a first end portion, a second end portion, a torsion state, and a relaxed state, wherein the implant is biased to the relaxed state and wherein, while the implant is in the torsion state, the proximal portion engages the first end portion, the distal portion engages the second end portion, and the implant applies a torque to the catheter.

Clause 234. The assembly of Clause 233, wherein the implant further comprises a helical member extending in a second helical direction, opposite the first helical direction.

Clause 235. The assembly of any of Clauses 233-234, wherein, while the implant is in the torsion state, adjacent pairs of the plurality of filaments are configured to contact each other.

Clause 236. The assembly of any of Clauses 233-235, wherein, while the implant is in the relaxed state, adjacent pairs of the plurality of filaments are configured to be separated from each other.

Clause 237. The assembly of any of Clauses 233-236, wherein, while the implant is in the relaxed state, the proximal portion is configured to disengage from the first end portion and/or the distal portion is configured to disengage from the second end portion.

Clause 238. The assembly of any of Clauses 233-237, wherein, while in the torsion state, the implant is configured to have a number of turns greater than a number of turns of the implant while in the relaxed state.

Clause 239. The assembly of any of Clauses 233-238, wherein, while in the torsion state, the implant is configured to have an outer diameter smaller than an outer diameter of the implant while than in the relaxed state.

Clause 240. The assembly of any of Clauses 233-239, wherein, while in the torsion state, the implant is configured to have a longitudinal length longer than a longitudinal length of the implant while in the relaxed state.

Clause 241. The assembly of any of Clauses 233-240, wherein the middle portion is configured to flex by separating the plurality of filaments on a side of the middle section.

Clause 242. A method of delivering an implantable device to a target location in a body lumen, comprising: advancing a catheter, holding an implant in a torsion state, to the target location, wherein a proximal portion of the catheter engages a first end portion of the implant, a distal portion of the catheter engages a second end portion of the implant, and the implant applies a torque to the catheter, the catheter having a helical kerf defining opposing sides along a helical coil; and disengaging the first end portion from the proximal portion and/or the second end portion from the distal portion, such that the implant achieves a relaxed state.

Clause 243. The method of Clause 242, wherein the torque causes a plurality of filaments extending in a first helical direction and connecting the proximal portion to the distal portion to be pulled toward each other.

Clause 244. A method of assembling an implant delivery system, comprising: providing an implant, in a relaxed state, to a catheter having a plurality of filaments extending in a first helical direction; engaging a first end portion of the implant with a proximal portion of the catheter; and engaging a second end portion of the implant with a distal portion of the catheter, such that the implant is held in a torsion state by the catheter, and such that the implant applies a torque to the catheter.

Clause 245. The method of Clause 244, wherein the torque causes the adjacent pairs of the plurality of filaments to be pulled toward each other.

Clause 246. The method of any of Clauses 244-245, wherein the implant further comprises a helical member extending in a second helical direction, opposite the first helical direction.

Clause 247. An expandable device comprising any of the features recited in any of the preceding clauses or herein.

Clause 248. A method of delivering an expandable device comprising any of the features recited in any of the preceding clauses or herein.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIG. 4A shows a perspective view of an implant support frame on a catheter distal section of an implant carrier assembly, according to some embodiments.

FIG. 4C shows a sectional view of FIG. 4A of an implant support frame on a catheter distal section of an implant carrier assembly, according to some embodiments.

FIG. 14 shows a partial side view of a proximal engagement mechanism for supporting the implant support frame of FIG. 12 on the catheter, according to some embodiments.

FIG. 15A shows an enlarged, partial side view of the proximal engagement mechanism for supporting the implant support frame of FIG. 12 on the catheter, according to some embodiments.

FIG. 15B shows an enlarged, partial side view of a distal engagement mechanism for supporting the implant support frame of FIG. 12 on the catheter, according to some embodiments.

FIG. 23A shows a cross-sectional view of an implant in a compressed state, according to some embodiments.

FIG. 23B shows a cross-sectional view of a portion of a strut joining with an end member in a compressed state, according to some embodiments.

FIG. 23C shows a cross-sectional view of a portion of a strut joining with an end member in an expanded state, according to some embodiments.

FIG. 23D shows first and second portions of a strut joining in a compressed state, according to some embodiments.

FIG. 23E shows first and second portions of a strut joining in an expanded state, according to some embodiments.

FIG. 29A shows a perspective view of an implant in a compressed state, according to some embodiments.

FIG. 29B shows a side view of an implant in a compressed state, according to some embodiments.

FIG. 29C shows a perspective view of an implant in an expanded state, according to some embodiments.

FIG. 29D shows a side view of an implant in an expanded state, according to some embodiments.

FIG. 29G shows a side view of an implant in an expanded state, according to some embodiments.

FIG. 29H shows a front view of an implant in an expanded state, according to some embodiments.

FIG. 29I shows a side view of two implants in expanded states, according to some embodiments.

FIG. 30C shows a perspective view of a catheter and two implants in the expanded states, according to some embodiments.

FIG. 33A shows a perspective view of a support frame of an implant, according to some embodiments.

FIG. 33B shows a side view of a support frame of an implant, according to some embodiments.

FIG. 33C shows a front view of a support frame of an implant, according to some embodiments.

FIG. 33D shows a perspective view of an implant having a support frame and a cover, according to some embodiments.

FIG. 34 shows a perspective view of a support frame of an implant in a collapsed configuration, according to some embodiments.

FIG. 35A shows a perspective view of an implant in a collapsed configuration within a catheter, according to some embodiments.

FIG. 35B shows a perspective view of an implant in an expanded configuration within a body vessel, according to some embodiments.

FIG. 37A shows a perspective view of a support frame of an implant, according to some embodiments.

FIG. 37B shows a side view of a portion of a support frame of an implant, according to some embodiments.

FIG. 38 shows a side view of a support frame of an implant, according to some embodiments.

FIG. 39 shows a side view of a support frame of an implant, according to some embodiments.

FIG. 40A shows a perspective view of a support frame of an implant, according to some embodiments.

FIG. 40B shows a side view of a support frame of an implant, according to some embodiments.

FIG. 40C shows a front view of a support frame of an implant, according to some embodiments.

FIG. 40D shows a perspective view of a support frame of an implant in a collapsed configuration, according to some embodiments.

FIG. 42D shows a perspective view of an implant having a support frame and a cover, according to some embodiments.

FIG. 43A shows a perspective view of a support frame of an implant, according to some embodiments.

FIG. 43B shows a side view of a support frame of an implant, according to some embodiments.

FIG. 43C shows a front view of a support frame of an implant, according to some embodiments.

FIG. 43D shows a perspective view of an implant having a support frame and a cover, according to some embodiments.

FIG. 44A shows a perspective view of an implant, according to some embodiments.

FIG. 44B shows a side view of an implant, according to some embodiments.

FIG. 44C shows a front view of an implant, according to some embodiments.

FIG. 44D shows a perspective view of an implant in a collapsed configuration, according to some embodiments.

FIG. 45A shows a perspective view of an implant in a collapsed configuration within a catheter, according to some embodiments.

FIG. 45B shows a perspective view of an implant in an expanded configuration within a body vessel, according to some embodiments.

FIG. 46 is a perspective view of an implant, according to some embodiments.

Figure 2:
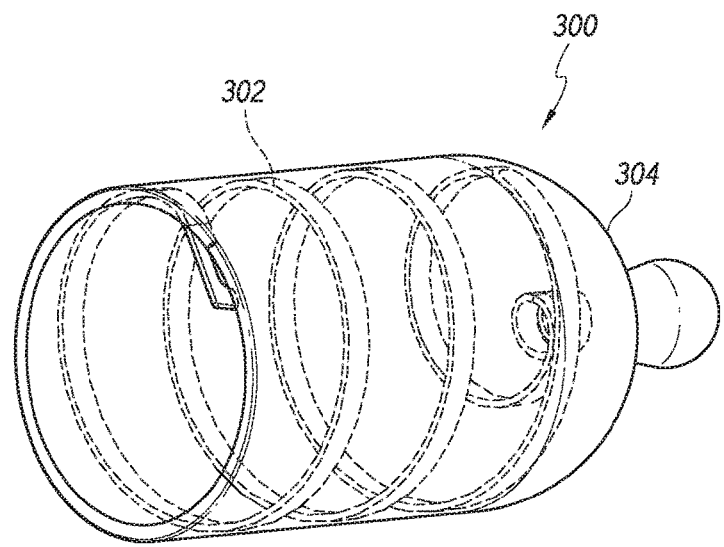
FIG. 2 shows a perspective view of an implant, according to some embodiments.
Figure 47:
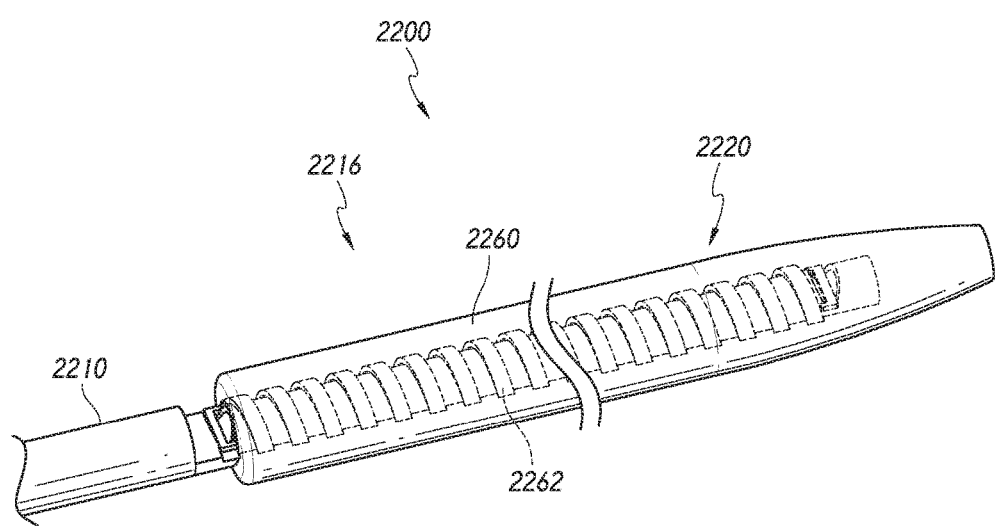

FIG. 47 is a perspective view of the implant of FIG. 2, illustrating a support component thereof, according to some embodiments.

Figure 48:
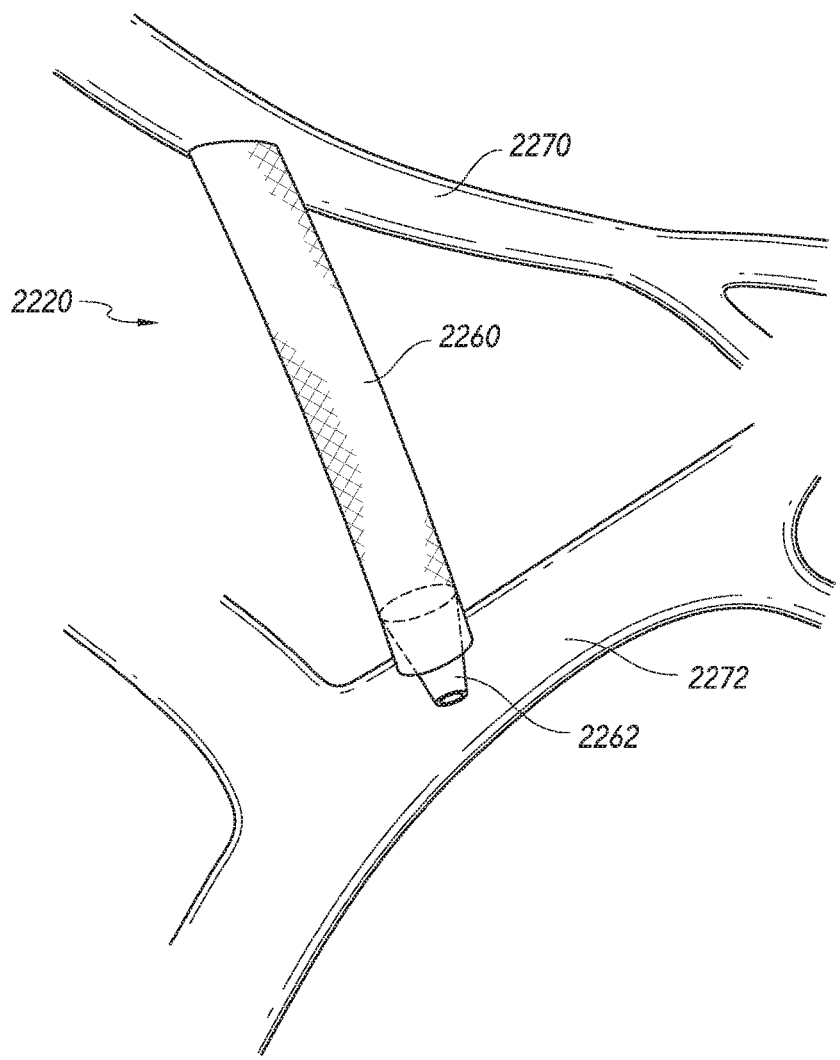

FIG. 48 is a schematic view of an assembly implanted between portal and hepatic veins to perform a transjugular intrahepatic portosystemic shunt procedure, according to some embodiments.

Figure 49:
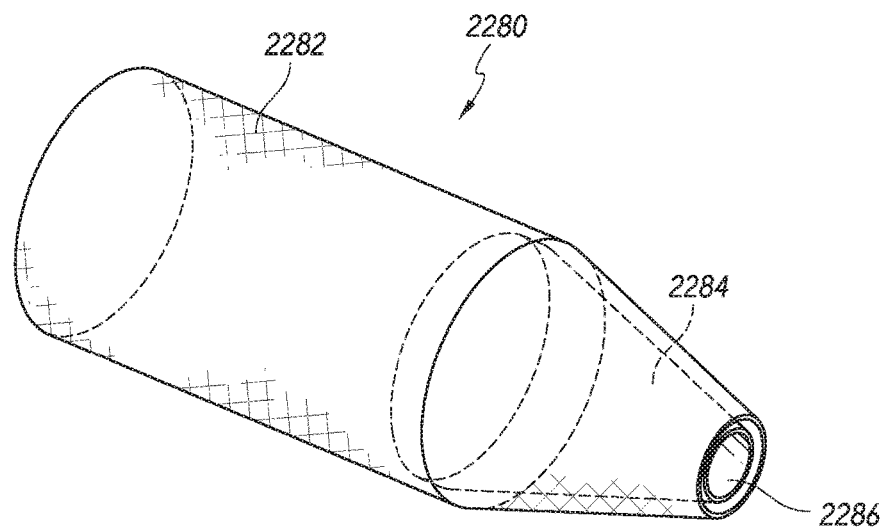

FIG. 49 illustrates a flow regulating implant assembly, according to some embodiments.

Figure 50:
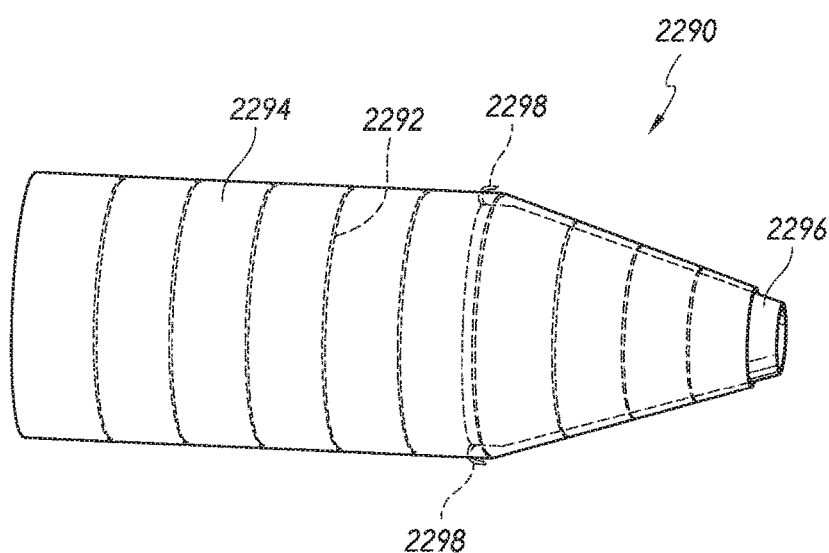

FIG. 50 illustrates the implant assembly of FIG. 5, illustrating an internal structure thereof, according to some embodiments.

Figure 51:
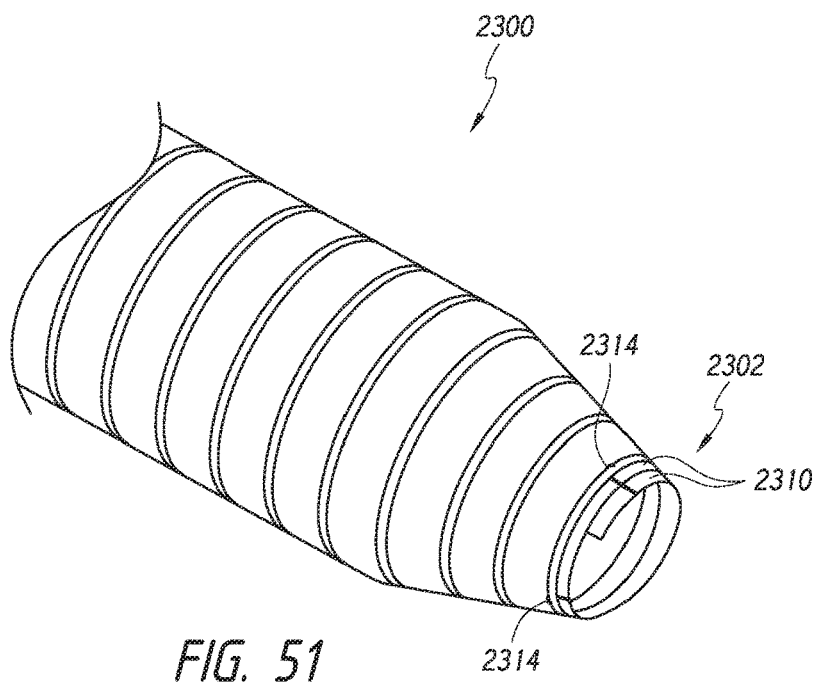
Figure 52:
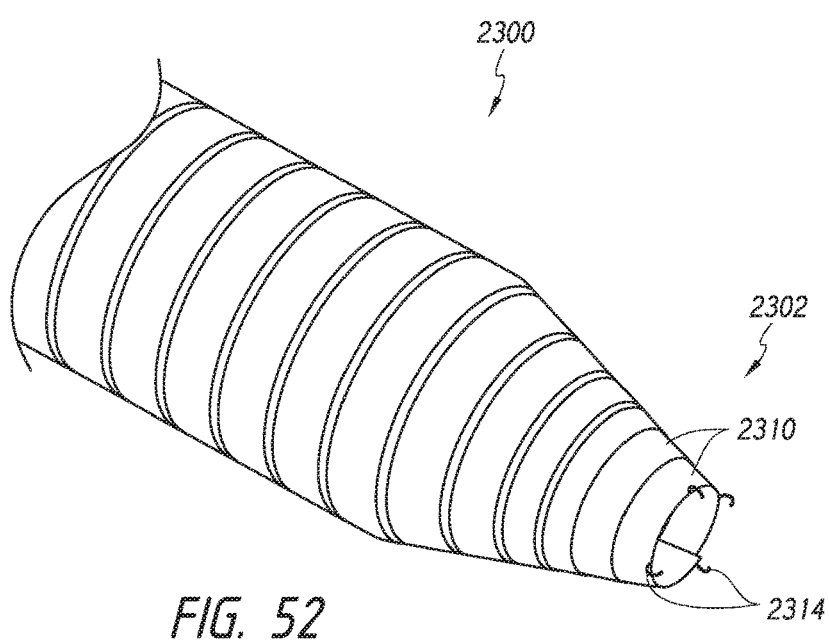

FIGS. 51-52 illustrate operative positions of a flow regulating implant assembly, according to some embodiments.

Figure 53A:
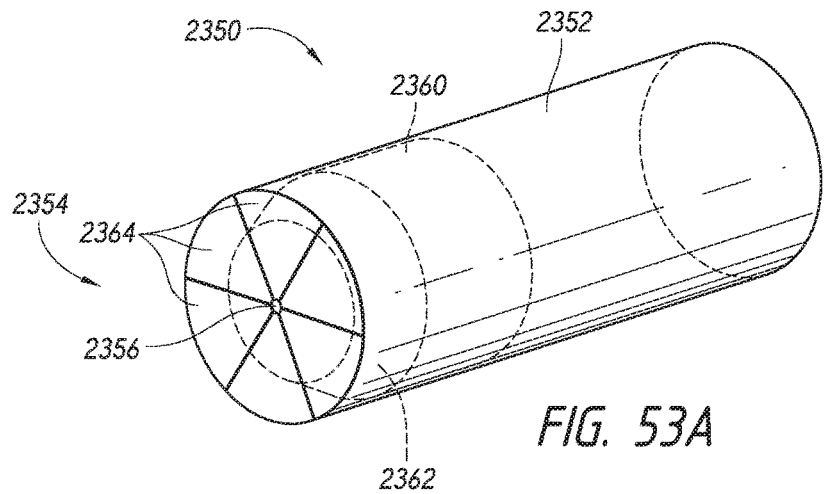
Figure 53B:
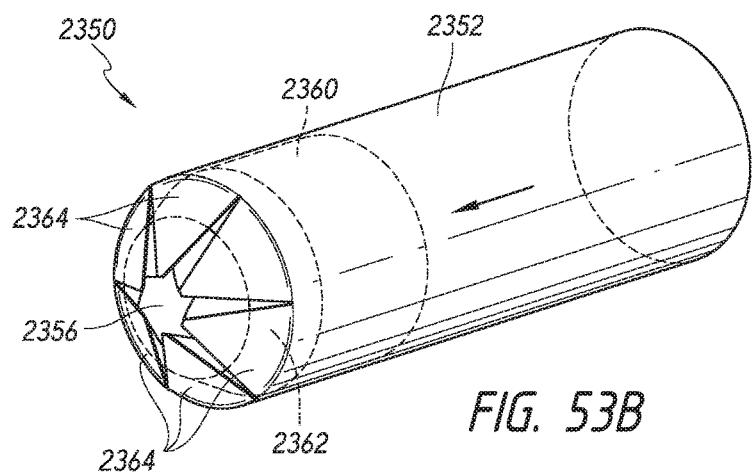
Figure 53C:
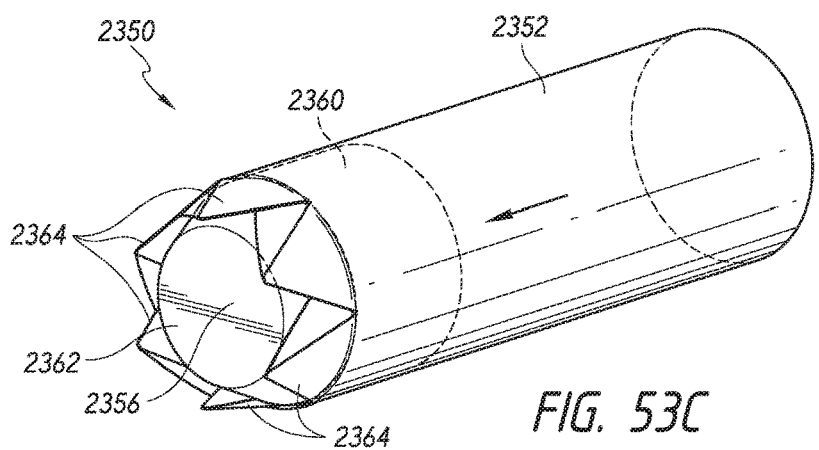

FIGS. 53A-53C illustrate operation of a flow regulating implant assembly, according to some embodiments.

FIGS. 54-57 illustrate side, cross-sectional views of operation of an implant assembly, according to some embodiments.

Figure 58:
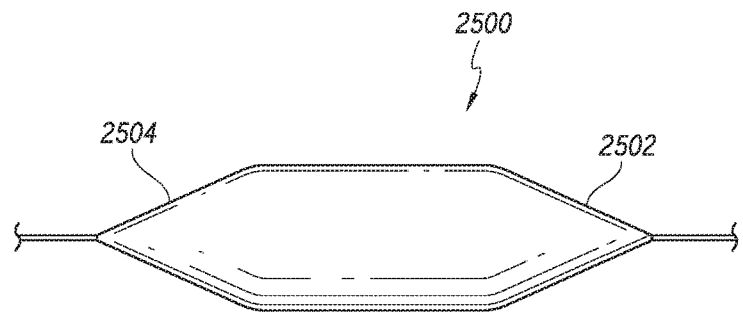
Figure 59:
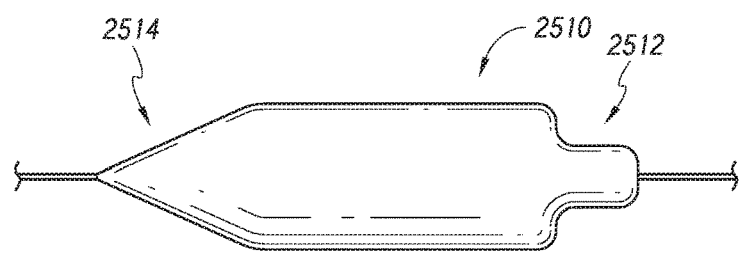
Figure 60:
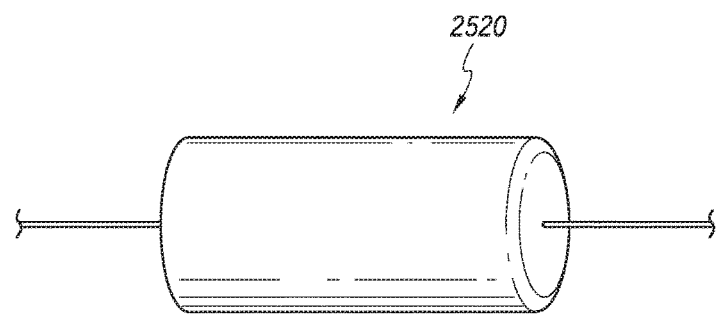

FIGS. 58-60 illustrate side views of balloon shapes, according to some embodiments.

FIG. 61 illustrates aspects of catheter distal section of an implant carrier assembly having a keyed coil, according to some embodiments.

FIG. 62 shows a perspective view of an implant support frame on a catheter distal section of an implant carrier assembly having a keyed coil, according to some embodiments.

Figure 63:
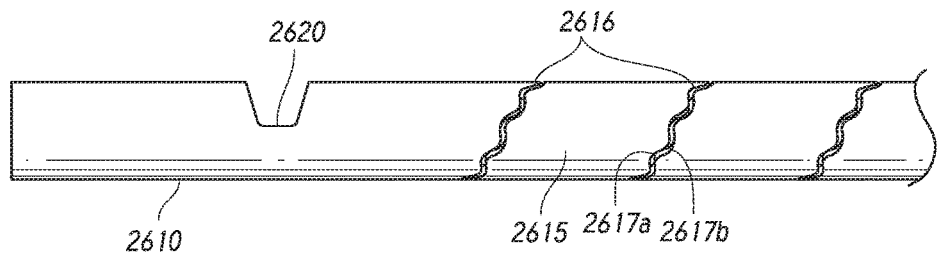

FIG. 63 illustrates aspects of catheter distal section of an implant carrier assembly having a keyed coil, according to some embodiments.

FIGS. 64A-64E illustrate aspects of catheter distal section of an implant carrier assembly having a keyed coil, according to some embodiments.

Figure 65:
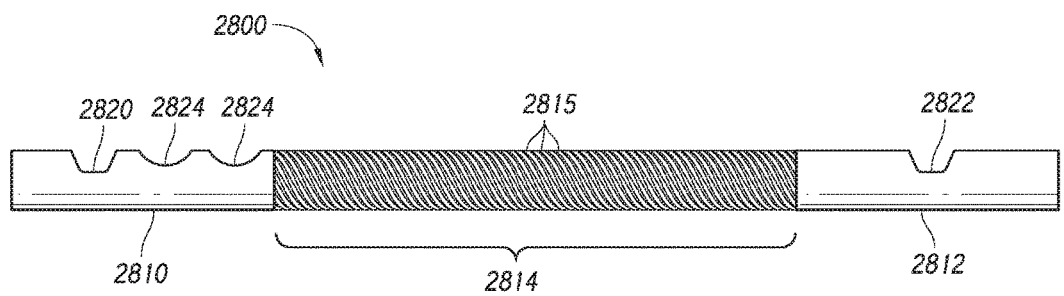

FIG. 65 illustrates aspects of catheter distal section of an implant carrier assembly having a multifilar coil, according to some embodiments.

Figure 66:
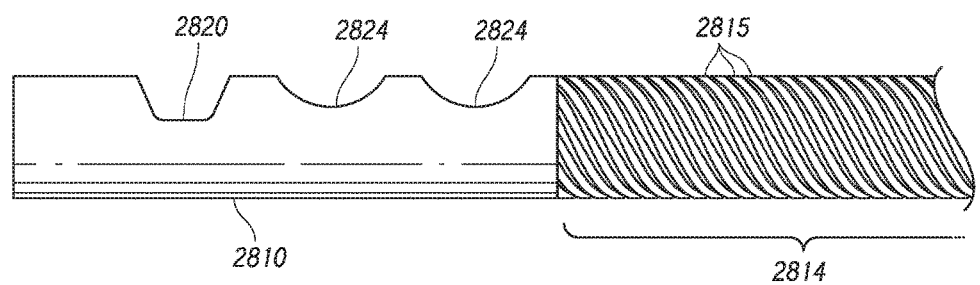

FIG. 66 illustrates aspects of catheter distal section of an implant carrier assembly having a multifilar coil, according to some embodiments.

Figure 67:
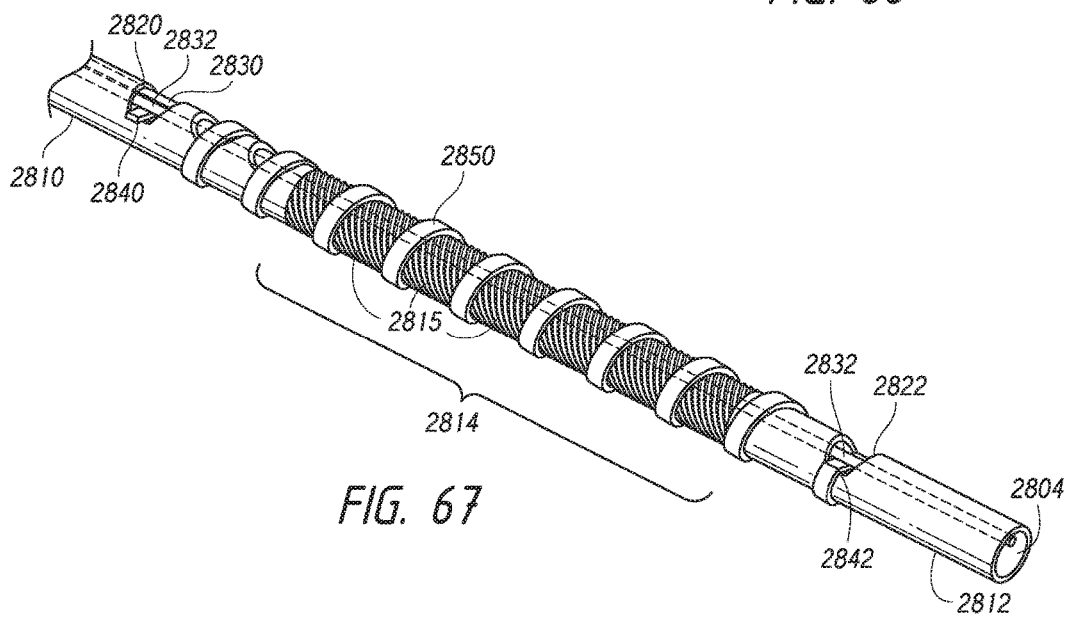
Figure 68A:
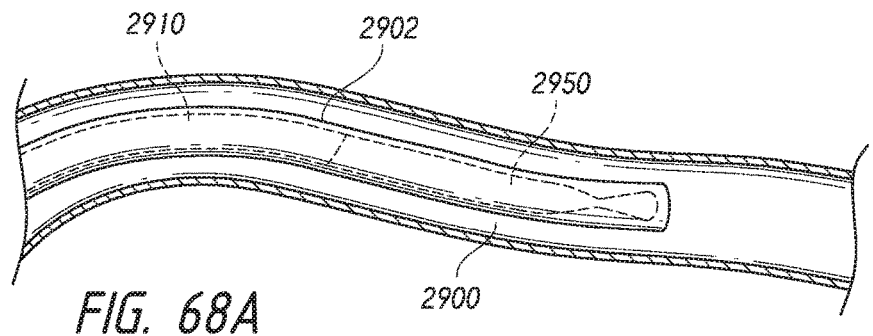
Figure 68B:
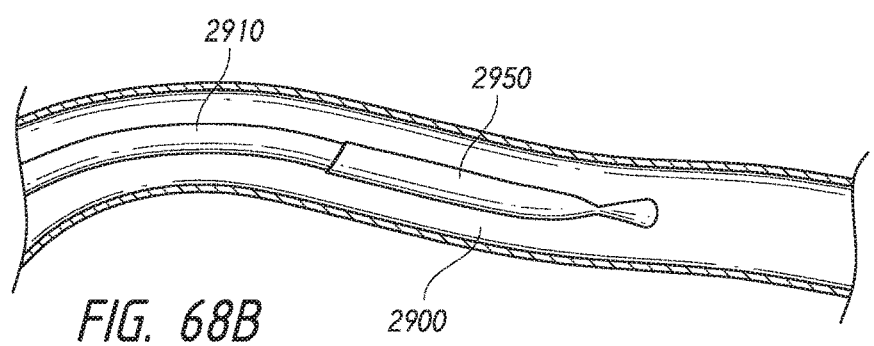
Figure 68C:
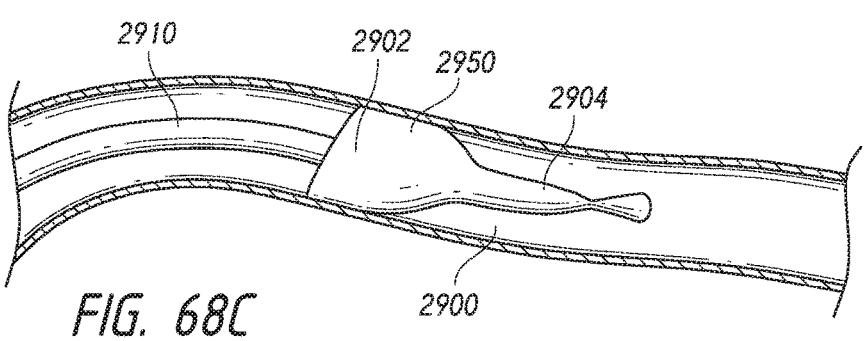
Figure 68D:
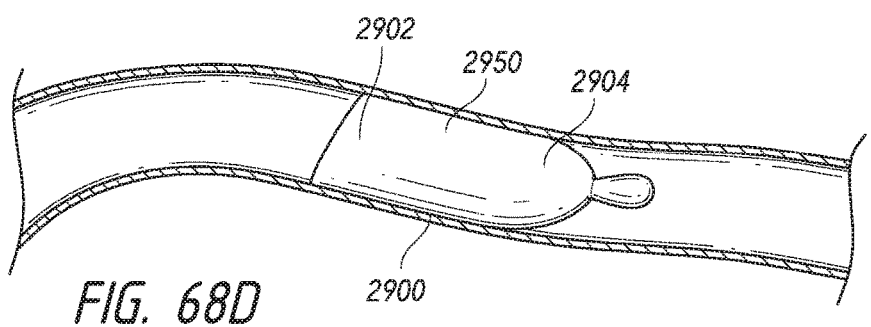

FIG. 67 shows a perspective view of an implant support frame on a catheter distal section of an implant carrier assembly having a multifilar coil, according to some embodiments.

FIGS. 68A-68D show sequential views of an expansion process of an implant, according to some embodiments.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

While the present description sets forth specific details of various embodiments, it will be appreciated that the description is illustrative only and should not be construed in any way as limiting. It is contemplated that although particular embodiments of the present inventions may be disclosed or shown in particular contexts, such embodiments can be used in a variety of endoluminal applications. Various applications of such embodiments and modifications thereto, which may occur to those who are skilled in the art, are also encompassed by the general concepts described herein.

The present disclosure provides various embodiments of an expandable device, such as a stent, and a catheter for supporting and delivering the stent, as well as methods of using the devices and catheters.

According to some embodiments, devices, catheters, systems, and methods disclosed herein can be used for percutaneous, peripheral occlusion of the arterial and venous vasculature. For example, some embodiments can be used to treat pelvic venous incompetence, varicocele, gonadal vein for pelvic varices in females with chronic pelvic pain, stop blood loss from a damaged blood vessel due to a traumatic arterial injury, stop hemorrhage caused by a neoplasia, and close an abnormal blood vessel or blood vessels supplying a vascular anomaly such as arteriovenous malformations or arteriovenous fistulas, and other conditions.

According to some embodiments, devices, catheters, systems, and methods disclosed herein can also be used for percutaneous, peripheral stenting of the arterial and venous vasculature.

According to some embodiments, an assembly can be provided including an expandable device and a catheter, which can be configured to engage, support, and/or house the device for delivery to a treatment location. The device can be engaged, supported, and/or housed along a distal portion of the device. Some embodiments can advantageously provide an assembly that has a cross-sectional profile that is much less than existing medical implant delivery assemblies.

For example, the catheter can define an outer diameter from about 2 Fr to about 12 Fr, as noted in Table 1 below and discussed further herein. These dimensions are provided for illustrative purposes only, and the sizes of the components disclosed herein can vary from those sizes listed below.

TABLE 1

| French Gauge | Diameter (mm) | Diameter (inches) |
| --- | --- | --- |
| 2 | 0.67 | 0.025 |
| 3 | 1 | 0.039 |
| 4 | 1.33 | 0.053 |
| 5 | 1.67 | 0.066 |
| 6 | 2 | 0.079 |
| 7 | 2.3 | 0.092 |
| 8 | 2.7 | 0.105 |
| 9 | 3 | 0.118 |
| 10 | 3.3 | 0.131 |
| 11 | 3.7 | 0.144 |
| 12 | 4 | 0.158 |

According to some embodiments, the reduced diameter or reduced cross-sectional profile can be achieved by using stent or frame structures that can have a nominal profile that is less than about five times the cross-sectional profile of the filament(s) or wire forming the stent or frame structure. For example, in some embodiments, the stent or frame structure can be formed using a single elongate wire that is drawn into a generally linear configuration and moved through a catheter lumen toward the target site. Some embodiments can comprise two or more elongate wires that can be drawn into generally elongate linear configurations. Accordingly, various embodiments can be provided in which the elongate wires are drawn into a minimum profile configuration that allows the stent to assume a collapsed configuration having a cross-sectional profile that allows the stent to be loaded and delivered using a very small gauge catheter.

In accordance with some embodiments, a medical implant can be provided that can be used in a variety of clinical applications, such as vessel occlusion, stenting, or other functions within a body vessel. The medical implant can comprise a frame and one or more secondary components.

As noted, in some embodiments, the implant can at least partially occlude or block flow in a body lumen, such as a blood vessel. Some embodiments can be configured to provide complete and immediate occlusion of target lumen. Further, some embodiments can be configured to prevent or reduce any tendency for migration of the deployed device under pulsatile blood pressure. Furthermore, some embodiments can be configured to facilitate precise and well controlled deployment of the device for structure with movement of the device in and out of the catheter up until the moment of final detachment.

The frame can comprise one or more resilient members, such as wires, which can be drawn out into a delivery configuration in which the frame is in a generally linear configuration and thereafter expand to an expanded state when released from a delivery device, such as a catheter.

Various embodiments of the frame can be comprise one or more features, such as having a variable pitch, an alternating pitch, a laminated configuration, a consistent pitch, upright configuration, a dual wire loop configuration, axial backbones interconnecting support elements, radial expandable arms, and/or other features disclosed herein. Further, embodiments of the frame can be used with occlusive structures, valves, occlusive covers, fibrous membranes, and the like.

Further, in accordance with some embodiments, the implants and delivery systems can be used in combination with image-guided placement techniques, such as fluoroscopy and the like.

Figure 1A:
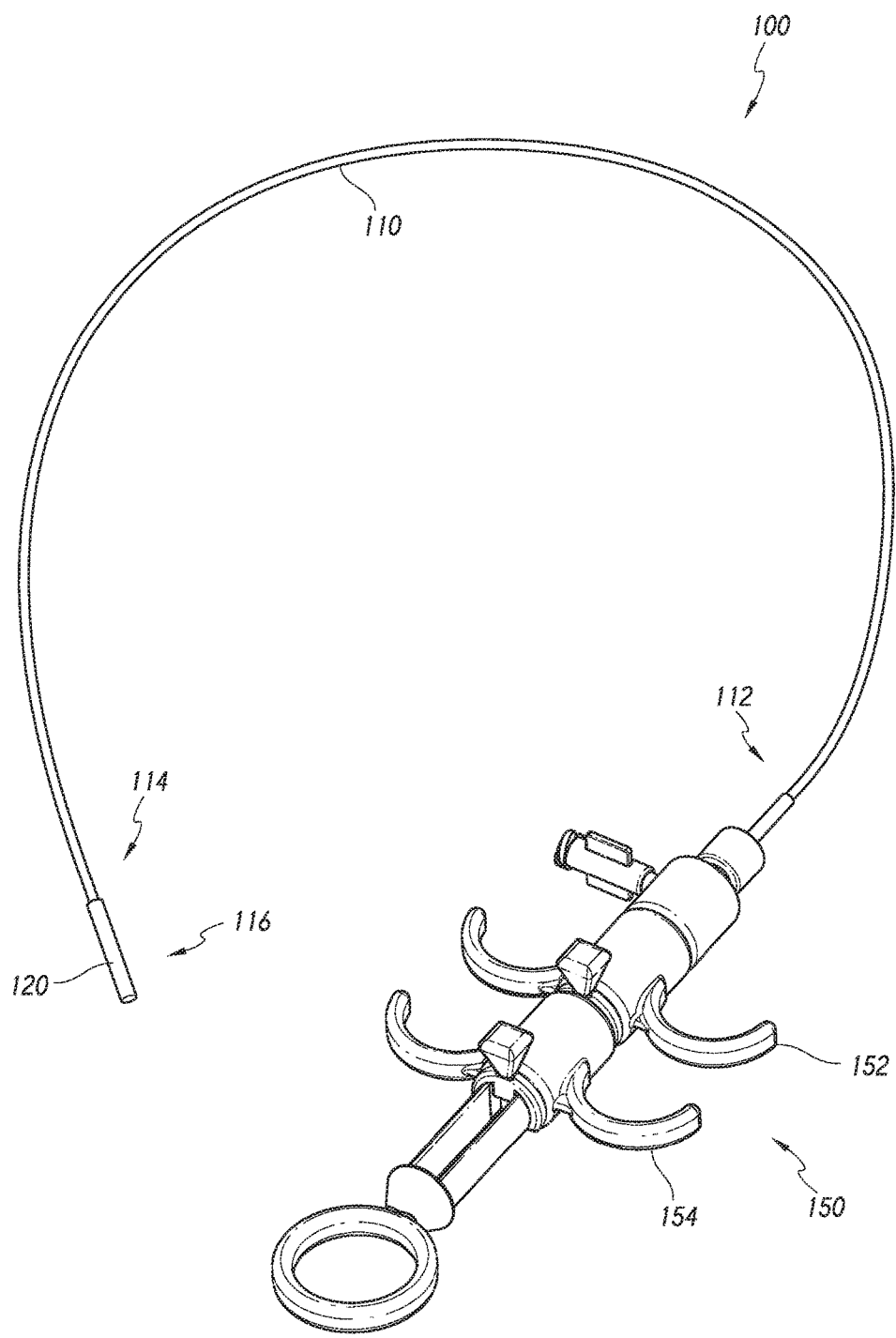
FIG. 1A is a perspective view of an implant carrier assembly, according to some embodiments.

FIG. 1A illustrates an embodiment of an implant carrier assembly 100, which can comprise a catheter 110 having a lumen that extends between a proximal portion 112 and a distal portion 114 of the catheter. The catheter 110 can also comprise an engagement section 116, which can be located along a distal portion of the catheter 110, configured to engage and/or restrain an implant positioned therealong. Thus, the implant can be supported, engaged, or restrained along an exterior surface of the catheter.

Figure 1B:
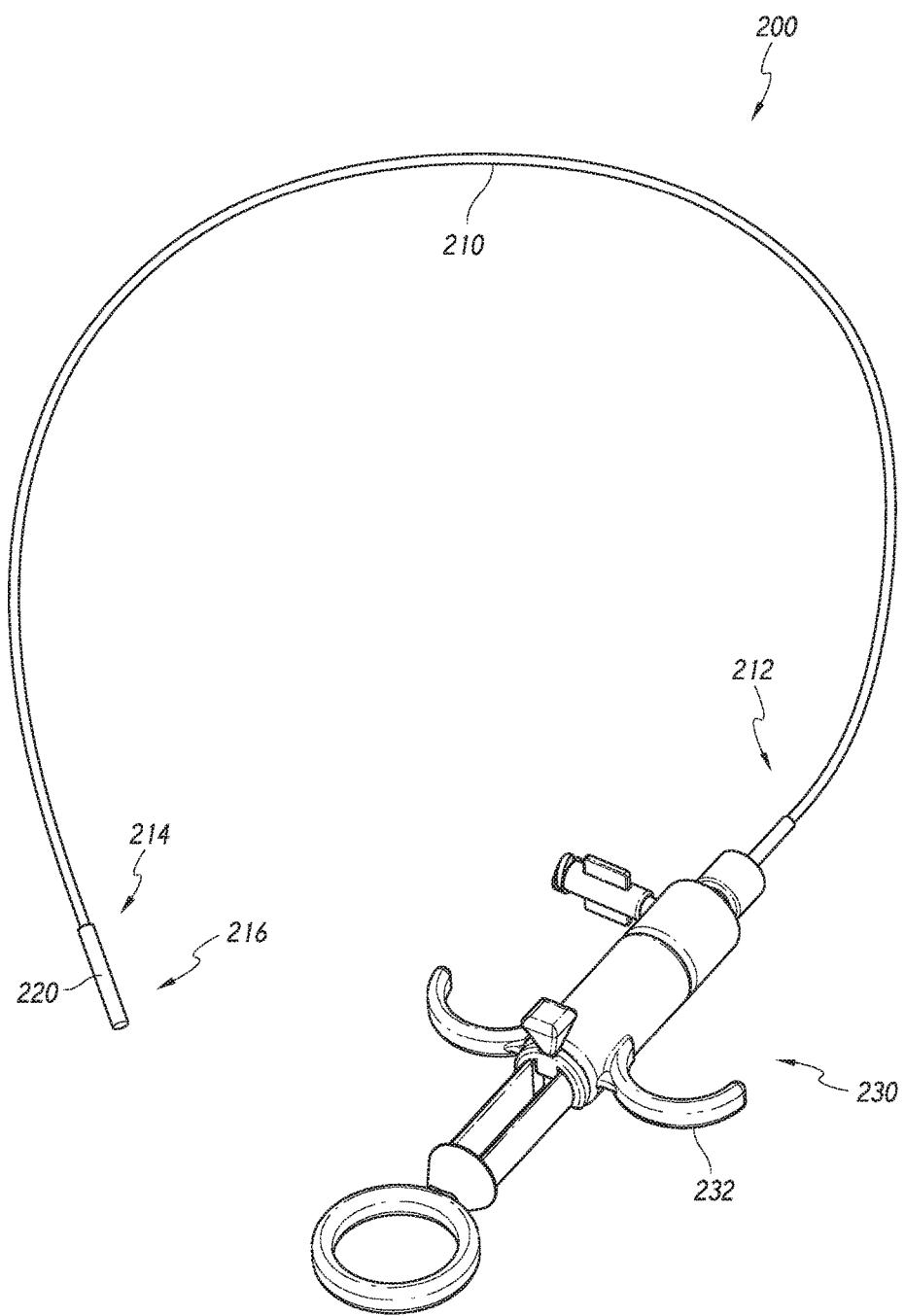
FIG. 1B illustrates a perspective view of another implant carrier assembly, according to some embodiments.

Similarly, FIG. 1B illustrates an embodiment of an implant carrier assembly 200, which can comprise a catheter 210 having a lumen that extends between a proximal portion 212 and a distal portion 214 of the catheter. The catheter 210 can also comprise an engagement section 216, which can be located along a distal portion of the catheter 210, configured to engage and/or restrain an implant positioned therealong.

In some embodiments, the catheter 110, 210 can define a length from about 50 cm to about 200 cm, from about 70 cm to about 160 cm, or in some embodiments, about 120 cm, with a working length of from about 85 cm to about 140 cm, from about 95 cm to about 130 cm. In accordance with some embodiments, the total length of the implant carrier assembly (with handle) can be about 117 cm, with a working length of 97 cm.

The catheter 110, 210 can be configured to move within a guide sheath when advancing the assembly 100, 200 into a patient for treatment. The proximal portion 112, 212 of the catheter 110, 210 can be configured to be relatively stiff in order to enhance the pushability of the catheter 110, 210 through the guide sheath. Further, the distal portion 114, 214 can be relatively flexible in order to improve the maneuverability and trackability of the catheter 110, 210 as it is advanced through the guide sheath.

The assembly 100, 200 can also comprise an implant or device 120, 220. As shown in FIGS. 1A-1B, the implant 120, 220 can be supported on the engagement section 116, 216 of the catheter 110, 210.

Further, the assembly 100 can also comprise a deployment handle assembly 150 attached to the catheter proximal portion 112. The deployment handle assembly 150 shown in FIG. 1A includes two pull members 152, 154, whereas the deployment handle 230 shown in FIG. 1B includes a single pull member 232. As discussed further herein and in co-pending U.S. patent application Ser. No. 14/044,794, filed Oct. 2, 2013, the entirety of which is incorporated herein by reference, the pull members 152, 154 can be used to release the implant 120 from engagement with the engagement section 116 of the catheter 110. In some embodiments, both deployment handles 150, 230 can be used to release distal and proximal portions of the implant 120, 220. Either embodiment can be used with any of the implant embodiments disclosed herein to perform any of the methods and procedures disclosed herein.

For example, the deployment handle 150 can be configured to provide separate, dedicated pull members 152, 154 for releasing each of the distal and proximal portions of the implant 120. The pull member 152 can be coupled to a first elongate member, and the pull member 154 can be coupled to a second elongate member. The first and second elongate members can extend distally toward the engagement section 116. The first and second elongate members can be releasably engageable with respective proximal or distal portion of the implant 120. In use, the pull member 154 can be proximally withdrawn, causing the second elongate member to move proximally and disengage with the proximal or distal end of the implant 120. Further, the pull member 152 can then be proximally withdrawn, causing the first elongate member to move proximally and disengage with the other of the proximal or distal end of the implant 120. The assembly 100 can thereby provide either sequential or simultaneous controlled deployment of the proximal and distal ends of the implant 120.

Additionally, the deployment handle 230 uses a single pull member 232 that can be, for example, moved a first distance to release the distal portion of the implant 220 and pulled a second distance to release the proximal portion of the implant 220. The pull member 232 can be coupled to an elongate member that extends distally toward the engagement section 216. The elongate member can be releasably engageable with proximal and distal portion of the implant 220. In use, the pull member 232 can be proximally withdrawn at a first axial distance, causing the elongate member to move proximally and disengage with the proximal or distal end of the implant 220. Further, the pull member 232 can then be proximally withdrawn a second axial distance, greater than the first axial distance, causing the first elongate member to move proximally and disengage with the other of the proximal or distal end of the implant 120. The assembly 100 can thereby provide either sequential or simultaneous controlled deployment of the proximal and distal ends of the implant 120.

Further, in some embodiments, whether a single or multiple pull members are used, the pull members can be pushed distally relative to the handle assembly 150, 230 to cause release of a portion of the implant from engagement with the assembly 100, 200. Thus, the pull members can move in either direct, and in any order, to release one or more portions of the implant (e.g., the distal or proximal ends of the implant), whether sequentially or simultaneously.

The implant carrier assemblies 100, 200 may be used in combination with any of the implants disclosed herein, including variations and combinations thereof.

Figure 3:
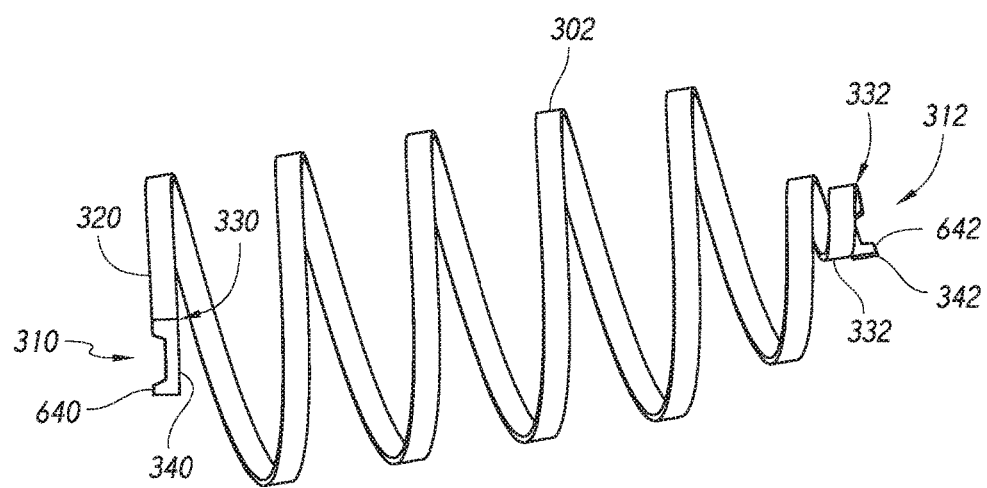
FIG. 3 shows a perspective view of a support frame of an implant, according to some embodiments.

For example, referring now to FIGS. 2-3, features of an exemplary embodiment of an implant 300 are illustrated. The implant 300 can comprise a support frame 302 and a membrane 304 supported by the support frame 302. The support frame 302 can be formed from a variety of materials, which can be flexible or deformable. Additionally, the membrane 304 can comprise one or more of a variety of materials that can be impermeable or have low permeability. When implanted into a vessel, the implant 300 can be configured to provide sufficient radial strength against a vessel wall under normal blood pressure in order to minimize post-deployment migration.

Referring now to FIG. 3, in some embodiments, the implant support frame 302 can be formed as a helical body. For example, the support frame 302 can include proximal and distal sections 310, 312. Generally, the body of the support frame 302 can extend along a curvilinear, helical path. However, in accordance with some embodiments, one or both of the proximal or distal sections 310, 312 can bend at elbows 330, 332 from the helical path radially inwardly or with a smaller radius of curvature than that of the support frame 302 at a portion between the proximal and distal sections 310, 312. From the elbows 330, 332, planar portions 340, 342 may extend, providing an engagement mechanism. For example, reduced cross-sectional segments 320, 322 can be provided in the planar portions 340, 342. The reduced cross-sectional segments 320, 322 can be indentations, protrusions, slots, and/or apertures extending through the support frame 302. As discussed further below, the segments 320, 322 can be configured to interact with respective structures of the engagement section 216 of the catheter 210. The proximal or distal sections 310, 312 can comprise an end or tab 640, 642 extending therefrom.

As shown in FIG. 4A, the distal engagement section 216 can be configured to receive and facilitate engagement with an implant 300 or a portion thereof (e.g., the support frame 302) to maintain the implant 300 engaged with the distal end 214 of the catheter 210. In accordance with some embodiments, the implant carrier assembly 200 comprises at least one elongate member 420 that extends at least partially through a catheter lumen 400 and engages the support frame 302, for example at one or both of the segments 320, 322. The elongate member 420 can be selectively actuated, withdrawn, or controlled using the handle assembly 250 to disengage from the support frame 302.

The catheter 210 can comprise a proximal aperture 600 and a distal aperture 602. The proximal and distal aperture 600, 602 are configured to extend through the wall 402 of the catheter 210 as slots or notches that extend transversely relative to a longitudinal axis of the catheter lumen 400. Each of the proximal or distal sections 310, 312 of the support frame 302 extends within the respective proximal or distal aperture 600, 602 of the catheter 210. As shown in FIG. 4C, the proximal section 310 can sit within the aperture 600 and provide enough clearance between the proximal section 310 and wall 402 or the inner surface of the wall 402 such that the elongate member 420 can be positioned intermediate the wall 402 and the proximal section 310.

Accordingly, some embodiments can be configured such that the proximal and/or distal sections 310, 312 can be constrained against movement in an axial direction 646, a radial direction 648, and a transverse direction 650. Thus, when the support frame 302 is coiled about the engagement section 216 of the catheter 210, the proximal and distal sections 310, 312 of the support frame 302 can be secured in various directions to be engaged during delivery of the support frame 302 to the treatment site. When the support frame 302 reaches the treatment site, the support frame 302 can then be released and expanded.

Figure 4B:
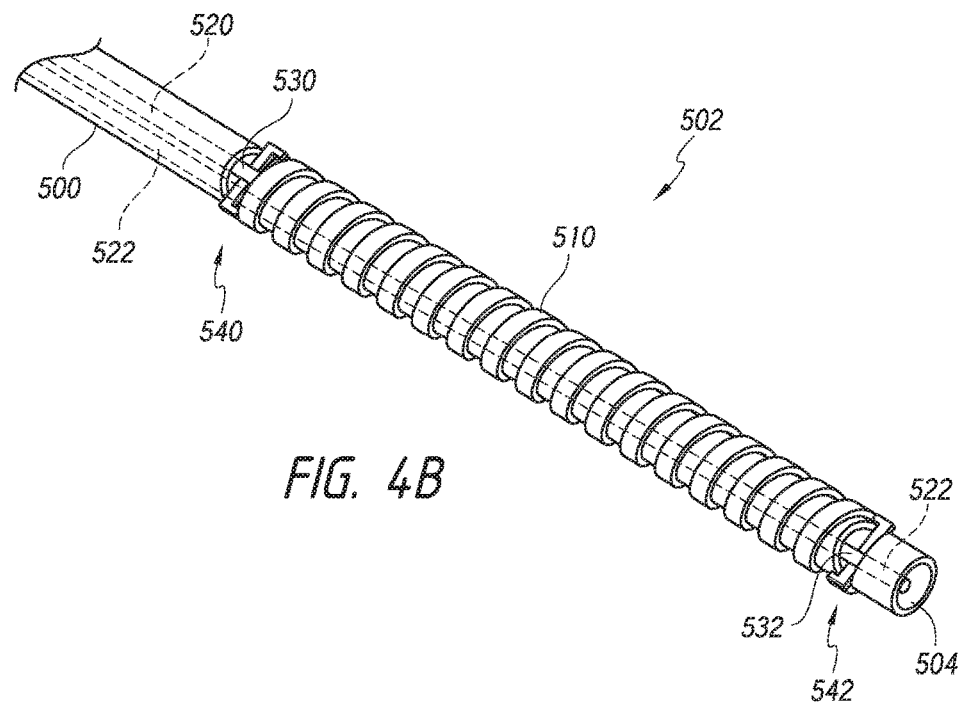
FIG. 4B shows a perspective view of an implant support frame on a catheter distal section of an implant carrier assembly, according to some embodiments.

As shown in FIG. 4B, a catheter 500 comprises an engagement section 502 and a lumen 504. The assembly can comprise an implant or support frame 510 supported on the engagement section 502. The assembly can comprise a first elongate member 520 and a second elongate member 522 configured to engage the support frame 510. As shown, a distal portion 530 of the elongate member 520 can engage a proximal portion 540 of support frame 510 and a distal portion 532 of the elongate member 522 can engage a distal portion 542 of the support frame 510.

The support frame 302 is mounted, collapsed, or wound around the catheter distal portion. Before the support frame 302 is released, the support frame 302 is helically wound tightly around the catheter 210. The winding of the support frame 302 about the catheter distal portion can put the support frame 302 into a stressed state. As discussed further below, the support frame 302 will tend to rebound or expand from the stressed, mounted, collapsed, or wound position.

Figure 4D:
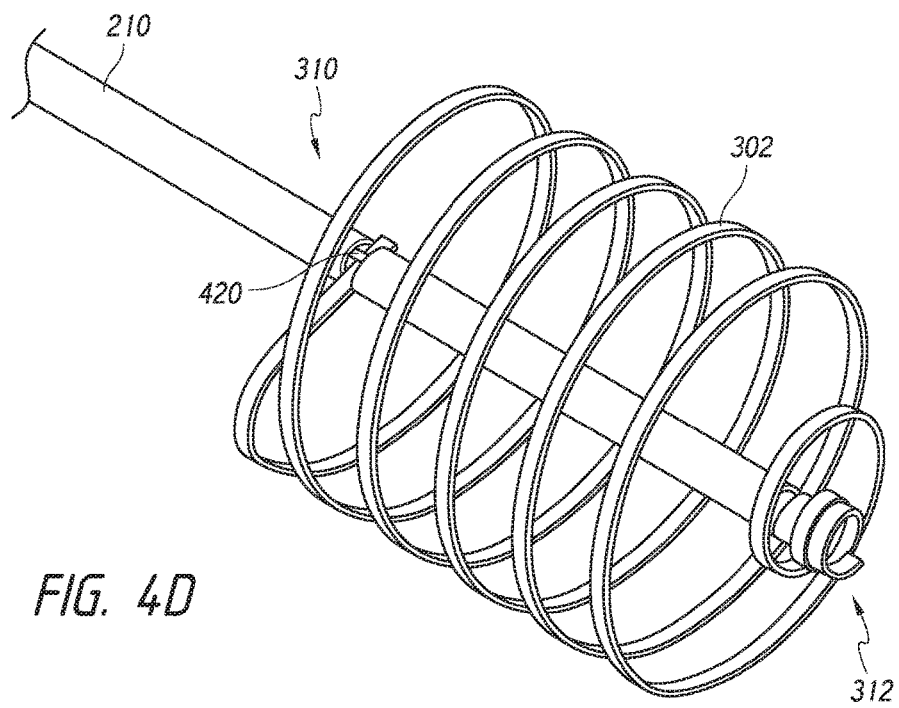
FIG. 4D shows a perspective view of an implant support frame partially released from a catheter distal section of an implant carrier assembly, according to some embodiments.

An initial phase of the implant expansion is illustrated in FIG. 4D. As shown, the proximal portion 310 of the support frame 302 is engaged or retained by an elongate member 420. However, the support frame 302 has expanded from a mounted, collapsed, or torsion state (shown in FIG. 4B) to an expanded or relaxed state (shown in FIG. 4D) because the distal section 312 of the support frame 302 has been released from engagement with the catheter 210. When released, the stress in the wound support frame 302 can be released as the implant distal section 312 unwinds (perhaps along with a portion of the support frame 302 intermediate the proximal and distal sections 310, 312). For example, the distal and proximal sections 310, 312 can rotate or unwind relative to each other, allowing the diameter of the implant 300 to expand while it unwinds or rotates. Thereafter, in order to fully release the support frame 302, the engagement member 420 can be moved to disengage from the proximal section 310 of the support frame 302.

Figure 5A:
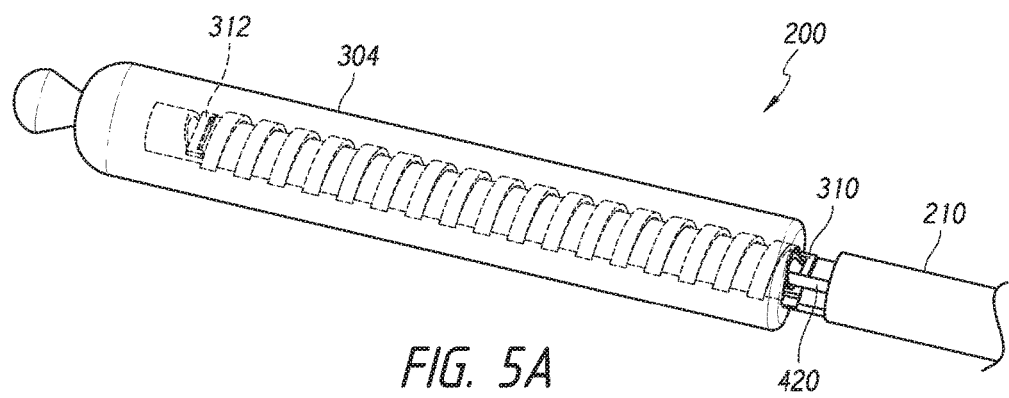
FIGS. 5A and 5B illustrate perspective views of an implant in a mounted or collapsed position on a catheter, according to some embodiments.
Figure 5B:
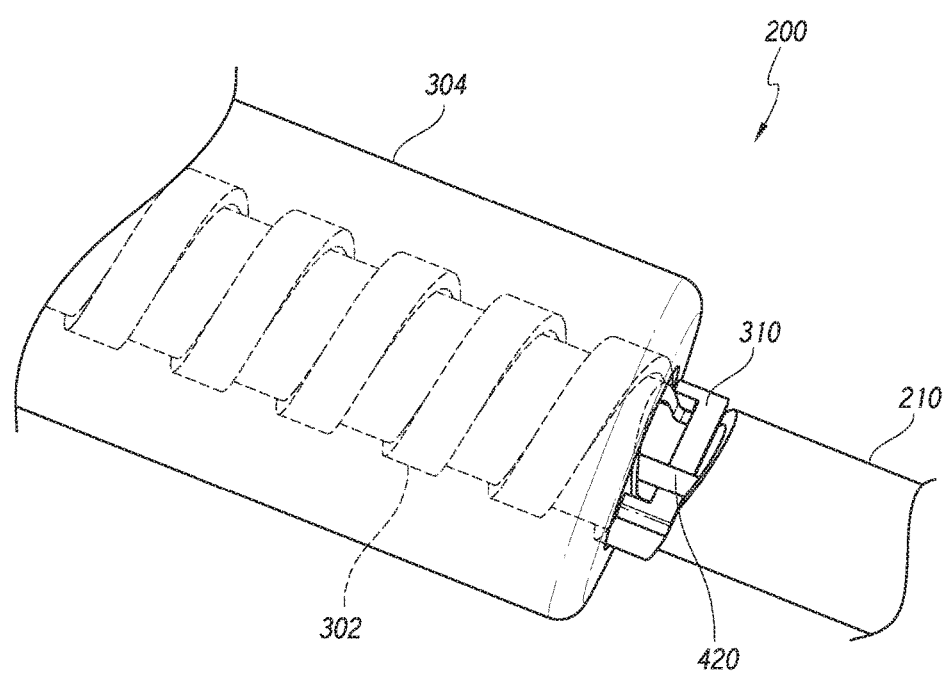

FIGS. 5A-5B illustrate perspective views of the implant carrier assembly 200, similar to the illustrations of FIGS. 4A-4B, but further including the implant membrane 304. As illustrated, the implant membrane can be positioned over the support frame 302 and delivered in a mounted or collapsed state. The elongate member 420 can be engaged with the proximal section 310 of the support frame 302. Further, as noted above, the elongate member 420 or a different elongate member can be engaged with the distal section 312 of the support frame 302.

In some embodiments, a length of support frame 302 may be between about 7 millimeters (mm) and about 9 mm. In some embodiments, the length of support frame 302 may be less than about 7 mm or greater than about 9 mm. In some embodiments, the length of distal portion may be less than about 3 mm or greater than about 4 mm. In some embodiments, a diameter of the proximal portion and/or the middle portion may be between about 2 mm and about 10 mm. In some embodiments, the diameter of the proximal portion and/or the middle portion may be less than about 2 mm or greater than about 10 mm.

In some embodiments, radio-opaque markers may be located on support frame 302 or occlusion membrane 304 for endovascular or other image-guided procedures. For example, a radio-opaque marker may be placed on a first coil of support frame 302. In some embodiments, an outer cross sectional dimension of the first coil is less than an outer cross sectional dimension of a second coil of support frame 302, which will allow space for the radio-opaque marker to surround, at least in part, an exterior of the first coil. In some embodiments, the first coil is adjacent to the second coil, and occlusion membrane 304 may be coupled to the second coil. In this regard, having the radio-opaque marker placed on the first coil adjacent to the second coil that is coupled to occlusion membrane 304 will allow an operator to identify where embolization may occur, for example. In some embodiments, the radio-opaque marker may be a platinum iridium alloy or other suitable markers known to those of ordinary skill in the art.

According to various embodiments of the subject technology, occlusion membrane 304 may be used to occlude, partially or completely, luminal structure in which an implant is deployed. In some embodiments as used herein, occlusion may refer to either partial or complete occlusion.

Some embodiments can also comprise a frame having a laminated configuration. The laminated configuration can be achieved using two or more interconnected frame components that overlay each other in either a radial or longitudinal direction.

Figure 6A:
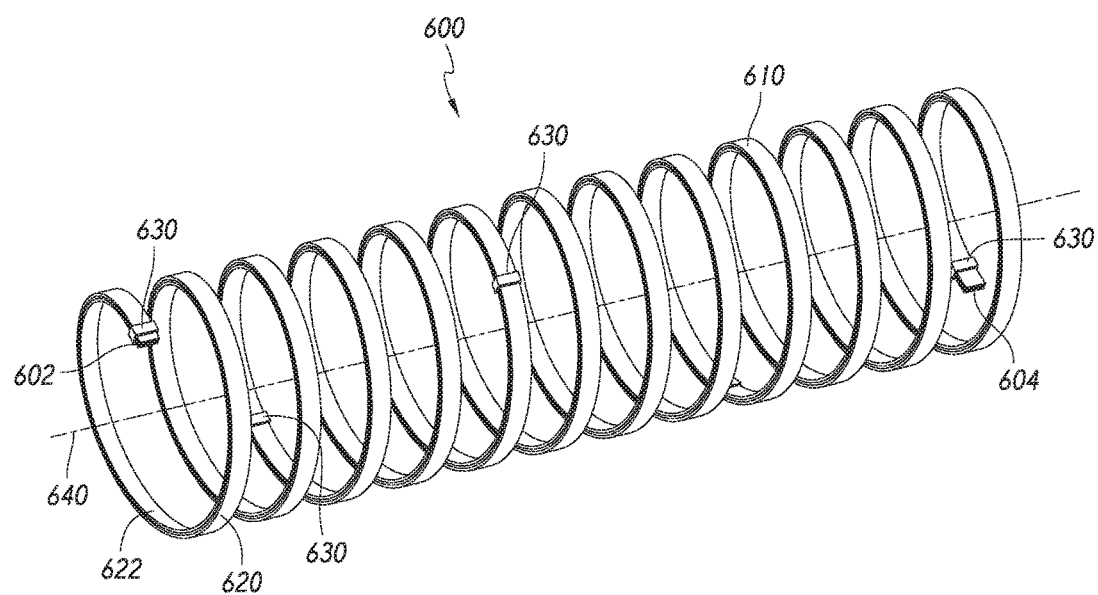
FIG. 6A shows a perspective view of an implant with overlapping coils, according to some embodiments.

For example, as illustrated below in FIGS. 6A-6B, an implant 600 includes a first helical member 620 and a second helical member 622 can both be positioned coaxially relative to the same axis 640. The first helical member 620 and the second helical member 622 may each be formed as a flat wire coil. The first helical member 620 and the second helical member 622 can be aligned along the full length of a frame 610. For example, as shown in FIG. 6A, the first and second helical members 620, 622 radially overlap along an entire length from a first end 602 to a second end 604. Alternatively, the first and second helical members 620, 622 can radially overlap along a portion of the length from the first end 602 to the second end 604. For example, the first helical member 620 may define a lumen, wherein the second helical member 622 is disposed within the lumen defined by the first helical member 620.

The first and second helical member 620, 622 can contact each other at opposing surfaces along the length of the frame 610. Accordingly, the second helical member 622 may have an outer diameter equal to the inner diameter of the first helical member 620. Alternatively, the first and second helical member 620, 622 can face each other with opposing surfaces separated by a helical gap. Accordingly, the second helical member 622 may have an outer diameter smaller than the inner diameter of the first helical member 620.

The first and second helical members 620, 622 can be connected at one or more of their ends 602, 604 or at one or more positions along the length of the frame 610 by coupling members 630. The coupling members 630 may be wires, ties, cuffs, coils, rings, adhesion, welding, and/or other connection mechanisms, which can be radiopaque, such as cuffs, coils, or bands used to maintain relative positioning of the first and second helical members 620, 622. The coils, cuffs, or bands used to connect coils may be constructed of a radiopaque material such as gold, platinum, tungsten, or plastic impregnated with a radiopaque material.

According to some embodiments, a laminated frame 610 configuration can enable smaller delivery diameters with the utilization of thinner wire, but maintain radial force applied against vessel wall after deployment to secure location of implant. The frame 610 may have consistent pitch, alternating pitch, or have variable pitch intended to improve stability after deployment. Alternate design options can include a tapered diameter, or varying diameter constructs, as disclosed herein.

Figure 6B:
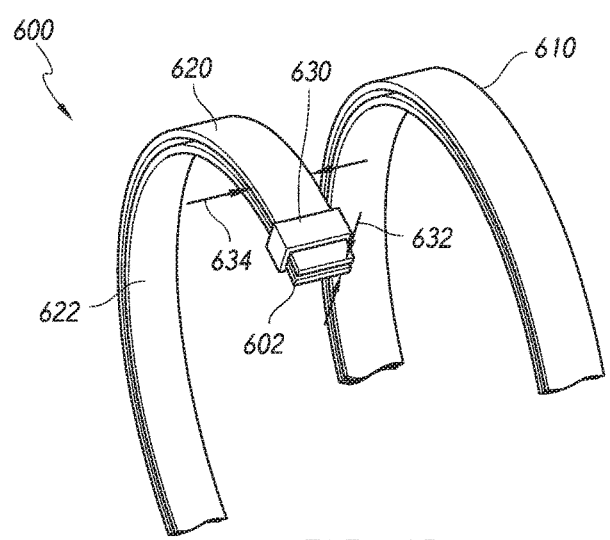
FIG. 6B shows a close view of the implant of FIG. 6A, according to some embodiments.

FIG. 6B illustrates an enlarged view of separate coils of the laminated frame shown in FIG. 6A. As shown in FIG. 6A, the first helical members 620 may have a wire shape that is rectangular in cross-section. The cross-sectional shape provides a radial thickness 632 defined by a length from a radially inner surface of the first helical member 620 to a radially outer surface of the first helical member 620, i.e., as measured in a radial direction transverse to the central axis 640. The cross-sectional shape further provides an axial width 634 defined by a length from a first axial side of a segment of the first helical member 620 to a second axial side of the segment of the first helical member 620, i.e., as measured in an axial direction parallel to the central axis 640. As shown in FIG. 6A, the axial width 634 may be greater than the radial thickness 632. The second helical member 622 may provide a correspondingly similar cross-sectional shape.

Although according to some embodiments, the first and second helical members 620, 622 can have a wire shape that is rectangular in cross section, the wire shape can also be oval shaped, diamond shaped, etc., having an axial width that is greater than a radial thickness.

Figure 6C:
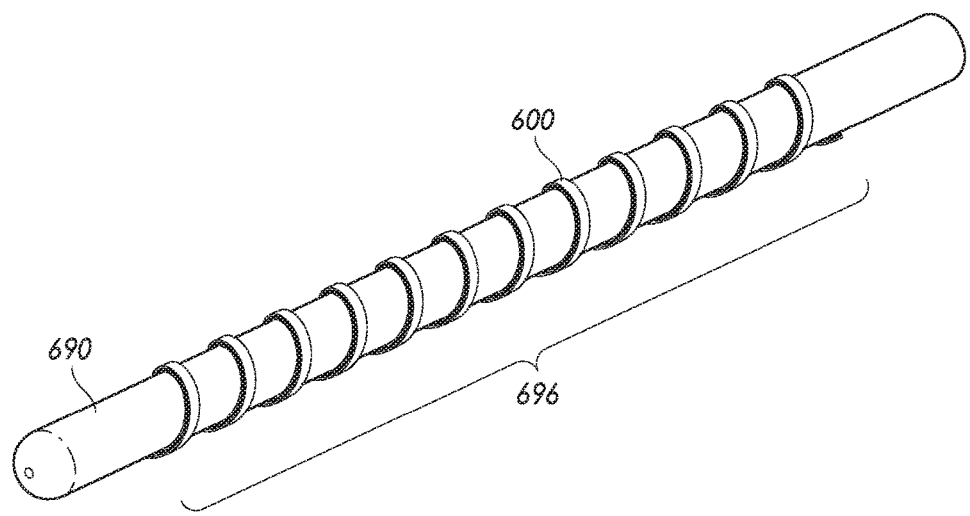
FIG. 6C shows a perspective view of an implant on a catheter for delivery to a target location in a vessel, according to some embodiments.
Figure 6D:
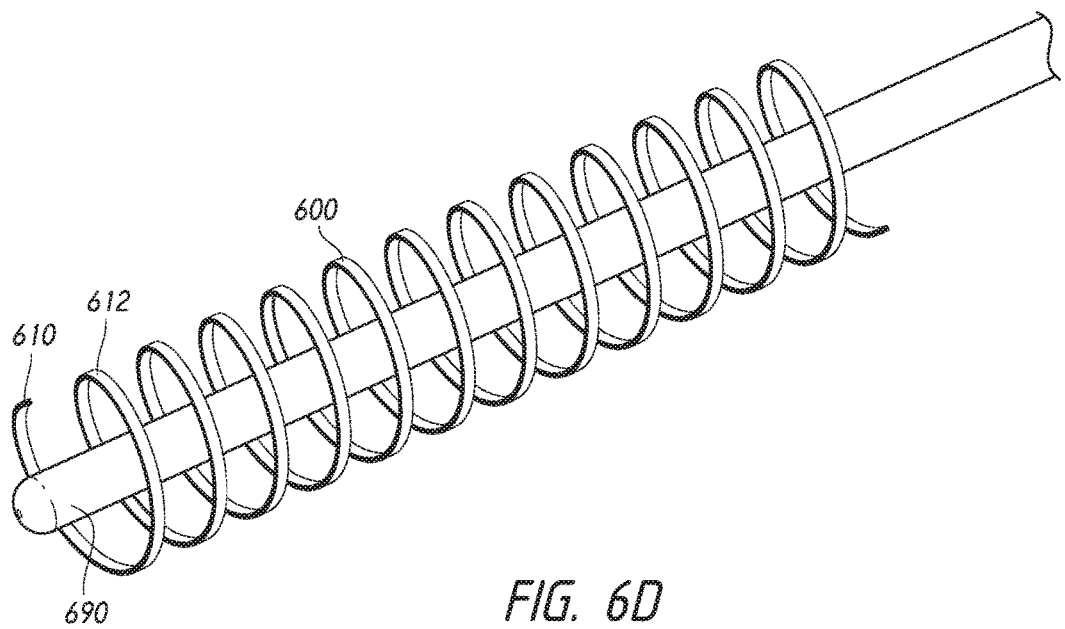
FIG. 6D shows a perspective view of the implant of FIG. 6C, expanded from the catheter, according to some embodiments.

In accordance with some embodiments, as shown in FIG. 6C, the implant 600 may be tightly wound around a catheter 690 in a delivery or collapsed state, for delivery to a target location in a body vessel. In accordance with some embodiments, as shown in FIG. 6D, the implant 600 may be released from the catheter 690 to freely expand to an expanded state, for expansion into the blood vessel.

Figure 7A:
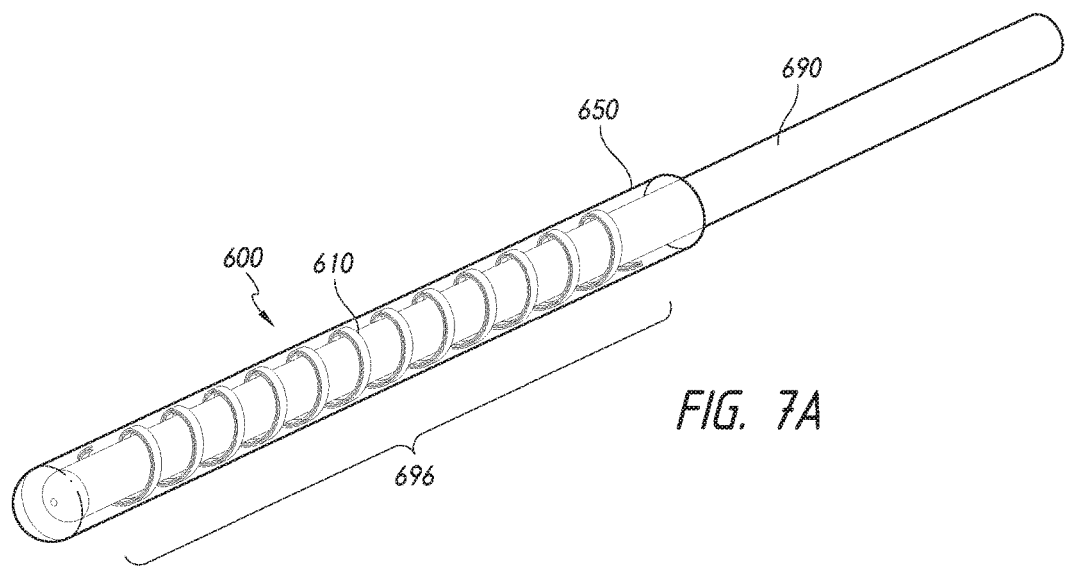
FIG. 7A shows a perspective view of an implant with a cover on a catheter, according to some embodiments.
Figure 7B:
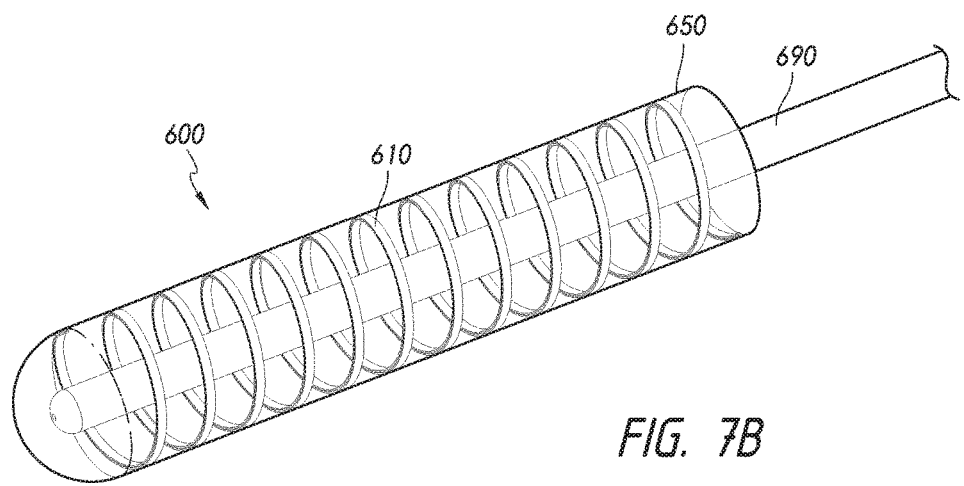
FIG. 7B shows a perspective view of the implant with a cover of FIG. 7A, expanded from the catheter, according to some embodiments.

FIG. 7A illustrates the laminated frame shown in FIG. 6A-6D, further including a cover 650 assembled to frame 610. The frame 610 and the cover 650 can form the implant 700 that can be deployed for occluding a vessel, as disclosed generally herein. The cover 650 can be assembled to the frame 610 with one or both closed ends to achieve occlusion. The cover 650 may reside on the outside surface of the frame 610, radially between the first and second helical members 620, 622, or partially inside and partially outside of the frame 610 to aid in attachment and size reduction. FIG. 7B illustrates the laminated frame 610 shown in FIG. 7A, in which the frame 610 has been expanded to an expanded state within the cover 650. Thus, the frame 610 and the cover 650 collectively form an implant 600 for occlusion of blood flow, according to some embodiments.

In accordance with some embodiments, an implant can comprise an upright frame in a coiled configuration. In such embodiments, a frame can be formed by a coiled wire having a cross-section with a radial thickness that is greater than its longitudinal or axial width. For example, the frame can comprise a flat coil that extends in a helical direction and has cross-section having a radial thickness that is greater than its axial or longitudinal width.

For example, as illustrated below in FIGS. 8A-8B, an implant 700 can comprise a flat wire coiled in a helical shape from a first end 702 to a second end 704. The frame 710 may define a lumen.

The upright frame 710 may have consistent pitch, alternating pitch, or have variable pitch intended to improve stability after deployment. Alternate design options can include a tapered diameter, or varying diameter constructs, as disclosed herein.

Figure 8A:
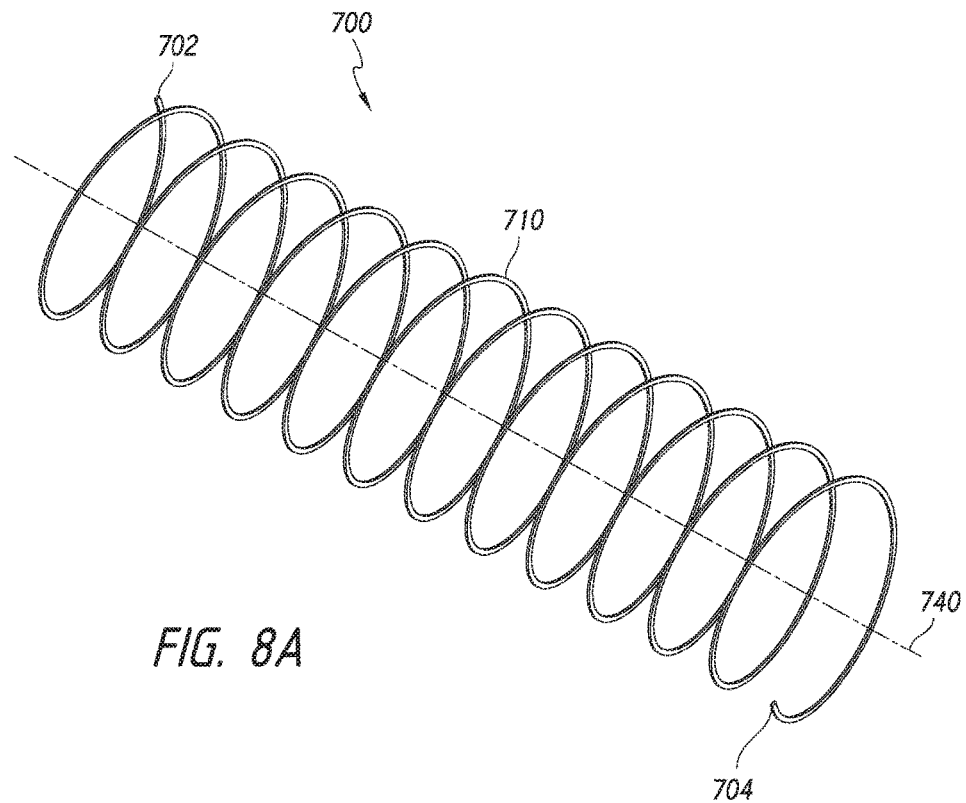
FIG. 8A shows a perspective view of an implant, according to some embodiments.
Figure 8B:
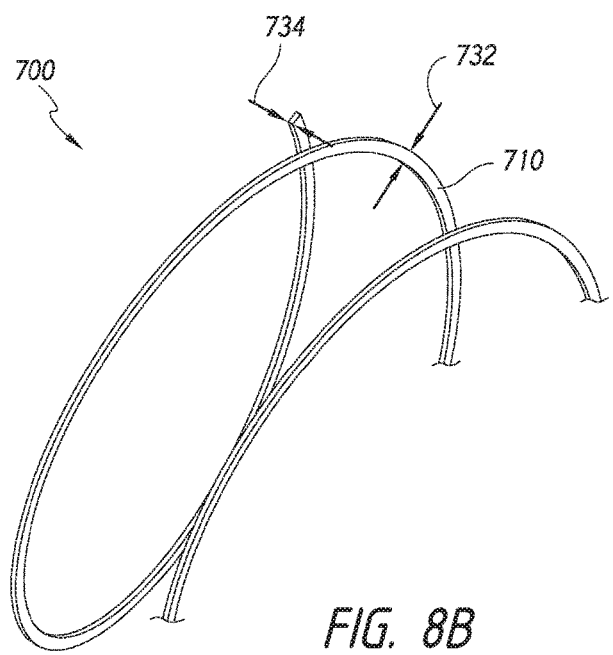
FIG. 8B shows a close view of the implant of FIG. 8A, according to some embodiments.

FIG. 8B illustrates an enlarged view of the implant 700 shown in FIG. 8A. As shown in FIG. 8A, the upright frame 710 may have a wire shape that is rectangular in cross-section. The cross-sectional shape provides a radial thickness 732 defined by a length from a radially inner surface of the frame 710 to a radially outer surface of the frame 710, i.e., as measured in a radial direction transverse to the central axis 740. The cross-sectional shape further provides an axial width 734 defined by a length from a first axial side of a segment of the frame 710 to a second axial side of the segment of the frame 710, i.e., as measured in an axial direction parallel to the central axis 740. As shown in FIG. 8A, the radial thickness 732 may be greater than the axial width 734.

According to some embodiments, the cross section of the frame 710 can have a radial thickness that is between about 1.5 to about 10 times as great as the axial width of the frame. Further, in some embodiments, the cross section of the frame can have a radial thickness that is between about 2 to about 8 times as great as the axial width of the frame. Additionally, in some embodiments, the cross section of the frame can have a radial thickness that is between about 2.5 to about 6 times as great as the axial width of the frame. Furthermore, in some embodiments, the cross section of the frame can have a radial thickness that is between about 3 to about 4 times as great as the axial width of the frame.

Although according to some embodiments, the upright frame 710 can have a wire shape that is rectangular in cross section, the wire shape can also be oval shaped, diamond shaped, etc., having a radial thickness that is greater than an axial width.

FIG. 8A also illustrates an upright frame 710 having a consistent pitch. However, a variable pitch frame can be provided in order to improve stability after deployment.

According to an aspect of some embodiments, the upright frame 710 can be configured to assume a generally linear state during delivery. Alternatively, the upright frame 710 can be configured to assume a compressed state during delivery, wherein, while in the compressed state the frame 710 has a cross-sectional dimension less than in an expanded state. For example, the upright frame 710 can be held straight or in a tight coil during delivery to target location and as the frame is moved out of the delivery device (such as a catheter), the frame 710 can expand to a coiled, expanded state, as illustrated in FIG. 8A.

Figure 9A:
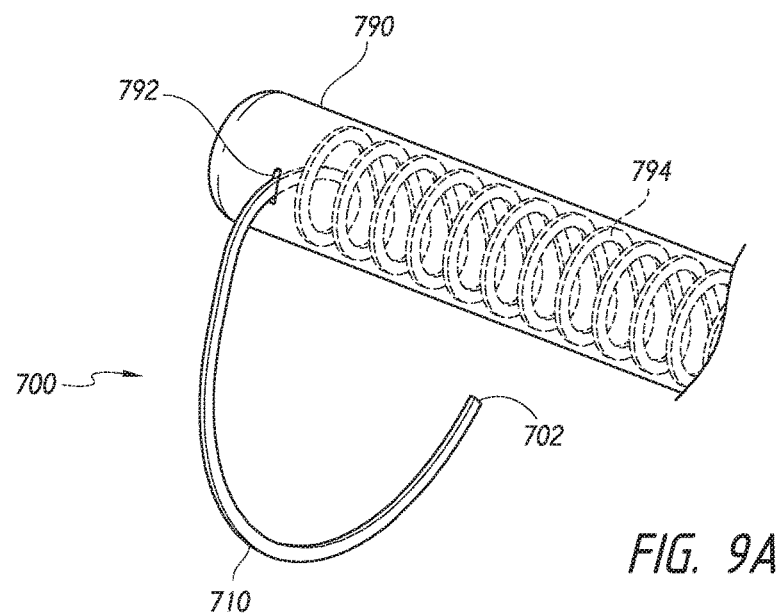
FIG. 9A shows a perspective view of a partial delivery of an implant from within a catheter, according to some embodiments.

The upright frame 710 can be delivered from a delivery device 790 out of a distal aperture (not shown) of a lumen 794 of the delivery device 790. However, as illustrated in FIG. 9A, in accordance with some embodiments, the delivery device 790 can be configured to comprise a side aperture 792 that extends transversely to a lumen 794 of the device. Thus, the upright frame 710 can be deployed through an aperture 792 in a side of a catheter 790, which can facilitate the alignment and expansion of the upright frame 710 such that the upright orientation of coil is maintained as the frame 710 exits the aperture 792. The aperture 792 can have a cross-section that generally matches the cross section (i.e., wire shape) of the upright frame 710, which can be generally rectangular. Such embodiments can allow a clinician to deliver the frame 710 from a straight or compressed state within the lumen 794 to minimize the device profile.

Figure 9B:
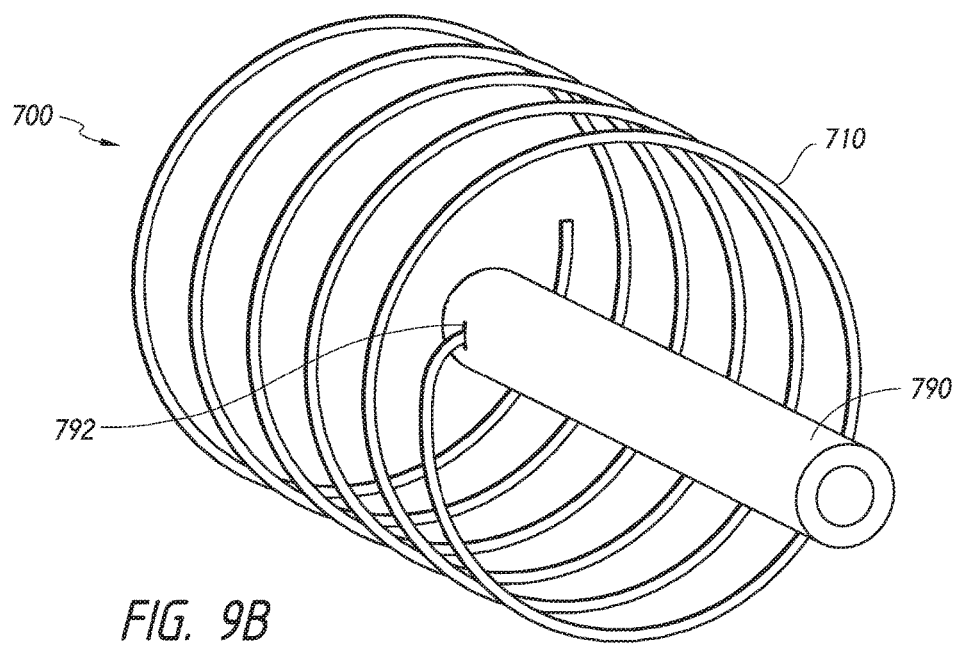
FIG. 9B shows a perspective view of a partial delivery of an implant from a catheter, according to some embodiments.

FIG. 9A illustrates partial delivery of an upright frame 710 from a catheter 790, according to some embodiments. In some embodiments, the upright frame 710 can be pre-loaded into the catheter 790, with only a portion of the distal end 702 of the upright frame 710 extending through the aperture 792 of the catheter 790. For example, the upright frame 710 can define a catch, distal hook, or enlarged portion (not shown) that is disposed at a distal end 702 thereof and configured to extend through or be disposed outside of the aperture 792. The catch, distal hook, or enlarged portion can be configured to prevent the distal end 702 of the upright coil 710 from being retracted fully into the lumen 794 of the catheter 790. The catch, distal hook, or enlarged portion can be formed or attached to a distal end 702 of the upright frame 710 after the distal end 702 has passed through the aperture 792, during assembly. Alternatively, the frame 710 may be inserted into the lumen 794 through the aperture 792 by feeding the proximal end 704 there through. FIG. 9B illustrates the further deployment and expansion of the upright frame 710 from the aperture 792 of the catheter 790.

Figure 10A:
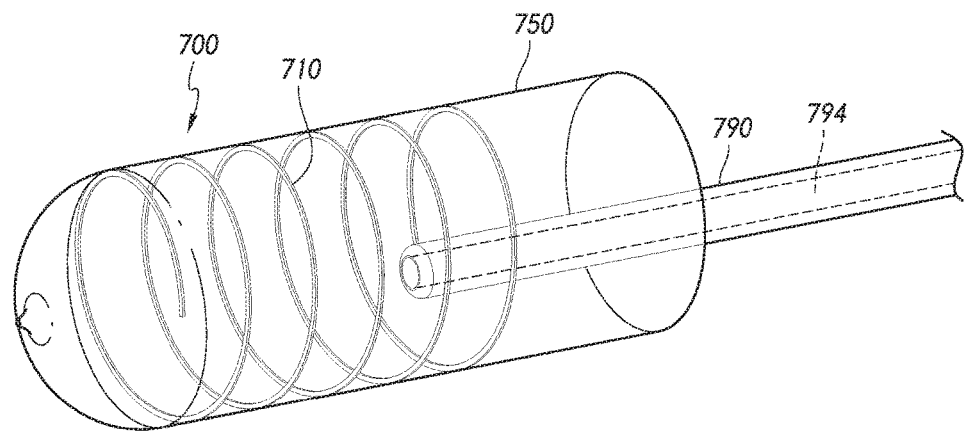
FIG. 10A shows a perspective view of an implant with a cover in a body vessel, according to some embodiments.

In accordance with some embodiments, as shown in FIG. 10A, a frame 710 of a medical implant 700 can be provided with an upright feature and can be used in a variety of clinical applications. For example, a cover 750 (e.g., occlusive structures, fibrous mesh, or other component) can be used with a frame 710 having an upright feature.

Figure 10B:
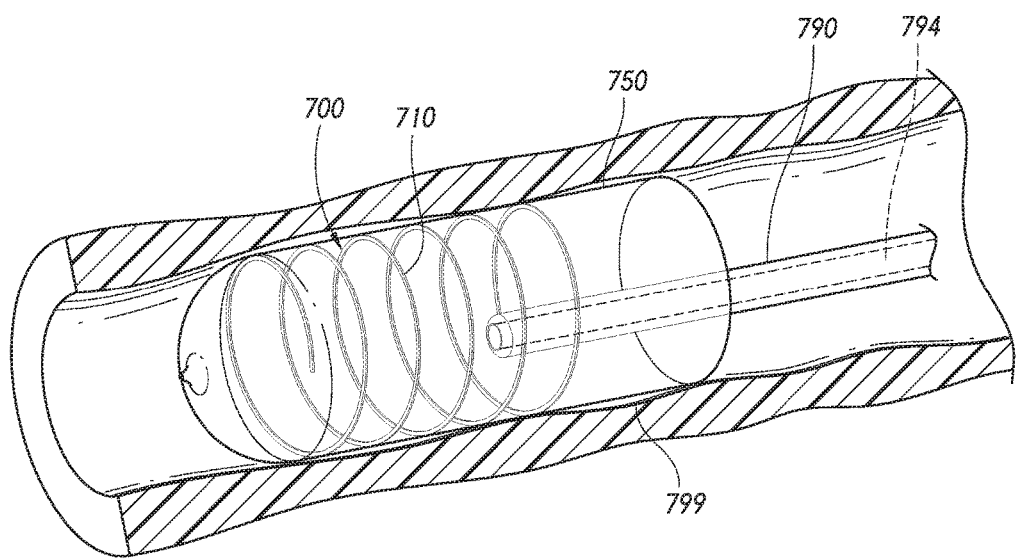
FIG. 10B shows a perspective view of an implant with a cover in a body vessel, according to some embodiments.

As shown in FIG. 10B the frame 710 can be positioned within a vessel 799 and extend in a helical direction having an upright configuration, which can provide superior radial strength. Such advantages can be useful in deploying an upright frame 710 along with a secondary component, such as a cover 750, where the secondary component must be pressed or pinched against a wall of the vessel 799.

The cover 750 may extend over a full or partial length of the frame 710. The cover 750 may reside outside, inside, or a combination of inside and outside of the frame 710. As shown in FIG. 10A-10B, the cover 750 may include at least one closed end to facilitate occlusion of blood flow through the vessel 799.

While various embodiments disclosed herein relate to "coil-type" implant support frames, defined a support frames that extend helically only in a single direction, some embodiments disclosed herein can comprise a "non-coil-type" implant support frames, defined as support frames that have do not extend helically in only a single direction (i.e., that reverse direction one or more times), implant support frames that have symmetrical halves that each extend about only a portion of a perimeter of the support frame and are coupled to each other to form a completed support frame, or support frames that do not extend helically at all.

For example, a non-coil-type support frame, such as a symmetrical dual-component implant support frame, can have symmetrical halves formed using dual wires that each extend about only a portion of a perimeter of the support frame and are coupled to each other to form a completed support frame. Such embodiments can provide various advantages over coil-type support frames. Generally, the maximum expanded diameter to which a coil-type support frame can resiliently expand is less than the maximum expanded diameter to which a non-coil-type or symmetrical support frame can resiliently expand. Further, the minimum collapsed diameter or profile of a coil-type support frame is greater than the minimum collapsed diameter or profile of a non-coil-type or symmetrical support frame.

Thus, a non-coil-type or symmetrical support frame can be delivered through a lower profile catheter and/or be released into vessels having a larger diameter than those treatable by a coil-type support frame. Further, even if a coil-type support frame is designed to provide the same minimum collapsed profile as a non-coil-type or symmetrical support frame, the non-coil-type or symmetrical support frame can have a greater maximum expanded diameter than the coil-type support frame. Furthermore, even if a coil-type support frame is designed to provide the same maximum expanded diameter as a non-coil-type or symmetrical support frame, the non-coil-type or symmetrical support frame can have a smaller minimum collapsed profile than a coil-type support frame.

In addition, because a non-coil-type or symmetrical support frame need not be torsionally constrained when mounted or supported on a support member (e.g., a catheter), the non-coil-type or symmetrical support frame will not tend to exert any torsional force or torque on the support member. Thus, the support member carrying a non-coil-type or symmetrical support frame need not provide any significant torque resistance to accommodate torque exerted by the non-coil-type or symmetrical support frame (which would otherwise be necessary if a coil-type support frame were used).

Figure 11:
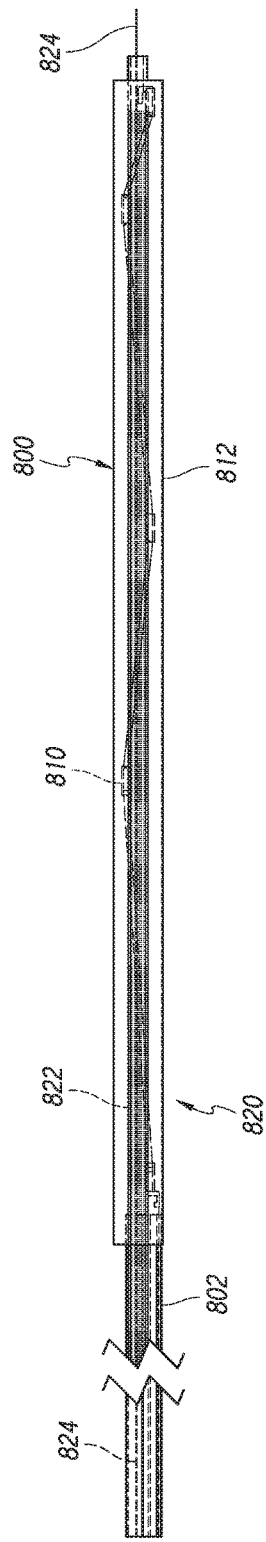
FIG. 11 shows a side view of an implant on a catheter, according to some embodiments.

Some embodiments of a non-coil-type or symmetrical support frame are illustrated in FIGS. 11-18D. FIG. 11 shows a side view of an implant 800 supported on a support member 802, such as a catheter, according to some embodiments. The implant 800 can comprise a support frame 810 and a membrane or occlusive member 812. The support member 802 can comprise a distal portion 820 having an implant support section 822.

Similar to some of the embodiments disclosed herein, the support member 802 can comprise one or more lumens and be configured to be delivered over the wire ("OTW") to the target or treatment site. FIG. 11 illustrates a guide wire 824 extending through a lumen of the support member 802.

Figure 12:
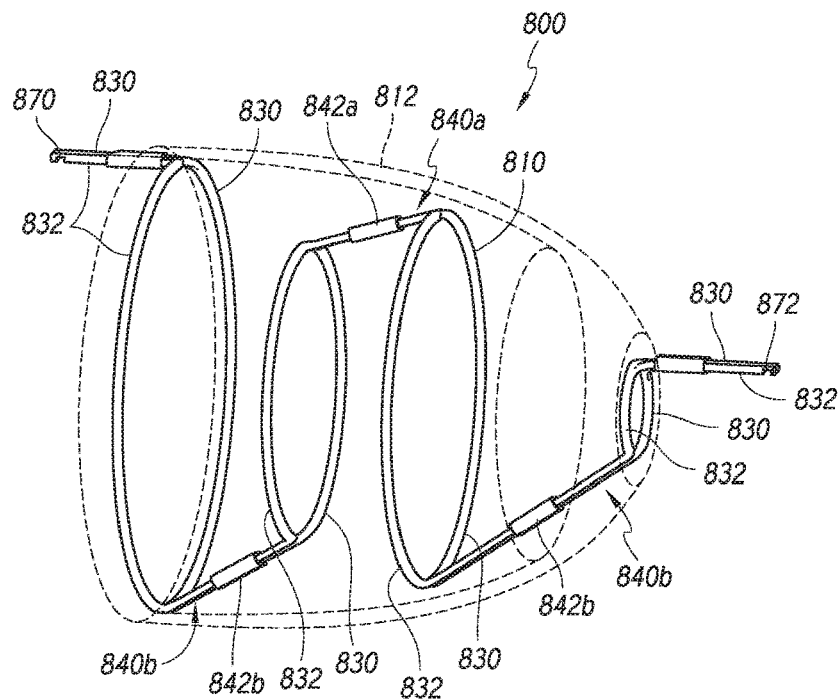
FIG. 12 shows a perspective view of an implant support frame in an expanded state, according to some embodiments.
Figure 13A:
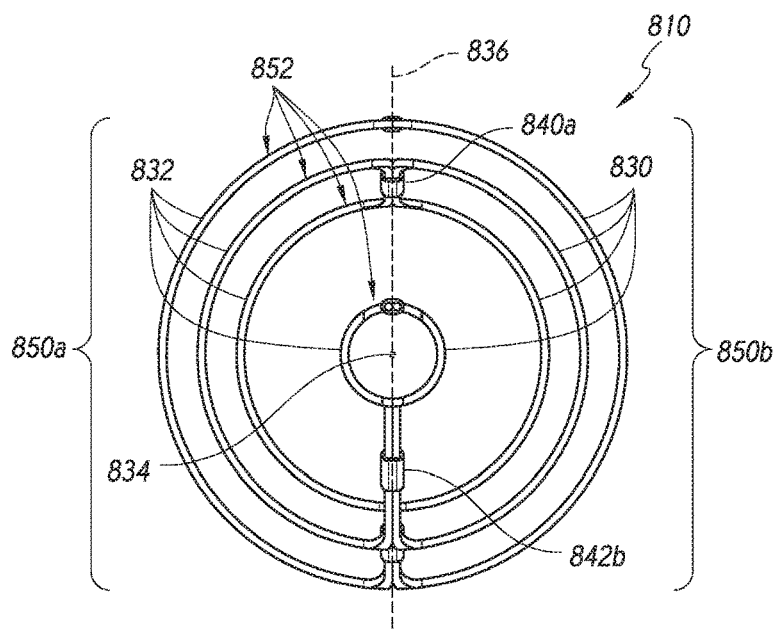
FIG. 13A shows an end view of the implant support frame of FIG. 12, according to some embodiments.

FIG. 12 illustrates a perspective view of the implant support frame 810 and the membrane 812 (shown in dashed lines) in an expanded state, according to some embodiments. In some embodiments, similar to the frame discussed below with respect to FIGS. 12-13C, separate wires 830, 832 can be generally mirror images of each other along a longitudinal center plane 834 (extending through the central axis 836) of the frame 810, as illustrated in FIG. 13A. The wires 830, 832 extend from a first end 902 to a second and 904 of the frame 900. Additional wires (e.g., 3, 4, or more wires) may be coupled together as disclosed herein. In some embodiments, whether a single or multiple wires are used, the wires can comprise a nitinol or titanium material.

The wires 830, 832 may be coupled together and extend axially along axial portions 840a and 840b. The axial portions 840a may be radially opposite the axial portions 840b across the central axis 836. Along the axial portions 840a, 840b, the wires 830, 832 may be adjacent and/or contacting. The wires 830, 832 may be joined or coupled together with connectors 842a at the axial portions 840a and with connectors 842b at the axial portions 840b. As shown in FIGS. 12-13C, the connectors 842a, 842b may be bands, cuffs, rings, clips, coil windings, combinations thereof, and the like. The connectors 842a, 842b may also be adhesive, glue, welding, combinations thereof, and the like. The connectors 842a, 842b may also be radiopaque for visualization.

The wires 830, 832 may extend circumferentially along circumferential portions 850a and 850b. The circumferential portions 850a may be radially opposite the circumferential portions 850b across or about the central axis 836. Each of the circumferential portions 850a, 850b may extend from an axial portion 840a to an axial portion 840b, radially opposite the axial portion 840a. The circumferential portions 850a, 850b can collectively define one or more rings or support elements 852, as illustrated in FIG. 13A. The axial portions 840a, 840b between which a single circumferential portion 850a or 850b extends may be axially displaced relative to each other. Each wire 830, 832 may extend entirely on a respective radial side of the frame 810. Each circumferential portion 850*a* or 850*b* may extend along at least a portion of a cylindrical path in a clockwise circumferential direction toward a given axial portion 840*a* or 840*b*, and each circumferential portion 850*a* or 850*b* may extend along at least a portion of the cylindrical path in a counterclockwise circumferential direction away from the given axial portion 840*a* or 840*b*. Each wire 830, 832 may contact all or less than all of the connectors 842*a*, 842*b*.

Thus, the interconnections of the separate wires 830, 832 can lie substantially in a common plane. However, the separate wires 830, 832 can also form interconnections that are not mirror images or that do not lie in a common plane. For example, in some embodiments in which the frame 810 defines a generally tubular shape, the interconnections can be located at different and varied circumferential locations. For example, the interconnections can be distributed across one, two, three, four, five, or more circumferential locations. The pattern can be a repeating pattern or randomized, which can provide a desired flexibility or strength characteristics for the frame.

Additionally, the separate wires 830, 832 can be of a common gauge or can have different gauges, in order to impart a desired strength characteristics.

The support elements 852 of the support frame 810 can be generally circular. However, the support elements 852 can be formed in any of a variety of shapes, including square, triangle, rectangle, oval, or other polygons (having five, six, seven, eight, nine, or more sides). Additionally, as illustrated in FIGS. 12-13C, the support elements 852 can each have different expanded or outer diameters.

For example, the support elements 852 can have expanded diameters from about 2 mm to about 30 mm or more. In some embodiments, the expanded diameter of a given support element 852 can be between about 2 mm and about 20 mm, between about 3 mm and about 16 mm, between about 4 mm and about 12 mm, or between about 5 mm and about 8 mm. For example, a given support element 852 can have an expanded diameter of about 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, or more.

In some embodiments, each of the support elements 852 can have an expanded diameter that is different from the other support elements 852 of the frame 810.

For example, as shown in FIG. 13C, a first support element 860 can have an expanded diameter of about 2 mm, a second support element 862 can have an expanded diameter of about 8 mm, a third support element 864 can have an expanded diameter of about 6 mm, and a fourth support element 868 can have an expanded diameter of about 10 mm.

According to some embodiments, the variation of expanded diameter sizes of the support elements 852 can allow the implant 802 self-adjust to different vessel diameters and/or provide anti-migration benefits. In accordance with some embodiments, the support frame 810 illustrated in FIG. 13C can be placed into a vessel having a diameter of between less than 2 mm and about 8 mm.

For example, when the embodiment of FIG. 13C is placed in a smaller size vessel, the larger support elements 862, 868 can extend longitudinally or axially within the vessel in an oval shape that tracks the inner wall of the vessel (extending in a slanted direction relative to a longitudinal axis of the vessel), while the smaller support elements 860, 864 may be fully expanded into apposition with the vessel wall and oriented generally perpendicularly relative to the longitudinal axis of the vessel. Further, when the embodiment of FIG. 13C is placed in a larger size vessel, the larger support elements 862, 868 will tend to extend more perpendicularly relative to the longitudinal axis of the vessel (more so than in a small vessel) while being fully expanded into apposition with the vessel wall, while the smaller support elements 860, 864 may not tend to provide full contact or engagement with the vessel wall if the expanded diameters of the support elements 860, 864 is less than the internal diameter of the vessel.

Such embodiments can advantageously permit the implant to be used with a range of vessel sizes.

Further, as similarly noted above, the implant 800 can advantageously be used in a greater range of vessel diameters than coil-type implant support frames that extend helically in a single direction. For example, some embodiments, such as that illustrated in FIGS. 12-13C, can be used in vessel diameters between 2 mm and greater than 20 mm. Such a broad range of vessel diameters for a single implant has not been possible using coil-type implant support frames that extend helically in a single direction, due to the limitations of the coil-type support frames.

For example, with some non-coil-type embodiments, such as the implant 800, the ratio of the minimum collapsed profile to the maximum expanded profile (which can be measured in a diameter that circumscribes the collapsed or expanded profile) can be between about 1:20, about 1:18, about 1:16, about 1:15, about 1:14, about 1:13, about 1:12, about 1:11, about 1:10, about 1:9, about 1:8, about 1:7, about 1:6, about 1:5, about 1:4, about 1:3, or about 1:2.

Additionally, due to the exceptional minimum collapsed profile achievable using some non-coil-type embodiments, such as the implant 800, the implant 800 can be fitted into a delivery catheter having a profile of less than about 5 Fr, less than about 4 Fr, less than about 3 Fr, or smaller.

In accordance with some embodiments, the support frame 810 can also be formed using a plurality of support elements 852 that are interconnected with one or more backbone members or axial portions. The backbone members can extend in a longitudinal or axial direction such that the support elements 852 are spaced apart along the longitudinal axis of the support frame 810. Thus, instead of having a pair of wires 830, 832, the support frame 810 can be formed using a series of same-sized or differently sized rings or support elements 852 that are interconnected to each other using backbone members that are welded or otherwise coupled to the adjacent rings to form a cylindrical structure that has a constant diameter (in the case of using support elements that have a common diameter) or a cylindrical structure that has a varying diameter (in the case of using support elements that have different diameters, as in FIG. 12).

The backbone member(s) can extend intermittently on opposing sides of the support elements 852 as shown in FIG. 12) or continuously along a single side of the support elements 852. When the backbone members or axial portions extend intermittently along opposing sides of the support elements 852, as in the case of axial portions 840*a*, 840*b*, the length of the support frame 810 can be longitudinally stretched when positioned onto the support member 802. Accordingly, when expanding from the collapsed configuration, the support elements 852 can be longitudinally drawn towards each other and the outer profile or diameter of the implant 800 can increase. Further, when only a single backbone member or axial portion is used, the support elements 852 can be coupled to the backbone member at positions spaced apart from each other their along. In such embodiments, the support frame 810 may not tend to longitudinally elongate when in the collapsed configuration. However, in either implementation of the backbone member(s), the support elements 852 can be biased towards a position that is substantially orthogonal relative to the backbone member(s). In being "substantially orthogonal," the support element can assume a position that is oriented within about 35° relative to a normal line of a longitudinal axis of a backbone member.

Figure 13B:
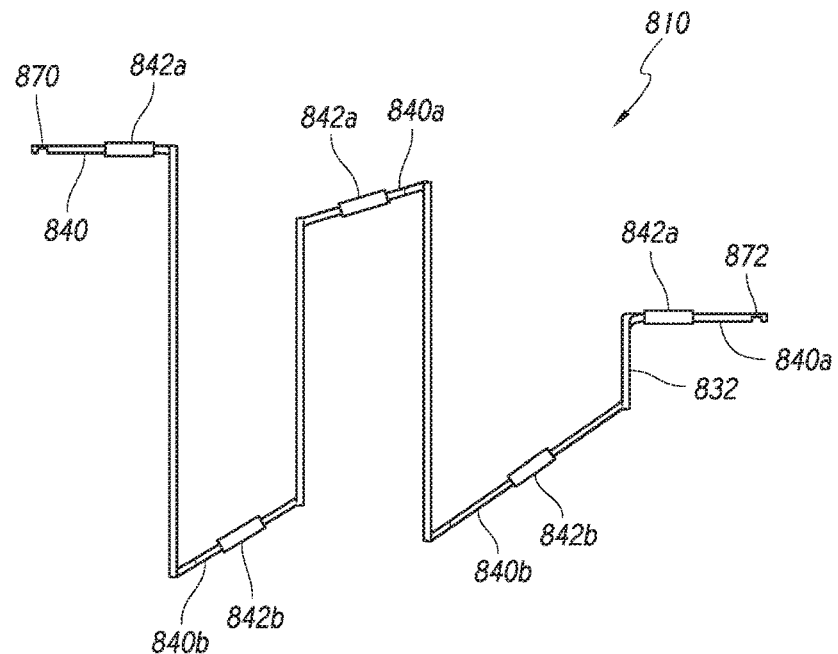
FIG. 13B shows a side view of the implant support frame of FIG. 12, according to some embodiments.
Figure 13C:
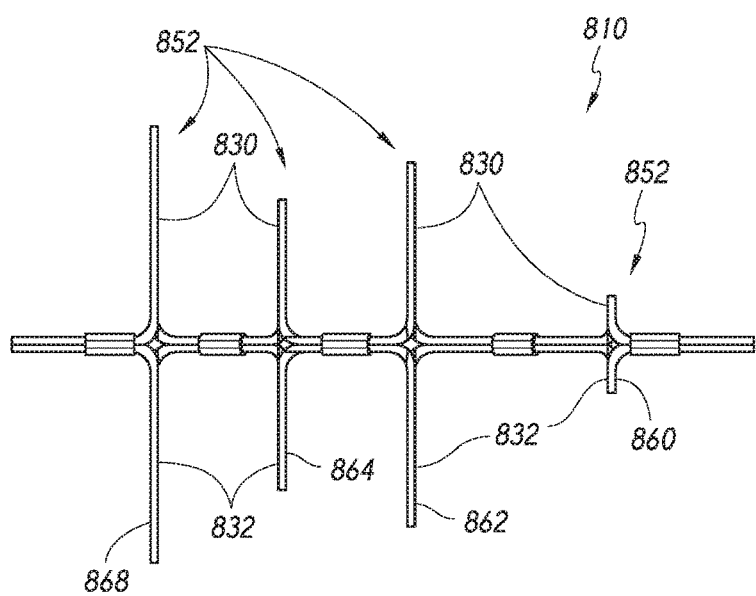
FIG. 13C shows a top view of the implant support frame of FIG. 12, according to some embodiments.

As also illustrated in FIGS. 12 and 13B, the support frame 810 can comprise proximal and distal coupling members 870, 872. The coupling members 870, 872 can be coupled to the wires 830, 832 and be configured to engage with a respective engagement mechanism of the support member 802.

For example, FIG. 14 shows a partial side view of a proximal engagement mechanism 880 for engaging and supporting the implant support frame 810 on the support member 802, according to some embodiments. As shown, the proximal engagement mechanism 880 of the support member 802 can comprise a protrusion 882 configured to engage with the proximal coupling member 870 of the support frame 810. Further, the system can also be configured such that the support member 802 comprises a distal engagement mechanism 884 having a protrusion 886 configured to engage with the distal coupling member 872 of the support frame 810. These features are illustrated in FIGS. 15A-15B, which show enlarged, partial side views of the proximal and distal engagement mechanisms 880, 884 for supporting the implant support frame 810 on the support member 802, according to some embodiments.

As illustrated, the protrusions 882, 886 can comprise a notch into which a corresponding protrusion of the proximal and distal coupling members 870, 872 can be fitted in order to restrict longitudinal or axial movement of the coupling members 870, 872 relative to the proximal and distal engagement mechanisms 880, 884. Accordingly, when engaged, the support frame can be drawn or stretched along the implant support section 822 of the support member 802.

In some embodiments, the protrusions 882, 886 of the proximal and distal engagement mechanisms 880, 884 can be formed on the support member 802. For example, the protrusions 882, 886 can be formed as radial notches in the support member 802 or as depressions in an outer surface of the support member 802. The proximal and distal engagement mechanisms 880, 884 also be attached or coupled to the support member 802, such as by welding or adhesive means.

Furthermore, in some embodiments, as shown in FIG. 14, the proximal and distal engagement mechanisms 880, 884 can be formed as notches in an elongate wire, which create the protrusions 882, 886. For example, an elongate wire 888 can extend through a lumen 889 of the support member 802 and comprise the protrusions 882, 886 that form the proximal and distal engagement mechanisms 880, 884.

Although in some embodiments, the proximal and distal engagement mechanisms 880, 884 can remain at a fixed longitudinal position relative to the support member 802, the proximal and distal engagement mechanisms 880, 884 can also be moved relative to the support member 802 in order to facilitate engagement or disengagement of the support frame 810 to or from the proximal and distal engagement mechanisms 880, 884.

The proximal and distal coupling members 870, 872 can be releasably engaged by the protrusions 882, 886. In some embodiments, the engagement can be substantially only a mechanical engagement, while in other embodiments, release of the engagement can be actuated by overcoming an adhesive. Further, the proximal and distal coupling members 870, 872 can be continuous with the protrusions 882, 886, such that an electrolytic detachment mechanism can be used to break the connection between the support member 802 and the support frame 810.

Further, in some embodiments, the distal coupling member 872 can be releasably engaged with the protrusion 886 to form a locking mechanism that is engaged only when the distal coupling member 872 and the protrusion 886 are disposed within a lumen of a catheter 890, as illustrated in FIG. 14. A wall of the catheter 890 can radially constrained the distal coupling member 872 against the protrusion 886, thereby preventing this engagement between the distal coupling member 872 and the protrusion 886. The same principle can be effective in maintaining and removing an engagement between the proximal coupling member 870 and the protrusion 882. Thus, the proximal and distal engagement mechanisms 880, 884 can be sized such that when fitted within a lumen 892 of the catheter 890 and when engaged with the proximal and distal coupling members 870, 872, the proximal and distal coupling members are radially and longitudinally constrained such that the support frame 810 is maintained in an engaged state.

Additionally, in some embodiments, the proximal and distal ends of the implant 800 can be engaged using the engagement mechanisms illustrated in discussed with regard to FIGS. 1A-1B.

However, when the distal engagement mechanism 884 exits the lumen 892, the distal coupling member 872 will radially shift and expand to disengage from the distal engagement mechanism 884, thus permitting a distal end of the support frame 810 to begin to expand within the vessel. This process is illustrated in FIGS. 16A-16D.

Additionally, in embodiments using a mechanical locking mechanism, in order to assemble the support frame 810 with the support member 802, the support member 802 can be positioned within a guide catheter 890 such that the support section 822 of the support member 802 is positioned distally beyond a distal end of the guide catheter 890. In this position, the proximal engagement mechanism 880 can be engaged with the proximal coupling member 870 and the support member 802 can then be drawn proximally into the lumen 892 of the catheter 890, thereby radially constrained the proximal engagement mechanism 880 with the proximal coupling member 870, which also longitudinally constrains relative movement of the proximal engagement mechanism 880 relative to the proximal coupling member 870. When completed, the support member 802 can be further proximally withdrawn into and relative to the catheter 890 until the distal engagement mechanism 884 and the distal coupling member 872 are positioned adjacent to a distal end of the catheter 890. At that point, the distal engagement mechanism 884 and the distal coupling member 872 can be aligned or engaged with each other and the support member 802 can be further proximally withdrawn into and relative to the catheter 890 until the distal engagement mechanism 884 is fully received within the lumen 892 of the catheter 890. Thereafter, the assembly can be used.

Furthermore, the membrane 812 can be positioned on top of the support member 802 prior to placing the support frame 810 onto the support member 802 or drawn or pulled under the support frame 810 all the support frame is initially engaged or fitted over the support member 802, in a manner similar to that disclosed in co-pending U.S. patent application Ser. No. 14/044,794, filed on Oct. 2, 2013, the entirety of which is Incorporated herein by reference.

Figure 16A:
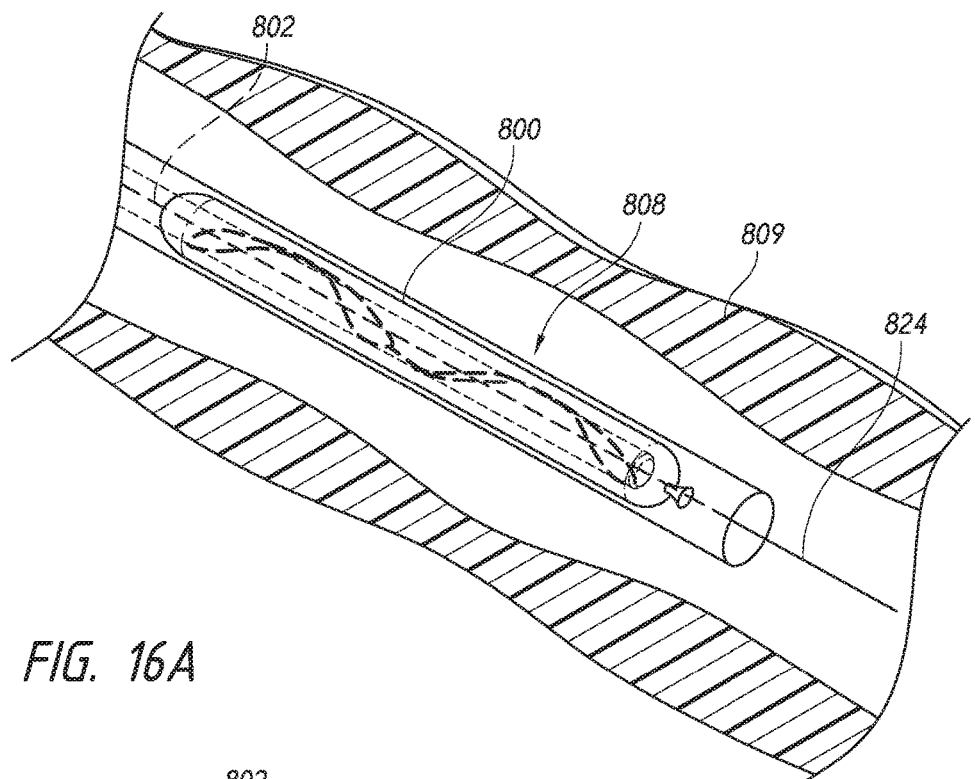
FIGS. 16A-16D show perspective views of stages in which an implant carrier assembly releases an implant into a body lumen, according to some embodiments.

FIGS. 16A-16D show perspective views of stages in which an implant carrier assembly 808 releases the implant 800 into a body lumen 896, according to some embodiments. In FIG. 16A, the assembly 808 is advanced over a guide wire 824 to a target area within a vessel 809. The use of an OTW delivery mechanism can allow the assembly 808 to be more steerable and controllable. The guide wire 824 can comprise a diameter of between about 0.010 inches and about 0.025 inches, and in some embodiments, between about 0.013 inches and about 0.018 inches. Such sizes can facilitate the use of a smaller profile catheter and assembly, such as 5 Fr, 4 Fr, 3 Fr, or smaller.

Figure 16B:
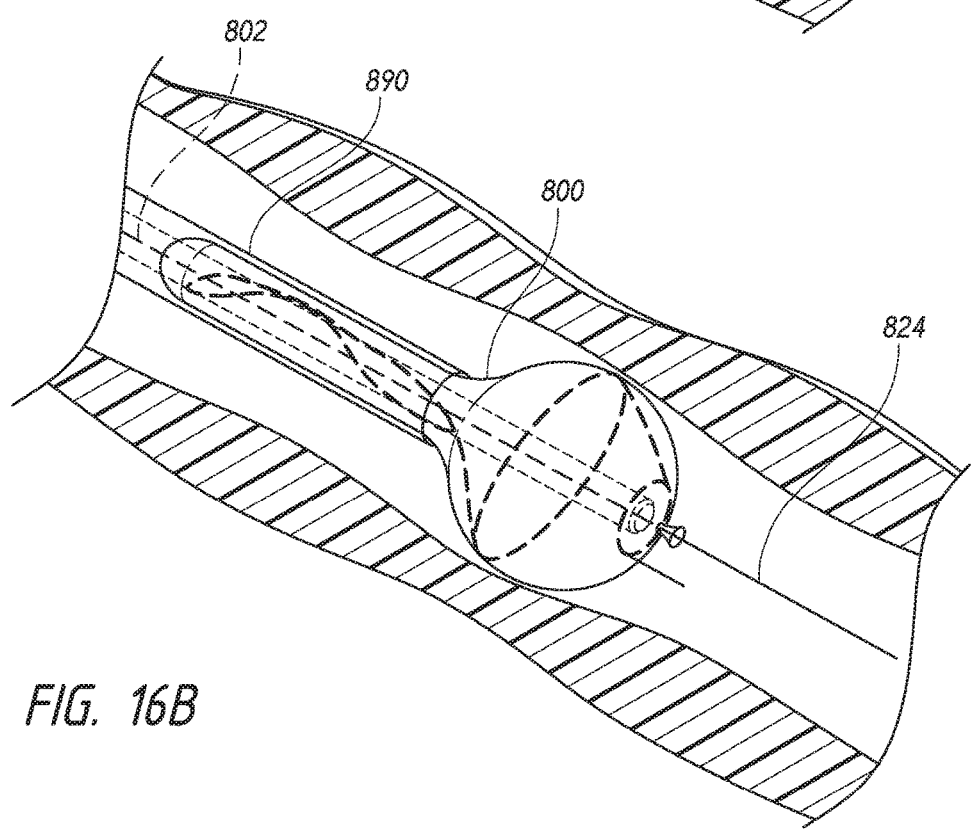

Once in position, the catheter 890 and the support member 802 can be moved relative to each other such that the support member 802 begins to exit the distal end of the catheter 890, thereby allowing the distal engagement mechanism 884 to disengage from the distal coupling member 872. Once this occurs, the distal end of the implant 800 begins to expand, as illustrated in FIG. 16B.

Thereafter, as the catheter 890 continues to be withdrawn or proximally, the implant 800 continues to expand and contact the wall of the vessel 809. As this occurs, the support elements 852 urge the membrane 812 into contact with the vessel wall.

Should the placement of the implant 800 be undesirable, prior to releasing a proximal end of the implant 800, the implant 800 can be proximally withdrawn into the catheter 890 by urging the catheter 890 distally over the implant 800, thereby causing the implant 800 to be radially collapsed and pulled into or within the catheter 890. Thereafter, the implant 800 can be repositioned and a distal end of the implant 800 can be re-released. Once the positioning of the implant 800 is verified, the proximal end of the implant 800 can be released from the assembly 808.

Figure 16C:
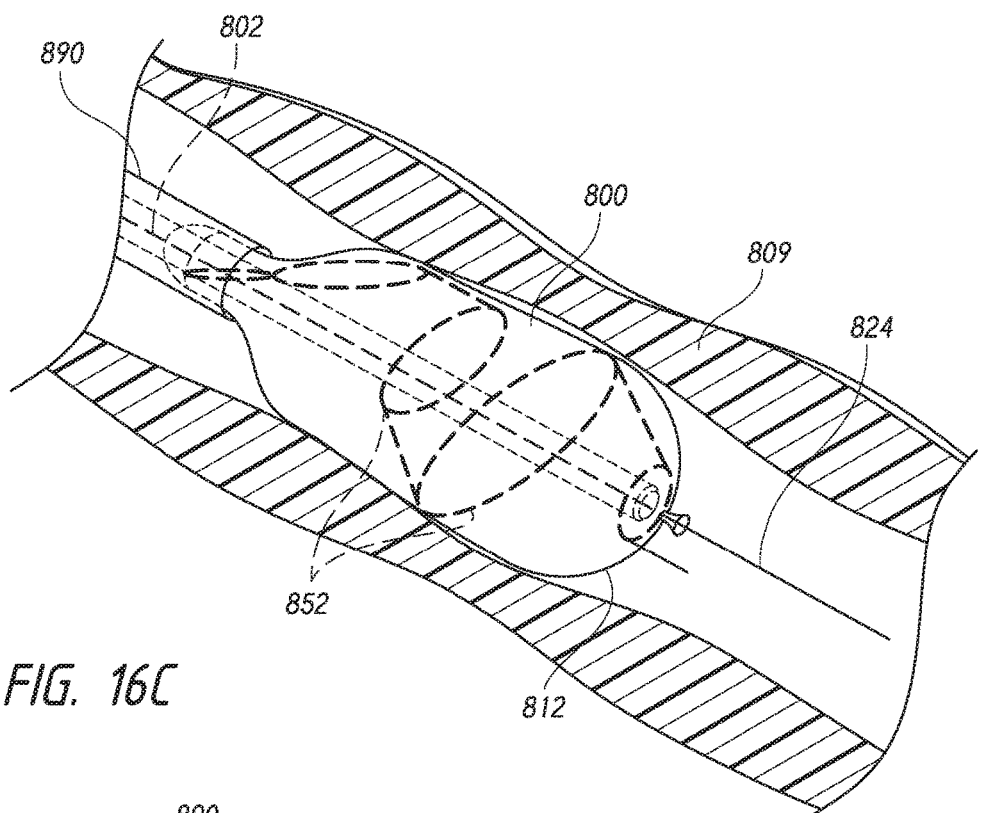
Figure 16D:
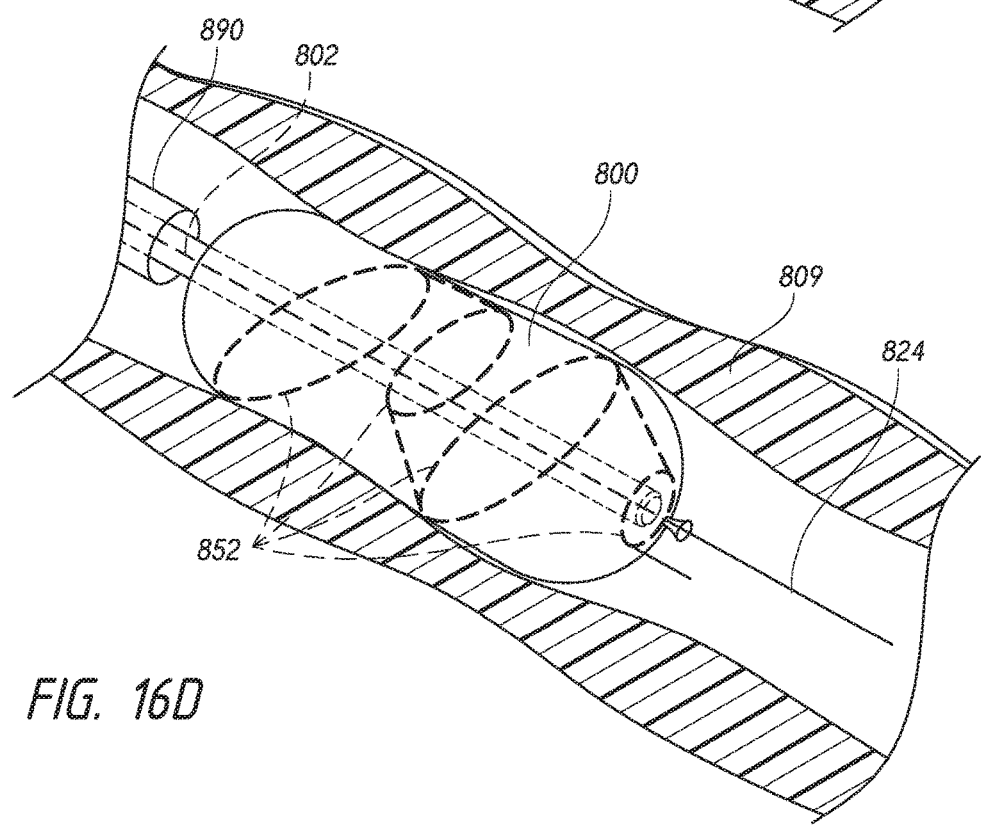

As shown in FIGS. 16C-16D, some of the support elements 852 may be larger in diameter or profile than the inner diameter of the vessel. As such, when the implant is released, as shown in FIG. 16D (when the proximal engagement mechanism 880 becomes disengage from the proximal coupling member 870 as the catheter 890 is retracted proximally of the proximal end of the implant 800), one or more of the support members 852 can be engaged with a sidewall of the vessel 809 such that the implant 800 is longitudinally engaged within the vessel 809.

Figure 17:
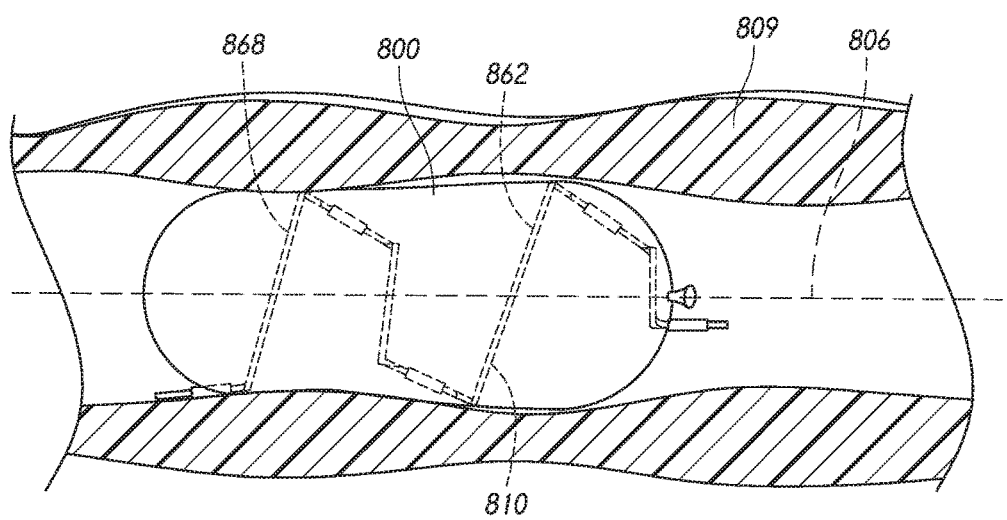
FIG. 17 shows a side view of the implant of FIG. 16D released into the body lumen, according to some embodiments.

As shown in FIGS. 16D and 17, in some embodiments, one or more of the support members (shown as support members 862 and 868) can be slanted relative to a longitudinal axis 806 of the vessel 809. This orientation of the support members 862 and 868 can tend to cause the implant support frame 810 to be positioned in a stressed or tensioned state within the vessel 809, thus tending to provide an anti-migration effect for the implant 800.

In accordance with some embodiments, the implant 800 can also comprise a valve mechanism that permits the guide wire 824 to be passed therethrough while the assembly 808 is advanced to the target region. However, in some implementations, the guide wire a toy four can be removed after the assembly 808 reaches the target region. Thereafter, the valve mechanism of the implant 800 can allow the distal end of the implant 800 to close and occlude flow when the implant 800 is released into the vessel 809. Further, the implant 800 can be used with a valve or cover component in a manner suitable for deploying an embolic material to a target region, such as for cancer therapy, as disclosed in copending U.S. patent application Ser. No. 14/101,171, filed Dec. 9, 2013, the entirety of which is incorporated herein by reference.

In accordance with some embodiments, a medical implant 900 can form a frame including one or more dual wire loop features. A dual wire loop feature can be formed by using one or more individual wires that are shaped to form a partial coil For example, two separate wires 910, 912 can be configured to have opposite (clockwise and counterclockwise) directions of winding, and the separate wires 910, 912 can be connected to form full loops.

Figure 18A:
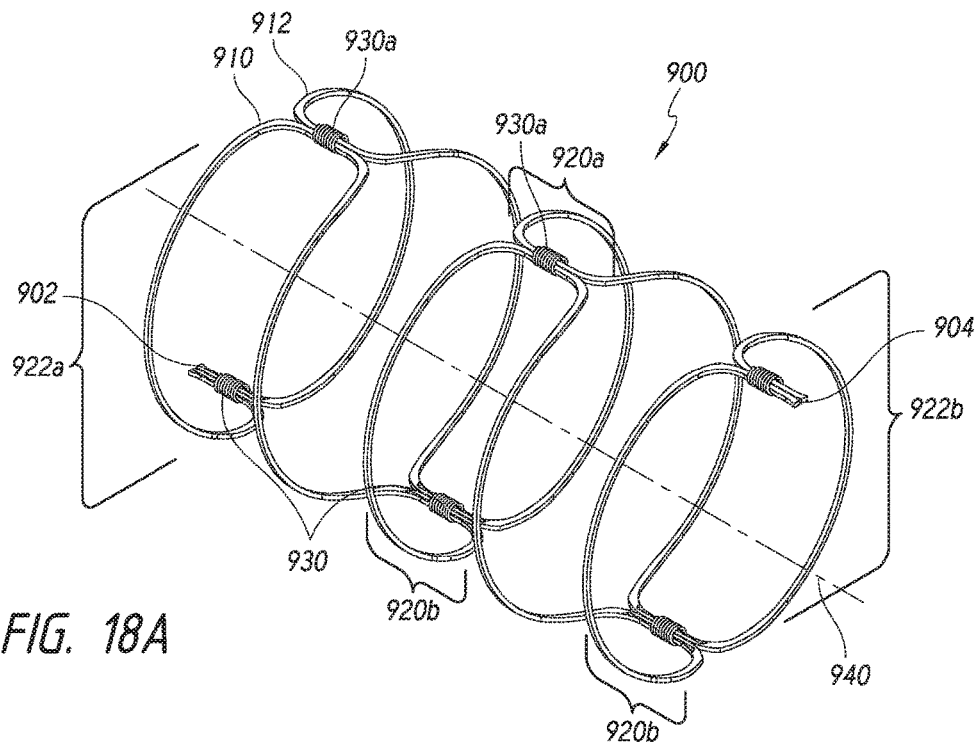
FIG. 18A shows a perspective view of a frame with wires joined by connectors, deployed configuration, according to some embodiments.

In some embodiments, the separate wires 910, 912 can be generally mirror images of each other along a longitudinal center plane (extending through the central axis 940) of the frame 900, as illustrated in FIG. 18A. The wires 910, 912 extend from a first end 902 to a second and 904 of the frame 900. Additional wires (e.g., 3, 4, or more wires) may be coupled together as disclosed herein.

Figure 18B:
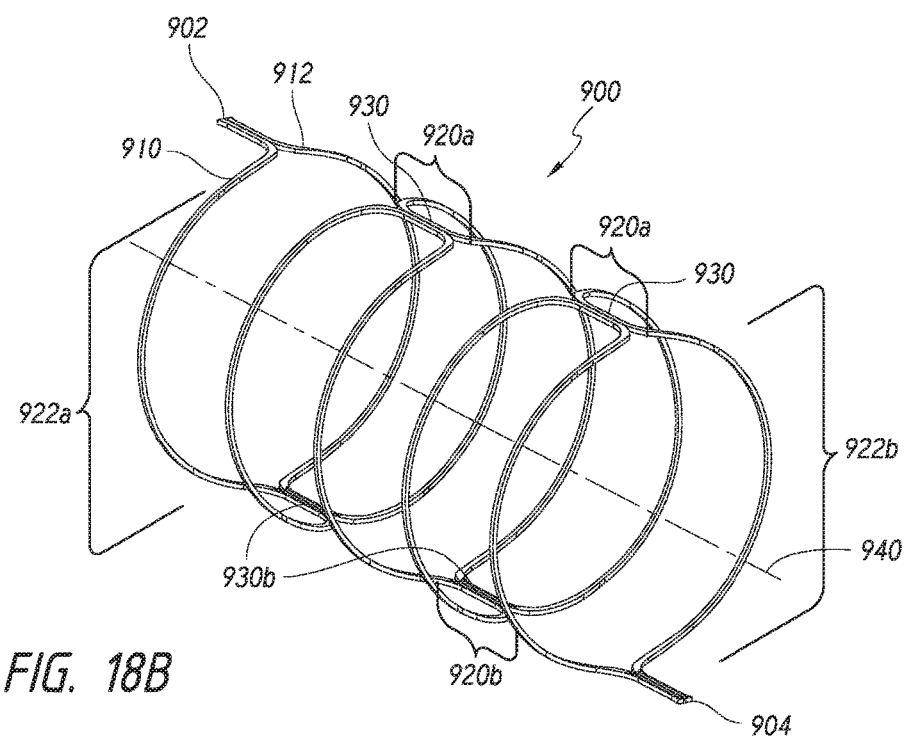
FIG. 18B shows a perspective view of a frame with wires joined at connection locations, according to some embodiments.
Figure 18C:
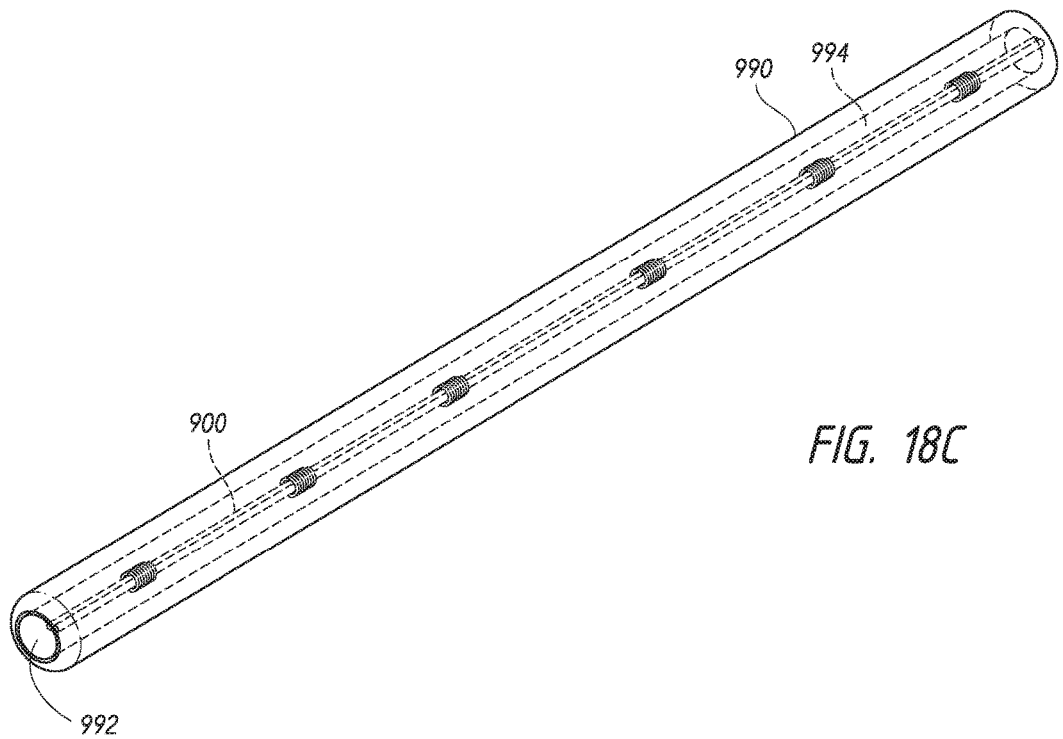
FIG. 18C shows a perspective view of a frame in a compressed state within a deliver catheter, according to some embodiments.

The wires 910, 912 may extend axially along axial portions 920a and 920b. The axial portions 920a may be radially opposite the axial portions 920b across the central axis 940. Along the axial portions 920a, 920b, the wires 910, 912 may be adjacent and/or contacting. The wires 910, 912 may be joined or coupled together with connectors 930a at the axial portions 920a and with connectors 930b at the axial portions 920b. As shown in FIG. 18A, the connectors 930a, 930b may be bands, cuffs, rings, clips, coil windings, combinations thereof, and the like. As shown in FIG. 18B, the connectors 930a, 930b may be adhesive, glue, welding, combinations thereof, and the like. The connectors 930a, 930b may be radiopaque for visualization.

The wires 910, 912 may extend circumferentially along circumferential portions 922a and 922b. The circumferential portions 922a may be radially opposite the circumferential portions 922b across or about the central axis 940. Each of the circumferential portions 922a, 922b may extend from an axial portion 920a to an axial portion 920b, radially opposite the axial portion 920a. The axial portions 920a, 920b between which a single circumferential portion 922a or 922b extends may be axially displaced relative to each other. Each wire 910, 912 may extend entirely on a respective radial side of the frame 900. Each circumferential portion 922a or 922b may extend along at least a portion of a cylindrical path in a clockwise circumferential direction toward a given axial portion 920a or 920b, and each circumferential portion 922a or 922b may extend along at least a portion of the cylindrical path in a counterclockwise circumferential direction away from the given axial portion 920a or 920b. Each wire 910, 912 may contact all or less than all of the connectors 930a, 930b.

Thus, the interconnections of the separate wires 910, 912 can lie substantially in a common plane. However, the separate wires 910, 912 can also form interconnections that are not mirror images or that do not lie in a common plane. For example, in embodiments in which the frame 900 defines a generally tubular shape, the interconnections can be located at different and varied circumferential locations. For example, the interconnections can be distributed across one, two, three, four, five, or more circumferential locations. The pattern can be a repeating pattern or randomized, which can provide a desired flexibility or strength characteristics for the frame.

Additionally, the separate wires 910, 912 can be of a common gauge or can have different gauges, in order to impart a desired strength characteristics.

Figure 18D:
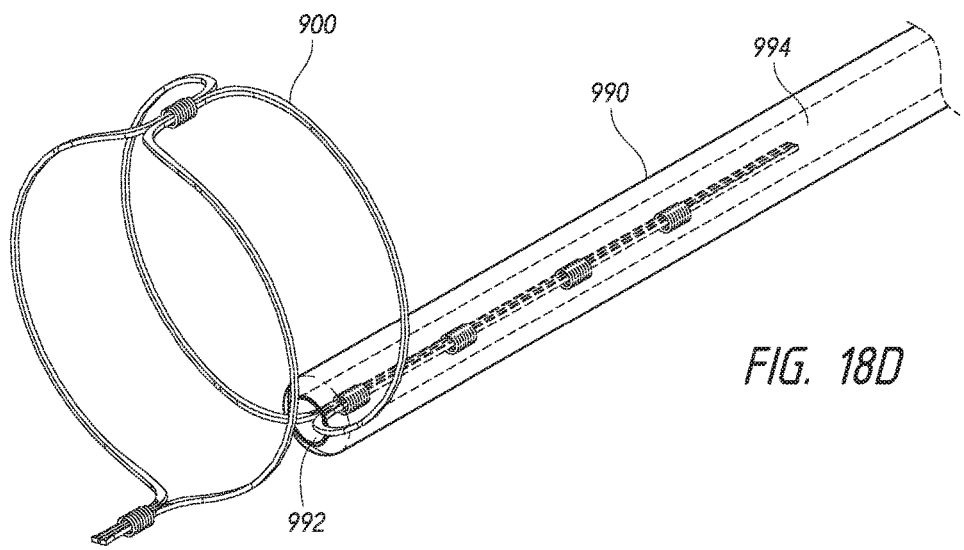
FIG. 18D shows a perspective view of a frame partially expanded from a delivery catheter, according to some embodiments.

Additionally, as illustrated above and in FIG. 18C, as with various embodiments discussed herein, a frame 900 having dual wire loop features can be held in a generally linear or straight configuration within a lumen 994 of a catheter 990. For example, ends 902, 904 of the frame 900 can be pulled or separated which can create tension between the ends 902, 904 to allow the frame 900, when deployed, to return an expanded shape consisting of one or more loops, as illustrated in FIG. 18D, as the frame 900 exits from a distal end 992 of the catheter 990.

In accordance with some embodiments, the medical implant can comprise a frame 1010 that incorporates a fibrous membrane feature. The fibrous membrane feature can be implemented using one or more filaments 1030 and/or membranes 1060 that extend between one or more engagement members of the frame 1010. The fibrous membrane 1060 can be porous or comprise one or more portions that are nonporous, such as impermeable occlusive structures or other such sections. The engagement members can be configured as holes, apertures, slits, protrusions, cavities, adhesive connections, or other features that allow interconnection with one or more filaments.

Figure 19A:
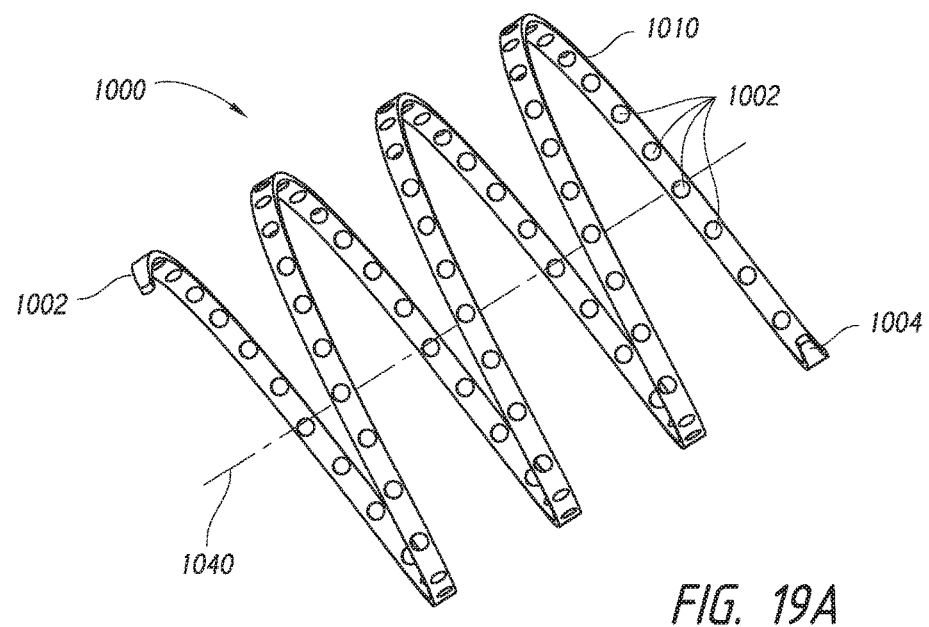
FIG. 19A shows a perspective view of a frame having holes for securing a fibrous membrane, according to some embodiments.
Figure 19B:
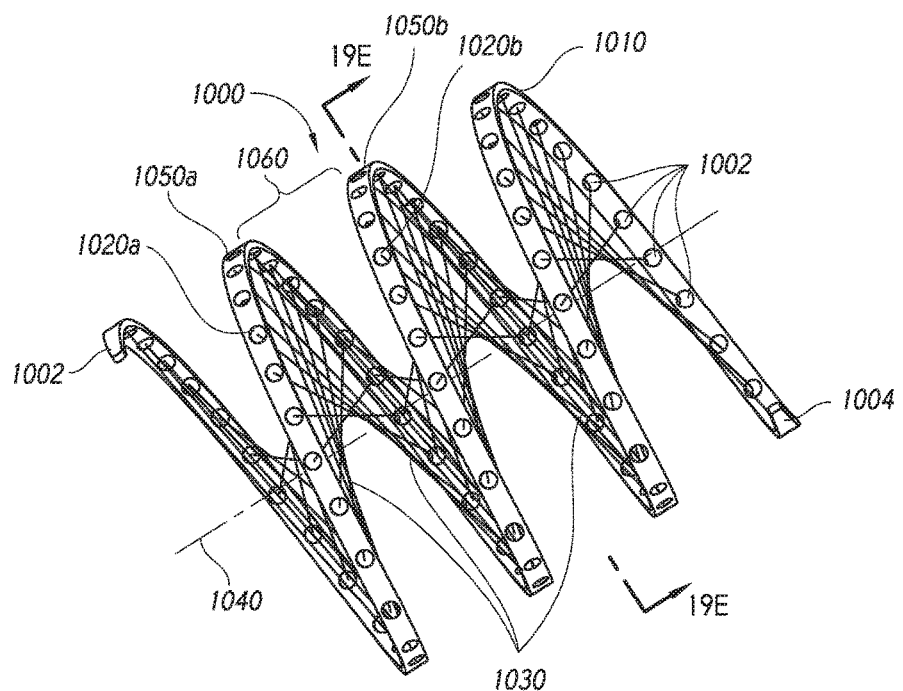
FIG. 19B shows a perspective view of a frame having holes securing a fibrous membrane, according to some embodiments.

In accordance with some embodiments, FIG. 19A illustrates a frame 1010 with a plurality of holes 1020 for attachment of filaments, a fibrous membrane, or a patch. In accordance with some embodiments, FIG. 19B illustrates a frame 1010 with a representative fibrous membrane 1060 over, across, or within a center region of the frame 1010. The fibrous membrane 1060 can be configured such that blood flow through the central luminal opening of the frame 1010 is obstructed or occluded. As illustrated, in some embodiments, the holes 1020 can be provided along a helical pathway defined by the frame 110. The holes 1020 can extend radially through the frame 1010. The membrane 1060 may provide a net-like, fibrous, or elastic patch to be constructed.

For example, the frame 1010 can comprise a fibrous membrane 1060 having one or more filaments 1030 that are interconnected between apertures or holes 1020 in the frame 1010. In accordance with some embodiments, a flat coil frame 1010 can be provided that comprises a plurality of holes 1020 extending along the length of the frame 1010. The plurality of holes 1020 can be used to interconnect with a plurality of fibers 1030 or aspects of a membrane 1060 or cover, as illustrated in FIG. 19B.

From a hole 1020a, a filament 1030 may extend to another hole 1020b. The holes 1020a, 1020b may be axially displaced relative to each other. For example, the holes 1020a, 1020b may be disposed on separate helical turns 1050a and 1050b of the frame 1010. The separate turns 1050a, 1050b may be axially adjacent or separated by yet other helical turns of the frame 1010. As shown in FIG. 19B, the filament 1030 may alternate between holes 1020a of the first turn 1050a and the holes 1020b of the second turn 1050b. Each filament 1030 may be woven through holes 1020 of multiple turns (e.g., in an alternating over-under pattern) in a first direction and woven through the same or different holes 1020 of the multiple turns in a second direction.

The holes 1020a, 1020b may have a common circumferential location, regardless of axial location. For example, the filament 1030 may extend axially between the holes 1020a, 1020b in a direction that is parallel to the central axis 1040. Alternatively, the holes 1020a, 1020b may have different circumferential locations. Accordingly, the filament 1030 may extend helically or non-axially between the holes 1020a, 1020b.

According to some embodiments, the fibrous membrane or patch 1060 can extend along only an axial portion of the frame 1010. For example, the fibrous membrane or patch can extend along a central axial portion, a distal axial portion, and/or a proximal axial portion of the frame 1010, which can be determined based on the application and in response to the vessel geometry. However, in some embodiments, the fibrous membrane or patch 1060 can be configured to extend along the entire axial length of the frame 1010.

Figure 19C:
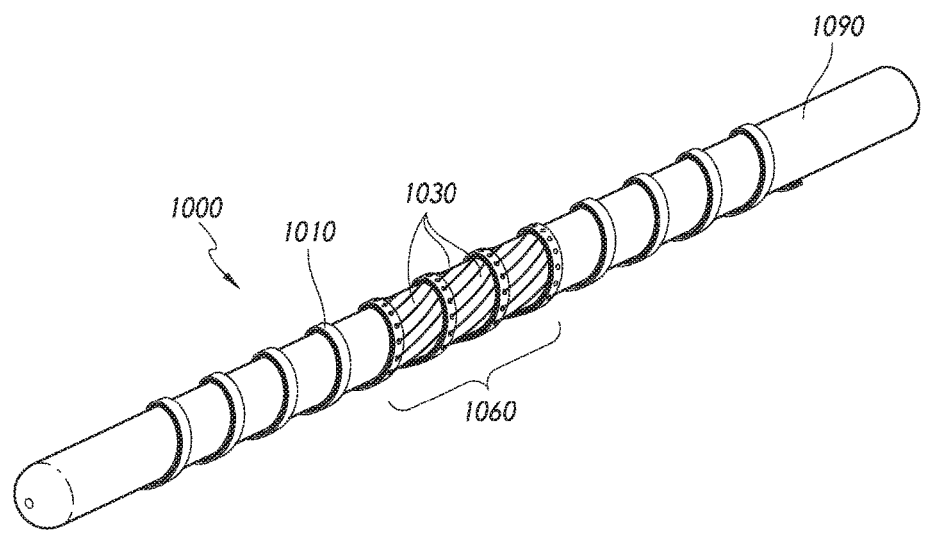
FIG. 19C shows a perspective view of a frame on a delivery device, the frame having a fibrous membrane, according to some embodiments.
Figure 19D:
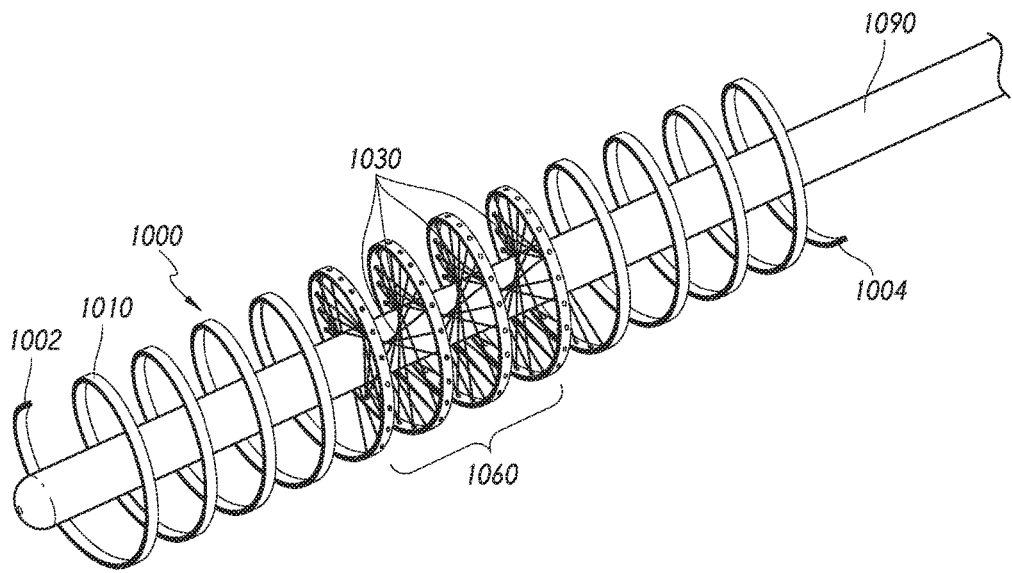
FIG. 19D shows a perspective view of a frame expanded from a delivery device, the frame having a fibrous membrane, according to some embodiments.

FIG. 19C illustrates a delivery device 1090 on which a frame 1010 having a fibrous membrane or patch 1060 prior to delivery is loaded for delivery in a collapsed or delivery configuration. FIG. 19D is a perspective view of the frame 1010 shown in FIG. 19C, in which the frame 1010 has moved to an expanded state. In the expanded state, the fibrous membrane or patch 1060 is shown as being positioned in an axially central region of frame 1010. However, the fibrous membrane or patch 1060 can be positioned along any axial length or location of the expanded frame 1010, as discussed above.

Figure 19E:
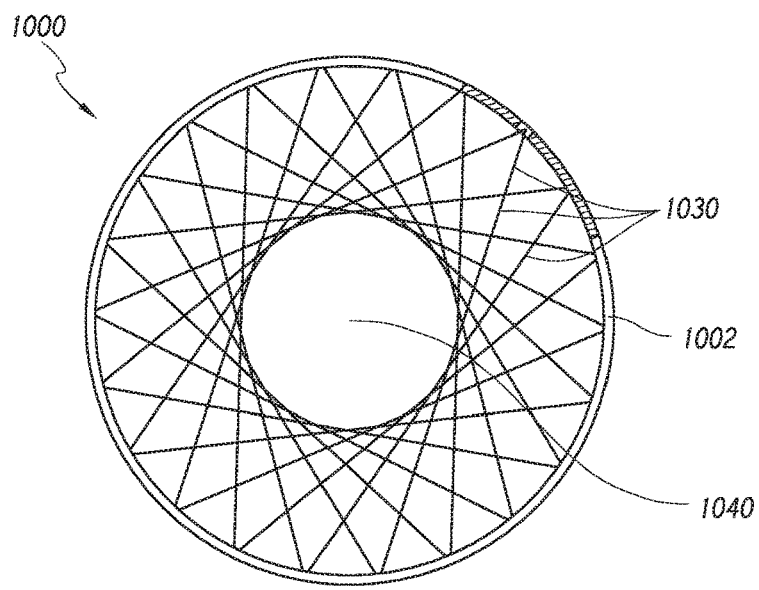
FIG. 19E shows a cross-sectional view of the frame of FIG. 12B, the frame having a fibrous membrane, according to some embodiments.
Figure 19F:
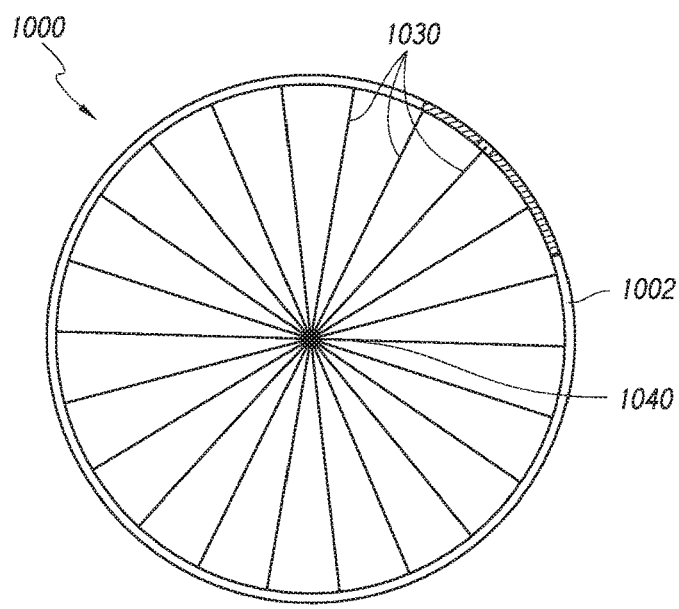
FIG. 19F shows a cross-sectional view of the frame of FIG. 12B, the frame having a fibrous membrane, according to some embodiments.

FIGS. 19E-19F illustrate cross-sectional end views of frames 1010, each having a fibrous membrane or patch 1060 with the respective frame 1010 in an expanded state. In the expanded state, the filaments 1030, or segments thereof, of the fibrous membrane or patch 1060 are shown as extending across a lumen of the frame 1010 from one aperture or hole 1020 to another aperture or hole 1020. In some embodiments, as shown in FIG. 19E, the filaments 1030 can extend across the lumen without passing through a central axis 1040. The remaining opening at and around the central axis 1040 may receive the delivery device 1090. In some embodiments, as shown in FIG. 19F, the filaments 1030 can extend across the lumen by passing through a central axis 1040. For example, each of the filaments 1030 can extend from one aperture or hole 1020 to a radially opposite aperture or hole 1020. In some embodiments, some of the filaments 1030 pass through the central axis 1040 and others of the filaments 1030 do not pass through the central axis 1040.

Figure 20A:
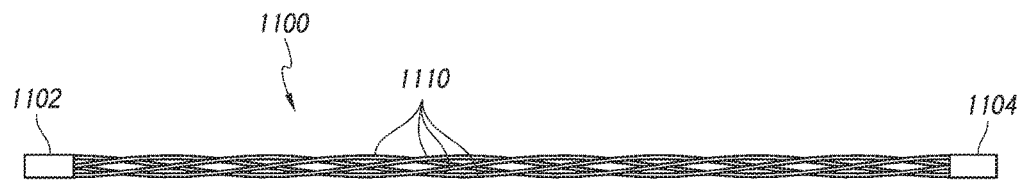
FIG. 20A shows a side view of an implant in a compressed state, according to some embodiments.
Figure 20B:
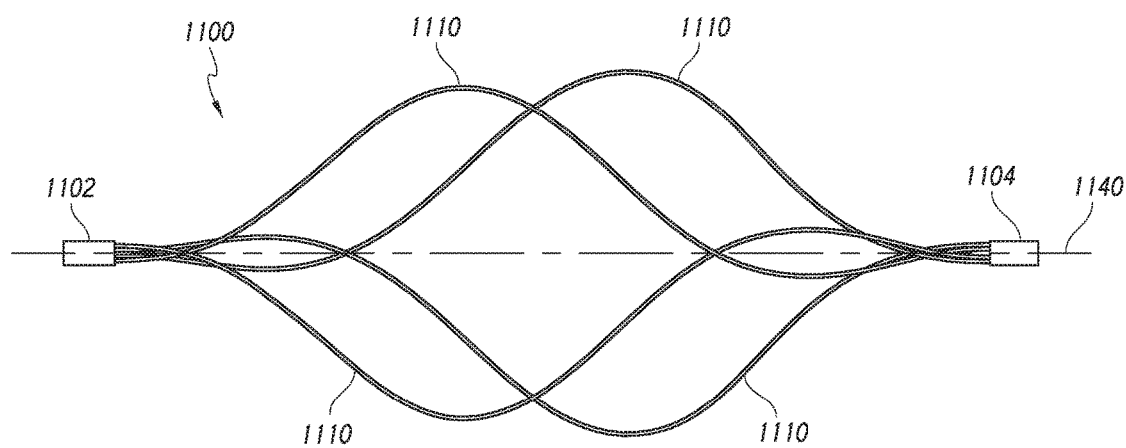
FIG. 20B shows a side view of an implant in a partially expanded state, according to some embodiments.
Figure 20C:
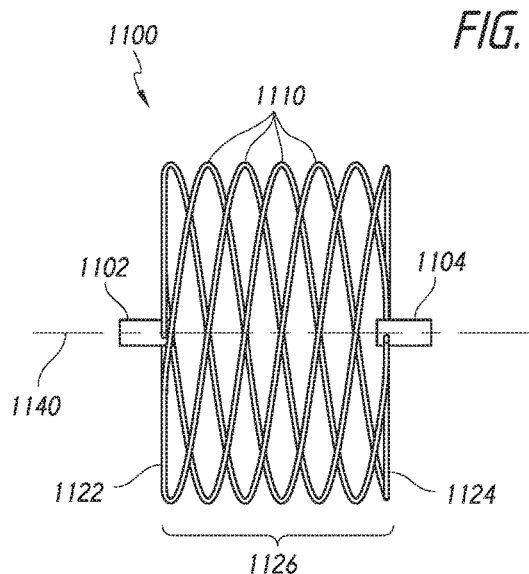
FIG. 20C shows a side view of an implant in an expanded state, according to some embodiments.

In accordance with some embodiments, FIGS. 20A-20D illustrate an implant 1100 including a plurality of filaments 1110 extending helically between a first end member 1102 and a second end member 1104. FIG. 20A illustrates the implant 1100 in a straight or linear configuration. FIG. 20B illustrates the implant 1100 in a partially expanded state. FIG. 20C illustrates the implant 1100 in a fully expanded state.

Figure 20D:
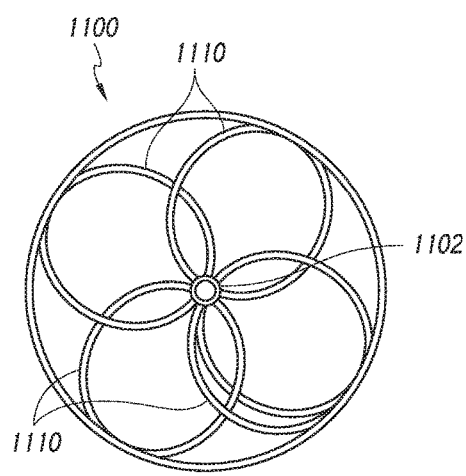
FIG. 20D shows front view of an implant in an expanded state, according to some embodiments.

Multiple filaments 1110 can be shaped in a coil or helical configuration. As shown in FIG. 20C, the filaments 1110 may be equally spaced axially along a length of the implant 1100. Likewise, as shown in FIG. 20D, the filaments 1110 may be equally spaced circumferentially about an outer circumference of the implants 1100. All of the filaments 1110 can be coiled in the same direction (e.g., clockwise).

The filaments 1110 may define a first (e.g., proximal) face 1122 near the first end member 1102, and a second (e.g., distal) face 1124 near the second end member 1104. One or both of the first and second faces 1122, 1124 may define a surface that is transverse (e.g., orthogonal) to the central axis 1140. Alternatively, one or both of the first and second faces 1122, 1124 may define a surface that is hemispherical, conical, frustoconical, concave, convex, combinations thereof, and the like.

In the expanded state, the filaments 1110 can define a substantially cylindrical profile in a middle region 1126 between the end members 1102, 1104, as shown in FIGS. 20C-20D. The middle region 1126 can define one or more other profiles, such as conical, frustoconical, curved, or tapering without departing from the scope of the subject technology. For example, the middle region 1126 may be designed to conform to a wall of a blood vessel 1199 when expanded therein.

The first end member 1102 may be axially opposite the second end member 1104 along an axis 1140. The end members 1102, 1104 may be of a radiopaque material or may include a separate component (not shown) being of a radiopaque material, for visualization during a procedure.

The filaments 1110 can extend helically between the end members 1102, 1104. The filaments 1110 can be fixed to the end members 1102, 1104 by attachment (e.g., welding). The filaments 1110 can be integrally formed with the end members 1102, 1104. For example, the filaments 1110 and the end members 1102, 1104 may all be cut from a single tube, rather than assembling from separate components.

As the implant 1100 transitions from a compressed state (as shown in FIG. 20A) to an expanded state (as shown in FIG. 20C), the end members 1102, 1104 move axially toward each other, such that the implant 1100 foreshortens axially. As the implant 1100 transitions from the compressed state to the expanded state, the filaments 1110 expand radially. The implant 1100 allows for decreased length in the expanded state, while maintaining several turns of the filaments 1110 in the expanded form.

In accordance with some embodiments, as shown in FIGS. 21A-21E, a non-permeable cover 1150 may be attached to one or both of the end members 1102, 1104 to provide occlusion in a blood vessel 1199. The cover 1150 can extend from one or both of the end members 1102, 1104 over a middle portion of the implant 1100. The cover 1150 may be a silicone tube fit tightly around the collapsed construct, which stretches to expand with the coil. Alternatively, the cover 1150 may be ePTFE that can be mechanically attached to each end member 1102, 1104 of the implant 1100, and has a diameter that fits tightly around the expanded diameter of the filaments 1110. The cover 1150 may be on an external surface of the filaments 1110, on an internal surface of the filaments 1110, or a combination of the internal and external surfaces of the filaments 1110.

Figure 21A:
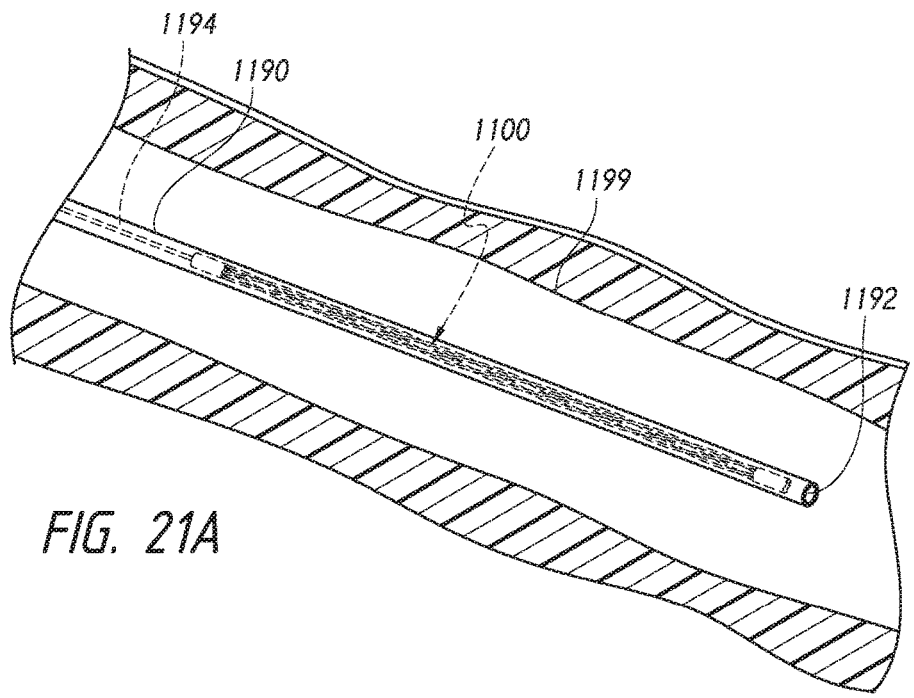
FIG. 21A shows a perspective view of an implant in a compressed state in a catheter within a vessel, according to some embodiments.
Figure 21B:
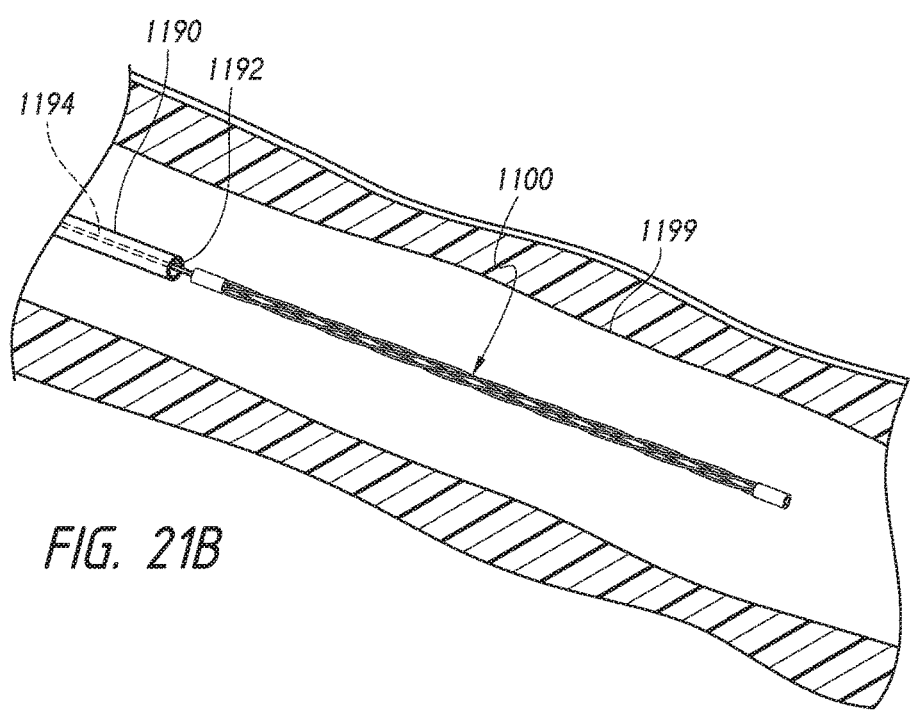
FIG. 21B shows a perspective view of an implant advanced out of a catheter and within a vessel, according to some embodiments.
Figure 21C:
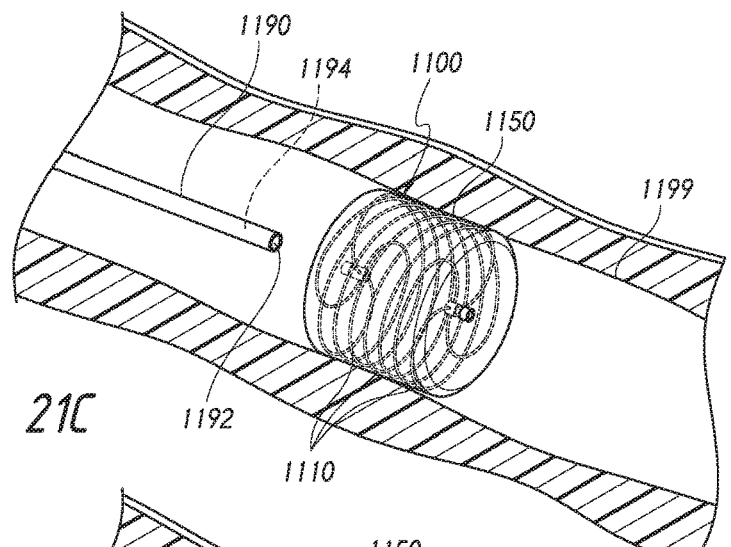
FIG. 21C shows a perspective view of an implant in an expanded state within a vessel, according to some embodiments.
Figure 21D:
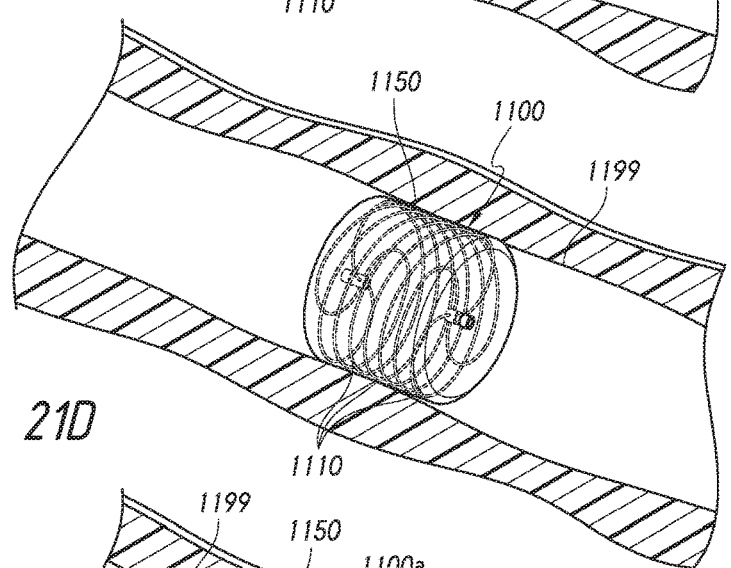
FIG. 21D shows a perspective view of an implant in an expanded state within a vessel, according to some embodiments.

In accordance with some embodiments, as shown in FIGS. 21A-21E, the implant 1100 may be shape-set in the expanded state, and pulled into a lumen 1194 of a catheter 1190 to collapse to the compressed state. As shown in FIG. 21A, the catheter 1190 containing the implant 1100 is be provided to a site within a vessel 1199. As shown in FIG. 21B, the implant 1100 is advanced relative to the catheter 1190, such that the implant 1100 exits from the lumen 1194 of the catheter 1190 through a port 1192 at a distal end of the catheter 1190. As shown in FIG. 21C, the implant 1100 expands from a compressed state to an expanded state upon exiting the catheter 1190. In the expanded state, the filaments 1110 of the implant 1100 holds a portion of the cover 1150 against a wall of the vessel 1199. As shown in FIG. 21D, the catheter 1190 may be withdrawn after expansion of the implant 1100.

Figure 21E:
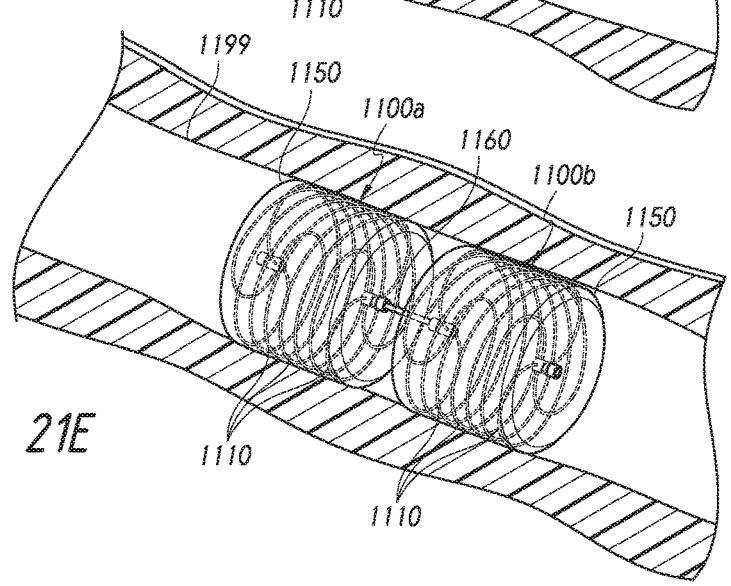
FIG. 21E shows a perspective view of a dual-section implant in an expanded state within a vessel, according to some embodiments.

In accordance with some embodiments, as shown in FIG. 21E, the first implant 1100a and a second implant 1100b may be connected by a connector 1160. Each of the implants 1100a, 1100b may be constructed substantially as disclosed herein. The connector 1160 may attach or extend through axially adjacent end members of the implants 1100a, 1100b. The implants 1100a, 1100b may be connected prior to, during, or after delivery thereof, or the implants 1100a, 1100b may be separately delivered and attached by connector 1160 in situ.

In accordance with some embodiments, as shown in FIGS. 21A-21E, the implant 1100 may contain a wire 1180 fixedly attached to one of the end members 1102, 1104. The wire 1180 may be configured to slide through an opening of the other of the end members 1102, 1104. For example, the wire 1180 may be configured such that it snaps into the proximal end member 1102 when pulled or pushed to the fully expanded position. The wire 1180 may act as a pusher for the implant 1100. The wire 1180 may require action by the user to push or pull the wire 1180, causing the compression and expansion of the implant 1100. Opposite motion with the wire 1180 would allow collapse, readjustment of position, or removal.

In accordance with some embodiments, the implant 1100 may contain a wire 1180 through the center that can be attached to the distal end member 1104, and slides through the proximal end member 1102. The implant 1100 would be shape-set to the expanded state. The implant 1100 can be deployed by advancing the wire 1180 to push the implant 1100 out of a lumen 1194 of the catheter 1190, at which point the proximal end member 1102 would spring axially towards the distal end member 1104. The wire 1180 may then be detached and removed. Detachment of the wire 1180 may include retraction that overcomes a holding force (e.g., friction), removal of an interference fit, electrolytic detachment, thermal detachment, combinations thereof, and the like.

Figure 22A:
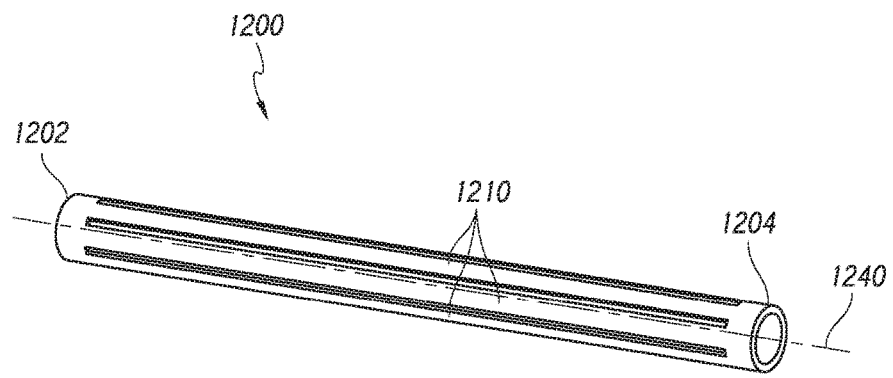
FIG. 22A shows a perspective view of an implant in a compressed state, according to some embodiments.
Figure 22B:
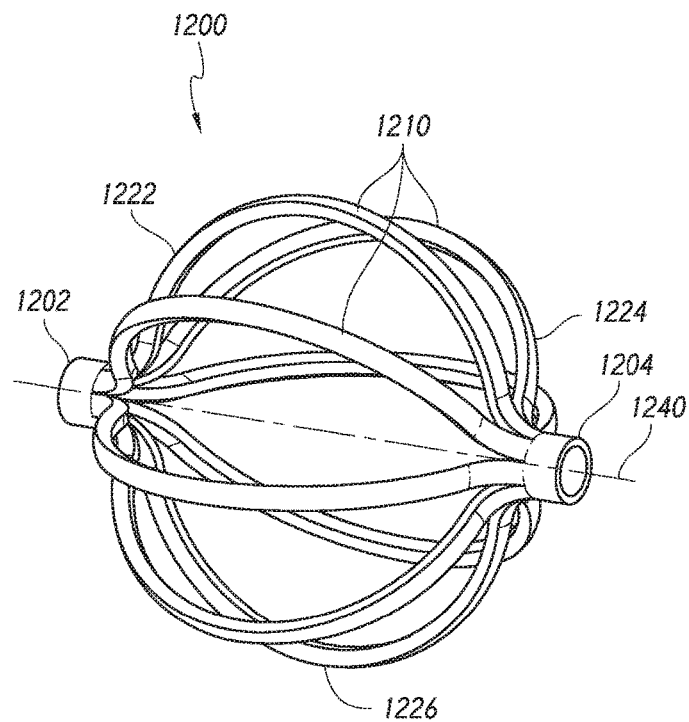
FIG. 22B shows a perspective view of an implant in an expanded state, according to some embodiments.
Figure 22C:
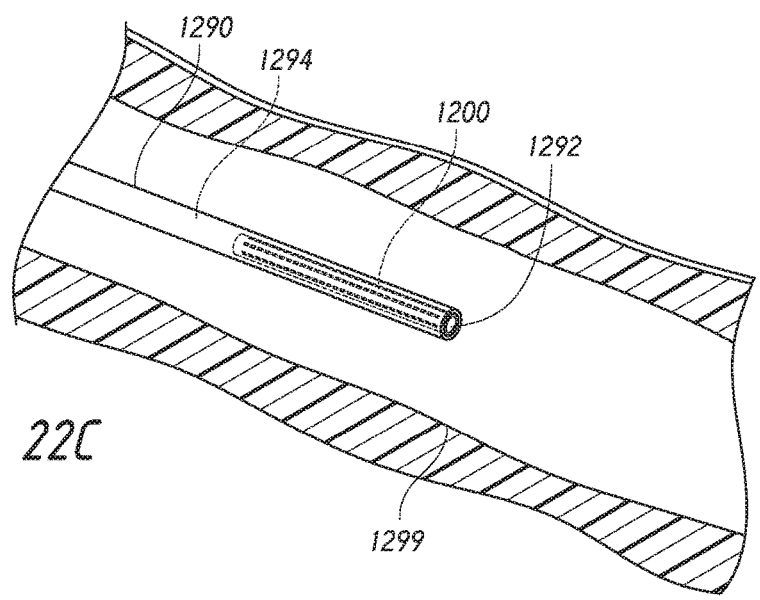
FIG. 22C shows a perspective view of an implant in a compressed state in a catheter within a vessel, according to some embodiments.

In accordance with some embodiments, FIGS. 22A-22B illustrate an implant 1200 including a plurality of struts 1210 extending between a first end member 1202 and a second end member 1204. FIG. 22A illustrates the implant 1200 in a straight or linear configuration. FIG. 22B illustrates the implant 1200 in a partially expanded state. FIG. 22C illustrates the implant 1200 in a fully expanded state.

Multiple struts 1210 can be shaped in a configuration that is substantially linear in a compressed state (FIG. 22A) and follows an arcuate pathway in an expanded state. The struts 1210 may extend longitudinally along at least a partial circumferential path. For example, as shown in FIG. 15B, the struts 1210 may extend from the first end member 1202 to the second end member 1204 along a path that substantially conforms to a sphere. As further shown in FIG. 22B, the struts 1210 may extend axially, such that the struts 1210 do not extend helically about a central axis 1240. As shown in FIG. 22B, the struts 1210 may be equally spaced circumferentially about an outer circumference of the implant 1200. Alternatively, the struts 1210 may be distributed asymmetrically about the circumference.

The struts 1210 may define a first (e.g., proximal) face 1222 near the first end member 1202, and a second (e.g., distal) face 1224 near the second end member 1204. One or both of the first and second faces 1222, 1224 may define a surface that is hemispherical, conical, frustoconical, concave, convex, combinations thereof, and the like. In the expanded state, the struts 1210 can define a substantially spherical profile between the end members 1202, 1204, as shown in FIG. 22B. The struts 1210 may define an equator 1226 between the first and second faces 1222, 1224.

The first end member 1202 may be axially opposite the second end member 1204 along the axis 1240. The end members 1202, 1204 may be of a radiopaque material or may include a separate component (not shown) being of a radiopaque material, for visualization during a procedure.

The struts 1210 can be fixed to the end members 1202, 1204 by attachment (e.g., welding). The struts 1210 can be integrally formed with the end members 1202, 1204. For example, the struts 1210 and the end members 1202, 1204 may all be cut from a single tube, rather than assembling from separate components.

As the implant 1200 transitions from a compressed state (as shown in FIG. 22A) to an expanded state (as shown in FIG. 22B), the end members 1202, 1204 move axially toward each other, such that the implant 1200 foreshortens axially. As the implant 1200 transitions from the compressed state to the expanded state, the struts 1210 expand radially.

Figure 22D:
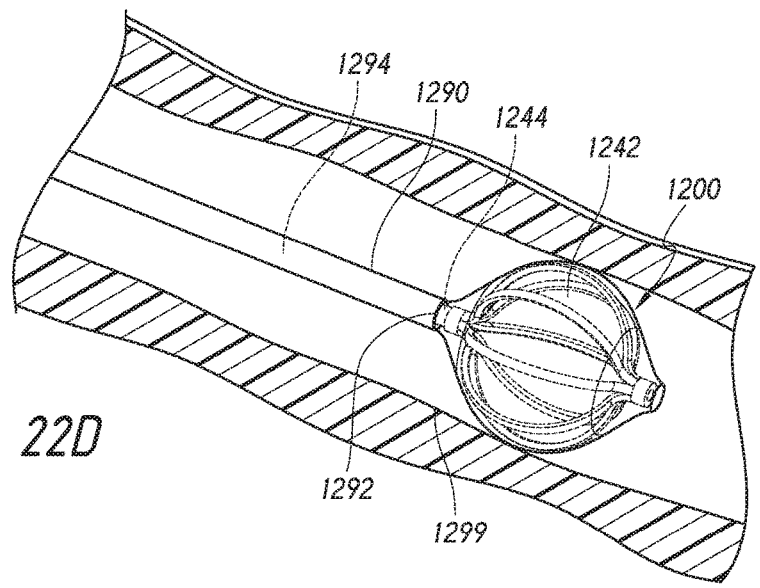
FIG. 22D shows a perspective view of an implant in an expanded state within a vessel, according to some embodiments.

In accordance with some embodiments, as shown in FIG. 22D, a non-permeable cover 1242 may be attached to one or both of the end members 1202, 1204 to provide occlusion in a blood vessel 1299. The cover 1242 can extend from one or both of the end members 1202, 1204 over a middle portion of the implant 1200. The cover 1242 may be a silicone tube fit tightly around the collapsed construct, which stretches to expand with the coil. Alternatively, the cover 1242 may be ePTFE that can be mechanically attached to each end member 1202, 1204 of the implant 1200, and has a diameter that fits tightly around the expanded diameter of the struts 1210. The cover 1242 may be on an external surface of the struts 1210, on an internal surface of the struts 1210, or a combination of the internal and external surfaces of the struts 1210.

In accordance with some embodiments, as shown in FIGS. 22C-22D, the implant 1200 may be shape-set in the expanded state, and pulled into a lumen 1294 of a catheter 1290 to collapse to the compressed state. As shown in FIG. 22C, the catheter 1290 containing the implant 1200 may be provided to a site within a vessel 1299. As shown in FIG. 22D, the implant 1200 may be advanced relative to the catheter 1290, such that the implant 1200 exits from the lumen 1294 of the catheter 1290 through a port 1292 at a distal end of the catheter 1290. The implant 1200 expands from a compressed state to an expanded state upon exiting the catheter 1290. In the expanded state, the struts 1210 of the implant 1200 may hold a portion of the cover 1242 against a wall of the vessel 1299. The catheter 1290 may be withdrawn after expansion of the implant 1200.

In accordance with some embodiments, as shown in FIG. 22D, the implant 1200 may contain a wire 1244 fixedly attached to one of the end members 1202, 1204. The wire 1244 may be configured to slide through an opening of the other of the end members 1202, 1204. For example, the wire 1244 may be configured such that it snaps into the proximal end member 1202 when pulled or pushed to the fully expanded position. The wire 1244 may act as a pusher for the implant 1200. The wire 1244 may require action by the user to push or pull the wire 1244, causing the compression and expansion of the implant 1200. Opposite motion with the wire 1244 would allow collapse, readjustment of position, or removal.

In accordance with some embodiments, the implant 1200 may contain a wire 1244 through the center that can be attached to the distal end member 1204, and slides through the proximal end member 1202. The implant 1200 would be shape-set to the expanded state. The implant 1200 can be deployed by advancing the wire 1244 to push the implant 1200 out of a lumen 1294 of the catheter 1290, at which point the proximal end member 1202 would spring axially towards the distal end member 1204. The wire 1244 may then be detached and removed. Detachment of the wire 1244 may include retraction that overcomes a holding force (e.g., friction), removal of an interference fit, electrolytic detachment, thermal detachment, combinations thereof, and the like.

Figure 23F:
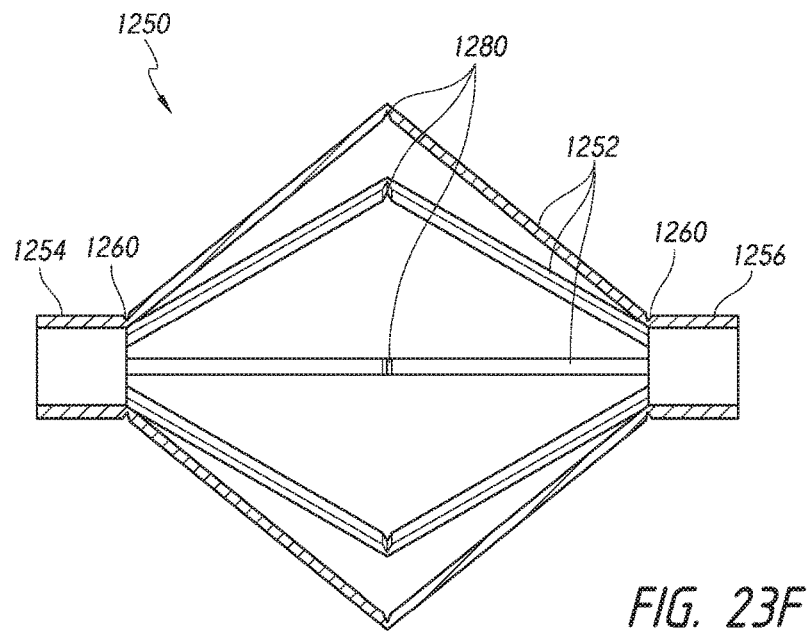
FIG. 23F shows a cross-sectional view of an implant in an expanded state, according to some embodiments.

In accordance with some embodiments, FIGS. 23A-23G illustrate an implant 1250 including a plurality of struts 1252 extending between a first end member 1254 and a second end member 1256. FIG. 23A illustrates the implant 1250 in a straight or linear configuration. FIG. 23F illustrates the implant 1250 in an expanded state.

As shown in FIG. 23A, the implant 1250 can include an end notch 1260 where each of the plurality of struts 1252 joins with the first end member 1254 and where each of the plurality of struts 1252 joins with the second end member 1254. Each end notch 1260 may be formed as a recess or indentation on a radially outer surface of the implant 1250. As shown in FIGS. 23B-23C, opposing sides 1262, 1264 of the end notch 1260 form an angle 1226 there between. As the implant transitions from a compressed state (FIG. 23B) to an expanded state (FIG. 23C), the opposing sides 1262, 1264 move toward each other and the angle 1266 decreases. The opposing sides 1262, 1264 may approach or contact each other in the expanded state. The angle 1266 may be smaller in the expanded state than in the compressed state. The end notch 1260 provides ease of bending by providing a thinner cross-sectional dimension than at the struts 1252, the first end member 1254, or the second end member 1256. This provides a predictable location of bending and reduces the force required to bend at the location of the end notch 1260.

As shown in FIG. 23A, the implant 1250 can include a middle notch 1280 along a length of each strut 1252 such that the strut 1252 is divided into two segments. The middle notch 1280 may be located along the strut 1252 between the first end member 1254 and the second end member 1256. For example, the middle notch 1280 may be halfway between the first end member 1254 and the second end member 1256. More than one middle notch 1280 may be provided, such that each strut 1252 is divided into more than two segments. For example, a segment of each strut 1252 may be configured to be parallel to a vessel wall when deployed. Each middle notch 1280 may be formed as a recess or indentation on a radially inner surface of the implant 1250. As shown in FIGS. 23D-23E, opposing sides 1262, 1264 of the end notch 1260 form an angle 1266 there between. As the implant transitions from a compressed state (FIG. 23D) to an expanded state (FIG. 23E), the opposing sides 1282, 1284 move toward each other and the angle 1236 decreases. The opposing sides 1282, 1284 may approach or contact each other in the expanded state. The angle 1236 may be smaller in the expanded state than in the compressed state. The middle notch 1280 provides ease of bending by providing a thinner cross-sectional dimension than at the struts 1252 on either side of the middle notch 1280. This provides a predictable location of bending and reduces the force required to bend at the location of the middle notch 1280.

Figure 23G:
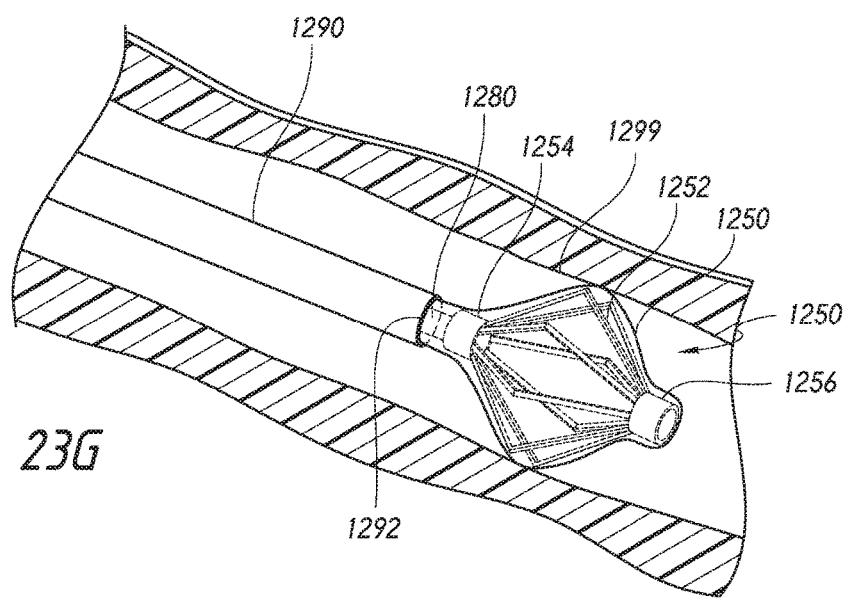
FIG. 23G shows a perspective view of an implant in an expanded state within a vessel, according to some embodiments.

In accordance with some embodiments, as shown in FIG. 23G, a non-permeable cover 1242 may be attached to one or both of the end members 1254, 1256 to provide occlusion in a blood vessel 1299. The cover 1242 can extend from one or both of the end members 1254, 1256 over a middle portion of the implant 1250, including the middle notch 1280.

In accordance with some embodiments, the implant 1250 may be shape-set in the expanded state, and pulled into a lumen 1294 of a catheter 1290 to collapse to the compressed state. The catheter 1290 containing the implant 1250 may be provided to a site within a vessel 1299. As shown in FIG. 23G, the implant 1250 may be advanced relative to the catheter 1290, such that the implant 1250 exits from the lumen 1294 of the catheter 1290 through a port 1292 at a distal end of the catheter 1290. The implant 1250 expands from a compressed state to an expanded state upon exiting the catheter 1290 by bending at the end notches 1260 and the middle notches 1280. In the expanded state, the struts 1252 of the implant 1250 may hold a portion of the cover 1242 against a wall of the vessel 1299. The catheter 1290 may be withdrawn after expansion of the implant 1250.

Figure 24A:
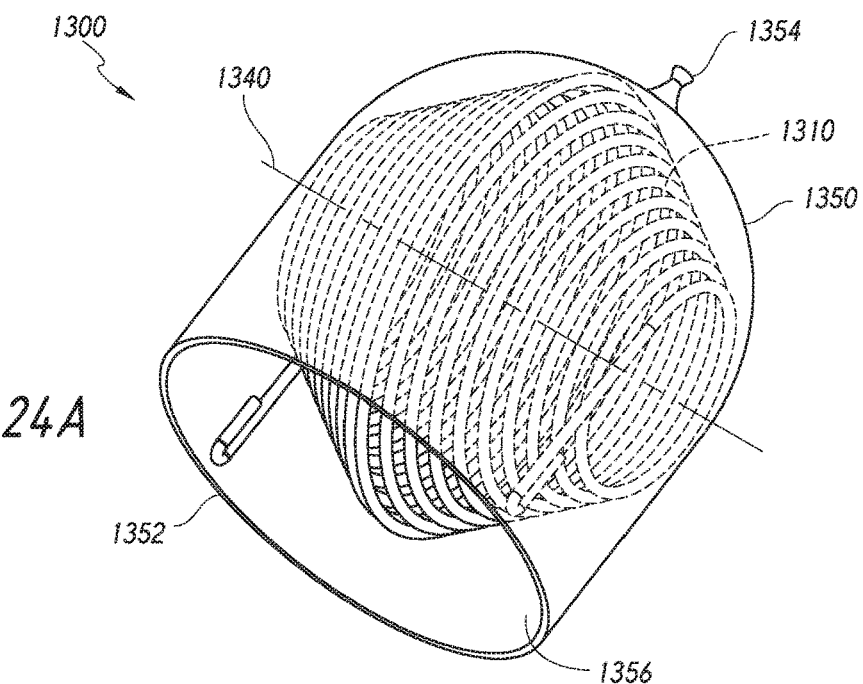
FIG. 24A shows a perspective view of an implant in an expanded state with a cover, according to some embodiments.
Figure 24B:
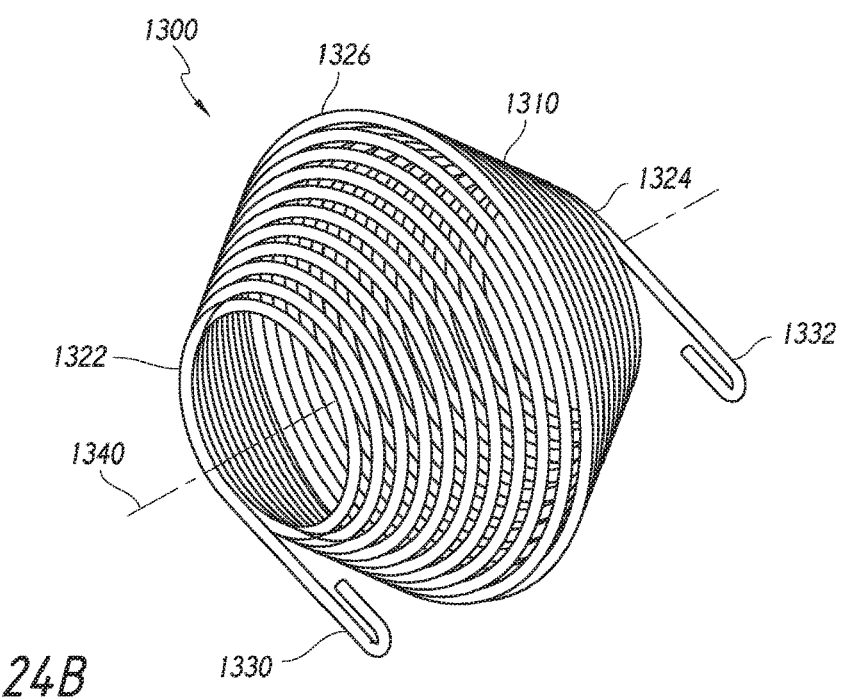
FIG. 24B shows a perspective view of an implant in an expanded state with a cover, according to some embodiments.

In accordance with some embodiments, FIGS. 24A-24B illustrate an implant 1300 including a filament 1310 wound in a shape, such that the filament 1310 extends from a first side 1322 to a second side 1324, opposite the first side 1322 along a central axis 1340. FIG. 24A illustrates the implant 1300 in a fully expanded state with the filament 1310 within a cover 1350.

The filament 1310 may form a three-dimensional shape in the expanded state. The shape can be configured to approximate the diameter of a target vessel for occlusion thereof. As shown in FIGS. 24A-24B, the filament 1310 may form multiple turns of a helical winding. The helical winding may be cylindrical, such that the turns of the winding have the same outer cross-sectional dimension, as measured in a plane transverse to the central axis 1340. As shown in FIGS. 24A-24B, the turns of the winding may have varying cross-sectional dimension.

For example, the cross-sectional dimension of a turn at the first side 1322 may be less than a cross-sectional dimension of a turn at a middle section (e.g., an equator) 1326, as measured in a plane transverse to the central axis 1340. By further example, the cross-sectional dimension of a turn at the second side 1324 may be less than a cross-sectional dimension of a turn at the middle section 1326, as measured in a plane transverse to the central axis 1340. The cross-sectional dimension may increase from the first side 1322 to the middle section 1326. The cross-sectional dimension may increase from the second side 1324 to the middle section 1326. The cross-sectional dimension of a turn at the first side 1322 may be the cross-sectional dimension of a turn at the second side 1324.

For example, the section between the first side 1322 and the middle section 1326 may be hemispherical, conical, frustoconical, concave, convex, combinations thereof, and the like. By further example, the section between the second side 1324 and the middle section 1326 may be hemispherical, conical, frustoconical, concave, convex, combinations thereof, and the like. The filament 1310 in the expanded state may generally form a sphere, an ovoid, a polyhedron, another smooth or angular three-dimensional shape, combinations thereof, and the like.

In accordance with some embodiments, the filament 1310 may be heat set or otherwise biased to an expanded state, as shown in an exemplary view in FIGS. 24A-24B. For example, the filament 1310 may be wound about a mandrel and/or encompassed by an exterior support structure, such that the filament 1310 is held into the target expanded state while heat or another treatment is applied. Thereafter, the filament 1310 has a tendency to form the expanded state when unrestrained. The filament 1310 may be elongated into a straight or compressed state, e.g., within a catheter 1390, with the ability to return to the expanded state when released from the catheter 1390.

In accordance with some embodiments, as shown in FIG. 24B, the filament may a first end region 1330 and second end region 1332. Each end region 1330, 1332 may have a straight (i.e., linear) portion, such that the end regions 1330, 1332 stabilize the filament 1310 in a given orientation when expanded in a vessel 1399. The end regions 1330, 1332 may be oriented so as to extend in a direction along a longitudinal length of the vessel 1399. For example, the end regions 1330, 1332 may be parallel by extending in the same or opposite directions. As further shown in FIG. 24B, the end regions 1330, 1332 may have a rounded or curved feature to provide atraumatic interaction with surrounding structures, such as the cover 1350 or walls of the vessel 1399 into which the implant 1300 is delivered.

As shown in FIG. 24B, the implant 1300 may form a fully expanded state with the filament 1310 within an interior region 1356 of a cover 1350. The cover may have a first end 1352 and a second end 1354. One of the ends 1352, 1354 may be open (as shown at the first end 1352 in FIG. 24A). The other of the ends 1352, 1354 may be closed (as shown at the second end 1354 in FIG. 24A). Alternatively, both of the ends 1352, 1354 may be open, or both of the ends 1352, 1354 may be closed. Either an open end or a closed end may be oriented toward upstream flow in the vessel 1399. The cover 1350 may be disposed partially or entirely on an exterior of the filament 1310.

Figure 25A:
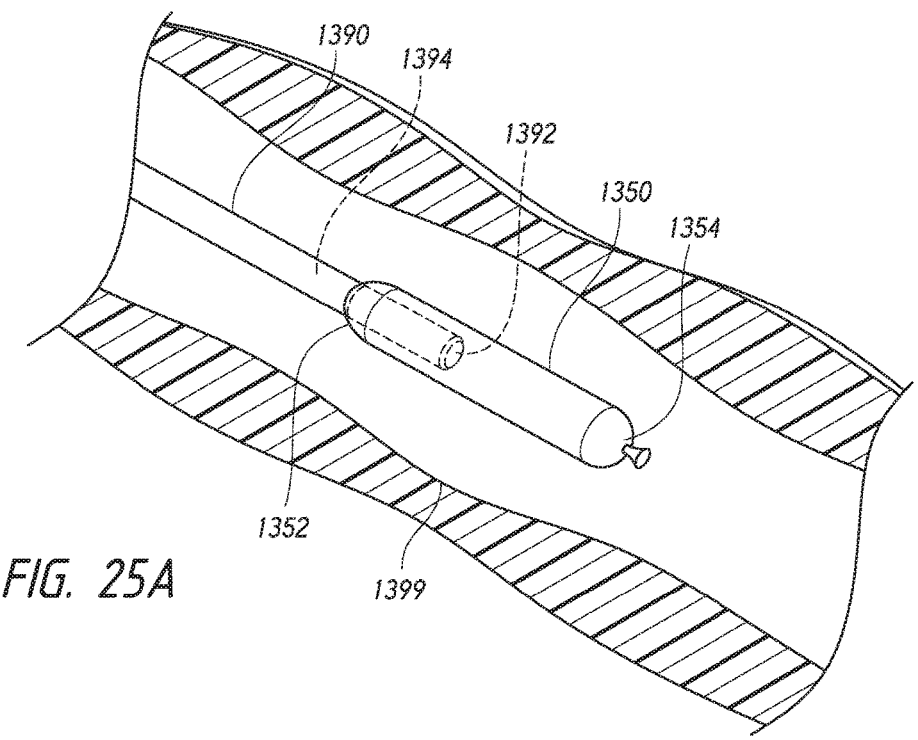
FIG. 25A shows a perspective view of a catheter within a vessel, according to some embodiments.
Figure 25B:
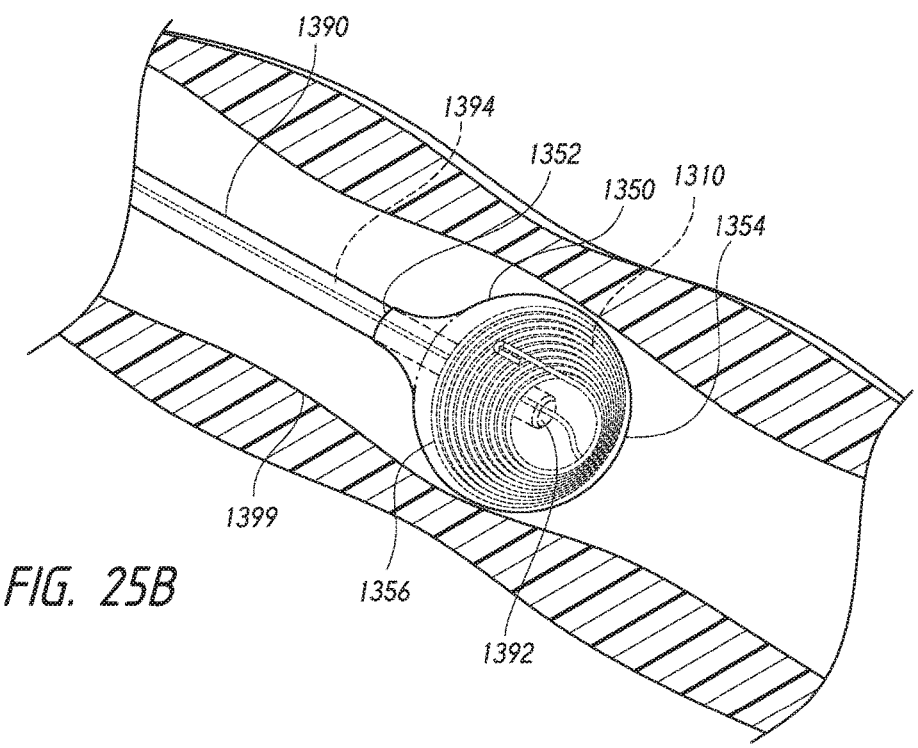
FIG. 25B shows a perspective view of a filament partially expanded from a catheter into a cover, according to some embodiments.
Figure 25C:
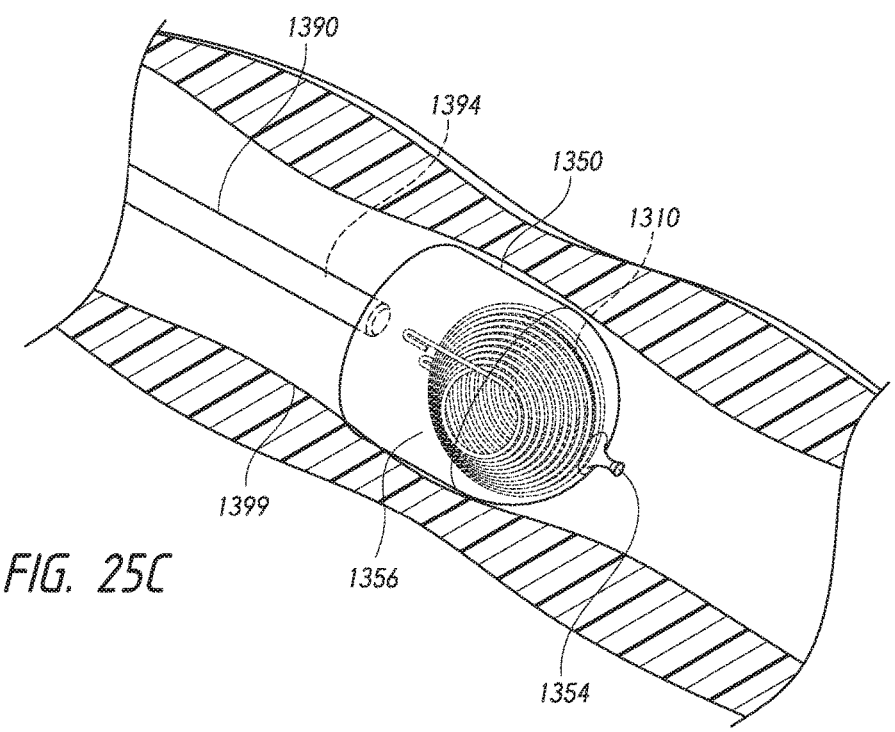
FIG. 25C shows a perspective view of an implant in an expanded state having a filament and a cover, according to some embodiments.

In accordance with some embodiments, as shown in FIG. 25A, a catheter 1390 may be provided within the vessel 1399. The cover 1350 may be controllably held on a distal region of the catheter 1390. For example, the first end 1352 of the cover 1350 may be held on a portion of the catheter 1390, with the second end 1354 of the cover 1350 extending distally of the port 1392 of the catheter 1390. The first end 1352 may be releasably held, for example, by clasps, graspers, adhesive, friction, pins, combinations thereof, and the like. A perforated section may be provided to controllably tear along a perforation. A lumen 1394 of the catheter 1390 is provided with access to the interior region 1356 of the cover 1350 via the port 1392. As shown in FIG. 25B, the filament 1310 is provided in the lumen 1394 in a compressed (e.g. straight or linear) state. The 1310 is advanced out of the port 1392 of the catheter 1390. Upon exiting the catheter 1390, portions of the filament 1310 coil or otherwise expand to an expanded state within the cover 1350. The first end 1352 of the cover 1350 may remain secured to the catheter 1390 during at least a portion of this process. As shown in FIG. 25C, once the filament 1310 is partially or entirely advanced out of the catheter 1390 and released to the expanded state, the first end 1352 of the cover 1350 may be released from the catheter 1390. Radially expansive forces of the filament 1310 in the expanded state may hold the cover 1350 against a wall of the vessel 1399. For example, the filament 1310 may tend to a cross-sectional dimension that exceeds the diameter of the blood vessel. The cover 1350 blocks fluid flow through the vessel 1399.

In accordance with some embodiments, FIGS. 26A-26D illustrate an implant 1400 including a plurality of filaments 1420 extending from a central hub 1410. The filaments 1420 each have a first end, attached to the hub 1410, and a second end, free of any attachment. The filaments 1420 may flex and/or pivot about a region of attachment to the hub 1410, such that the filaments 1420 move from an axial orientation to a radial or partially radial orientation, e.g., transverse to a longitudinal axis.

A control rod 1432 is provided to move axially through the hub 1410. A user at a proximal location may have access to and control over each of the control rod 1432 and the hub 1410 such that the user may move them axially relative to each other. The control rod 1432 is releasably attached to an expander 1430 at a distal end thereof. The expander 1430 includes a flange or another radial extension having a cross-sectional dimension greater than a distance between radially opposite filaments 1420 while in the compressed state. The expander 1430 is configured to move axially and separate the filaments 1420 such that they move radially outwardly when brought into contact with the expander 1430. The filaments 1420 may have notches at a location between the filaments 1420 and the hub 1410, as disclosed with respect to the implant 1250.

Figure 26A:
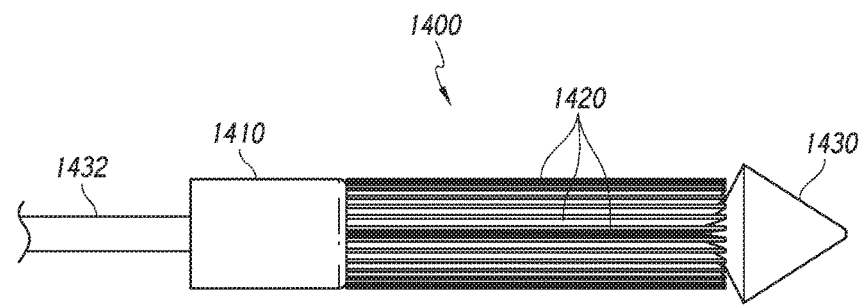
FIG. 26A shows a side view of an implant in a compressed state, according to some embodiments.
Figure 26B:
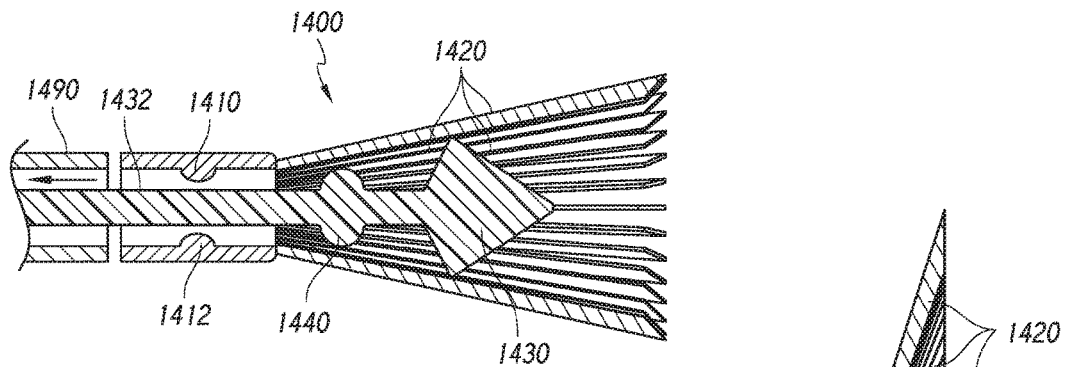
FIG. 26B shows a cross-sectional view of an implant in a partially expanded state, according to some embodiments.
Figure 26C:
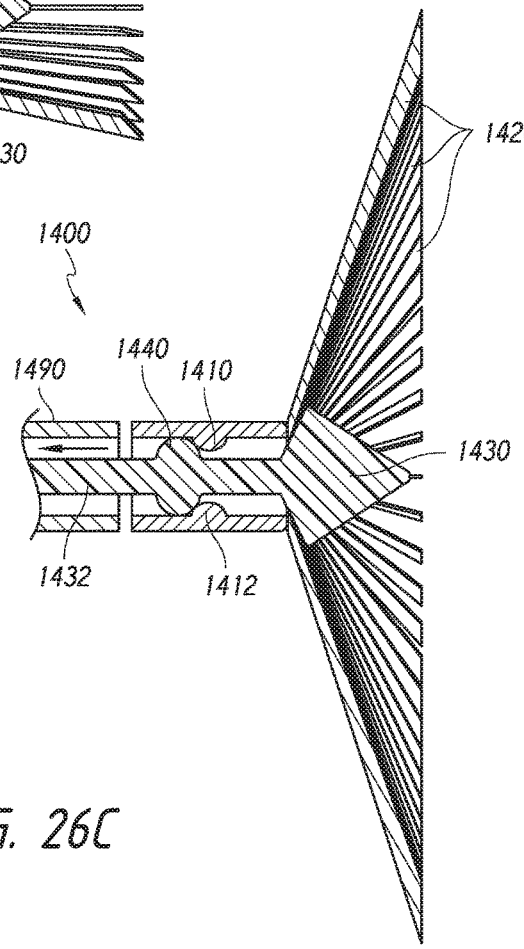
FIG. 26C shows a cross-sectional view of an implant in a fully expanded state, according to some embodiments.

FIG. 26A illustrates the implant 1400 in a fully compressed state with the filaments 1420 extending axially from the hub 1410. The compressed state of the filaments 1420 may be the relaxed state thereof, to which the filaments 1420 tend when unrestrained. The filaments 1420 define an inner cross-sectional dimension determined by the distance between radially opposite filaments 1420. The expander 1430 is positioned distal to the distal, free ends of the filaments 1420. FIG. 26B illustrates the implant 1400 in a partially expanded state with the filaments 1420 beginning to extend radially outwardly. This is accomplished as the expander 1430 is moved proximally relative to the hub 1410 (e.g., pulling the control rod 1432 proximally while pushing the hub 1410 distally with the catheter 1490). The maximum outer cross-sectional dimension of the expander 1430 applies a force on the radially adjacent portions of the filaments 1420, pressing them radially outwardly. FIG. 26C illustrates the implant 1400 in a fully expanded state with the filaments 1420 extending at least partially radially outwardly. As shown in FIGS. 26C and 26E, the filaments 1420 may extend both radially and axially from the hub 1410 in the fully expanded state. The expander 1430 is brought into contact with a portion of the filaments 1420 at or near the hub 1410.

Figure 26D:
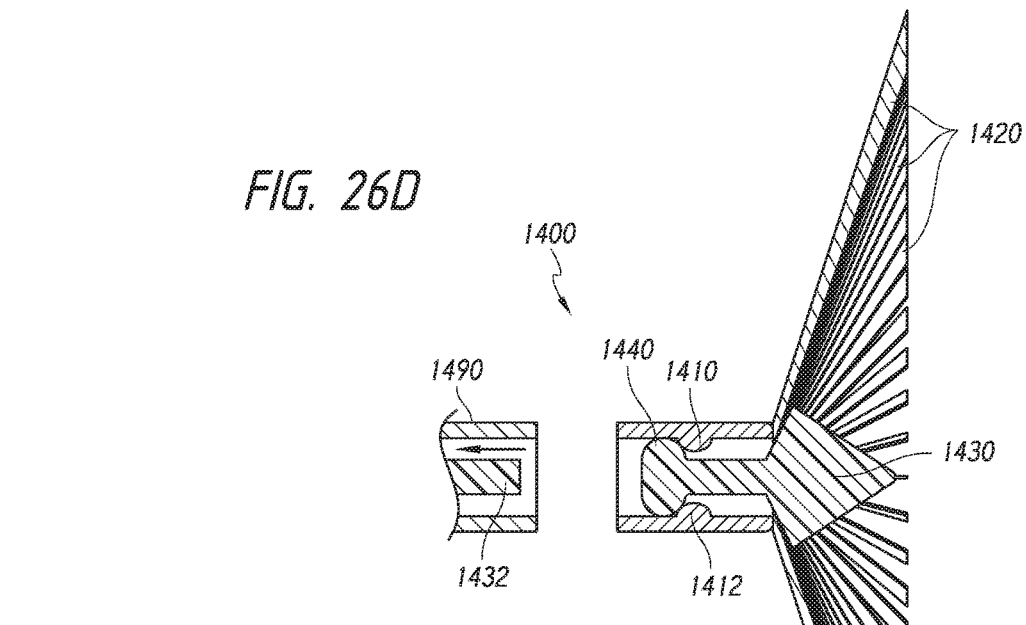
FIG. 26D shows a cross-sectional view of an implant in a fully expanded state, according to some embodiments.
Figure 26E:
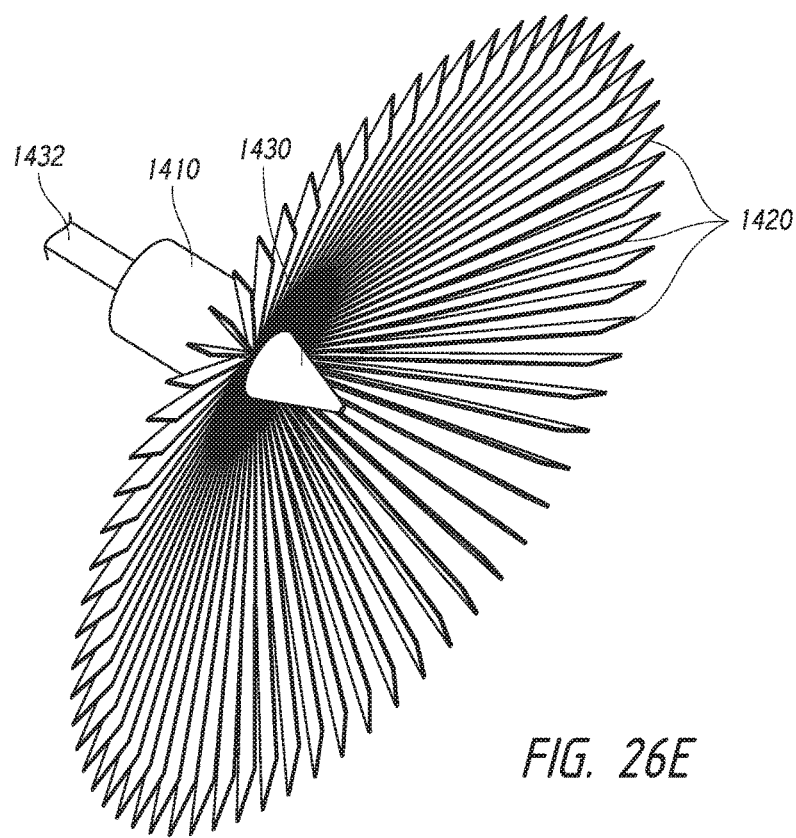
FIG. 26E shows a perspective view of an implant in a fully expanded state, according to some embodiments.

In accordance with some embodiments, as shown in FIGS. 26B-26D, the implant 1400 may be provided with a mechanism for retaining the filaments 1420 in the fully expanded state. As shown in FIGS. 26B-26D, the hub 1410 may include an inner protrusion 1412. The inner protrusion may extend from an inner wall of the hub 1410, such that the interior of the hub 1410 has variable cross-sectional dimensions. The inner protrusion 1412 may be an annular ring, one or more non-circumferential protrusions, or another structure that provides a relatively smaller cross-sectional dimension within the hub 1410. The inner protrusion 1412 is configured to provide an inner cross-sectional dimension within the hub 1410 that is less than an outer cross-sectional dimension of an enlarged member 1440 connected to the expander 1430. As shown in FIG. 26B, the enlarged member 1440 may be moved from a position distal to the inner protrusion 1412 (see FIG. 26B) to a position proximal to the inner protrusion 1412 (see FIG. 26C). One or both of the inner protrusion 1412 and the enlarged member 1440 may be elastically deformable, such that the enlarged member 1440 having an outer cross-sectional dimension greater than an inner cross-sectional dimension at the inner protrusion 1412 may move proximally past the inner protrusion 1412 when a sufficient proximally directed force is applied to the enlarged member 1440. Subsequently, the outer cross-sectional dimension of the enlarged member 1440 remains greater than the inner cross-sectional dimension at the inner protrusion 1412, such that distal movement of the enlarged member 1440 past the inner protrusion 1412 is prevented.

In the fully expanded state, the filaments 1420 may apply a force (e.g., spring force) upon the expander 1430, which may be transferred to the enlarged member 1440. A force required to pass the enlarged member 1440 past the inner protrusion 1412, at least in a distal direction, can be greater than the force of the filaments 1420 on the expander 1430. For example the shape and geometries of the enlarged member 1440 and the inner protrusion 1412 may be such that proximal movement of the enlarged member 1440 past the inner protrusion 1412 is permitted while distal movement of the enlarged member 1440 past the inner protrusion 1412 is prevented. The enlarged member 1440 and/or the inner protrusion 1412 may include or form a ratchet, a pawl, or the like. For example, the enlarged member 1440 may include a section with triangular teeth that slope in one direction (e.g., facing proximally). The inner protrusion 1412 may include a flexible pawl that rides up the slope of the teeth of the enlarged member 1440 when moved past the inner protrusion 1412. The pawl engages the backside (e.g., facing distally) of the teeth to arrest distal motion thereof beyond a certain point.

In accordance with some embodiments, as shown in FIGS. 26A-26D, the control rod 1432 may be detachable from the enlarged member 1440 and/or the expander 1430. The control rod 1432 may detach by one or more of a variety of mechanisms. For example, the control rod 1432 may be frictionally engaged with the enlarged member 1440 and/or the expander 1430, such that a sufficiently large proximal force detaches the control rod 1432 from the enlarged member 1440 and/or the expander 1430 (e.g., while applying a distally directed force to the enlarged member 1440 and/or the expander 1430 via the catheter 1490 and/or the hub 1410). A force required to detach the control rod 1432 from the enlarged member 1440 may be greater than the force required to pass the enlarged member 1440 past the inner protrusion 1412, at least in a proximal direction, such that the control rod 1432 does not detach merely by pulling the enlarged member 1440 past the inner protrusion 1412. Other detachment mechanisms are contemplated, including removal of an interference fit, electrolytic detachment, thermal detachment, combinations thereof, and the like.

Figure 27A:
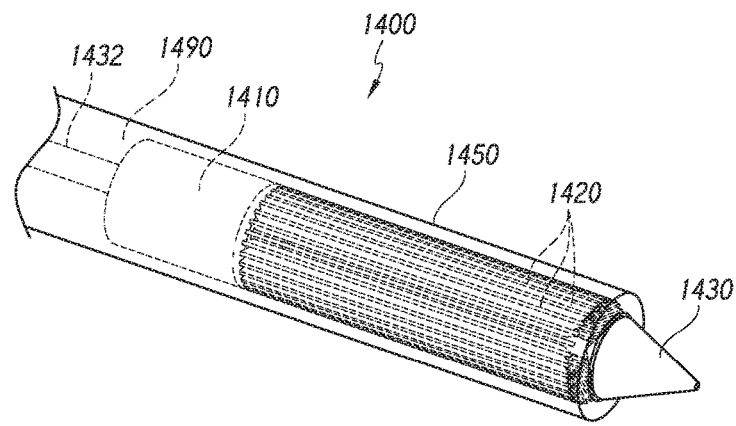
FIG. 27A shows a perspective view of an implant in a compressed state with a cover, according to some embodiments.
Figure 27B:
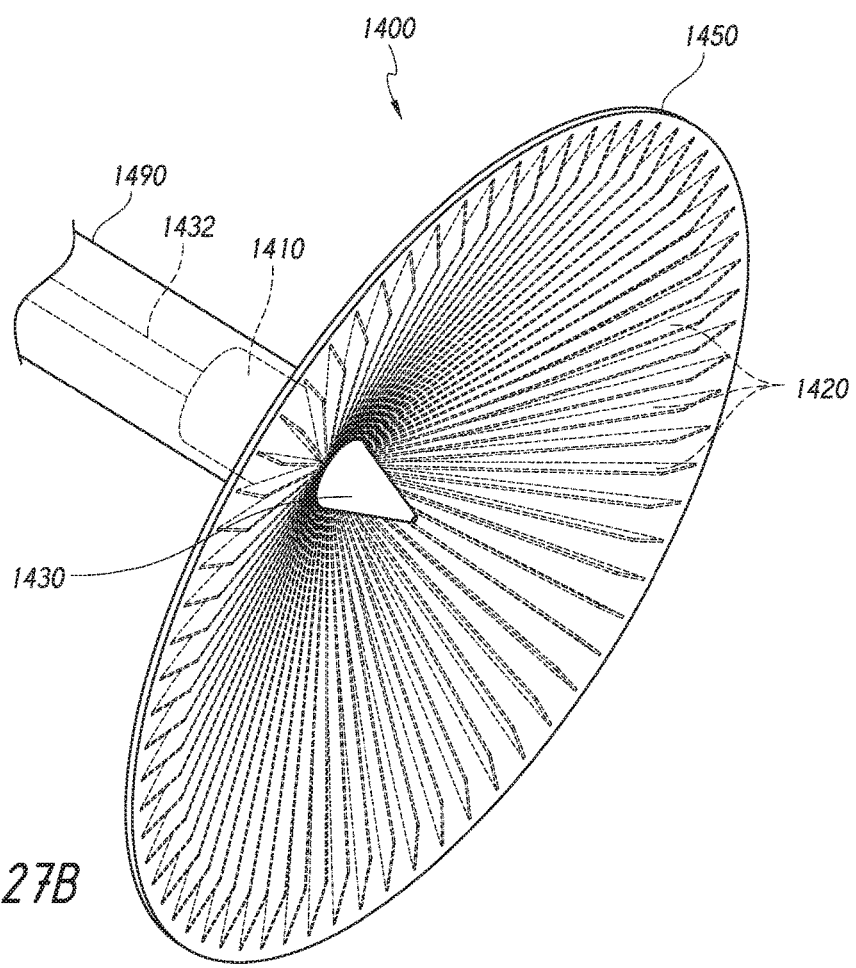
FIG. 27B shows a perspective view of an implant in a fully expanded state with a cover, according to some embodiments.

In accordance with some embodiments, as shown in FIGS. 27A-B, the implant 1400 may include a cover 1450 provided over or with the filaments 1420 and/or the hub 1420. The cover 1450 may be provided to the filament 1420 collectively or individually. The cover 1450 may occlude openings between the filaments 1420.

Figure 28A:
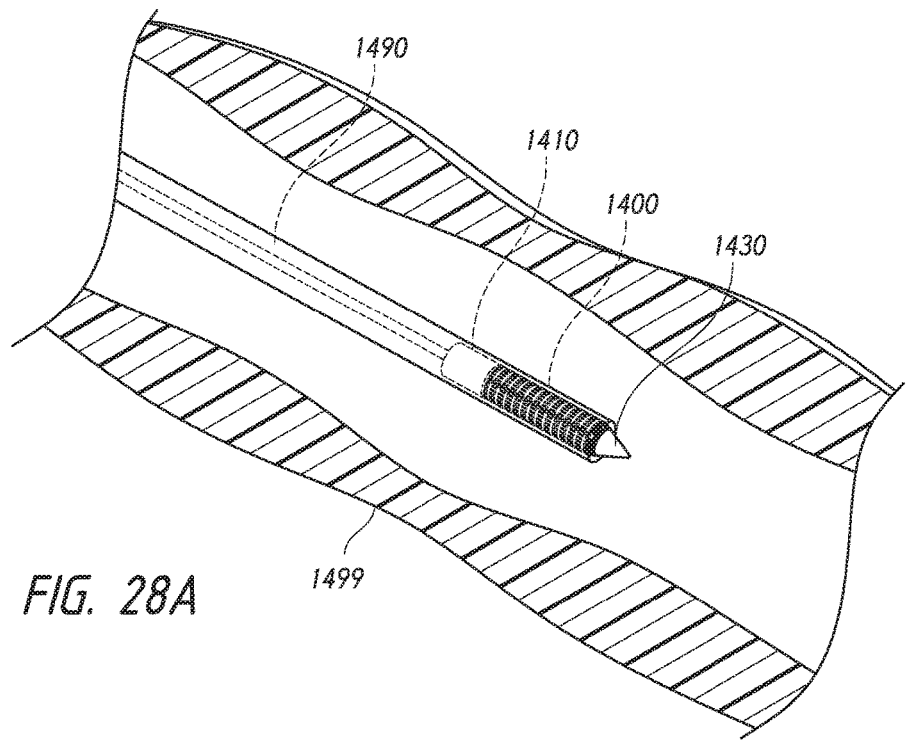
FIG. 28A shows a perspective view of a catheter and an implant in a compressed state, according to some embodiments.
Figure 28B:
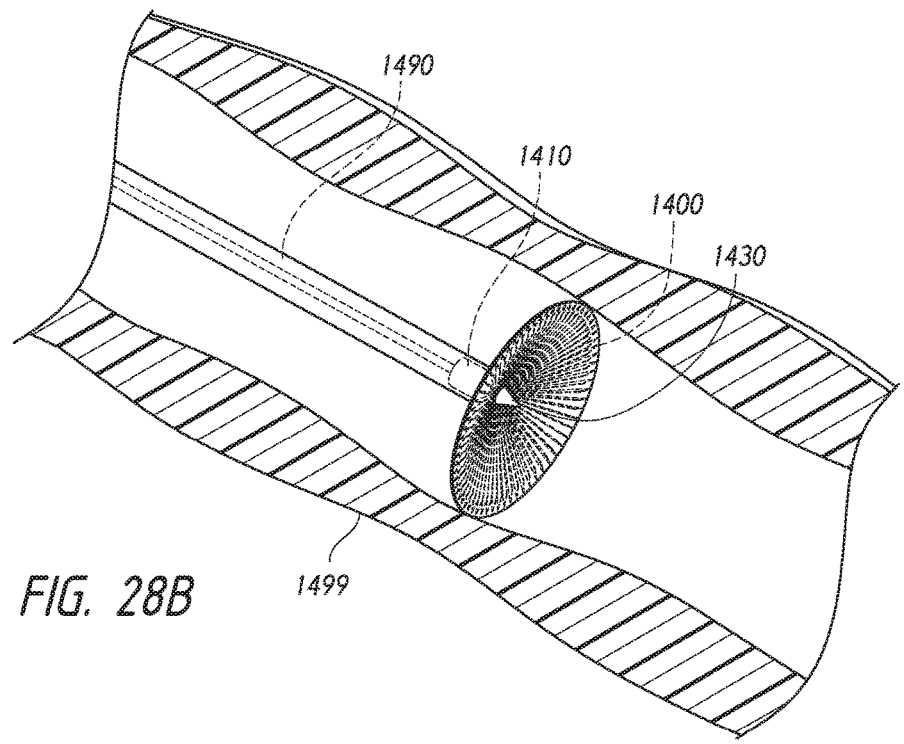
FIG. 28B shows a perspective view of a catheter and an implant in a fully expanded state, according to some embodiments.
Figure 28C:
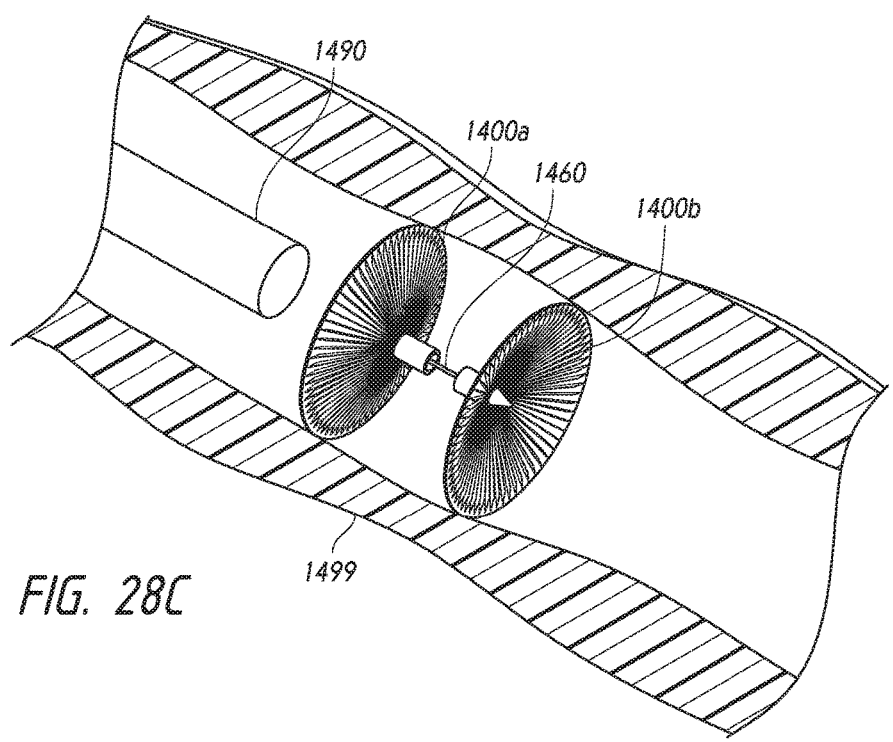
FIG. 28C shows a perspective view of two connected implants in fully expanded states, according to some embodiments.

In accordance with some embodiments, as shown in FIGS. 28A-28C, the implant 1400 and a catheter 1490 are provided to a site within a vessel 1499. As shown in FIG. 28B, the implant 1400 expands from a compressed state to an expanded state by action of the expander 1430. In the expanded state, the filaments 1420 of the implant 1400 hold a portion of the cover 1450 against a wall of the vessel 1499. The catheter 1490 may be withdrawn after expansion of the implant 1400.

In accordance with some embodiments, as shown in FIG. 28C, a first implant 1400*a* and a second implant 1400*b* may be connected by a connector 1460. Each of the implants 1400*a*, 1400*b* may be constructed substantially as disclosed herein. The connector 1460 may attach or extend through axially adjacent hubs of the implants 1400*a*, 1400*b*. The implants 1400*a*, 1400*b* may be connected prior to, during, or after delivery thereof, or the implants 1400*a*, 1400*b* may be separately delivered and attached by connector 1460 in situ. The opposing directions of the implants 1400*a*, 1400*b* effectively occludes flow in either direction with the vessel 1499.

Figure 28D:
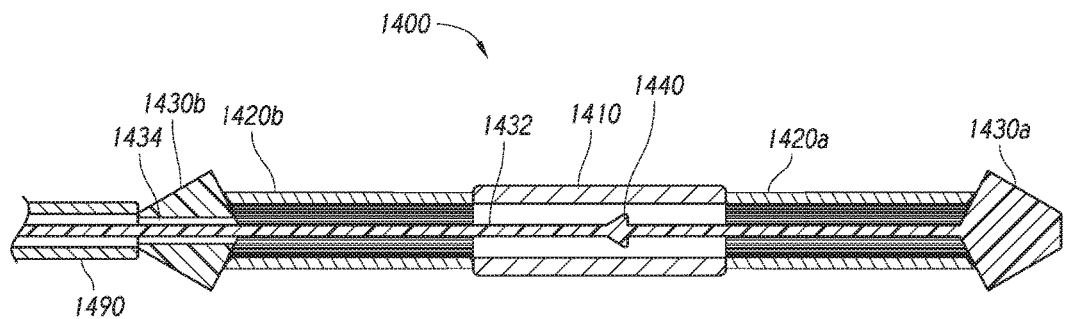
FIG. 28D shows a cross-sectional view of an implant in a compressed state, according to some embodiments.
Figure 28E:
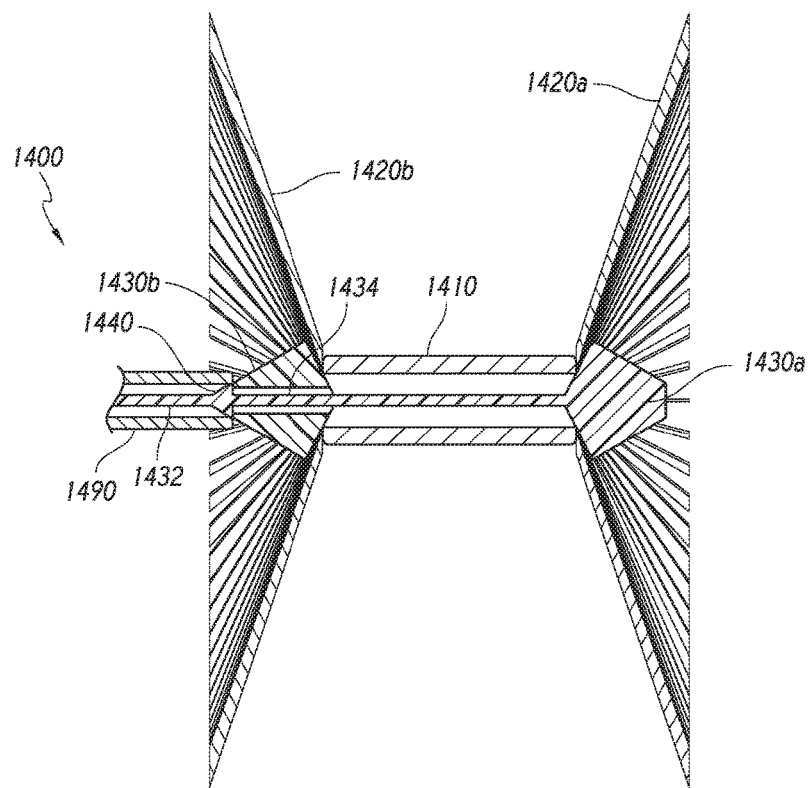
FIG. 28E shows a cross-sectional view of an implant in a fully expanded state, according to some embodiments.
Figure 28F:
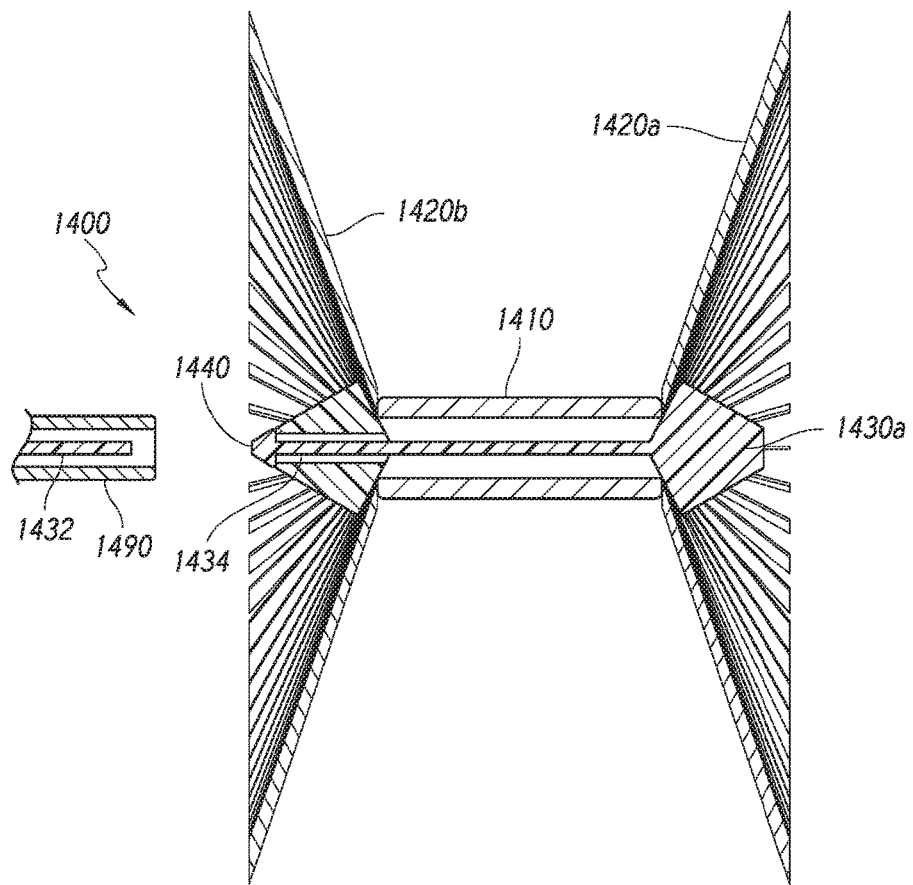
FIG. 28F shows a cross-sectional view of an implant in a fully expanded state and detached state, according to some embodiments.

In accordance with some embodiments, FIGS. 28D-28F illustrate an implant 1400 including distal filaments 1420*a* at a distal end of a central hub 1410 and proximal filaments 1420*b* at a proximal end of the central hub 1410. The filaments 1420*a*, 1420*b* each have a first end, attached to the hub 1410, and a second end, free of any attachment. The filaments 1420*a*, 1420*b* may flex and/or pivot about a region of attachment to the hub 1410, such that the filaments 1420 move from an axial orientation to a radial or partially radial orientation.

A control rod 1432 is provided to move axially through the hub 1410 and a lumen 1434 of a proximal expander 1430*b*. A user at a proximal location may have access to and control over each of the control rod 1432 and a delivery device 1490, such that the user may move them axially relative to each other. The control rod 1432 is releasably attached to a distal expander 1430*a* at a distal end of the implant 1400. The expanders 1430*a*, 1430*b* include a flange or another radial extension having a cross-sectional dimension greater than a distance between radially opposite filaments 1420*a*, 1420*b* while in the compressed state. The expanders 1430*a*, 1430*b* are configured to move axially relative to each other and separate the filaments 1420*a*, 1420*b* such that they move radially outwardly when brought into contact with the corresponding expander 1430*a*, 1430*b*.

FIG. 28D illustrates the implant 1400 in a fully compressed state with the filaments 1420*a*, 1420*b* extending axially from the hub 1410. The distal expander 1430*a* is positioned distal to the distal, free ends of the first filaments 1420*a*, and the proximal expander 1430*b* is positioned proximal to the proximal, free ends of the second filaments 1420*b*. FIG. 28E illustrates the implant 1400 in a fully expanded state with the filaments 1420*a*, 1420*b* extending at least partially radially outwardly. As shown in FIGS. 28D-28E, the delivery device 1490 is moved relative to the control rod 1432. Accordingly, the delivery device 1490 applies a distally directed force on the proximal expander 1430*b*, and the control rod 1432 applies a proximally directed force to the proximal expander 1430*b*. The distal expander 1430*a* is brought into contact with a portion of the distal filaments 1420*a* at or near the hub 1410, and the proximal expander 1430*b* is brought into contact with a portion of the proximal filaments 1420*b* at or near the hub 1410.

In accordance with some embodiments, as shown in FIGS. 28D-28F, the implant 1400 may be provided with a mechanism for retaining the filaments 1420*a*, 1420*b* in the fully expanded state. As shown in FIGS. 28D-28F, the control rod 1432 may include an enlarged member 1440 having a cross-sectional dimension larger than a cross-sectional dimension of other portions of the control rod 1432. The lumen 1434 of the proximal expander 1430*b* provides a relatively smaller cross-sectional dimension than a maximum cross-sectional dimension of the enlarged member 1440. The proximal expander 1430*b* is configured to provide an inner cross-sectional dimension within the lumen 1434 that is less than an outer cross-sectional dimension of an enlarged member 1440 connected to the distal expander 1430*a*. As shown in FIGS. 28D-28F, the enlarged member 1440 may be moved from a position distal to the proximal expander 1430*b* (see FIG. 28D) to a position proximal to the proximal expander 1430*b* (see FIG. 28E). One or both of the proximal expander 1430*b* and the enlarged member 1440 may be elastically deformable, such that the enlarged member 1440 having an outer cross-sectional dimension greater than an inner cross-sectional dimension at the lumen 1434 may move proximally past the proximal expander 1430*b* when a sufficient proximally directed force is applied to the enlarged member 1440. Subsequently, the outer cross-sectional dimension of the enlarged member 1440 remains greater than the inner cross-sectional dimension at the lumen 1434, such that distal movement of the enlarged member 1440 past the proximal expander 1430*b* is prevented.

In the fully expanded state, the filaments 1420*a*, 1420*b* may apply a force (e.g., spring force) upon the expanders 1430*a*, 1430*b*, which may be transferred to the enlarged member 1440. A force required to pass the enlarged member 1440 past the proximal expander 1430*b*, at least in a distal direction, can be greater than the force of the filaments 1420 on the expander 1430. For example the shape and geometries of the enlarged member 1440 and the proximal expander 1430*b* may be such that proximal movement of the enlarged member 1440 past the proximal expander 1430*b* is permitted while distal movement of the enlarged member 1440 past the proximal expander 1430*b* is prevented. The enlarged member 1440 and/or the proximal expander 1430*b* may include or form a ratchet, a pawl, or the like. For example, the enlarged member 1440 may include a section with triangular teeth that slope in one direction (e.g., facing proximally). The proximal expander 1430*b* may include a flexible pawl that rides up the slope of the teeth of the enlarged member 1440 when moved proximally out of the lumen 1434 and proximally past the proximal expander 1430*b*. The pawl engages the backside (e.g., facing distally) of the teeth to arrest distal motion thereof beyond a certain point.

In accordance with some embodiments, as shown in FIGS. 28E-28D, the control rod 1432 may be detachable from the enlarged member 1440 and/or the distal expander 1430*a*. The control rod 1432 may detach by one or more of a variety of mechanisms. For example, the control rod 1432 may be frictionally engaged with the enlarged member 1440 and/or the distal expander 1430*a*, such that a sufficiently large proximal force detaches the control rod 1432 from the enlarged member 1440 and/or the distal expander 1430*a* (e.g., while applying a distally directed force to the enlarged member 1440 and/or the distal expander 1430*a* via the catheter 1490 and/or the hub 1410). A force required to detach the control rod 1432 from the enlarged member 1440 may be greater than the force required to pass the enlarged member 1440 past the proximal expander 1430*b*, at least in a proximal direction, such that the control rod 1432 does not detach merely by pulling the enlarged member 1440 past the proximal expander 1430*b*. Other detachment mechanisms are contemplated, including removal of an interference fit, electrolytic detachment, thermal detachment, combinations thereof, and the like.

Figure 29E:
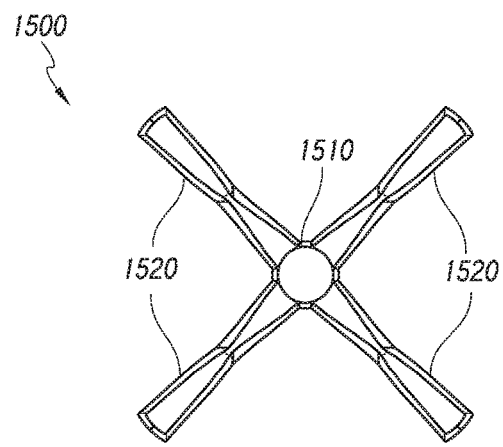
FIG. 29E shows a front view of an implant in an expanded state, according to some embodiments.

In accordance with some embodiments, FIGS. 29A-29D illustrate an implant 1500 including a plurality of arms 1520 extending from a central hub 1510. The arms 1520 each have a first end, attached to the hub 1510, and a second end, free of any attachment. The arms 1520 may flex, bend, and/or pivot about a region of attachment to the hub 1510, such that the arms 1520 move from an axial orientation, as shown in FIGS. 29A-29B, to a radial orientation, as shown in FIGS. 29C-29E.

Multiple arms 1520 can be shaped in a configuration that is substantially linear in a compressed state and follows an arcuate pathway in an expanded state. In the expanded state, the arms 1520 may follow a serpentine pathway. For example, as shown in FIG. 29D, a proximal portion of the arms 1520 adjacent to the hub 1510 may be convex on its outer surface, and a distal portion of the arms 1520 may be concave on its outer surface. The arms 1520 may define a maximum cross-sectional dimension between radially opposite arms 1520. A maximum cross-sectional dimension of the arms 1520 may be provided at a terminal ends of the arms 1520. Alternatively, a maximum cross-sectional dimension of the arms 1520 may be provided at a middle region between the terminal ends of the arms 1520 and the hub 1510. As such, the terminal ends of the arms 1520 may provide a cross-sectional dimension that is less than a maximum cross-sectional dimension of the arms 1520.

Any number of arms 1520 may be provided. For example, the implant 1500 may include three, four, five, six, seven, eight, or more arms 1520. The arms 1520 may be equally spaced circumferentially about an outer circumference of the implant 1500. Alternatively, the arms 1520 may be distributed asymmetrically about the circumference of the implant 1500.

FIGS. 29A-29B illustrates the implant 1500 in a compressed state with the arms 1520 extending axially from the hub 1510. The compressed state of the arms 1520 may be achieved by restraining the implant 1500, for example within a catheter. The arms 1520 can be fixed to the hub 1510 by attachment (e.g., welding). The arms 1520 can be integrally formed with the hub 1510. For example, the arms 1520 and the hub 1510 may both be cut from a single tube, rather than assembling from separate components.

As shown in FIGS. 29C-29E, the arms 1520 may extend both radially and axially from the hub 1510 in a fully expanded state. The expanded state of the arms 1520 may be the relaxed state thereof, to which the arms 1520 tend when unrestrained. The arms 1520 define a maximum cross-sectional dimension determined by the greatest distance between radially opposite arms 1520. In the fully expanded state, the arms 1520 may apply a force radially outwardly against a vessel. The cross-sectional dimension of the vessel may be less than a cross-sectional dimension of the arms 1520 in a freely expanded state.

In accordance with some embodiments, the implant 1500 may include a cover 1550 (not shown) provided over or with the arms 1520 and/or the hub 1520. The cover 1550 may be provided to the arm 1520 collectively or individually. The cover 1550 may occlude openings between the arms 1520.

Figure 29F:
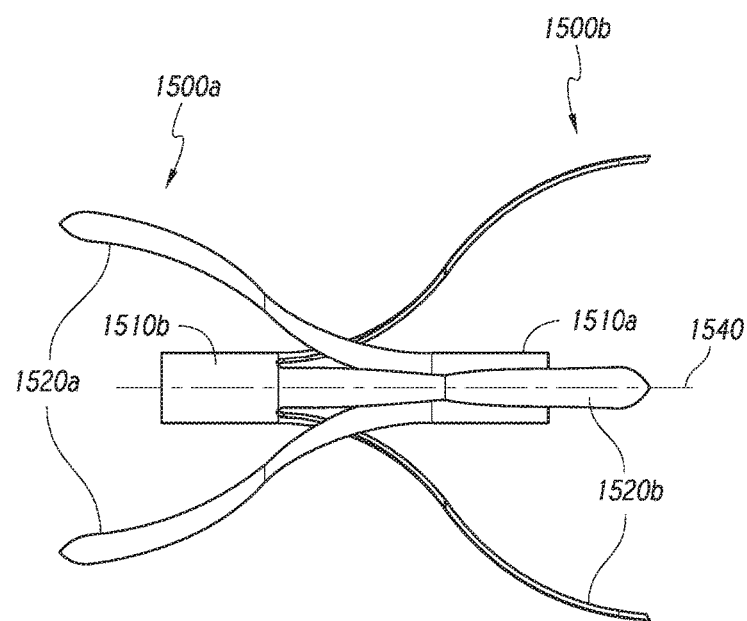
FIG. 29F shows a side view of two implants in expanded states, according to some embodiments.

As shown in FIG. 29F, two implants 1500a, 1500b may be provided. As shown in FIG. 29F, the implants 1500a, 1500b may be aligned along a common axis 1540. The implants 1500a, 1500b may have opposite orientations, such that the implants 1500a, 1500b face in opposite axial directions. For example, the hub 1510a of a first implant 1500a may face axially away from the hub 1510b a second implant 1500b. The implants 1500a, 1500b may overlap, such that each arm 1520a of the first implant 1500a is disposed between circumferentially adjacent arms 1520b of the second implant 1500b. Likewise, each arm 1520b of the second implant 1500b is disposed between circumferentially adjacent arms 1520a of the first implant 1500a. Accordingly, the arms 1520a, 1520b may be angularly offset, such that the arms 1520a, 1520b have different angular positions relative to a common axis 1540 of the implants 1500a, 1500b.

In accordance with some embodiments, as shown in FIGS. 29G-29H, one or more of the arms 1520 may include a prong 1530 on one or both lateral sides of the respective arm 1520. Each of the prongs 1530 can provide a substantially flat or curved surface. Each of the prongs 1530 can have a first edge facing the terminal ends of the arms 1520 and a second edge facing the hub 1510. The first edge and the second edge may have different angles relative to the arm 1520. For example, as shown in FIG. 29G, an edge of the prongs 1530 facing the hub 1510 can form an angle that is substantially orthogonal to the arms 1520. As further shown in FIG. 29G, an edge of the prongs 1530 facing the terminal distal ends of the arms 1520 can form an angle that is substantially oblique relative to the arms 1520.

In accordance with some embodiments, as shown in FIGS. 29I, two implants 1500a, 1500b can interlock by engaging respective prongs 1530a, 1530b. First prongs 1530a of a first implant 1530a can be positioned between second prongs 1530b and a second hub 1510b of a second implant 1500b. Second prongs 1530b of a second implant 1530b can be positioned between first prongs 1530a and a first hub 1510a of a first implant 1500a. Accordingly, the prongs 1530a, 1530b engage each other to limit or prevent separation of the two implants 1500a, 1500b. Edges of the prongs 1530a, 1530b can be oriented to allow the prongs to move past each other as the two implants 1500a, 1500b engage each other. Other edges of the prongs 1530a, 1530b can be oriented to limit or prevent separation of the two implants 1500a, 1500b.

Figure 30A:
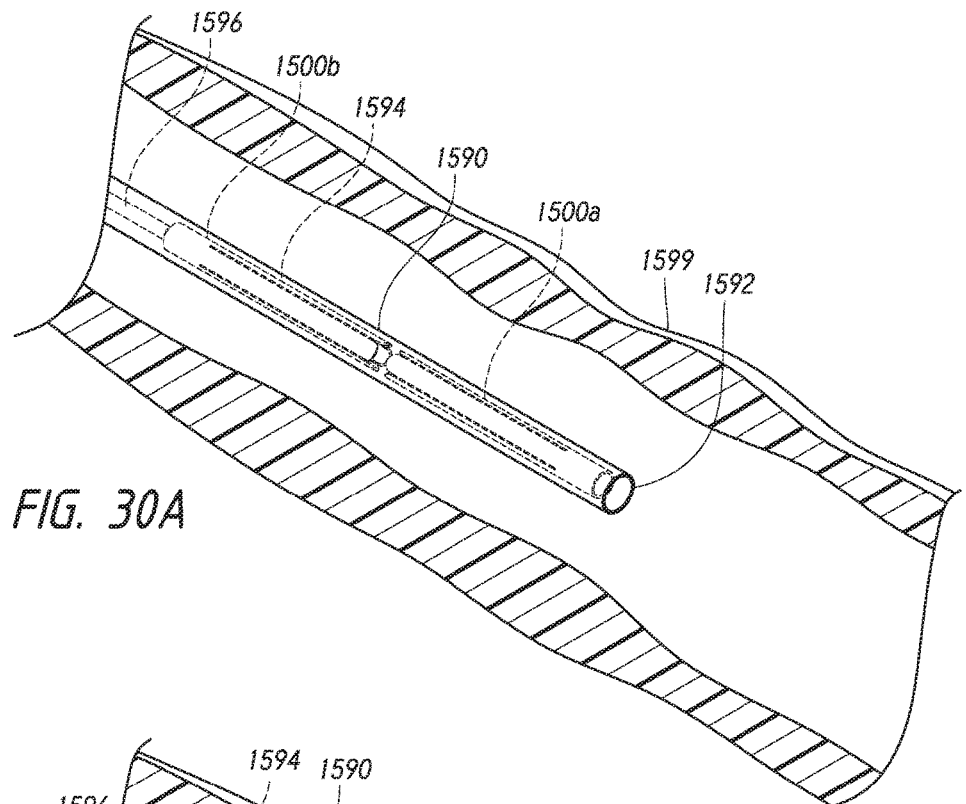
FIG. 30A shows a perspective view of a catheter and two implants in compressed states, according to some embodiments.
Figure 30B:
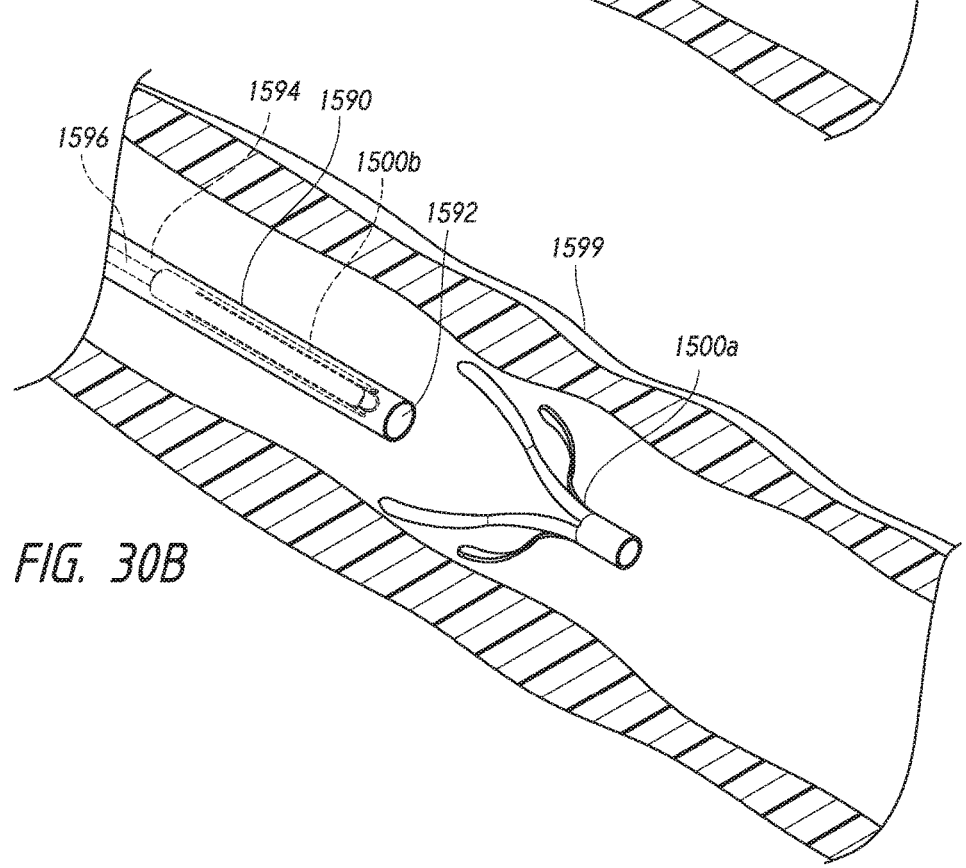
FIG. 30B shows a perspective view of a catheter, an implant in an expanded state, and an implant in the compressed state according to some embodiments.

In accordance with some embodiments, as shown in FIGS. 30A-30C, the first and second implants 1500a, 1500b and a catheter 1590 are provided to a site within a vessel 1599. The first and second implants 1500a, 1500b are axially aligned with opposite axial orientations within a lumen 1594 of the catheter 1590, such that the respective arms of the first and second implants 1500a, 1500b face each other. Terminal ends of the arms 1520a, 1520b of the first and second implants 1500a, 1500b may be shaped to provide a complementary fit. For example, as shown in FIG. 30B, the terminal ends of the first implant 1500a may be pointed or curved, such that terminal ends of the second implant 1500b with the opposite axial orientation and being angularly offset may fit against the terminal ends of the first implant 1500a. Accordingly, the angular offset of the first and second implants 1500a, 1500b may be achieved or maintained by pushing the terminal ends of the arms 1520a, 1520b against each other.

As shown in FIG. 30B, the first implant 1500a is advanced out of a port 1592 of the catheter 1590 and expands from a compressed state to an expanded state. The first implant 1500a may be advanced by a force transmitted by a pusher 1596. The force may be transmitted directly to the first implant 1500a or indirectly via the second implant 1500b. In the expanded state, the arms 1510a of the first implant 1500a engage a wall of the vessel 1599.

After expansion of the first implant 1500a and before expansion of the second implant 1500b, the catheter 1590 may be advanced toward the expanded first implant 1500a. As shown in FIG. 30C, the second implant 1500b is advanced out of the port 1592 of the catheter 1590 and expands from a compressed state to an expanded state. The second implant 1500b may be advanced by a force transmitted by the pusher 1596. In the expanded state, the arms 1510b of the second implant 1500b engage a wall of the vessel 1599. In the expanded state, each arm 1520a of the first implant 1500a is disposed between circumferentially adjacent arms 1520b of the second implant 1500b, and each arm 1520b of the second implant 1500b is disposed between circumferentially adjacent arms 1520a of the first implant 1500a. The opposing directions of the first and second implants 1500a, 1500b effectively occludes flow in either direction with the vessel 1599. The catheter 1590 may be withdrawn after expansion of the first and second implants 1500a, 1500b.

In accordance with some embodiments, the pusher 1596 may be detachably connected to at least one of the first and second implants 1500a, 1500b. The pusher 1596 may detach by one or more of a variety of mechanisms. For example, the pusher 1596 may be frictionally engaged with a hub 1510. Other detachment mechanisms are contemplated, including removal of an interference fit, electrolytic detachment, thermal detachment, combinations thereof, and the like.

Figure 31:
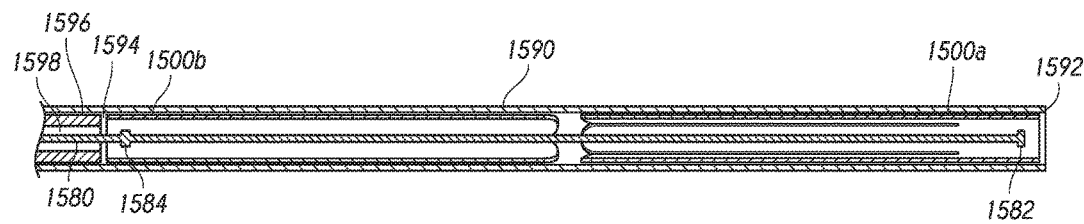
FIG. 31 shows a cross-sectional view of a catheter and two implants in compressed states, according to some embodiments.
Figure 32A:
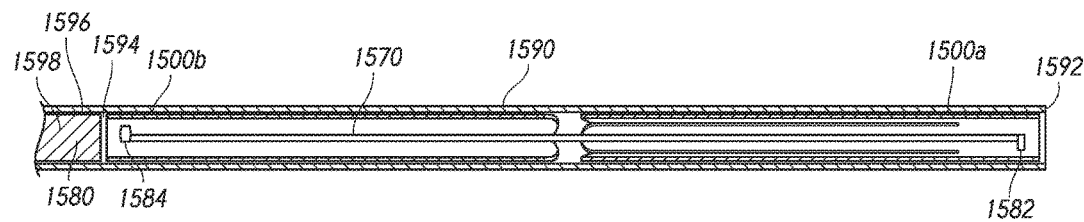
FIG. 32A shows a cross-sectional view of a catheter and two implants in compressed states, according to some embodiments.
Figure 32B:
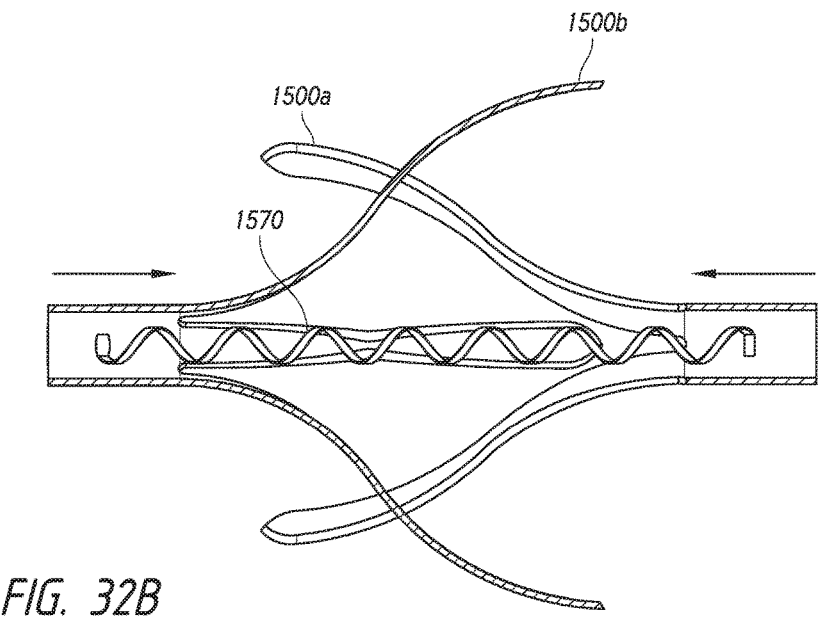
FIG. 32B shows a cross-sectional view of a catheter and two implants in the expanded states, according to some embodiments.

In accordance with some embodiments, as shown in FIGS. 31 and 32A-32B, one or both of the first and second implants 1500a, 1500b may be connected to a tether 1580. For example, the tether 1580 may attach to and/or extend between hubs 1510a, 1510b of the first and second implants 1500a, 1500b, respectively. The tether 1580 may extend through a lumen 1598 of the pusher 1596 or adjacent to the pusher 1596. The first and second implants 1500a, 1500b may be connected prior to, during, or after delivery thereof, or the first and second implants 1500a, 1500b may be separately delivered and attached in situ. For example, the tether 1580 can be detachably connected to the first implant 1500a at a first connection point 1582. By further example, the tether 1580 can be detachably connected to the second implant 1500b at a second connection point 1584. One or both of the implants 1500a, 1500b can be deployed from the catheter 1590. Thereafter, one of the connections 1584 or 1852 may be maintained to adjust the position of the connected implant relative to the other implant. For example, the first implant 1500a can be deployed (and detached if necessary) to a location, and the second implant 1500b can be moved relative to the first implant 1500a by pushing or pulling the tether 1580. By further example, the second implant 1500b can be deployed (and detached if necessary) to a location, and the first implant 1500a can be moved relative to the second implant 1500b by pushing or pulling the tether 1580.

In accordance with some embodiments, as shown in FIGS. 32A-32B, the first and second implants 1500a, 1500b may be connected to each other by a band 1570. The band 1570 can be connected to the first implant 1500a at a first connection point 1582, and the band 1570 can be connected to the second implant 1500b at a second connection point 1584. As shown in FIG. 32A, as the implants 1500a, 1500b are in the compressed state in the catheter 1590, the band 1570 may be elongated and straight. As shown in FIG. 32B, when released from the catheter 1590, the implants 1500a, 1500b can move to an expanded state, and the band 1570 can transition to a shortened configuration, such that the implants 1500a, 1500b are drawn toward each other. The band 1570 can be configured to shorten axially by coiling, bending, or expanding radially.

Referring now to FIGS. 33A-33D, features of an exemplary embodiment of an implant 1600 are illustrated. The implant 1600 can include a support frame 1602 and an occlusive cover 1660 supported by the support frame 1602. When implanted into a vessel, the implant 1600 can be configured to provide sufficient radial strength against a vessel wall under normal blood pressure in order to minimize post-deployment migration.

Referring now to FIG. 33A, in some embodiments, the support frame 1602 can include a proximal anchor 1610, a connection bridge 1620, and a distal anchor 1630. The support frame 1602 can be formed as a unitary body. For example, the support frame 1602 can be formed of a single, continuous wire. The support frame 1602 can be designed to be secured at a target location and hold an occlusive cover 1660 against a wall of the body vessel.

As shown in FIGS. 33A-33B, the body of the proximal anchor 1610 can extend along a curvilinear, helical path. A helical coil formed by the proximal anchor 1610 can extend about a central axis of the implant 1600. Alternatively or in combination, the proximal anchor 1610 can form other substantially cylindrical structures, such as a braided stent, a stent cut from a tube, or a series of interconnected hoops. One or both of the proximal anchor 1610 and the distal anchor 1630 can be oversized to have, in an unrestrained configuration, an outer cross-sectional dimension that exceeds the cross-sectional dimension of the body vessel at a target location for implantation. Such a configuration can provide proper wall apposition for lumen occlusion and device stability. Accordingly, the proximal anchor 1610 can provide securement of the implant 1600 at a target location by generating a frictional force against a wall of the body vessel.

As shown in FIGS. 33A-33B, the body of the distal anchor 1630 can extend along a circumferentially continuous path. The distal anchor 1630 can include a plurality of struts 1640. The struts 1640, or portions thereof, can extend longitudinally so as to be parallel to a central axis of the implant 1600. Alternatively, the struts 1640, or portions thereof, can extend transversely to the central axis of the implant. The plurality of struts 1640 can be connected to each other by proximal bends 1650a and distal bends 1650b. For example, each of the struts 1640 can be connected to a circumferentially adjacent strut by one of the proximal bends 1650a. Each of the struts 1640 can also be connected to a circumferentially adjacent strut by one of the distal bends 1650b.

The distal anchor 1630 can also extend along a circumferential path by forming other repeating or non-repeating patterns, such as sinusoidal waves, square waves, triangular waves, sawtooth waves, and combinations thereof. The distal anchor 1630 can otherwise extend a given axial length from a proximal end thereof to a distal end thereof. The axial length can be sufficiently large relative to the cross-sectional diameter of the anchor portion 1630 to provide sufficient stability. For example, the axial length of the anchor portion 1630 can be at least about 30%, 40%, 50%, 60%, 70%, 80%, 90%, or 100% the cross-sectional diameter of the anchor portion 1630. By further example, the axial length of the anchor portion 1630 can be greater than the cross-sectional diameter of the anchor portion 1630.

As further shown in FIGS. 33A-33B, the connection bridge 1620 can connect the proximal anchor 1610 to the distal anchor 1630. The connection bridge 1620 can extend longitudinally and parallel to the central axis of the frame 1602. Alternatively, the connection bridge 1620 can extend helically about a central axis of the frame 1602. The connection bridge 1620 can be located to contact a wall of the body vessel when implanted. Multiple connection bridge is 1620 can be provided about the circumference of the frame 1602 to connect the proximal anchor 1610 to the distal anchor 1630. The connection bridge 1620 can be 1-5 mm long or long enough to allow sufficient flexibility and maneuverability of the device and its major components. For example, the connection bridge 1620 can provide a pivoting action that allows the proximal anchor 1610 to be oriented differently than the distal anchor 1630. Accordingly, the frame 1602 can be placed within tortuous anatomy while still allowing the proximal anchor 1610 and the distal anchor 1630 to adequately conform to a wall of the body vessel.

In some embodiments, no connection bridge 1620 is provided, such that the proximal anchor 1610 connects directly to the distal anchor 1630.

Referring now to FIG. 33C, in some embodiments, the profile of the frame 1602 is formed such that the outer radial surface of the frame 1602 conforms to a shape that corresponds to a target location of a body vessel. In some embodiments, the profile of the frame 1602 is formed such that the inner radial surface of the frame 1602 defines a lumen extending therethrough, with no portion of the frame 1602 extending radially into or across the lumen. Accordingly, each of the proximal anchor 1610 the connection bridge 1620 and the distal anchor 1630 can be confined within a cross-sectional profile as shown in FIG. 33C and described herein.

In some embodiments, a length of the support frame 1602 can be between about 7 millimeters (mm) and about 9 mm. In some embodiments, the length of the support frame 1602 can be less than about 7 mm or greater than about 9 mm. In some embodiments, the length of the distal anchor 1630 can be between about 3 millimeters (mm) and about 5 mm. In some embodiments, the length of the distal anchor 1630 can be less than about 3 mm or greater than about 5 mm. In some embodiments, a diameter of the proximal anchor 1610 and/or the distal anchor 1630 can be between about 2 mm and about 10 mm. In some embodiments, the diameter of the proximal anchor 1610 and/or the distal anchor 1630 can be less than about 2 mm or greater than about 10 mm.

FIG. 33D illustrates a perspective view of the implant 1600, similar to the illustrations of FIGS. 33A-33C, but further including an implant occlusive cover 1660. As illustrated, the implant occlusive cover 1660 can be positioned over at least a portion of the support frame 1602 (e.g., the distal anchor 1630) and delivered in a mounted or collapsed configuration. In some embodiments, the occlusive cover 1660 includes an open proximal end 1662 and a closed distal end 1664. The proximal end 1662 can be located proximal to, coterminous with, or distal to a proximal end of the distal anchor 1630. The distal end 1664 can be located distal to the distal end of the distal anchor 1630. The occlusive covers 1660 can cover an entirety of or a portion of a radially outer surface of the distal anchor 1630.

In some embodiments, the occlusive cover 1660 can be fixed to the frame 1602. For example, the occlusive cover 1660 can be tied, glued, sutured, adhered, or otherwise fixedly attached to the frame 1602. Alternatively, the occlusive cover 1660 can be loosely provided about a portion of the frame 1602, such that the frame 1602 maintains contact with the occlusive cover by friction via an outward radial force. The outward radial force can hold the distal anchor 1660 against the occlusive covers 1660 in a catheter or against a wall of a body vessel.

Referring now to FIG. 34, in some embodiments, the frame 1602 can achieve or be provided in a collapsed configuration, wherein the frame 1602 has a reduced cross-sectional dimension. As shown in FIG. 34, the frame 1602, having a reduced cross-sectional dimension, can have an increased axial length. For example, the proximal anchor 1610 can be compressed to form a helical coil, undulating curvilinear shape, or straight line that has a reduced cross-sectional dimension and an enlarged axial length. By further example, the distal anchor 1630 can be compressed to form a shape that has a reduced cross-sectional dimension and an enlarged axial length. The struts 1640 can move radially inward to increase their relative circumferential proximity. Furthermore, the proximal bends 1650a and the distal bends 1650b can decrease a radius of curvature along a portion thereof. Other portions of the proximal bends 1650a and the distal bends 1650b can straighten to align with axially adjacent struts 1640.

Referring now to FIGS. 35A-35B, the implant 1600 can be advanced within a body vessel to a target location. The implant 1600 can be carried within a catheter 1690 that provides a lumen 1694 and a distal port 1692. In accordance with some embodiments, the implant 1600 can be shape-set in an expanded configuration, and pulled into the lumen 1694 of the catheter 1690 to collapse to the collapsed configuration. As shown in FIG. 35A, the catheter 1690 containing the implant 1600 can be provided to a site within a vessel 1699. As shown in FIG. 35B, the implant 1600 can be advanced relative to the catheter 1690, such that the implant 1600 exits from the lumen 1694 of the catheter 1690 through the port 1692 at the distal end of the catheter 1690. The implant 1600 expands from a collapsed configuration to an expanded configuration upon exiting the catheter 1690. In the expanded configuration, the distal anchor 1630 can hold a portion of the occlusive cover 1660 against a wall of the vessel 1699. The catheter 1690 can be withdrawn after expansion of the implant 1600.

In accordance with some embodiments, as shown in FIG. 35A-35B, the implant 1600 can contain a pusher 1696 contacting a proximal end of the proximal anchor 1610. The pusher 1696 causes ejection of the implant 1600 out of the distal port 1692 by advancement of the pusher 1696 within the lumen 1694. In accordance with some embodiments, the pusher 1696 can be a wire that is detachably connected to a portion of the frame 1602. For example, the pusher 1696 can advance the implant 1600 out of the catheter 1690 and remain attached to the frame 1602 until a subsequent operation is performed. For example, the pusher 1696 can be electrolytically, mechanically, thermally, or chemically detached from the frame 1602 at a designated time determined by the user.

The implant 1600 can fit into a 4 F catheter or smaller and possess the ability for controlled deployment and optional retrieval back into the catheter until desired positioning and detachment is complete. The implant 1600 can provide total occlusion of a blood vessel or vascular structure within the human body. The construct is applicable to all endovascular applications, specifically neurovascular vessels of 3-6 mm diameter, and peripheral vasculature of 3-14 mm. The implant 1600 can be used for delivery via a 4 F or smaller catheter system. The construct can be formed to various diameters (3-6 mm, and 6-14 mm) for use within appropriate vessels and vascular structures.

According to various embodiments of the subject technology, the implant occlusive cover 1660 can be used to occlude, partially or completely, a body vessel in which an implant 1600 is deployed. In some embodiments as used herein, occlusion can refer to either partial or complete occlusion. Occlusion provided by the occlusive covers 1660 can limit, impede, reduce, prevent, or eliminate flow within the body vessel distal to the occlusive covers 1660.

According to some embodiments of the subject technology, an implant 1600a can include an anchor 1630a and an occlusive cover 1660a. The anchor 1630a can include features and attributes of the distal anchor 1630, including features of the distal anchor 1630 with respect to the occlusive covers 1660, as disclosed herein. The anchor 1630a can include features and attributes of other structures disclosed herein, including but not limited to any of the distal anchors disclosed herein. The anchor 1630a can be provided with neither a proximal anchor nor a connection bridge. As such, the implant 1600a can include only an anchor 1630a and an occlusive covers 1660a. The anchor 1630a can be positioned entirely within or partially within the occlusive cover 1660a.

Figure 36A:
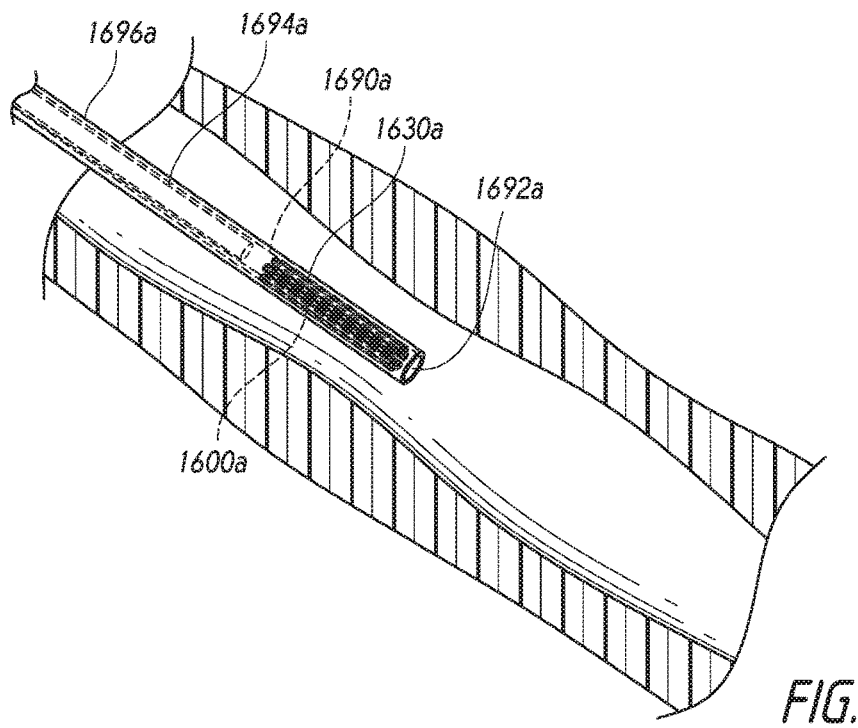
FIG. 36A shows a perspective view of an implant in a collapsed configuration within a catheter, according to some embodiments.
Figure 36B:
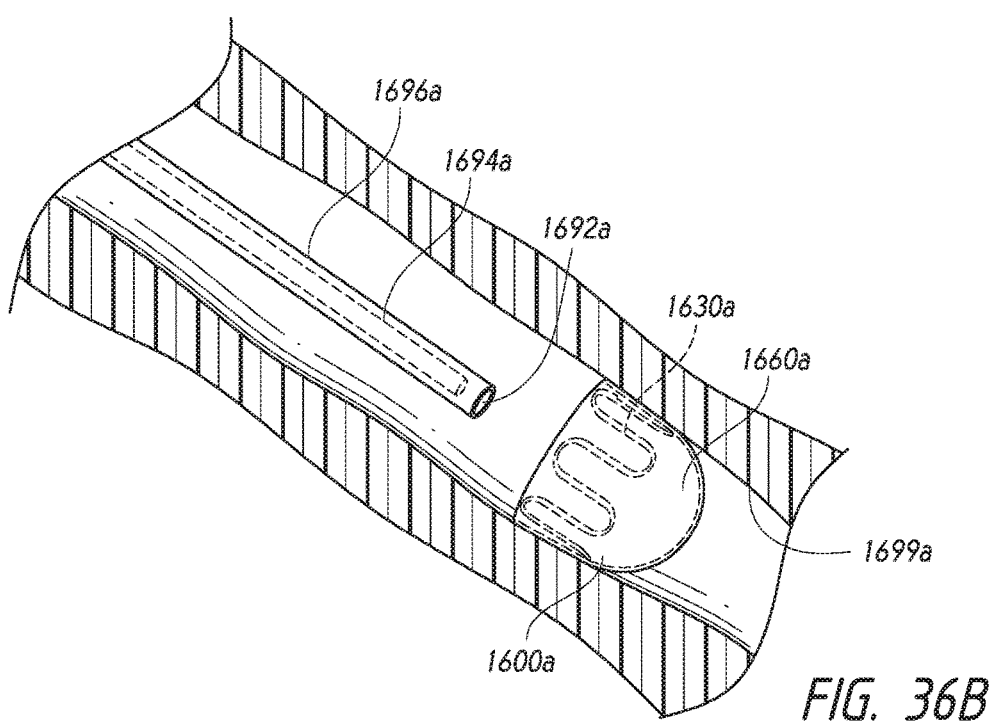
FIG. 36B shows a perspective view of an implant in an expanded configuration within a body vessel, according to some embodiments.

Referring now to FIGS. 36A-36B, the implant 1600a can be advanced within a body vessel to a target location. The implant 1600a can be carried within a catheter 1690a that provides a lumen 1694a and a distal port 1692a. In accordance with some embodiments, the implant 1600a can be shape-set in an expanded configuration, and pulled into the lumen 1694a of the catheter 1690a to collapse to the collapsed configuration. As shown in FIG. 36A, the catheter 1690a containing the implant 1600a can be provided to a site within a vessel 1699a. As shown in FIG. 36B, the implant 1600a can be advanced relative to the catheter 1690a, such that the implant 1600a exits from the lumen 1694a of the catheter 1690a through the port 1692a at the distal end of the catheter 1690a. The implant 1600a expands from a collapsed configuration to an expanded configuration upon exiting the catheter 1690a. In the expanded configuration, the distal anchor 1630a can hold a portion of the occlusive cover 1660a against a wall of the vessel 1699a. The catheter 1690a can be withdrawn after expansion of the implant 1600a.

In accordance with some embodiments, as shown in FIG. 36A-36B, the implant 1600a can include a pusher 1696a contacting a proximal end of the anchor 1630a. The pusher 1696a causes ejection of the implant 1600a out of the distal port 1692a by advancement of the pusher 1696a within the lumen 1694a. In accordance with some embodiments, the pusher 1696a can be a wire that is detachably connected to a portion of the anchor 1630a. For example, the pusher 1696a can advance the implant 1600a out of the catheter 1690a and remain attached to the anchor 1630a until a subsequent operation is performed. For example, the pusher 1696a can be electrolytically, mechanically, thermally, or chemically detached from the anchor 1630a at a designated time determined by the user.

Referring now to FIGS. 37A-37B, in accordance with some embodiments, the distal anchor 1630 can include struts 1640 having a circumferential width 1642, as measured along a circumference of the distal anchor 1630 or along a line tangent to the circumference of the distal anchor 1630. The struts 1640 can have the same circumferential width 1642 or varying circumferential width 1642 relative to each other. In accordance with some embodiments, each of the proximal bends 1650a and distal bends 1650b has an axial width 1652, as measured along a line parallel to a central axis of the distal anchor 1630 or the implant 1600. The proximal bends 1650a and distal bends 1650b can have the same axial width 1652 or varying axial width 1652 relative to each other. In accordance with some embodiments, a circumferential width 1642 of each of the plurality of struts 1640 exceeds an axial width 1652 of the proximal bends 1650a and distal bends 1650b. Accordingly, when transitioning from an expanded configuration to a collapsed configuration, the proximal bends 1650a and distal bends 1650b provide greater flexibility for bending than the flexibility of the struts 1640. The struts 1640, the proximal bends 1650a, and the distal bends 1650b can have the same or different radial thicknesses.

Referring now to FIG. 38, in accordance with some embodiments, a distal anchor 1630b of a frame 1602b can have a radially largest outer cross-sectional dimension at a distal end of the distal anchor 1630b (i.e., at the distal bends 1650bb). Alternatively or in combination, a distal anchor 1630b can have a radially largest outer cross-sectional dimension at a proximal end of the distal anchor 1630b (i.e., at the proximal bends 1650ab). Alternatively or in combination, a distal anchor 1630b can have a radially largest outer cross-sectional dimension at a middle portion of the distal anchor 1630b (e.g., at struts 1640b). The distal anchor 1630b can have a collapsed configuration substantially similar to the configuration of the distal anchor 1630 shown in FIG. 34. In accordance with some embodiments, the distal anchor 1630b can connect via a connection bridge 1620b to a proximal anchor and include other features of the frame 1602 of the implant 1600. Accordingly, the distal anchor 1630b can be delivered to within a body vessel by a method substantially similar to the method illustrated in FIGS. 35A-35B. Alternatively, the distal anchor 1630b can be provided independent of a connection bridge 1620b or a proximal anchor. Accordingly, the distal anchor 1630b can be delivered to within a body vessel by a method substantially similar to the method illustrated in FIGS. 36A-36B.

Referring now to FIG. 39, in accordance with some embodiments, a distal anchor 1630c of a frame 1602c can have a radially smallest outer cross-sectional dimension at a distal end of the distal anchor 1630c (i.e., at the distal bends 1650bc). Alternatively or in combination, a distal anchor 1630c can have a radially smallest outer cross-sectional dimension at a proximal end of the distal anchor 1630c (i.e., at the proximal bends 1650ac). Alternatively or in combination, a distal anchor 1630c can have a radially smallest outer cross-sectional dimension at a middle portion of the distal anchor 1630c (e.g., at struts 1640c). The distal anchor 1630c can have a collapsed configuration substantially similar to the configuration of the distal anchor 1630 shown in FIG. 34. In accordance with some embodiments, the distal anchor 1630c can connect via a connection bridge 1620c to a proximal anchor and include other features of the frame 1602 of the implant 1600. Accordingly, the distal anchor 1630c can be delivered to within a body vessel by a method substantially similar to the method illustrated in FIGS. 35A-35B. Alternatively, the distal anchor 1630c can be provided independent of a connection bridge 1620c or a proximal anchor. Accordingly, the distal anchor 1630c can be delivered to within a body vessel by a method substantially similar to the method illustrated in FIGS. 36A-36B.

Referring now to FIGS. 40A-40D, in accordance with some embodiments, a distal anchor 1730 of a frame 1702 can include a plurality of circumferential rings. For example, as shown in FIGS. 40A-40B, three circumferential rings 1770a, 1770b, and 1770c can be provided axially in series. By further example, the distal anchor 1730 can include two circumferential rings or more than three circumferential rings. Each of the circumferential rings 1770a, 1770b, 1770c can have features and attributes corresponding to the distal anchor 1630, as disclosed herein. For example, each of the circumferential rings 1770a, 1770b, 1770c can include a plurality of parallel struts 1740 connected by bends 1750a, 1750b, 1750c, 1750d, 1750e, and/or 1750f.

In accordance with some embodiments, pairs of axially adjacent circumferential rings 1770a, 1770b, 1770c can be welded together at one or more contact points. Alternatively or in combination, pairs of axially adjacent circumferential rings 1770a, 1770b, 1770c can be interwoven with an alternating over-and-under pattern, wherein portions of a first circumferential ring lie radially over portions of a second circumferential ring, and other portions of the first circumferential ring lie radially under other portions of the second circumferential ring. Alternatively or in combination, pairs of axially adjacent circumferential rings 1770a, 1770b, 1770c can be tied, adhered, or otherwise fixedly attached to each other. Pairs of struts 1740 across pairs of axially adjacent circumferential rings 1770a, 1770b, 1770c can be circumferentially aligned or circumferentially offset relative to each other.

The distal anchor 1730 can have a collapsed configuration as shown in FIG. 40D. As shown in FIG. 40D, the distal anchor 1730 can be compressed to form a shape that has a reduced cross-sectional dimension and an enlarged axial length. The struts 1740 can move radially inward to increase their relative circumferential proximity. Furthermore, the bends 1750a, 1750b, 1750c, 1750d, 1750e, 1750f can decrease a radius of curvature along a portion thereof. Other portions of the bends 1750a, 1750b, 1750c, 1750d, 1750e, 1750f can straighten to align with axially adjacent struts 1740.

In accordance with some embodiments, the distal anchor 1730 can connect via a connection bridge 1720 to a proximal anchor and include other features of the frame 1602 of the implant 1600. Accordingly, the distal anchor 1730 can be delivered to within a body vessel by a method substantially similar to the method illustrated in FIGS. 35A-35B. Alternatively, the distal anchor 1730 can be provided independent of a connection bridge 1720 or a proximal anchor. Accordingly, the distal anchor 1730 can be delivered to within a body vessel by a method substantially similar to the method illustrated in FIGS. 36A-36B.

Referring now to FIGS. 41A-41D, in accordance with some embodiments, a distal anchor 1830 of a frame 1802 can extend along a circumferentially continuous path formed by struts 1840, proximal bends 1850a, and distal bends 1850b. The distal anchor 1830 can attach to a hoop 1822 that extends at least partially circumferentially at a proximal end of the distal anchor 1830. The hoop 1822 can weave through portions of the distal anchor 1830 by passing over radially outward surfaces of portions of the distal anchor 1830 and by passing under radially inwards surfaces of other portions of the distal anchor 1830. Alternatively or in combination, the hoop 1822 can be fixedly attached to the distal anchor 1830 by a weld, a tie, an adhesive, or combinations thereof. The hoop 1822 can connect to connection bridges 1820a and 1820b.

Figure 41A:
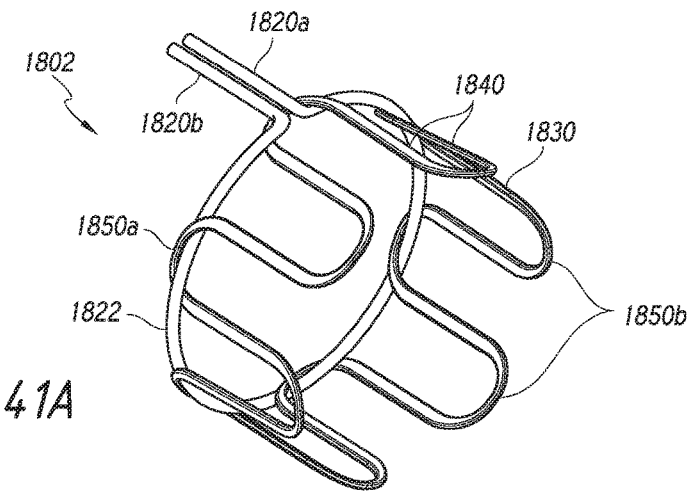
FIG. 41A shows a perspective view of a support frame of an implant, according to some embodiments.
Figure 41B:
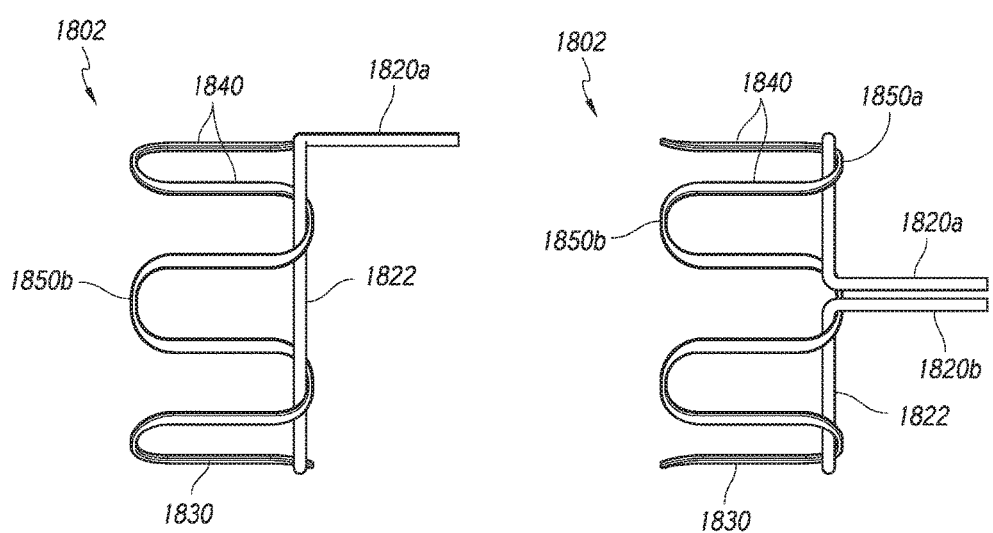
FIG. 41B shows a side view of a support frame of an implant, according to some embodiments.
Figure 41C:
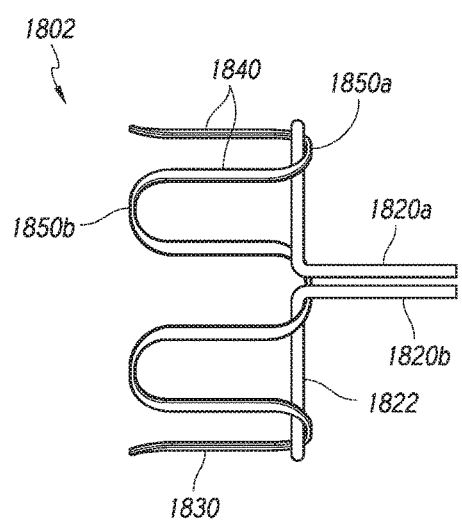
FIG. 41C shows a top view of a support frame of an implant, according to some embodiments.
Figure 41D:
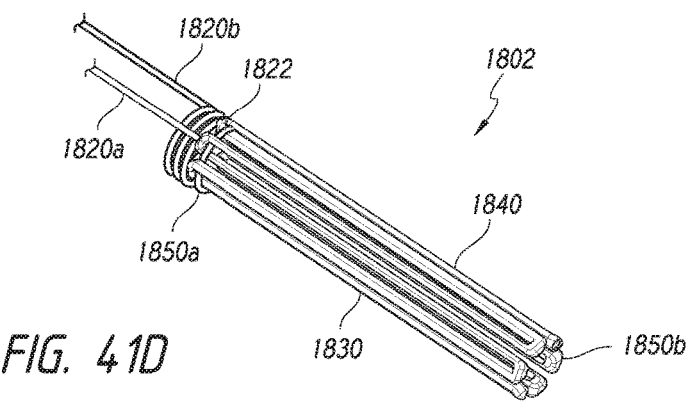
FIG. 41D shows a perspective view of a support frame of an implant in a collapsed configuration, according to some embodiments.

The distal anchor 1830 can have a collapsed configuration as shown in FIG. 41D. As shown in FIG. 41D, the distal anchor 1830 can be compressed to form a shape that has a reduced cross-sectional dimension and an enlarged axial length. The struts 1840 can move radially inward to increase their relative circumferential proximity. Furthermore, the bends 1850a, 1850b can decrease a radius of curvature along a portion thereof. Other portions of the bends 1850a, 1850b can straighten to align with axially adjacent struts 1840. In the collapsed configuration, the hoop 1822 can transition to form multiple windings of a helical coil. For example, the connection bridges 1820a, 1820b can wind circumferentially past each other one or more times to form the multiple windings of the helical coil.

In accordance with some embodiments, the distal anchor 1830 can connect via one or more of the connection bridges 1820a, 1820b to a proximal anchor and include other features of the frame 1602 of the implant 1600. Accordingly, the distal anchor 1830 can be delivered to within a body vessel by a method substantially similar to the method illustrated in FIGS. 35A-35B. Alternatively, the distal anchor 1830 can be provided independent of any connection bridges 1820a, 1820b or a proximal anchor. Accordingly, the distal anchor 1830 can be delivered to within a body vessel by a method substantially similar to the method illustrated in FIGS. 36A-36B.

Figure 42A:
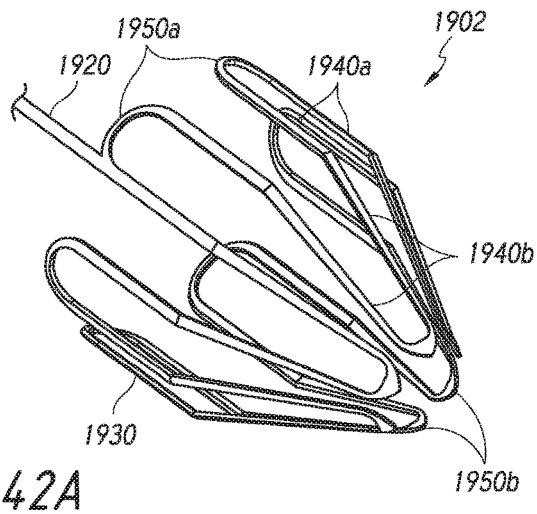
FIG. 42A shows a perspective view of a support frame of an implant, according to some embodiments.
Figure 42B:
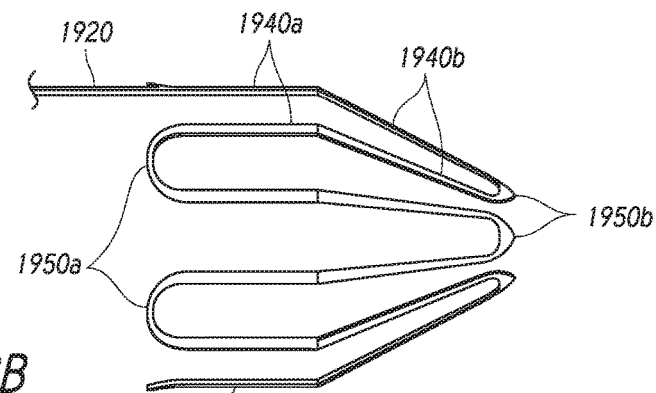
FIG. 42B shows a side view of a support frame of an implant, according to some embodiments.
Figures 42C, 42D:
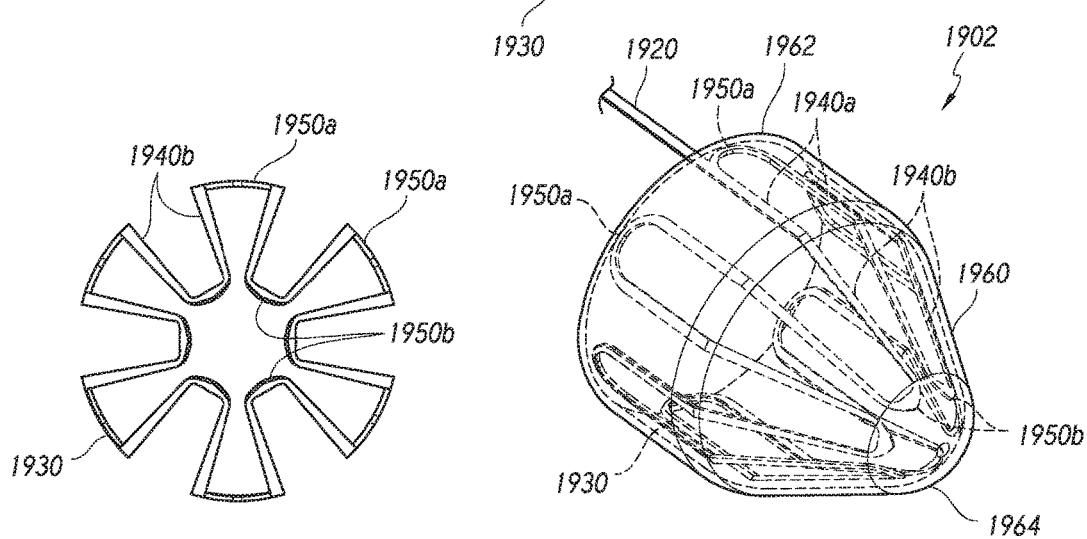
FIG. 42C shows a front view of a support frame of an implant, according to some embodiments.

Referring now to FIGS. 42A-42D, in accordance with some embodiments, a distal anchor 1930 of a frame 1902 can extend along a circumferentially continuous path formed by proximal struts 1940a, distal struts 1940b, proximal bends 1950a, and distal bends 1950b. The proximal struts 1940a can define a proximal section of the distal anchor 1930, and the distal struts 1940b can define a distal section of the distal anchor 1930. The proximal struts 1940a of the proximal section define a first outer cross-sectional dimension and extend axially at the first outer cross-sectional dimension. The first outer cross-sectional dimension can correspond to (e.g. be equal to or exceed, in an expanded configuration) and inner diameter of the body vessel. The distal struts 1940b of the distal section can taper along an axial length thereof from the first outer cross-sectional dimension to a second outer cross-sectional dimension, less than the first outer cross-sectional dimension. The taper of the distal section can be linear, curvilinear, stepwise, or combinations thereof. As shown in FIG. 42D, at least a portion of the distal anchor 1930 can be provided with an occlusive cover 1960 having an open proximal end 1962 and a closed distal end 1964.

The distal anchor 1930 can have a collapsed configuration substantially similar to the configuration of the distal anchor 1630 shown in FIG. 34. In accordance with some embodiments, the distal anchor 1930 can connect via a connection bridge 1920 to a proximal anchor and include other features of the frame 1602 of the implant 1600. Accordingly, the distal anchor 1930 can be delivered to within a body vessel by a method substantially similar to the method illustrated in FIGS. 35A-35B. Alternatively, the distal anchor 1930 can be provided independent of a connection bridge 1920 or a proximal anchor. Accordingly, the distal anchor 1930 can be delivered to within a body vessel by a method substantially similar to the method illustrated in FIGS. 36A-36B.

Referring now to FIGS. 43A-43D, in accordance with some embodiments, a distal anchor 2030 of a frame 2002 can extend along a circumferentially continuous path formed by proximal struts 2040a, middle struts 2040b, distal struts 2040c, proximal bends 2050a, and distal bends 2050b. The proximal struts 2040a can define a proximal section of the distal anchor 2030, the middle struts 2040b can define a middle section of the distal anchor 2030, and the distal struts 2040c can define a distal section of the distal anchor 2030. The proximal struts 2040a of the proximal section define a first outer cross-sectional dimension and extend axially at the first outer cross-sectional dimension. The first outer cross-sectional dimension can correspond to (e.g. be equal to or exceed, in an expanded configuration) an inner diameter of a portion of the body vessel. The middle struts 2040b of the middle section can taper along an axial length thereof from the first outer cross-sectional dimension to a second outer cross-sectional dimension, less than the first outer cross-sectional dimension. The taper of the middle section can be linear, curvilinear, stepwise, or combinations thereof. The distal struts 2040c of the distal section further define the second outer cross-sectional dimension and extend axially at the second outer cross-sectional dimension. The second outer cross-sectional dimension can correspond to (e.g. be equal to or exceed, in an expanded configuration) and inner diameter of a different portion of the body vessel. As shown in FIG. 43D, at least a portion of the distal anchor 2030 can be provided with an occlusive cover 2060 having an open proximal end 2062 and a closed distal end 2064.

The distal anchor 2030 can have a collapsed configuration substantially similar to the configuration of the distal anchor 1630 shown in FIG. 34. In accordance with some embodiments, the distal anchor 2030 can connect via a connection bridge 2020 to a proximal anchor and include other features of the frame 1602 of the implant 1600. Accordingly, the distal anchor 2030 can be delivered to within a body vessel by a method substantially similar to the method illustrated in FIGS. 35A-35B. Alternatively, the distal anchor 2030 can be provided independent of a connection bridge 2020 or a proximal anchor. Accordingly, the distal anchor 2030 can be delivered to within a body vessel by a method substantially similar to the method illustrated in FIGS. 36A-36B.

Referring now to FIGS. 44A-44D, features of an exemplary embodiment of an implant 2100 are illustrated. The implant 2100 can include a proximal anchor 2110, a connection bridge 2120, and a spherical member 2130. The implant 2100 can be designed to be secured at a target location.

As shown in FIGS. 44A-44B, the body of the proximal anchor 2110 can extend along a curvilinear, helical path. A helical coil formed by the proximal anchor 2110 can extend about a central axis of the implant 2110. Alternatively or in combination, the proximal anchor 2110 can form other substantially cylindrical structures, such as a braided stent, a stent cut from a tube, or a series of interconnected hoops. One or both of the proximal anchor 2110 and the spherical member 2130 can be oversized to have, in an unrestrained configuration, an outer cross-sectional dimension that exceeds the cross-sectional dimension of the body vessel at a target location for implantation. Such a configuration can provide proper wall apposition for lumen occlusion and device stability. Accordingly, the proximal anchor 2110 can provide securement of the implant 2100 at a target location by generating a frictional force against a wall of the body vessel.

As further shown in FIGS. 44A-44B, the connection bridge 2120 can connect the proximal anchor 2110 to the spherical member 2130. The connection bridge 2120 can extend along or parallel to the central axis of the implant 2100. The connection bridge 2120 can be 1-5 mm long or long enough to allow sufficient flexibility and maneuverability of the device and its major components. For example, the connection bridge 2120 can provide a pivoting action that allows the proximal anchor 2110 to be oriented differently than the spherical member 2130. Accordingly, the implant 2100 can be placed within tortuous anatomy while still allowing the proximal anchor 2110 and the spherical member 2130 to adequately conform to a wall of the body vessel.

In accordance with some embodiments, the spherical member 2130 can be constructed by a plurality of interwoven strands. For example, the spherical member 2130 can be a braided structure. The strands can extend from a proximal end member 2132 to a distal end member 2134 at opposite axial ends of the spherical member 2130. Alternatively or in combination, the spherical number 2130 can be constructed by a plurality of non-intersecting struts that extend from the proximal end member 2132 to the distal end member 2134. For example, the struts can extend axially or helically in a single direction. In accordance with some embodiments, the spherical member 2130 can be an inflatable balloon that is expandable by insufficient of a fluid. In accordance with some embodiments, the spherical member 2130 can be a swellable material that expands to form a sphere upon absorption of fluid.

In accordance with some embodiments, at least a portion of the spherical member 2130 occludes a passageway of the body vessel. For example, one or both of a proximally directed face of the spherical member 2130 and a distally directed face of the spherical member 2130 can form an occlusive surface. By further example, the structure of the spherical member 2130 (e.g., strands, struts, etc.) can partially or entirely include the body vessel. Alternatively or in combination, the spherical member 2130 can support an occlusive cover (not shown). The spherical member 2130 can be designed to be secured at a target location and hold the occlusive cover against a wall of the body vessel.

Referring now to FIG. 44D, in some embodiments, the implant 2100 can achieve or be provided in a collapsed configuration, wherein the implant 2100 has a reduced cross-sectional dimension. As shown in FIG. 34, the implant 2100, having a reduced cross-sectional dimension, can have an increased axial length. For example, the proximal anchor 2110 can be compressed to form a helical coil, undulating curvilinear shape, or straight line that has a reduced cross-sectional dimension and an enlarged axial length. By further example, the spherical member 2130 can be compressed to form a shape that has a reduced cross-sectional dimension and an enlarged axial length.

Figure 45A:
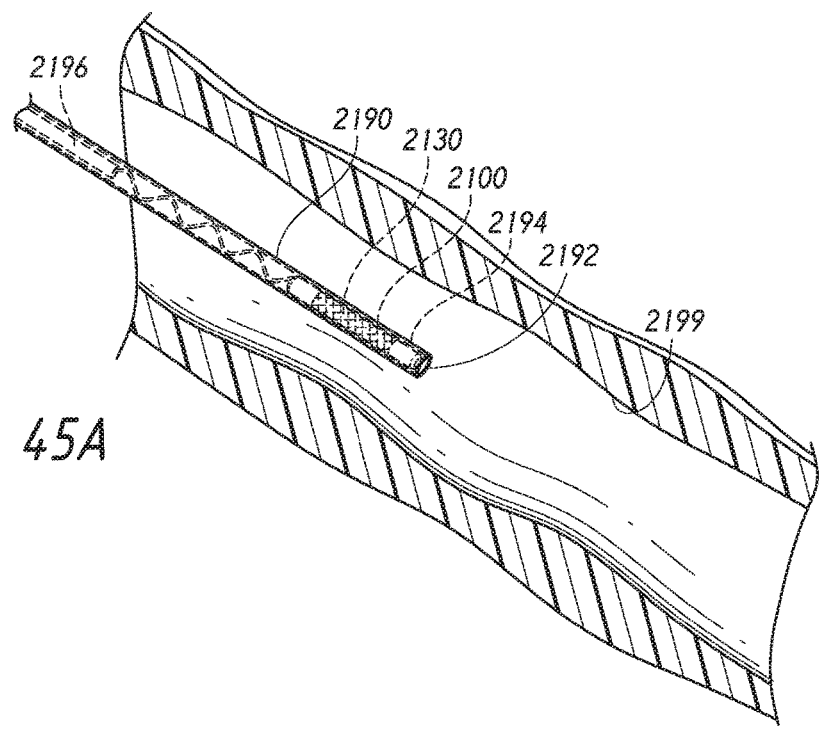
Figure 45B:
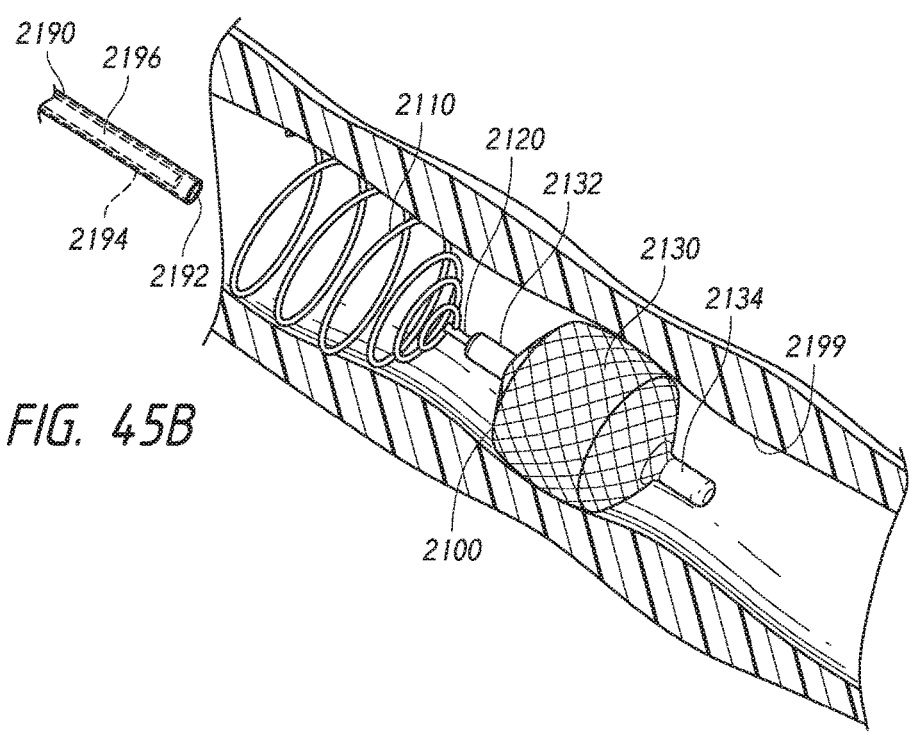

Referring now to FIGS. 45A-45B, the implant 2100 can be advanced within a body vessel to a target location. The implant 2100 can be carried within a catheter 2190 that provides a lumen 2194 and a distal port 2192. In accordance with some embodiments, the implant 2100 can be shape-set in an expanded configuration, and pulled into the lumen 2194 of the catheter 2190 to collapse to the collapsed configuration. As shown in FIG. 45A, the catheter 2190 containing the implant 2100 can be provided to a site within a vessel 2199. As shown in FIG. 45B, the implant 2100 can be advanced relative to the catheter 2190, such that the implant 2100 exits from the lumen 2194 of the catheter 2190 through the port 2192 at the distal end of the catheter 2190. The implant 2100 expands from a collapsed configuration to an expanded configuration upon exiting the catheter 2190. In the expanded configuration, the spherical member 2130 can hold a portion of an occlusive cover against a wall of the vessel 2199. The catheter 2190 can be withdrawn after expansion of the implant 2100.

In accordance with some embodiments, as shown in FIG. 45A-45B, the implant 2100 can include a pusher 2196 contacting a proximal end of the proximal anchor 2110. The pusher 2196 causes ejection of the implant 2100 out of the distal port 2192 by advancement of the pusher 2196 within the lumen 2194. In accordance with some embodiments, the pusher 2196 can be a wire that is detachably connected to a portion of the implant 2100. For example, the pusher 2196 can advance the implant 2100 out of the catheter 2190 and remain attached to the implant 2100 until a subsequent operation is performed. For example, the pusher 2196 can be electrolytically, mechanically, thermally, or chemically detached from the implant 2100 at a designated time determined by the user.

Some embodiments of the procedures, techniques, and implants disclosed herein can enable a clinician, in one or a several clinical procedures, to dynamically control the flow through a flow regulating implant. For example, according to some embodiments disclosed herein, procedures, techniques, and implants are provided by which a clinician can control or selectively adjust the flow through a shunt in order to optimize the pressure gradient between adjacent vessels, such as in the TIPS procedure or the distal splenorenal shunt procedure (DSRS) (i.e., splenorenal shunt procedure or Warren shunt). Further, methods and implants are provided in which a clinician can deposit embolic material into a target area downstream of an implanted shunt while preventing upstream flow or backflow of the particles away from the target area.

Some embodiments of the flow regulating implant can be configured to comprise a generally tubular member having a frame. In some embodiments, the tubular member can further comprise a graft, cover, or other material attached to the frame. Aspects of implants, catheters, and delivery devices that can be utilized in combination with the implants, systems, methods, and features disclosed herein are disclosed in: U.S. patent application Ser. No. 12/826,593, filed on Jun. 29, 2010 (086538-0012); U.S. patent application Ser. No. 13/367,338, filed on Feb. 6, 2012 (086538-0018); U.S. patent application Ser. No. 12/906,993, filed on Oct. 18, 2010 (086538-0014); U.S. patent application Ser. No. 13/828,974, filed on Mar. 14, 2013 (086538-0030); U.S. Patent Application No. 61/836,061, filed on Jun. 17, 2013 (086538-0038); U.S. patent application Ser. No. 14/044,794, filed on Oct. 2, 2013 (086538-0039); U.S.

patent application Ser. No. 14/281,797, filed on May 19, 2014 (086538-0055); U.S. Patent App. No. 61/835,406, filed on Jun. 14, 2013 (086538-0032); U.S. Patent App. No. 61/904,376, filed on Nov. 14, 2013 (086538-0041); U.S. Patent App. No. 61/904,379, filed on Nov. 14, 2013 (086538-0043); U.S. Patent App. No. 61/835,461, filed on Jun. 14, 2013 (086538-0034); U.S. Patent App. No. 61/900,321, filed on Nov. 5, 2013 (086538-0040); and U.S. patent application Ser. No. 14/101,171, filed on Dec. 9, 2013 (086538-0046), the entireties of which are incorporated herein by reference.

According to some embodiments, the flow regulating implant can comprise an implant having a tubular structure and a calibrated, adjustable tapered end by which flow through the implant can be controlled.

According to some embodiments, a desired flow resistance through the implant may be achieved through a mechanical alteration of one or more components of the implant, such as a movable, compressible, slidable, self-expandable, balloon-expandable, or telescopic portion of the implant. According to some embodiments, adjustment of the flow rate, flow restriction, or flow resistance through the implant can be substantially irreversible (e.g., a permanent alteration, such as by modifying a shape of a plastically deformable, non-resilient material, cutting, or otherwise removing a portion of a component, etc.). However, in some embodiments, adjustment of the flow rate, flow restriction, or flow resistance through the implant can be reversible (e.g., a temporary alteration, such as deflecting a resilient material, changing relative positions of components, etc.).

The implant can comprise a plurality of components, such as a structure with a variable aperture (e.g., an adjustable diaphragm, a series of deflectable leaflets, etc.) at the distal end of the implant. The adjustable end of the implant can be controlled, for example, by a balloon, an engagement member, and/or longitudinal movement of the catheter. Further, modifications to the adjustable and of the implant can be made intermittently, and can be formed performed, while optionally checking the pressure in the channel.

The implant can be delivered by image-guided catheter. Imaging may be provided by fluoroscopy or ultrasound. Although in some embodiments, the implant can comprise a shunt having a substantially constant diameter along at least a portion thereof, the implant may comprise one or more portions that are either not expandable, balloon-expandable, or self-expandable. Further, one or more components of the implant can be expandable and/or self-expandable while one or more other components of the implant can be balloon-expandable and/or self-expandable.

Figure 46:
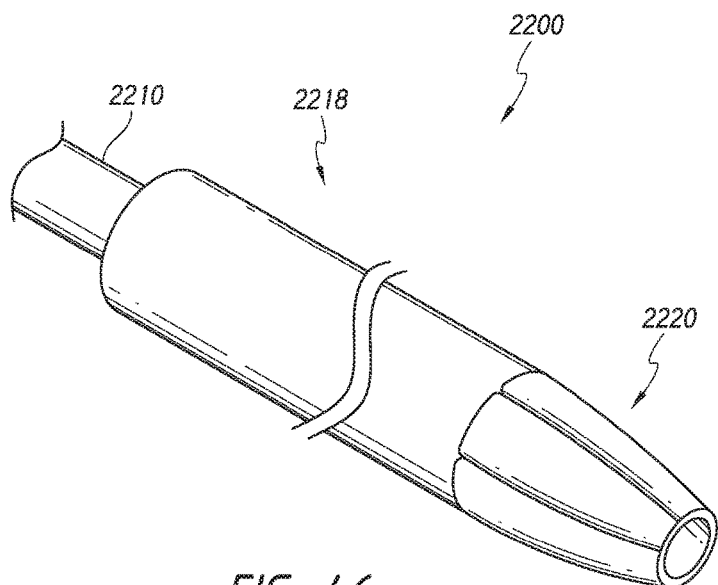

Referring to FIG. 46, the implant 2220 (or any of the other embodiments provided herein) can comprise one or more adjustable components that can be adjusted to regulate or modify flow of a bodily fluid through the implant 2220. The implant 2220 can comprise a plurality of components, such as one or more support components and one or more adjustable or flow restrictor components, which can be coupled to the support components and adjusted to regulate or modify flow through the implant 2220.

As shown in FIG. 47, according to some embodiments, the implant 2220 can comprise an outer, first component 2260 and an inner, second component 2262. The first component 2260 can comprise a shunt having a constant diameter along at least a first section thereof. The first component 2260 can be configured to receive the second component 2262 therewithin in order to selectively restrict flow through the first component 2260. For example, a shape or size of the second component 2262, or its position within the first component 2260 can be modified in order to achieve a desired flow resistance or flow rate through the first component 2260.

Thus, the implant 2220 can be configured such that the position of the second component 2262 relative to the first component 2260 can operate to adjust or restrict flow through the implant 2220.

For example, as illustrated in FIG. 48, embodiments of the implant 2220 can be used in a TIPS or other procedure in which a patient may benefit from flow control between two vessels. As shown in FIG. 48, a hepatic vein 2270 passing adjacent to a portal vein 2272 can be bridged in a TIPS procedure using the implant 2220. The diameter of the hepatic and portal veins vary depending on the age and degree of cirrhosis from 8.5 to 13 mm with mean diameters measured 11 mm+/−2 mm. The implant 2220 can comprise a first component 2260 and a second component 2262 that can be adjusted either based on its position within the lumen of the first component 2260 or by mechanically altering an attribute, size, or shape of the second component 2262. For example, the distal tip of the second component 2262 can be varied either through balloon expansion or by cutting or otherwise further opening the distal diameter thereof.

In accordance with some embodiments, although the first component 2260 can comprise a substantially constant diameter shunt along at least a portion thereof, the first component 2260 can comprise a substantially constant diameter portion and/or at least one expandable support member or portion (e.g., a stent or other structure (e.g., a braided, laser-cut, or coiled structure, etc., which can be self-expanding or balloon-expandable)) and/or at least one flexible member or sheath (e.g., a graft, PTFE cover, etc.). Further, the second component 2262 can comprise at least one expandable support member or portion (e.g., a stent or other structure (e.g., a braided, laser-cut, or coiled structure, etc., which can be self-expanding or balloon-expandable)) and/or at least one flexible member or sheath (e.g., a graft, PTFE cover, etc.). The first and second components 2260, 2262 can be manipulated, e.g., reconfigured or mechanically altered from one position to another, in order to provide a specific flow resistance or otherwise control a fluid flow rate through the first component 2260.

Therefore, in accordance with some embodiments, the second component 2262, whether formed integrally with or separately from the first component 2260 of the implant, can be movable, deformable, or otherwise mechanically alterable (by balloon or otherwise) in order to control or adjust a flow resistance or flow rate through the implant.

As noted herein, some embodiments of the implants and procedures disclosed herein can be used for the TIPS procedure. Accordingly, a given implant can be implanted so as to extend from a region of low pressure, such as the hepatic vein, to an area of high pressure, such as the portal vein. An implant, selected and configured to provide a specific resistance to flow, can be implanted and extend between the hepatic and portal veins, thus relieving some of the pressure from the portal vein. Optionally, the pressures of the portal and hepatic veins can be measured before and/or after the procedure.

FIGS. 49-60 illustrate features of some embodiments by which flow through the implant can be mechanically adjusted, regulated, or modified. The implant may be structured as a covered stent structure with tapered distal end to provide flow resistance and achievement of a desired gradient.

In accordance with some embodiments, the implant can be implanted in a series of steps. For example, implant implantation may be performed in the following sequence. Initially, a first portion (proximal or distal) of the implant can be implanted (such as implanting the shunt or implant 2220 from the hepatic vein 2270 to the portal vein 2272, as shown in FIG. 48). In some embodiments, the implant can be implanted and retain a specific diameter over at least a portion of its length or be expanded along at least a portion thereof to achieve a minimum diameter of about 3 mm to about 4 mm. Optionally, the flow and gradient achieved by the initial expansion can then be verified. If necessary, expansion of the second portion can then be performed. Optionally, the flow gradient can then be checked, if necessary. The implant can be further and repeatedly expanded or adjusted until a desired flow gradient is achieved. In some embodiments, the implant can be a balloon-expandable or self-expanding implant. In some embodiments, the implant can be implanted and configured to have a preset diameter and with a variable flow resistance that is controllable by adjusting a portion of the implant.

In accordance with some embodiments, FIG. 49 illustrates a generally tubular implant or structure 2280 having a first component 2282 and a tip or second component 2284. The first component 2282 and the second component 2284 can be interconnected and delivered into the body as a single unit into a lumen or vessel. However, the first and second components 2282, 2284 can also be delivered separately, with the first component 2282 being implanted into the body lumen first and thereafter, the second component 2284 being implanted and interconnected with the first component 2282.

A flow resistance or flow rate through the implant can determined, controlled, and/or modified by setting or adjusting the relative positions of the first and second components 2282, 2284 or otherwise modifying the configuration of at least one of the first and second components 2282, 2284, such as by using a balloon or mechanical alteration, such as cutting, folding, or otherwise removing a least a portion of at least one of the first and second components 2282, 2284. As noted above, the first component 2282 and/or the second component 2284 can comprise a substantially constant diameter portion and/or at least one expandable support member or portion (e.g., a stent or other structure (e.g., a braided, laser-cut, or coiled structure, etc., which can be self-expanding or balloon-expandable)) and/or at least one flexible member or sheath (e.g., a graft, PTFE cover, etc.).

In accordance with some embodiments, the first component 2282 can be formed from a braided material and comprise a preset tubular shape having a generally conical end. Further, the second component 2284 can comprise a plastically deformable structure, such as a non-resilient, laser cut conical structure that can be deformed by expansion, such as by balloon expansion, in order to increase the size of aperture 2286 of the second component 2284. Thus, in some embodiments, the size of the aperture 2286 can be increased in order to irreversibly decrease flow restriction through the aperture 2286. However, other embodiments can be configured for reversible or temporary flow restriction such that the flow restriction can be selectively increased or decreased, as desired.

For example, FIG. 50 illustrates a side view of an implant 2290 having a helical frame 2292 that supports a cover member 2294. The cover member 2294 can be an elastic or PTFE cover that fits over the frame 2292. The implant 2290 can further comprise a valve component 2296 that can be received within a distal end of the implant 2290. The valve component can comprise a one-way valve. The valve component 2296 can be attached to the frame 2292 using an attachment structure, such as hooks 2298. This attachment structure can allow the valve component 2296 to be placed at a plurality of positions within the implant 2290.

Optionally, after the implant 2290 has been implanted into the patient, the pressure gradient can be measured and the position (i.e., flow restriction) through the implant 2290 can be increased or decreased in order to achieve a desired pressure gradient.

Additionally, some embodiments can be provided, as in FIGS. 51 and 52, in which a flow regulating implant 2300 comprises a valve component 2302 having a plurality of telescoping or slidable sections 2310. The valve component 2302 can be biased towards a maximum flow restriction position (but not necessarily fully closed), but maintained in one or more open positions using a mechanical interconnection between the slidable sections 2310 themselves of the valve component 2302 or between the slidable sections 2310 and a frame 2312 of the implant 2300.

For example, in order to maintain the valve component 2302 in an open position, the slidable sections 2310 can be interconnected with a portion of the implant, such as with the frame 2312 using an engagement structure, such as hooks 2314. In use, the clinician can move the sections 2310 relative to the implant 2300 by disconnecting of one or more of the hooks 2314 in order to adjust the location of the sections 2310 relative to each other.

As illustrated FIG. 51, the hooks 2314 can be interconnected with the frame 2312 of the implant to position the valve component 2302 in a first position. Although not shown, the hooks 2314 can be interconnected with the frame 2312 in a more proximal or open position, such that the valve component 2302 is in a fully nested or collapsed configuration in which the valve component 2302 achieves a minimum flow restriction. Further, the hooks 2314 can also be disconnected from the frame 2312 in order allow the valve component 2302 to move distally towards a second, extended position in which the valve component 2302 achieves a maximum flow restriction.

For example, as illustrated in FIG. 52, the hooks 2314 have been disconnected entirely from the implant in order to allow the distalmost section to expand and slide distally. According to some embodiments, the distalmost section of the valve component 2302 can comprise an elastic or resilient material that is configured such that the distalmost section tends to converge or collapse to a maximum flow restriction position, which is illustrated in FIG. 52.

Furthermore, the engagement structure of the valve component 2302 can be deflectable from or biased toward an engaging position. For example, the hooks 2314 can be biased toward a collapsed position such that the hooks 2314 do not protrude into the vessel after being disengaged from the frame 2312. The hooks 2314 can comprise elongate protrusions or tabbed portions or cutouts attached to or formed from the slidable sections 2310.

Additional variability or adjustment of the valve component can be achieved using a variable diameter opening that is pressure sensitive. For example, a distal tip of the valve component can comprise a plurality of leaflets that are resiliently connected with the distal tip such that the leaflets are biased towards a first position in which a diameter of an aperture is maintained at a desired configuration. However, upon an increase in pressure through the implant, the leaflets can deflect from the first position toward a second position in which the leaflets are spread apart in order to allow the aperture to increase in size, thus reducing the flow restriction and permitting an increase in the flow rate or a reduction in flow resistance through the aperture.

FIGS. 53A-53C illustrate another embodiment of a flow regulating implant 2350. In this embodiment, the flow regulating implant 2350 comprises a first component 2352 having an adjustable distal end 2354. The distal end 2354 can be biased towards a closed position, as illustrated in FIG. 53A, such that an aperture 2356 of the distal end 2354 achieves maximum flow restriction (while the second component 2360 is in maximum flow restriction position). The implant 2350 can also comprise a second component 2360 disposed within a lumen of the first component 2352 and movable therewithin to adjust the flow restriction through the implant 2350.

For example, the second component 2360 can comprise a distal portion 2362 configured to contact the distal end 2354 of the implant 2350 in order to open the aperture 2356. In the illustrated embodiment, the distal end 2354 can comprise a plurality of leaflets 2364, the form an adjustable diaphragm. As the second component 2360 is urged distally, the distal portion 2362 can begin to push open the leaflets 2364 such that the aperture 2356 increases in size. As illustrated, the distal portion 2362 of the second component 2360 can be formed as a substantially conical shape in order to allow the second component 2362 incrementally contact the leaflets 2364, permitting a range of sizes or diameters for the aperture 2356. The second component 2360 can be moved towards a minimum flow restriction position, as in FIG. 53C, in which the leaflets 2364 are in a fully open position.

Additionally, the second component 2360 can be secured within the first component 2352 at one of a plurality of positions when a desired flow gradient is achieved. As in other embodiments, the size of the aperture 2356 can be modified, such as by moving the second component 2360 to one of a variety of positions within the lumen of the first component 2352 in order to selectively increase or decrease flow restriction through the first component 2352. The movement of the second component 2360 can allow the operator to change the diameter of the aperture 2356. Optionally, the clinician can measure the pressure in the respective vessels, adjusting the position and/or size of the second component 2360 to achieve a desired gradient, until it the gradient is found to be satisfactory. Once the pressure gradient is determined to be satisfactory, the second component 2360 can be fixed in position so as not to permit further closing or opening of the aperture 2356.

Flow can also be adjusted by balloon-assisted means. FIGS. 54-57 illustrate side, cross-sectional views of operation of another implant assembly 2400, according to some embodiments. As illustrated, a flow regulating implant 2402 can be carried on a catheter implant 2404. The implant 2402 can comprise at least one support component 2410, at least one cover component 2412, and an aperture 2414 extending through the cover component 2412. Flow through the implant 2402 can pass through a lumen 2416 of the implant 2402 and out through the aperture 2414. According to some embodiments, aspects of engagement, structural features, and other characteristics of the catheter implant 2404 and the support component 2410 can be provided such as those disclosed in co-pending U.S. patent application Ser. No. 14/044,794, filed Oct. 2, 2013, the entirety of which is incorporated herein by reference.

In some embodiments, the support component 2410 can comprise a self-expanding helical member extending along a distal portion of the catheter implant 2404. Once the assembly 2400 is advanced to the target area within the vasculature, the support component 2410 can be permitted to expand from a collapsed position, as shown in FIG. 54, to an initially expanded position, as shown in FIG. 55. For example, by proximally withdrawing an engagement component 2420, which can be used to engage distal and proximal ends 2422, 2424 of the support component 2410. In such embodiments, the engagement component 2420 can be coupled to a single slidable handle member, such as that illustrated in FIG. 1B, and moved proximally relative to the catheter 2404 and the handle assembly.

As illustrated in FIG. 55, in some embodiments, the support component 2410 can be configured to expand to a tapered configuration. The support component 2410 can expand to define a generally tubular section 2430 and a generally tapered or conical section 2432. As shown in FIG. 55, in the initially expanded position, the generally tapered or conical section 2432 will not tend to exert any outward force on the cover component 2412. Accordingly, the aperture 2414 can remain in a maximum restriction position, shown in FIG. 55.

The cover component 2412 can be attached to the tapered section 2432 or otherwise biased toward a closed position (shown in FIG. 55). Thus, when the tapered section 2432 is in its initially expanded position, the tapered section 2432 will either maintain the cover component 2412 in its closed position or not exert an outward radial force against the cover component 2412 that could otherwise open the cover component 2412 or urge it away from its closed position.

The cover component 2412 can comprise a flexible or rigid material that is attached to or positioned around the tapered section 2432. A first end 2440 of the cover component 2412 can be attached to one or more portions of the support component 2410. For example, as shown in FIGS. 54-57, the first end 2440 of the cover component 2412 can be attached to a winding of the helically extending support component 2410. In other embodiments, the cover component 2412 can be attached to the support component 2410 at one or more additional locations, such as by using a chemical (e.g., adhesive) or mechanical fastener.

In accordance with some embodiments, the cover component 2412 can comprise a plurality of deflectable leaflets that are configured to slide or move relative to each other in order to increase or decrease the size of the aperture 2414. However, as also disclosed in accordance with other embodiments, the cover component 2412 can be adjusted by mechanically altering an attribute, size, or shape of the cover component 2412, such as by balloon expansion or by cutting or otherwise further opening the distal diameter thereof.

For example, FIGS. 56-57 illustrate aspects of an embodiment in which the implant 2402 comprises a plastically deformable frame component 2450. The assembly 2400 can comprise a balloon 2452 that can be inflated, as shown in FIGS. 56 and 57. When inflated, the balloon 2452 can urge the frame component 2450 from a collapsed position (shown in FIGS. 54 and 55) toward an expanded position. FIG. 54 illustrates the balloon 2452 in a first state of expansion, with the frame component 2450 being moved to a first expanded position 2460. In the first expanded position 2460, the frame component 2450 exerts an outward radial force against the tapered section 2432 of the support component 2410 to cause expansion thereof. In turn, expansion of the tapered section 2432 causes the cover component 2412 to expand and dilate the aperture 2414. Accordingly, flow through the aperture 2414 is less restricted when the frame component 2450 is urged to the first expanded position 2460.

FIG. 57 illustrates the frame component 2450 in a second expanded position 2462. In order to move the frame component 2450 to the second expanded position 2462, the balloon 2452 can be further inflated. As illustrated, the aperture 2414 will tend to become further dilated or expanded, thus further reducing flow restriction therethrough.

Although FIGS. 54-57 illustrate an embodiment in which the implant comprises both self-expanding and plastically deformable components, some embodiments can be provided in which the implant comprises only plastically deformable or only self-expanding components.

For example, FIGS. 58-60 illustrate potential designs of a balloon that can be used to expand or adjust the shape of an implant having a plastically deformable support component. FIG. 58 illustrates a balloon 2500 having two tapered ends 2502, 2504. FIG. 59 illustrates a balloon 2510 having a step down portion 2512 and a tapered end 2514. Further, FIG. 60 illustrates a balloon 2520 having a generally constant cross-sectional profile 2522 (e.g., cylindrical or other shapes).

In accordance with some embodiments, the implants disclosed herein can be implanted and/or adjusted using any of a variety of balloon shapes, such as those illustrated in FIGS. 58-60. In accordance with some embodiments, the balloon can have a tapered end so the balloon may expand the proximal portion of the implant to a larger diameter than the distal portion thereof. Further, any of the balloon designs disclosed herein can comprise a plurality of expanded states such that the balloon can expand the implant, or at least a portion of the implant, to a plurality of different sizes in order to modify the flow restriction through the implant.

Some embodiments are also provided by which the assembly and/or catheter can be advanced over a guidewire, thus allowing treatment of more tortuous or distal, smaller vessels in the vasculature. Other features and characteristics of the assembly and/or catheter can be modified to include any of the structures or features discussed above, or as those disclosed in: U.S. patent application Ser. No. 12/826,593, filed on Jun. 29, 2010 (086538-0012); U.S. patent application Ser. No. 13/367,338, filed on Feb. 6, 2012 (086538-0018); U.S. patent application Ser. No. 12/906,993, filed on Oct. 18, 2010 (086538-0014); U.S. patent application Ser. No. 13/828,974, filed on Mar. 14, 2013 (086538-0030); U.S. Patent Application No. 61/836,061, filed on Jun. 17, 2013 (086538-0038); U.S. patent application Ser. No. 14/044,794, filed on Oct. 2, 2013 (086538-0039); U.S. patent application Ser. No. 14/281,797, filed on May 19, 2014 (086538-0055); U.S. Patent App. No. 61/835,406, filed on Jun. 14, 2013 (086538-0032); U.S. Patent App. No. 61/904,376, filed on Nov. 14, 2013 (086538-0041); U.S. Patent App. No. 61/904,379, filed on Nov. 14, 2013 (086538-0043); U.S. Patent App. No. 61/835,461, filed on Jun. 14, 2013 (086538-0034); U.S. Patent App. No. 61/900,321, filed on Nov. 5, 2013 (086538-0040); and U.S. patent application Ser. No. 14/101,171, filed on Dec. 9, 2013 (086538-0046), the entireties of which are incorporated herein by reference.

Some embodiments provide for advantageously configured distal structures that allow the delivery device to move smoothly through a catheter or body lumen with minimal force. For example, some embodiments comprise a delivery device that has a flexible, torque resistant distal tip configured to support or carry a medical implant. In some embodiments, a torque resistant distal tip can be segmented and/or coiled, such that the distal tip is able to flex, separate, or deflect to a greater extent than a solid tube. In some embodiments, a torque resistant distal tip provides high column strength in response to axially compressive forces. For example, column strength may be maintained for transmitting axial forces while providing enhanced flexibility to yield to lateral forces.

Some embodiments of the delivery device or catheter can provide a flexible core over which an implant may be loaded. The implant can be configured and loaded or wound onto the distal tip of the catheter such that the implant is maintained in a collapsed configuration by virtue of torque resistance provided by the distal tip of the catheter. When loaded onto the distal tip and in the collapsed or delivery configuration, the implant can transmit torque to the core in order to maintain a deliverable diameter.

The design of the carrier tip is intended to allow flexibility of the catheter tip, while holding an implant frame in its pre-deployment position. The tip further resists torque applied to the tip by an implant secured onto the tip. The tip provides a counter torque in response to the implant, thereby providing a segmented design for greater flexibility without being adversely impacted by a coiled implant secured to the tip in a compressed state.

Referring now to FIGS. 61-62, a distal tip of a delivery device or catheter can be configured to comprise a keyed coil feature, in accordance with some embodiments. As illustrated in FIGS. 61-62, a catheter 2600 includes a proximal portion 2610, a distal portion 2612, and a middle portion 2614 extending from the proximal portion 2610 to the distal portion 2612. As shown in FIG. 61, the proximal portion 2610 may include a proximal aperture 2620, and the distal portion 2612 may include a distal aperture 2622. The proximal and distal portions 2610, 2612 are configured to extend through a wall of the catheter 2600 has slots or notches. As shown in FIG. 62, the proximal aperture 2620 is configured to receive and/or engage a proximal section 2640 of a support frame 2650, and the distal aperture 2622 is configured to receive and/or engage a distal section 2642 of the support frame 2650. As further shown, an elongate member 2630 can engage the proximal section 2640 of the support frame 2650, and an elongate member 2632 can engage the distal section 2642 of the support frame 2650. Alternatively, a single elongate member can engage both the proximal distal sections 2640, 2642 of the support frame 2650. The elongate members 2630, 2632 can extend within a lumen 2604 of the catheter 2600.

According to some embodiments, the middle portion 2614 generally forms a tubular shape. A coil 2615 is formed along the middle portion 2614 by cutting a helical kerf 2616 along the length of the tubular middle portion 2614. As used here, "kerf" is a slit that extends from an outer surface of the catheter 2600 to a lumen 2604 of the catheter 2600. The coil 2615 is defined by the structure that remains after the kerf 2616 is cut. Both the coil 2615 and the kerf 2616 follow helical paths in the same direction (e.g., levorotary/"right-handed" or dextrorotary/"left-handed"). The coil 2615 may be formed by providing the kerf 2616 to a generally tubular structure. The generally tubular structure defining the middle portion 2614—as well as the proximal portion 2610 and the distal portion 2612—may be of a metallic material, such as stainless steel or nitinol. The material may have shape memory characteristics. The kerf 2616 may be provided by laser cutting, mechanical cutting, electrical discharge machining, etching, combinations thereof, and the like. Accordingly, the coil 2615 of the middle portion 2614 may be integrally connected to the proximal portion 2610 and/or the distal portion 2612.

The kerf 2616 may have a consistent pitch or varying pitch along the length of the middle portion 2614. Accordingly, the coil 2615 may have, at any segment thereof, the same or different longitudinal lengths extending between axially adjacent sections of the curve 2616. According to some embodiments, more than one kerf 2616 may be provided, such that each of the kerf 2616 are in the same helical direction and such that they do not cross or overlap.

The kerf 2616 provides a gap between adjacent segments along a longitudinal length of the middle portion 2614. As such, first and second sides 2617a and 2617b of segments of the coil 2615 disposed across a portion of the kerf 2616 are able to separate as needed in response to a bending force applied to the middle section 2614. The first and second sides 2617a, 2617b can separate on one radial side of the middle portion 2614 and approach each other or contact each other on an opposite radial side of the middle portion 2614 to curve and bend. The ability of the first and second sides 2617a, 2617b to separate on any radial side of the middle portion 2614 provides flexibility to the middle portion 2614. Whereas the support frame 2650 increases overall rigidity of the assembly when applied to the catheter 2600, the ability of the coil 2615 to flex and bend increases the combined flexibility of the support frame 2650 and the middle portion 2614.

As shown in FIG. 62, the proximal section 2640 of the support frame 2650 is secured at the proximal portion 2610 of the catheter 2600, and the proximal section 2642 of the support frame 2650 is secured at the distal portion 2612 of the catheter 2600. As such, the support frame 2650 is secured to the catheter 2600 at different axial locations thereof. The support frame 2650 may have a torsion state, as shown in FIG. 62, such that the support frame 2650 is subject to a torque and has a smaller outer diameter than in a relaxed state (as shown in FIG. 2, for example). In the torsion state, the support frame 2650 may have a greater number of turns than in the relaxed state. In the torsion state, the support frame 2650 may have a smaller outer diameter than in the relaxed state. In the torsion state, the support frame 2650 may have a longer longitudinal length than in the relaxed state. The support frame 2650 may be brought into the torsion state by being subjected to a torque applied to support frame 950 from the proximal section 2640 to the distal section 2642. The torque may be applied in the same helical direction as the winding of the support frame 2650, such that the outer diameter of the support frame 2650 decreases (e.g., even while maintaining a consistent longitudinal length). In the torsion state, the support frame 2650 stores potential energy in the form of a torque applied to the proximal and distal portions 2610, 2612 of the catheter 2600.

The kerf 2616 and the coil 2615 of the catheter 2600 may be oriented in a helical direction. The helical kerf 2616 and coil 2615 provide counter torque capabilities in response to a torque applied by the support frame 2650. A helically directed kerf, rather than a kerf along a longitudinal path or a partial circumferential path orthogonal to a longitudinal axis, can provide a continuous gap along an entire circumference of the middle portion 2614. In contrast, a circumferential gap orthogonal to a longitudinal axis can only be partially circumferential in order to maintain a longitudinal continuity along the length of the middle portion 2614. The helically directed kerf allows the first and second sides 2617a, 2617b to separate at any circumferential location. The helical direction of the kerf 2616 and/or the coil 2615 can be opposite the helical direction of the support frame 2650. For example, as shown in FIG. 62, the support frame 2650 is wound in a support frame helical direction (e.g., levorotary) and the coil 2615 and the kerf 2616 are wound in a catheter helical direction (e.g., dextrorotary), opposite the support frame helical direction. Where the support frame 2650 has been torqued in a direction of its support frame helical winding, the support frame 2650 will tend to its relaxed state by imparting a torque to the catheter 2600 in the direction opposite of the direction of that torque. As such, the support frame 2650 will impart a torque to the catheter 2600 in the catheter helical direction.

The torque applied to the catheter 2600 causes the proximal and distal portions 2610, 2612 to tend to rotate relative to each other. In response, the coil 2615 of the middle portion 2614 tends to compress radially and/or expand longitudinally. Where longitudinal expansion is limited, such as by tension applied by the support frame 2650, the tendency of the middle portion 2614 to compress radially causes opposing first and second sides 2617a, 2617b across the kerf 2616 to move toward each other and decrease the size of the gap defined by the kerf 2616. When the first and second sides 2617a, 2617b engage each other, further radial compression of the middle portion 2614 is limited, and the torque provided by the support frame 2650 is matched by the engagement of the first and second sides 2617a, 2617b.

Figure 64A:
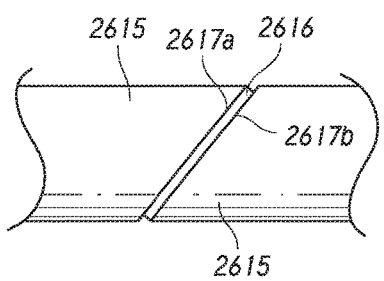

Referring now to FIGS. 64A-64E, the kerf 2616 has a profile that defines the manner in which the first and second sides 2617a, 2617b engage each other. As used herein, "profile" refers to the shape of a pattern apart from a helical path which it can follow. For example, a simple helix has a linear profile. As shown in FIG. 64A, the kerf 2616 may have a linear profile that follows a helical path. Such a linear profile may provide even distribution of engagement across the first and second sides 2617a, 2617b when a torque is applied in the direction of the helical path. Alternatively, the profile may be non-linear.

Figure 64B:
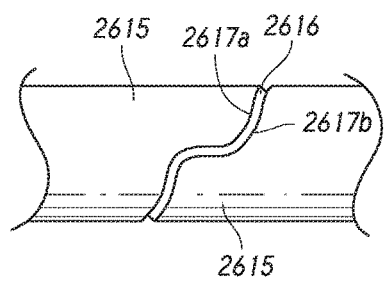

As shown in FIG. 64B, the kerf 2616 may have an undulating (e.g., sinusoidal) profile that follows a helical path. Such an undulating profile may facilitate engagement across the first and second sides 2617a, 2617b at particular portions thereof when a torque is applied in the direction of the helical path.

Figure 64C:
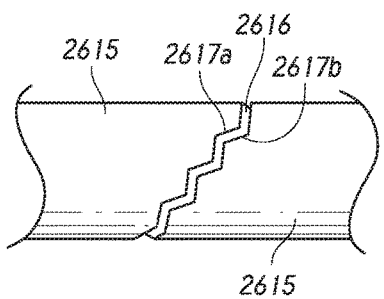

As shown in FIG. 64C, the kerf 2616 may have a triangular profile that follows a helical path. Each triangle may provide two exposed legs of equal length, as with an isosceles triangle. Such a triangle profile may facilitate engagement of the first and second sides 2617a, 2617b at only certain of the exposed legs when a torque is applied in the direction of the helical path.

Figure 64D:
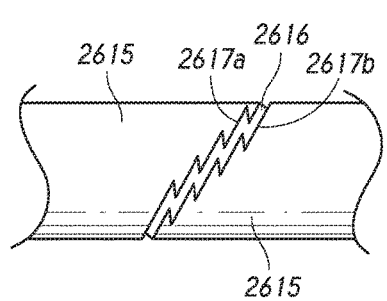

As shown in FIG. 64D, the kerf 2616 may have a sawtooth profile that follows a helical path. Each tooth may provide two exposed legs of different length, as with the legs of an asymmetric triangle. Such a sawtooth profile may facilitate more secure engagement of the first and second sides 2617a, 2617b with protrusions of one side fitting into complementary keyed shapes of the other side when a torque is applied in the direction of the helical path. The engagement of the complementary shapes may also resist axial elongation of the coil 2615.

Figure 64E:
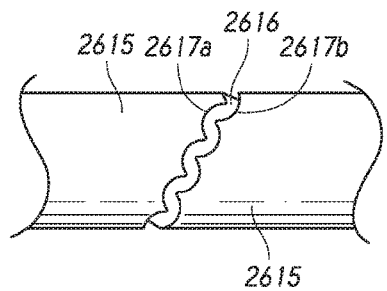

As shown in FIG. 64E, the kerf 2616 may have a profile that provides a series of concave portions following a helical path. Each concave portion of one of the first and second sides 2617a, 2617b bows away from the other of the first and second sides 2617a, 2617b. Adjacent concave portions meet together at a point where the portions extend toward the opposite side across the kerf 2616. Each point may extend in a location that is near or within a concave portion of the opposite side.

Therefore, the catheter 2600 provides enhanced flexibility for traversing tortuous vascular anatomy while resisting torque applied to the catheter 2600 by a support frame 2650 secured thereto.

Referring now to FIGS. 65-67, a distal tip of a delivery device or catheter can be configured to comprise a plurality of filaments, in accordance with some embodiments. As illustrated in FIGS. 65-67, a catheter 2800 includes a proximal portion 2810, a distal portion 2812, and a middle portion 2814 extending from the proximal portion 2810 to the distal portion 2812. As shown in FIG. 65, the proximal portion 2810 may include a proximal aperture 2820, and the distal portion 2812 may include a distal aperture 2822. The proximal and distal portions 2810, 2812 are configured to extend through a wall of the catheter 2800 has slots or notches. The proximal portion 2810 may further include one or more apertures 2824 for engaging a support frame 2850 or providing fluid communication across a wall of catheter 2800 into a lumen 2804 thereof. As shown in FIG. 67, the proximal aperture 2820 is configured to receive and/or engage a proximal section 2840 of a support frame 2850, and the distal aperture 2822 is configured to receive and/or engage a distal section 2842 of the support frame 2850. As further shown, an elongate member 2830 can engage the proximal section 2840 of the support frame 2850, and an elongate member 2832 can engage the distal section 2842 of the support frame 2850. Alternatively, a single elongate member can engage both the proximal distal sections 2840, 2842 of the support frame 2850. The elongate members 2830, 2832 can extend within the lumen 2804 of the catheter 2800.

According to some embodiments, the middle portion 2814 generally forms a tubular shape. A plurality of filaments 2815 are provided along the middle portion 2814. The plurality of filaments 2815 each follow a path in a helical direction (e.g., levorotary/"right-handed" or dextrorotary/ "left-handed"). The helical direction of each filament 2815 may be the same as the helical direction of every other filament 2815, such that only filaments in a given helical direction are provided. Alternatively, the helical direction of some of the filaments 2815 may be opposite the helical direction of others of the filaments 2815 (not shown). In such a configuration, the filaments 2815 may cross at intersection points to form a woven pattern. The filaments 2815 may have the same or different pitches. Each filament 2815 may have a consistent pitch or variable pitch. The filaments 2815 may have the same or different widths. Each filament 2815 may have a consistent width or a variable width along its length. The filaments 2815 may be equally or unequally spaced along a longitudinal length of the middle portion 2814. The filaments 2815 may be equally or unequally distributed circumferentially at either or both of the proximal and distal portions 2810, 2812.

The filaments 2815—as well as the proximal portion 2810 and the distal portion 2812—may be of a metallic material, such as stainless steel or nitinol. The filaments 2815 may be of the same or different materials. The material(s) may have shape memory characteristics. The filaments 2815 may be cut from a generally cylindrical tube section between the proximal and distal portions 2810, 2812 by laser cutting, mechanical cutting, electrical discharge machining (EDM), chemical etching, combinations thereof, and the like. Accordingly, the filaments 2815 of the middle portion 2814 may be integrally connected to the proximal portion 2810 and/or the distal portion 2812. Alternatively or in combination, the filaments 2815 may be formed apart from the proximal and distal portions 2810, 2812 and subsequently attached thereto (e.g., by adhesive bonding or welding).

The filaments 2815 are arranged to provide a gap between adjacent filaments 2815 along a longitudinal length of the middle portion 2814. As such, the filaments 2815 are able to separate from each other as needed in response to a bending force applied to the middle section 2814. The filaments 2815 can separate on one radial side of the middle portion 2814 and approach each other or contact each other on an opposite radial side of the middle portion 2814 to provide overall flexibility. The ability of the filaments 2815 to separate on any radial side of the middle section 2814 provides flexibility to the middle section 2814. Whereas the support frame 2850 increases overall rigidity of the assembly when applied to the catheter 2800, the ability of the filaments 2815 to flex and bend increases the combined flexibility of the support frame 2850 and the middle portion 2814.

As shown in FIG. 67, the proximal section 2840 of the support frame 2850 is secured at the proximal portion 2810 of the catheter 2800, and the proximal section 2842 of the support frame 2850 is secured at the distal portion 2812 of the catheter 2800. As such, the support frame 2850 is secured to the catheter 2800 at different axial locations thereof. The support frame 2850 may have a torsion state, as shown in FIG. 67, such that the support frame 2850 is subject to a torque and has a smaller outer diameter than in a relaxed state (as shown in FIG. 2, for example). In the torsion state, the support frame 2850 may have a greater number of turns than in the relaxed state. In the torsion state, the support frame 2850 may have a smaller outer diameter than in the relaxed state. In the torsion state, the support frame 2850 may have a longer longitudinal length than in the relaxed state. The support frame 2850 may be brought into the torsion state by being subjected to a torque applied to support frame 2850 from the proximal section 2840 to the distal section 2842. The torque may be applied in the same helical direction as the winding of the support frame 2850, such that the outer diameter of the support frame 2850 decreases (e.g., even while maintaining a consistent longitudinal length). In the torsion state, the support frame 2850 stores potential energy in the form of a torque applied to the proximal and distal portions 2810, 2812 of the catheter 2800.

The filaments 2815 of the catheter 2800 may be oriented in a helical direction opposite the helical direction of the support frame 2850. For example, as shown in FIG. 67, the support frame 2850 is wound in a support frame helical direction (e.g., dextrorotary) and the filaments 2815 are wound in a catheter helical direction (e.g., levorotary), opposite the support frame helical direction. Where the support frame 2850 has been torqued in a direction of its support frame helical winding, the support frame 2850 will tend to its relaxed state by imparting a torque to the catheter 2800 in the direction opposite of the direction of that torque. As such, the support frame 2850 will impart a torque to the catheter 2800 in the catheter helical direction.

The torque applied to the catheter 2800 causes the proximal and distal portions 2810, 2812 to tend to rotate relative to each other. In response, the filaments 2815 of the middle portion 2814 tend to compress radially and/or expand longitudinally. Where longitudinal expansion is limited, such as by tension applied by the support frame 2850, the tendency of the middle portion 2814 to compress radially causes adjacent filaments 2815 to move toward each other and decrease the size of the gap defined there between. The space between adjacent pairs of filaments 2815 may be eliminated, such that the filaments 2815 form a closed coil. When adjacent filaments 2815 engage each other, further radial compression of the middle portion 2814 is limited, and the torque provided by the support frame 2850 is matched by the engagement of the filaments 2815.

Therefore, the catheter 2800 provides enhanced flexibility for traversing tortuous vascular anatomy while resisting torque applied to the catheter 2800 by a support frame 2850 secured thereto.

Implant deployment can be performed as a two stage process, which is illustrated in FIGS. 68A-68D. A guide catheter 2910, a delivery catheter 2920, and an implant 2950 can first be moved to a target location 2900 (shown in FIG. 68A). The guide catheter 2910 can then be removed (shown in FIG. 68B). The implant 2950 may be engaged on the delivery catheter 2920 (see FIGS. 62 and 67). Any torque imparted by the implant 2950 upon the delivery catheter 2920 may be balanced or resisted by aspects of the delivery catheter 2920, according to embodiments disclosed herein. After a proximal-most retention clip is removed from the handle assembly, a proximal slider member of the handle assembly can be pulled proximally to release a proximal end 2902 of the implant 2950 (shown in FIG. 68C). When the proximal end 2902 is released, the physician can check the implant position and observe as the inner space of the implant 2950 fills with blood. Upon releasing at least one end of the implant 2950, the delivery catheter 2920 may be relieved of the torque imparted by the implant 2950. Some slight movement of the implant 2950 may be helpful to achieve precise placement. A second retention clip of the handle assembly can then be removed and a distal slider member of the handle assembly can be pulled proximally to release a distal end 2904 of the implant 2950 (shown in FIG. 68D), thus releasing the entire implant 2950.

Features of any of the implants, the support frames, and/or the membranes disclosed herein can be applied to other devices and implants disclosed herein. Any implant of the present disclosure may be configured to interact with structures of an engagement structure of a catheter disclosed herein. Features of a membrane disclosed herein can be applied to other membranes or implants disclosed herein.

According to some embodiments of the subject technology, the support frame may comprise at least one of stainless steel, nickel titanium (NiTi), cobalt chromium (CoCr), titanium, a polymer, a polyester based material, a tyrosine based polycarbonate, a polyethylene based material, Teflon (e.g., including expanded Teflon), and other suitable materials known to those of ordinary skill in the art. In some embodiments, support frame 302 may comprise at least one of polyethylene, polyglicolide, polylactide, ε-caprolactone, polycarbonate, hydroxyalkanote, para dioxinine, polytetrafluoroethylene (PTFE), expanded polytetrafluoroethylene (ePTFE), PLA, PGA, PLLA, PDLLA, PDO, PCL, and other suitable materials known to those of ordinary skill in the art. In some embodiments, support frame and/or occlusion membrane 304, may comprise a bioabsorbable material, beneficially allowing for their controlled degradation. In some embodiments, support frame and/or occlusion membrane may be formed of bioabsorbable material to have a controlled degradation anywhere between about 3 months to about 3 years depending on the desired application of support frame. In some embodiments, the controlled degradation may be less than about 3 months or greater than about 3 years. For example, hydrolysis of ester linkages or effects of enzymatic degradation may be utilized for the controlled degradation.

In some embodiments, the support frame may be coated with various suitable agents to allow support frame to expand within and engage the inner surface of the vessel or lumen. For example, support frame may be coated with biological glue. In some embodiments, support frame may be coated with a friction-resistant coating (e.g., a friction-resistant polymer coating). In some embodiments, radio-opaque markers may be located on support frame or occlusion membrane for endovascular or other image-guided procedures. In some embodiments, the radio-opaque marker may be a platinum iridium alloy or other suitable markers known to those of ordinary skill in the art.

According to various embodiments of the subject technology, occlusion membrane 304 may be used to occlude, partially or completely, luminal structure in which an implant is deployed. In some embodiments as used herein, occlusion may refer to either partial or complete occlusion.

According to some embodiments, implants disclosed herein can incorporate any one or more of the features disclosed in the Figures or discussion herein. For example, any of the implants can be configured to comprise a fibrous membrane feature, as discussed above.

According to some embodiments, implants disclosed herein can have an expanded diameter of between about 4 mm to about 22 mm. Additionally, some embodiments can be used in vessels having diameters between about 3 mm to about 20 mm.

According to some embodiments, implants disclosed herein can be deployed in vessels having dimensions of between about 3 mm to about 20 mm. The target delivery profile can be about 8 Fr, about 7 Fr, about 6 Fr, about 5 Fr, about 4 Fr, about 3 Fr, or smaller.

Furthermore, implants disclosed herein can also be configured for use in venous stenting and can comprise any of the features taught herein to facilitate such use, including incorporating a fibrous membrane into the implant frame. For example, stenting of vessels having diameters between about 3 mm to about 20 mm can be possible using embodiments disclosed herein. This exceptional and advantageous ability of embodiments of the medical implants disclosed herein to provide stenting in such small vessels is made possible, for example, due to the minimal delivery profile can be achieved using such embodiments. As noted above with other embodiments, deployment of an implant having a fibrous membrane feature can exert an outward radial force against inside wall of a vein in order to improve blood flow, or minimize vein insufficiency. Further, the delivery profile can be about 8 Fr or smaller, as discussed herein.

According to various aspects of the subject technology, implants disclosed herein may be used for various applications for reducing or stopping flow through a luminal structure in a patient. Implants of the subject technology may be used for rapid, well-controlled, and reliable occlusion of luminal structures. For example, the luminal structure may comprise at least one of a blood vessel, a body organ, a lung, an airway, a Fallopian tube, a cervical canal, a vagina, a cervix, a vas deferens, a bronchus, a ureter, a colon, a rectum, an anus, a bio duct, a pancreatic duct, or other suitable tubular structures known to those of ordinary skill in the art. In some embodiments, implants of the present disclosure may be used for temporary occlusion in cases of lung disease, or for temporary occlusion of female reproductive organs for contraceptive purposes. In some embodiments, implants of the present disclosure may be removed, or flow may be restored through the luminal structure to restore original organ functions.

In some embodiments, implants of the present disclosure may be used for various endoluminal occlusion procedures, including procedures for the lungs (e.g., selective endobronchial occlusion for lung reduction, occlusion of bronchopleural or bronchocutaneous fistulas, endovascular occlusion of pulmonary AVMs and fistulas or aortopulmonary anastomoses) and procedures for reproductive organs (e.g., endoluminal occlusion of vas deferens or Fallopian tubes for minimally-invasive contraceptive intervention, endovascular occlusion of varicocele in males and low abdominal gonadal veins for reducing or completely eliminating chronic pelvic pain syndrome in females). In some embodiments, implants of the present disclosure may be used for stopping blood loss from a damaged blood vessel, closing an abnormal blood vessel or a blood vessel supplying a vascular anomaly, or interrupting blood supply to an organ or part of an organ for permanent devascularization (e.g., closure of splenic artery in spleen laceration, devascularization of tissues involved by neoplastic process, either pre-operatively or as a palliative measure). In some embodiments, implants of the present disclosure may be used for various endovascular (e.g., neural and peripheral) procedures including procedures for giant cerebral and skull base aneurysms (ruptured and non-ruptured), head and neck arteriovenous fistulas, dissecting intracranial and extracranial vessels, traumatic and non-traumatic vessel injury or rupture (e.g., pelvic hemorrhages in trauma patients, carotid blow-out in patients with head and neck cancers, hemorrhage induced by a neoplasia, etc.), and devascularization prior to (or as an alternative to) surgical resection of various organs or tumors.

In certain embodiments, implants of the present disclosure may be used for various organs, including for example, the spleen (e.g., endovascular occlusion as a preoperative intervention or as an alternative to surgical resection with indications including traumatic hemorrhage, hypersplenism, bleeding secondary to portal hypertension or splenic vein thrombosis, and various disorders such as thalassemia major, thrombocytopenia, idiopathic thrombocytopenic purpura, Gaucher disease, and Hodgkin disease), the liver (e.g., occlusion of portal veins collaterals as adjunct to a transjugular intrahepatic portosystemic shunt (TIPS), occlusion of the TIPS itself in cases of encephalopathy, occlusion of intrahepatic arterioportal fistulas), the kidney (e.g., endoluminal ureteral occlusion for intractable lower urinary tract fistula with urine leakage, or for the treatment of ureteroarterial fistulae, endovascular occlusion as an alternative to surgical resection for end-stage renal disease or renovascular hypertension requiring unilateral or bilateral nephrectomy and renal transplant with native kidneys in situ), and the heart (e.g., occlusion of coronary arteriovenous fistulas, transarterial embolization of Blalock-Taussig shunts). The application of implants of the present disclosure is not limited to applications for human patients, but may also include veterinary applications.

According to some embodiments, a cover component or patch can be attached to an implant. Cover components may be attached to one or both ends or an implant and/or a middle region of an implant.

According to various embodiments of the subject technology, a cover component of an implant may be used to occlude, partially or completely, luminal structure in which a respective implant is deployed. In some embodiments as used herein, occlusion may refer to either partial or complete occlusion. In some embodiments, cover components can comprise at least one of a polyurethane, a polyanhidrate, PTFE, ePTFE, silicone, and other suitable materials known to those of ordinary skill in the art. In some embodiments, cover components may be elastic. In some embodiments, cover components may be permeable or non-permeable.

In some embodiments, an average thickness of a cover component can be between about 0.0005 inches and about 0.006 inches. In some aspects, the average thickness of a cover component may be less than about 0.0005 inches or greater than about 0.006 inches. In certain embodiments, an average thickness of a distal portion of a cover component is greater than an average thickness of a proximal portion of a cover component. Such a configuration may ensure that more flow may be reduced at the distal portion of a cover component. In some embodiments, the average thickness of the distal portion of a cover component is between about 0.002 inches and about 0.012 inches. In some embodiments, the average thickness of the distal portion of a cover component may be less than about 0.002 inches or greater than about 0.012 inches. In some embodiments, the average thickness of the proximal portion of a cover component is between about 0.0005 inches and about 0.006 inches. In some embodiments, the average thickness of the proximal portion of a cover component may be less than about 0.0005 inches or greater than about 0.006 inches.

The foregoing description is provided to enable a person skilled in the art to practice the various configurations described herein. While the subject technology has been particularly described with reference to the various Figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method Claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the Claims, such term is intended to be inclusive in a manner similar to the term "comprise" as "comprise" is interpreted when employed as a transitional word in a Claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the inventions have been described, these have been presented by way of example only, and are not intended to limit the scope of the inventions. Indeed, the novel methods and systems described herein may be embodied in a variety of other forms without departing from the spirit thereof. The accompanying Claims and their equivalents are intended to cover such forms or modifications as would fall within the scope and spirit of the inventions.

What is claimed is:

1. A method of assembling an implant delivery system, comprising:
    providing an implant, in a relaxed state, to a catheter having a kerf (1) extending from and through an outer surface of the catheter into a lumen of the catheter, and (2) extending in a first helical direction and defining opposing sides along a helical coil;
    engaging a first end portion of the implant with a proximal portion of the catheter; and
    engaging a second end portion of the implant with a distal portion of the catheter, such that the implant is held in a torsional state by the catheter, and such that the implant applies a torque to the catheter to cause opposing sides of adjacent windings of the coil between the proximal portion and the distal portion to be pulled toward each other.

2. The method of claim 1, wherein the kerf has a non-linear profile following a helical path.

3. The method of claim 2, wherein, the non-linear profile comprises a triangular profile.

4. The method of claim 2, wherein, the non-linear profile comprises a sawtooth profile.

5. The method of claim 2, wherein, the non-linear profile comprises an undulating profile.

6. The method of claim 1, wherein the implant further comprises a helical member extending in a second helical direction, opposite the first helical direction.

7. The method of claim 1, wherein, while the implant is in the relaxed state, the proximal portion is configured to disengage from the first end portion and/or the distal portion is configured to disengage from the second end portion.

8. The method of claim 1, wherein the kerf is defined between adjacent windings of the helical coil, and while the implant is in the torsional state, the adjacent windings of the helical coil contact each other.

9. The method of claim 1, wherein the kerf is defined between adjacent windings of the helical coil, and while the implant is in the relaxed state, the adjacent windings of the coil are spaced apart from each other by a gap.

10. The method of claim 1, wherein the torque causes opposing sides of adjacent windings of the coil between the proximal portion and the distal portion to be pulled toward each other.

11. The method of claim 1, wherein the kerf extends between adjacent windings of the coil.

12. A method of assembling an implant delivery system, the method comprising:
    providing a catheter comprising a proximal portion, a distal portion, and a helical coil extending in a first helical direction and connecting the proximal portion to the distal portion, the coil being defined by a kerf between adjacent windings of the coil;
    engaging a first end portion of an implant with the catheter proximal portion, the implant being biased to a relaxed state;
    moving the implant away from the relaxed state to a collapsed state and engaging a second end portion of the implant with the catheter distal portion such that the implant applies a torque to the catheter to reduce a width or pitch of the kerf between adjacent windings of the catheter coil.

13. The method of claim 12, wherein the kerf has a non-linear profile following a helical path.

14. The method of claim 12, wherein the implant further comprises a helical member extending in a second helical direction, opposite the first helical direction.

15. The method of claim 12, wherein, while the implant is in the relaxed state, the adjacent windings of the coil are spaced apart from each other by a gap.

16. The method of claim 12, wherein, while the implant is in the relaxed state, the proximal portion is configured to disengage from the first end portion and/or the distal portion is configured to disengage from the second end portion.

17. A method of assembling an implant delivery system, the method comprising:
    providing a catheter comprising a proximal portion, a distal portion, and a kerf that defines windings of the catheter that connect the proximal portion to the distal portion and are movable relative to each other; and
    compressing an implant onto the catheter to couple (i) a first end portion of the implant to the catheter proximal portion and (ii) a second end portion of the implant to the catheter distal portion such that the implant is engaged on the catheter in a collapsed state to apply a torque to the catheter, thereby reducing a width or pitch of a gap between adjacent windings.

18. The method of claim 17, wherein the catheter comprises a coil wherealong the kerf extends between adjacent windings of the coil.

19. The method of claim 17, wherein the kerf has a non-linear profile following a helical path.

* * * * *